(12) United States Patent
Shoda et al.

(10) Patent No.: US 7,531,533 B2
(45) Date of Patent: May 12, 2009

(54) 6-MEMBERED HETEROCYCLIC COMPOUND AND USE THEREOF

(75) Inventors: Motoshi Shoda, Tokyo (JP); Toshinori Ishizuya, Tokyo (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 327 days.

(21) Appl. No.: 11/339,803

(22) Filed: Jan. 26, 2006

(65) Prior Publication Data

US 2007/0060590 A1    Mar. 15, 2007

Related U.S. Application Data

(60) Provisional application No. 60/647,382, filed on Jan. 28, 2005, provisional application No. 60/737,390, filed on Nov. 17, 2005.

(30) Foreign Application Priority Data

Jan. 27, 2005 (JP) ............................... 2005-019185
Nov. 15, 2005 (JP) ............................... 2005-330079

(51) Int. Cl.
*C07D 285/18* (2006.01)
*A61K 31/54* (2006.01)
*A61K 31/541* (2006.01)

(52) U.S. Cl. ........................................ 514/222.5; 544/8

(58) Field of Classification Search .................... 544/8; 514/222.5

See application file for complete search history.

(56) References Cited

U.S. PATENT DOCUMENTS 6,747,037 B1  6/2004  Old et al.
7,015,243 B2  3/2006  Old et al.

FOREIGN PATENT DOCUMENTS

| EP | 1110949 A1 | 6/2001 |
|---|---|---|
| EP | 1232757 A1 | 8/2002 |
| WO | WO-02/24647 A1 | 3/2002 |
| WO | WO-02/42268 A2 | 5/2002 |
| WO | WO-03/007941 A1 | 1/2003 |
| WO | WO-03/035064 A1 | 5/2003 |
| WO | WO-2004/063158 A1 | 7/2004 |
| WO | WO-2004/085430 A1 | 10/2004 |
| WO | WO-2004/085431 A1 | 10/2004 |
| WO | WO-2005/053707 A1 | 6/2005 |
| WO | WO-2006/014206 A1 | 2/2006 |
| WO | WO-2006/014207 A1 | 2/2006 |

OTHER PUBLICATIONS

Alvarez-Ibarra et al., J. Org. Chem., vol. 67, pp. 2789-2797, (2002).
Hitchcock et al., J. Org. Chem., vol. 69, pp. 714-718, (2004).

*Primary Examiner*—Kahsay T Habte
(74) *Attorney, Agent, or Firm*—Birch, Stewart, Kolasch & Birch, LLP

(57) ABSTRACT

A compound represented by the general formula (I) or a salt thereof:

[Formula 1]

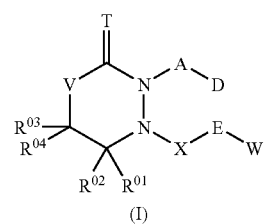

(I)

[T represents oxygen atom and the like; V represents $CH_2$ and the like; $R^{01}$ to $R^{04}$ represent hydrogen atom and the like; A represents a linear alkylene group or linear alkenylene group having 2 to 8 carbon atoms and the like; D represents carboxyl group and the like; X represents ethylene group, trimethylene group and the like; E represents —CH(OH)— group and the like; and W represent —$U^1$—($R^{W1}$)($R^{W2}$)—$U^2$—$U^3$ group ($U^1$ represents a single bond, an alkylene group having 1 to 4 carbon atoms and the like; $R^{W1}$ and $R^{W2}$ represent hydrogen atom and the like; $U^2$ represents a single bond, an alkylene group having 1 to 4 carbon atoms and the like; and $U^3$ represent an alkyl group having 1 to 8 carbon atoms and the like), or a residue of a carbon ring or heterocyclic compound], which can be utilized as an active ingredient of medicaments effective for prophylactic and/or therapeutic treatment of skeletal diseases such as osteoporosis and fracture, glaucoma, ulcerative colitis and the like.

5 Claims, No Drawings

US 7,531,533 B2

6-MEMBERED HETEROCYCLIC COMPOUND AND USE THEREOF

TECHNICAL FIELD

The present invention relates to a novel 6-membered heterocyclic compound. More specifically, the present invention relates to a 6-membered heterocyclic compound useful as an active ingredient of medicaments and a synthetic intermediate of the compound.

BACKGROUND ART

Osteoporosis is a disease in which bones pathologically are aged and become brittle. In general, the pathological conditions of osteoporosis, per se, are often non-symptomatic or with slight symptoms. However, if bone fracture is once caused, the disease may present severe symptoms depending on the position or degree of the fracture. Predilection sites of bone fractures are metaphyseal regions of appendicular skeletons and spines, and in particular, femoral neck fracture, compressed fracture of spine vertebra, fracture of distal end of radius, and fracture of proximal end of humerus are regarded as four major fractures in osteoporosis. It is generally difficult to reduce a fracture with osteoporosis by a therapeutic treatment because of the brittle property of the bone, and a problem arises that sufficient fixation can be hardly obtained even by osteosynthesis. Disuse of the whole body will readily advance with fractures, and various and severe complications such as muscular weakness, joint contracture, decubitus, dementia, urinary tract infection, and cardiopulmonary dysfunction are easily caused. Moreover, a vicious circle will likely occur in which disuse bone atrophy simultaneously advances, and as a result, osteoporosis is further aggravated.

As described above, fractures with osteoporosis degrade the quality of life (QOL) of patients, greatly affect the vital prognosis, and in addition, cause extremely serious social problems such as increases of caring burden and medical expense. Therefore, targets of therapeutic treatments of osteoporosis are to quickly promote osteogenesis to increase bone mass and thereby prevent bone fractures, and for patients suffered from existing fractures, to quickly increase bone mass in a similar manner to promote early leave from sickbeds and release the patients from risks of complications resulting from the bedridden status.

The pathological condition of bone fracture, per se, is an impairment which may occur all over generations due to various causes other than osteoporosis, and healing therefrom requires rather long period of time, if not with osteoporosis. For this reason, fractures significantly disturb activities of daily living (ADL) of patients, and clinical cases may sometimes occur in which normal recovery is not observed such as incomplete synostosis, protracted healing, and malunion. Therefore, for bone fractures, targets of the therapeutic treatments are also to quickly promote osteogenesis after injury to promptly increase bone mass and thereby shorten a period required for fixation of fractured site or period in bedridden status.

As prophylactic and/or therapeutic agents for skeletal diseases including osteoporosis and bone fracture, calcium preparations, estrogen preparations, selective estrogen receptor modulators (SERM), active vitamin D3 preparations, vitamin K preparations, ipriflavone preparations, calcitonin preparations, bisphosphonate preparations, parathyroid hormone preparations, anabolic hormone preparations, bone morphogenic proteins (BMP), fibroblast growth factors (FGF) and the like have been clinically used so far, or clinical applications thereof have been studied so far. However, despite the use of the variety of drugs, the number of patients of skeletal diseases has been increasing year by year. For example, the number of patients of femoral neck fracture is estimated to be 1,700,000 all over the world as of 1990, and the number is predicted to increase up to 6,300,000 in 2050. Therefore, the prophylactic and/or therapeutic effects of the conventional medicaments for the skeletal diseases are not fully satisfactory effects, and developments of innovative medicaments that exhibit higher effects than those of the conventional medicaments have been desired.

Prostaglandin $E_2$ (hereinafter abbreviated as "$PGE_2$") is known to have various physiological functions such as algesic action and oxytocic action, and regulatory action on bone metabolism is also reported. It is really reported that when $PGE_2$ is given to experimental animals such as rats or humans, osteogenesis rises and bone mass increases. It is also reported that when $PGE_2$ is topically administered to a bone in the form of a sustained release drug, osteogenesis of the site is promoted. Further, it is reported that when $PGE_2$ is added to a marrow cell culture system, the calcified bone-like node formation and the alkaline phosphatase activity as the marker of differentiation of osteoblasts increase, and therefore an efficacy of positively promoting osteogenesis can be expected for $PGE_2$. For this reason, in contrast to the conventional medicaments, which hardly achieve recovery from skeletal diseases although they delay the advance, $PGE_2$ may possibly be a medicament having extremely high usefulness.

However, since $PGE_2$ exhibits the side effects which should be avoided for continuous administration for a long period of time, such as the algesic action and oxytocic action as described above, researches have been extensively conducted aiming at obtaining $PGE_2$ derivatives which selectively act on bones. Four kinds of different receptor subtypes ($EP_1$, $EP_2$, $EP_3$, $EP_4$) are reported so far in human as receptors of $PGE_2$, and expression sites and intracellular signal transduction systems for the activation of these subtypes are different. Accordingly, for example, one attempt is to newly provide bone-selective $PGE_2$ derivatives by creating a subtype-specific agonist for each subtype.

At least two kinds of receptors, $EP_2$ and $EP_4$, have been reported as the receptors of $PGE_2$ expressed in osteoblasts, and in particular, $EP_4$ is reported to be deeply involved in the osteogenesis function, because an antagonist thereof suppresses the formation of the calcified bone-lime nodes in a marrow cell culture system (M. WEINEB, A. et al., Am. J. Physiol., 276, E376-E383, 1999). Therefore, $EP_4$ agonists are promising as skeletal disease curing agents. $EP_2$ also has a function of increasing cAMP in osteoblasts through conjugation with the Gs protein like $EP_4$. Accordingly, $EP_2$ agonists are also expected to be therapeutic agents for skeletal disease. Actual clinical applications of $EP_2$ agonists and $EP_4$ agonists as therapeutic agents for skeletal disease have been attempted. However, they are not clinically convenient because, for example, the route of administration thereof are limited to sustained release local administration, intravenous drip infusion and the like.

As heterocyclic compounds having similar action to that of the compounds of the present invention, compounds described in the following patent documents: International Patent Publications WO02/24647, WO02/42268, WO03/007941, WO03/035064, WO04/63158, WO04/85430, and U.S. Pat. No. 6,747,037 are known. However, structural features of any of these compounds are different from those of the compounds of the present invention.

DISCLOSURE OF THE INVENTION

Object to be Achieved by the Invention

An object of the present invention is to provide a novel compound that can be utilized as an active ingredient of a medicament extremely effective for prophylactic and/or therapeutic treatment of skeletal diseases such as osteoporosis and fracture. Another object of the present invention is to provide a novel compound useful as an $EP_4$ agonist. A further object of the present invention is to provide a medicament comprising the compound as an active ingredient. A still further object of the present invention is to provide an intermediate for the preparation of the compound.

Means for Achieving the Object

In order to achieve the aforementioned objects, the inventors of the present invention extensively searched for substances which promote osteogenesis. As a result, they found that the 6-membered heterocyclic compounds represented by the general formula mentioned below, which are novel compounds, had a superior osteogenesis promoting action, and that the compounds were useful as an active ingredient of a medicament for prophylactic and/or therapeutic treatment of skeletal diseases such as osteoporosis and bone fracture. The inventors of the present invention further found that the compounds were $EP_4$ agonists, and that the compounds were useful as an active ingredient for prophylactic and/or therapeutic treatment of glaucoma, ulcerative colitis and the like. The present invention was achieved on the basis of the aforementioned findings.

The present invention thus relates to the followings:

<1> A compound represented by the general formula (I) [hereafter also simply referred to as "Compound (I) of the invention"] or a salt thereof:

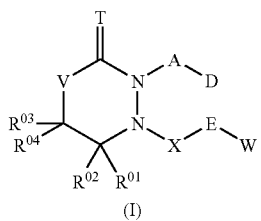

[Formula 1]

(I)

[wherein T represents (1) oxygen atom, or (2) sulfur atom;
V represents (1) $C(R^{O5})(R^{O6})$, (2) oxygen atom, or (3) sulfur atom;
$R^{O1}$, $R^{O2}$, $R^{O3}$, $R^{O4}$, $R^{O5}$, and $R^{O6}$ independently represent (1) hydrogen atom, or (2) an alkyl group having 1 to 4 carbon atoms;
A represents $A^1$ or $A^2$;
$A^1$ represents (1) a linear alkylene group having 2 to 8 carbon atoms which may be substituted with one or two alkyl groups having 1 to 4 carbon atoms, (2) a linear alkenylene group having 2 to 8 carbon atoms which may be substituted with one or two alkyl groups having 1 to 4 carbon atoms, or (3) a linear alkynylene group having 2 to 8 carbon atoms which may be substituted with one or two alkyl groups having 1 to 4 carbon atoms;

$A^2$ represents a -$G^1$-$G^2$-$G^3$- group;
$G^1$ represents (1) a linear alkylene group having 1 to 4 carbon atoms which may be substituted with one or two alkyl groups having 1 to 4 carbon atoms, (2) a linear alkenylene group having 2 to 4 carbon atoms which may be substituted with one or two alkyl groups having 1 to 4 carbon atoms, or (3) a linear alkynylene group having 2 to 4 carbon atoms which may be substituted with one or two alkyl groups having 1 to 4 carbon atoms;
$G^2$ represents (1) a —$Ar^1$— group, (2) a —Y—$Ar^1$— group, (3) a —$Ar^1$—Y— group, or (4) a —Y— group, Y represents (1) —S— group, (2) —S(O)— group, (3) —S(O)$_2$— group, (4) —O— group, or (5) a —N($R^{G1}$)— group;
$R^{G1}$ represents (1) hydrogen atom, (2) an alkyl group having 1 to 4 carbon atoms, or (3) an acyl group having 2 to 6 carbon atoms;
the group $Ar^1$ represents (1) a residue of a carbocyclic compound (ca1), or (2) a residue of a heterocyclic compound (qa1); the group $Ar^1$ may be substituted with 1 or the same or different 2 to 4 of groups $R^1$;
the group $R^1$ represents (1) an alkyl group having 1 to 4 carbon atoms, (2) an alkoxy group having 1 to 4 carbon atoms, or (3) a halogen atom;
$G^3$ represents (1) a single bond, (2) a linear alkylene group having 1 to 4 carbon atoms which may be substituted with one or two alkyl groups having 1 to 4 carbon atoms, (3) a linear alkenylene group having 2 to 4 carbon atoms which may be substituted with one or two alkyl groups having 1 to 4 carbon atoms, or (4) a linear alkynylene group having 2 to 4 carbon atoms which may be substituted with one or two alkyl groups having 1 to 4 carbon atoms (provided that when $G^2$ represents the —$Ar^1$—Y— group, or the —Y— group, $G^3$ represents any of those defined above except for a single bond);
D represents $D^1$ or $D^2$;
$D^1$ represents (1) a —$COOR^{D1}$ group, (2) tetrazol-5-yl group, or (3) a —$C(O)N(R^{D2})SO_2R^{D3}$ group;
$R^{D1}$ represents (1) hydrogen atom, (2) an alkyl group having 1 to 4 carbon atoms, (3) phenyl group, (4) an alkyl group having 1 to 4 carbon atoms substituted with phenyl group, or (5) a biphenyl group;
$R^{D2}$ represents (1) hydrogen atom, or (2) an alkyl group having 1 to 4 carbon atoms;
$R^{D3}$ represents (1) an alkyl group having 1 to 4 carbon atoms, or (2) phenyl group;
$D^2$ represents (1) a —$CH_2OR^{D4}$ group, (2) a —$OR^{D4}$ group, (3) formyl group, (4) a —$C(O)NR^{D5}R^{D6}$ group, (5) a —$C(O)N(R^{D5})SO_2R^{D7}$ group, (6) a —$C(O)$-$M_m$-OH group, (7) a —O-$M_m$-H group, (8) a —$COOR^{D8}$ group, (9) a —$OC(O)$—$R^{D9}$ group, (10) a —$COO$-$Z^1$-$Z^2$-$Z^3$ group, or (11) a substituent selected from the group consisting of the substituents $D^{2a1}$, $D^{2a2}$, $D^{2a3}$, $D^{2a4}$, and $D^{2a5}$ represented by the following formulas:

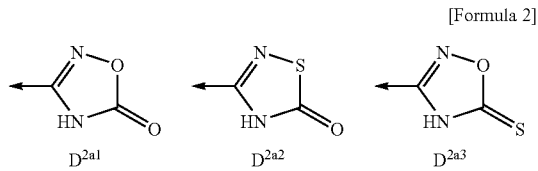

[Formula 2]

$D^{2a1}$     $D^{2a2}$     $D^{2a3}$

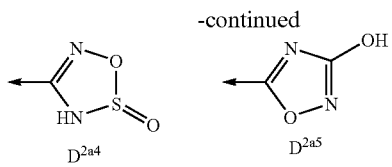

(wherein the arrows indicate a bond with the group A);
$R^{D4}$ represents (1) hydrogen atom, or (2) an alkyl group having 1 to 4 carbon atoms;
$R^{D5}$ and $R^{D6}$ independently represent (1) hydrogen atom, or (2) an alkyl group having 1 to 4 carbon atoms, or (3) $R^{D5}$ and $R^{D6}$ may bind to each other to form a saturated monocyclic heterocyclic ring (qb1) together with the nitrogen atom to which they bind;
$R^{D7}$ represents an alkyl group having 1 to 4 carbon atoms substituted with phenyl group;
$R^{D8}$ represents (1) an alkyl group having 1 to 4 carbon atoms substituted with a biphenyl group which may be substituted with 1 to 3 substituents selected from the group consisting of an alkyl group having 1 to 4 carbon atoms, an alkoxy group having 1 to 4 carbon atoms, and a halogen atom, or (2) a biphenyl group which may be substituted with 1 to 3 substituents selected from the group consisting of an alkyl group having 1 to 4 carbon atoms, an alkoxy group having 1 to 4 carbon atoms, and a halogen atom;
$R^{D9}$ represents (1) phenyl group, or (2) an alkyl group having 1 to 4 carbon atoms;
M represents a divalent group obtained by eliminating, from a compound having amino group and carboxyl group, hydrogen atom of the amino group and hydroxyl group of the carboxyl group;
m represents an integer of 1 or 2;
$Z^1$ represents (1) an alkylene group having 1 to 8 carbon atoms, (2) an alkenylene group having 2 to 8 carbon atoms, or (3) an alkynylene group having 2 to 8 carbon atoms;
$Z^2$ represents (1) —C(O)— group, (2) —OC(O)— group, (3) —COO— group, (4) a —C(O)N($R^{Z1}$)— group, (5) a —N($R^{Z2}$)C(O)— group, (6) —O— group, (7) —S— group, (8) —S(O)$_2$— group, (9) a —S(O)$_2$N($R^{Z2}$)— group, (10) a —N($R^{Z2}$)S(O)$_2$— group, (11) a —N($R^{Z3}$)— group, (12) a —N($R^{Z4}$)C(O)N($R^{Z5}$)— group, (13) a —N($R^{Z6}$)C(O)O— group, (14) a —OC(O)N($R^{Z7}$)— group, or (15) —OC(O)O— group;
$Z^3$ represents (1) hydrogen atom, (2) an alkyl group having 1 to 4 carbon atoms, (3) an alkenyl group having 2 to 4 carbon atoms, (4) an alkynyl group having 2 to 4 carbon atoms, (5) a ring Z, or (6) an alkoxy group having 1 to 4 carbon atoms, an alkylthio group having 1 to 4 carbon atoms, a —N($R^{Z8}$)($R^{Z9}$) group, or an alkyl group having 1 to 4 carbon atoms substituted with a ring Z;
the ring Z represents (1) a residue of a carbocyclic compound (ca2), or (2) a residue of a heterocyclic compound (qa2);
$R^{Z1}, R^{Z2}, R^{Z3}, R^{Z4}, R^{Z5}, R^{Z6}, R^{Z7}, R^{Z8}$, and $R^{Z9}$ independently represent hydrogen atom, or an alkyl group having 1 to 4 carbon atoms;
or $R^{Z1}$ and $Z^3$ may form a saturated monocyclic heterocyclic ring (qb2) together with the nitrogen atom to which they bind;
X represents (1) ethylene group, (2) trimethylene group, or (3) —CH$_2$CH=CH— group;
E represents (1) —CH(OH)— group, or (2) —C(O)— group;
W represents (1) a group Wa represented by the following formula:

[Formula 3]

$$\leftarrow U^1 \underset{\underset{R^{W2}}{|}}{\overset{\overset{R^{W1}}{|}}{C}} U^2 - U^3$$

(Wa)

(wherein the arrow indicates a bond with the group E), or (2) a group $Ar^2$;
$R^{W1}$ and $R^{W2}$ independently represent (1) hydrogen atom, (2) an alkyl group having 1 to 4 carbon atoms, or (3) fluorine atom, or (4) $R^{W1}$ and $R^{W2}$ may bind to each other to form a 3- to 7-membered saturated cycloalkane (cb) together with the carbon atom to which they bind;
the saturated cycloalkane (cb) may be substituted with 1 or the same or different 2 to 4 alkyl groups having 1 to 4 carbon atoms;
$U^1$ represents (1) a single bond, (2) an alkylene group having 1 to 4 carbon atoms, (3) an alkenylene group having 2 to 4 carbon atoms, or (4) an alkynylene group having 2 to 4 carbon atoms;
$U^2$ represents (1) a single bond, (2) an alkylene group having 1 to 4 carbon atoms, (3) an alkenylene group having 2 to 4 carbon atoms, (4) an alkynylene group having 2 to 4 carbon atoms, (5) —O— group, (6) —S— group, (7) —S(O)— group, (8) —S(O)$_2$— group, (9) a —N($R^{U1}$)— group, (10) —C(O)— group, (11) a —C(O)N($R^{U2}$)— group, (12) a —N($R^{U2}$)C(O)— group, (13) a —S(O)$_2$N($R^{U2}$)— group, or (14) a —N($R^{U2}$)S(O)$_2$— group;
$R^{U1}$ represents (1) hydrogen atom, (2) an alkyl group having 1 to 4 carbon atoms, or (3) an acyl group having 2 to 6 carbon atoms;
$R^{U2}$ represents (1) hydrogen atom, or (2) an alkyl group having 1 to 4 carbon atoms;
$U^3$ represents (1) an alkyl group having 1 to 8 carbon atoms which may be substituted with 1 or the same or different 2 to 4 substituents selected from the group consisting of an alkyl group having 1 to 4 carbon atoms, a halogen atom, hydroxyl group, an alkoxy group having 1 to 4 carbon atoms, an alkylthio group having 1 to 4 carbon atoms, and a —N($R^{U3}$)($R^{U4}$) group, (2) an alkenyl group having 2 to 8 carbon atoms which may be substituted with 1 or the same or different 2 to 4 substituents selected from the group consisting of an alkyl group having 1 to 4 carbon atoms, a halogen atom, hydroxyl group, an alkoxy group having 1 to 4 carbon atoms, an alkylthio group having 1 to 4 carbon atoms, and a —N($R^{U3}$)($R^{U4}$) group, (3) an alkynyl group having 2 to 8 carbon atoms which may be substituted with 1 or the same or different 2 to 4 substituents selected from the group consisting of an alkyl group having 1 to 4 carbon atoms, a halogen atom, hydroxyl group, an alkylthio group having 1 to 4 carbon atoms, and a —N($R^{U3}$)($R^{U4}$) group, (4) an alkyl group having 1 to 8 carbon atoms substituted with a group $Ar^3$, or (5) a group $Ar^3$;
$R^{U3}$ and $R^{U4}$ independently represent (1) hydrogen atom, or (2) an alkyl group having 1 to 4 carbon atoms, or (3) $R^{U3}$ and $R^{U4}$ may bind to each other to form a saturated monocyclic heterocyclic ring (qb3) together with the nitrogen atom to which they bind;
the group $Ar^2$ and the group $Ar^3$ independently represent (1) a residue of a carbocyclic compound (ca3), or (2) a residue of a heterocyclic compound (qa3);
the group $Ar^2$ and the group $Ar^3$ may be substituted with 1 or the same or different 2 to 4 of groups $R^2$;

$R^2$ represents (1) an alkyl group having 1 to 4 carbon atoms, (2) an alkoxy group having 1 to 4 carbon atoms, (3) an alkylthio group having 1 to 4 carbon atoms, (4) a halogen atom, (5) hydroxyl group, (6) nitro group, (7) a —N($R^{A1}$) ($R^{A2}$) group, (8) an alkyl group having 1 to 4 carbon atoms substituted with an alkoxy group having 1 to 4 carbon atoms, (9) an alkyl group having 1 to 4 carbon atoms substituted with 1 to 3 halogen atoms, (10) an alkyl group having 1 to 4 carbon atoms substituted with an alkoxy group having 1 to 4 carbon atoms substituted with 1 to 3 halogen atoms, (11) an alkyl group having 1 to 4 carbon atoms substituted with a —N($R^{A1}$)($R^{A2}$) group, (12) a group $Ar^4$, (13) a —O—$Ar^4$ group, (14) an alkyl group having 1 to 4 carbon atoms substituted with a group $Ar^4$, (15) an alkenyl group having 2 to 4 carbon atoms substituted with a group $Ar^4$, (16) an alkynyl group having 2 to 4 carbon atoms substituted with a group $Ar^4$, (17) an alkoxy group having 1 to 4 carbon atoms substituted with a group $Ar^4$, (18) an alkyl group having 1 to 4 carbon atoms substituted with a —O—$Ar^4$ group, (19) a —COO$R^{A3}$ group, (20) an alkoxy group having 1 to 4 carbon atoms substituted with 1 to 3 halogen atoms, (21) formyl group, (22) an alkyl group having 1 to 4 carbon atoms substituted with hydroxyl group, (23) an acyl group having 2 to 6 carbon atoms, (24) oxo group, or (25) thioxo group;

$R^{A1}$ and $R^{A2}$ independently represent (1) hydrogen atom, or (2) an alkyl group having 1 to 4 carbon atoms, or (3) $R^{A1}$ and $R^{A2}$ may bind to each other to form a saturated monocyclic heterocyclic ring (qb4) together with the nitrogen atom to which they bind;

$R^{A3}$ represents (1) hydrogen atom, or (2) an alkyl group having 1 to 4 carbon atoms;

the group $Ar^4$ represents (1) a residue of a carbocyclic compound (ca4), or (2) a residue of a heterocyclic compound (qa4);

residues of a carbocyclic compound ca1, ca2, ca3, and ca4 independently represent a residue of a completely unsaturated, or partially or completely saturated monocyclic compound having 3 to 11 carbon atoms, or a residue of condensed bicyclic carbocyclic compound having 8 to 11 carbon atoms;

the group $Ar^4$ may be substituted with 1 or the same or different 2 to 4 of groups $R^3$;

$R^3$ represents (1) an alkyl group having 1 to 4 carbon atoms, (2) an alkenyl group having 2 to 4 carbon atoms, (3) an alkynyl group having 2 to 4 carbon atoms, (4) an alkoxy group having 1 to 4 carbon atoms, (5) an alkyl group having 1 to 4 carbon atoms substituted with an alkoxy group having 1 to 4 carbon atoms, (6) a halogen atom, (7) hydroxyl group, (8) an alkyl group having 1 to 4 carbon atoms substituted with 1 to 3 halogen atoms, or (9) an alkyl group having 1 to 4 carbon atoms substituted with an alkoxy group having 1 to 4 carbon atoms substituted with 1 to 3 halogen atoms;

residues of a heterocyclic compound qa1, qa2, qa3, and qa4 independently represent a residue of a completely unsaturated, or partially or completely saturated monocyclic compound having 3 to 11 ring-constituting atoms (the monocyclic compound contains, as the ring-constituting atoms, one or more hetero atoms, which may be the same or different, selected from the group consisting of nitrogen atom, oxygen atom, and sulfur atom), or a residue of a condensed bicyclic heterocyclic compound (qa) having 7 to 11 ring-constituting atoms, the heterocyclic compound (qa) contains 1 to 4 hetero atoms, which may be the same or different, selected from the group consisting of nitrogen atom, oxygen atom, and sulfur atom as the ring-constituting atoms;

residues of a saturated monocyclic heterocyclic compound qb1, qb2, qb3, and qb4 independently represent a residue of a 5- to 7-membered nitrogen-containing saturated monocyclic heterocyclic compound (qb), and the heterocyclic compound (qb) may further contain one ring-constituting hetero atom selected from the group consisting of nitrogen atom, oxygen atom, and sulfur atom, and may be substituted with 1 or the same or different 2 to 4 alkyl groups having 1 to 4 carbon atoms].

<2> The compound or a salt thereof according to <1>, which compound is represented by the general formula (I-A):

[Formula 4]

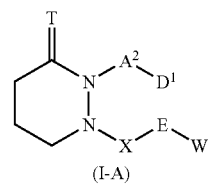

(I-A)

(wherein T, $A^2$, $D^1$, X, E, and W have the same meanings as those defined above).

<3> The compound or a salt thereof according to <1> or <2>, which compound is represented by the general formula (I-A-1):

[Formula 5]

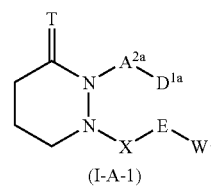

(I-A-1)

[wherein $A^{2a}$ represents (1) a -$G^{1a}$-$Ar^1$-$G^{3a}$- group, (2) a -$G^{1a}$-Y—$Ar^1$-$G^{3a}$- group, (3) a -$G^{1a}$-$Ar^1$—Y-$G^{3a}$- group, or (4) a -$G^{1a}$-Y-$G^{3a}$- group;

$G^{1a}$ represents a linear alkylene group having 1 to 4 carbon atoms;

$G^{3a}$ represents (1) a single bond, (2) a linear alkylene group having 1 to 4 carbon atoms, or (3) a linear alkenylene group having 2 to 4 carbon atoms;

$D^{1a}$ represents (1) a —COO$R^{D1}$ group, or (2) tetrazol-5-yl group;

$W^1$ represents (1) a group $Wa^1$ represented by the following formula:

[Formula 6]

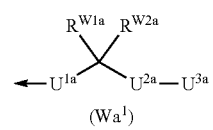

($Wa^1$)

(wherein the arrow indicates a bond with the group E), or (2) a group $Ar^2$;

$R^{W1a}$ and $R^{W2a}$ independently represent (1) hydrogen atom, (2) an alkyl group having 1 to 4 carbon atoms, or (3)

fluorine atom, or together represent (4) a substituent in which $R^{W1a}$ is $R^{W2a}$ bind to each other to form a 3- to 7-membered saturated cycloalkane (cb) together with the carbon atom to which they bind;

$U^{1a}$ represents (1) a single bond, or (2) an alkylene group having 1 to 4 carbon atoms;

$U^{2a}$ represents (1) a single bond, (2) an alkylene group having 1 to 4 carbon atoms, (3) —O— group, (4) —S— group, (5) —S(O)— group, (6) —S(O)$_2$— group, or (7) a —N($R^{U1}$)— group;

$U^{3a}$ represents (1) an alkyl group having 1 to 8 carbon atoms which may be substituted with 1 or the same or different 2 to 4 substituents selected from the group consisting of an alkyl group having 1 to 4 carbon atoms, a halogen atom, hydroxyl group, an alkoxy group having 1 to 4 carbon atoms, an alkylthio group having 1 to 4 carbon atoms, and a —N($R^{U3}$)($R^{U4}$) group, (2) an alkyl group having 1 to 8 carbon atoms substituted with a group $Ar^3$, or (3) a group $Ar^3$; and T, $Ar^1$, Y, $R^{D1}$, $Ar^2$, $R^{U1}$, $R^{U3}$, $R^{U4}$, and $Ar^3$ have the same meanings as those defined above].

<4> The compound or a salt thereof according to any one of <1> to <3>, which compound is represented by the general formula (I-A-1a):

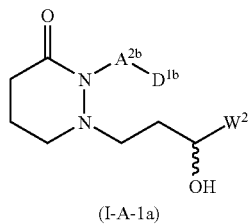

[Formula 7]

(I-A-1a)

[wherein $A^{2b}$ represents (1) a -$G^{1b}$-$Ar^{1a}$-$G^{3b}$- group, (2) a -$G^{1b}$-$Y^a$—$Ar^{1a}$-$G^{3b}$- group, (3) a -$G^{1b}$-$Ar^{1a}$—$Y^a$-$G^{3c}$- group, or (4) a -$G^{1b}$-$Y^a$-$G^{3c}$- group;

$G^{1b}$ represents (1) methylene group, (2) ethylene group, or (3) trimethylene group;

the group $Ar^{1a}$ represents (1) a residue of a completely unsaturated, or partially or completely saturated monocyclic carbocyclic compound having 3 to 7 carbon atoms (ca1m), or (2) a residue of a completely unsaturated, or partially or completely saturated monocyclic heterocyclic compound having 3 to 7 ring-constituting atoms and containing the same or different 1 to 3 hetero atoms selected from the group consisting of nitrogen atom, oxygen atom, and sulfur atom as the ring-constituting atoms (qa1m);

$Y^a$ represents (1) —O— group, or (2) —S— group;

$G^{3b}$ represents (1) a single bond, (2) methylene group, (3) ethylene group, or (4) ethenylene group;

$G^{3c}$ represents (1) methylene group, (2) ethylene group, or (3) ethenylene group;

$D^{1b}$ represents a —COOR$^{D1b}$ group, or tetrazol-5-yl group;

$R^{D1b}$ represents (1) hydrogen atom, or (2) an alkyl group having 1 to 4 carbon atoms;

$W^2$ represents (1) a group $Wa^2$ represented by the following formula:

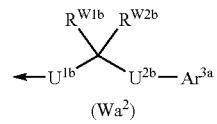

[Formula 8]

($Wa^2$)

(wherein the arrow indicates a bond with an adjacent carbon atom), or (2) a group $Ar^{2a}$;

$R^{W1b}$ and $R^{W2b}$ independently represent (1) hydrogen atom, or (2) methyl group, or together represent (3) a substituent in which $R^{W1b}$ and $R^{W2b}$ bind to each other to form cyclopropane, cyclobutane, cyclopentane, or cyclohexane together with the carbon atom to which they bind;

$U^{1b}$ represents (1) a single bond, (2) methylene group, (3) ethylene group, or (4) trimethylene group;

$U^{2b}$ represents (1) a single bond, (2) methylene group, (3) ethylene group, (4) trimethylene group, (5) —O— group, (6) —S— group, or (7) a —N($R^{U1'}$)—;

$R^{U1'}$ represents (1) hydrogen atom, or (2) an alkyl group having 1 to 4 carbon atoms;

the group $Ar^{2a}$ and the group $Ar^{3a}$ represent a residue of a cyclic compound selected from the group consisting of cyclopropane, cyclobutane, cyclopentane, cyclohexane, cycloheptane, benzene, azulene, naphthalene, dihydronaphthalene, tetrahydronaphthalene, adamantane, furan, thiophene, pyrrole, oxazole, isoxazole, thiazole, isothiazole, imidazole, pyrazole, triazole, furazan, oxadiazole, thiadiazole, tetrazole, pyridine, pyridazine, pyrimidine, pyrazine, triazine, oxazine, oxadiazine, thiazine, thiadiazine, indoline, isoindoline, dihydrobenzofuran, chroman, 4H-chromene, benzofuran, benzo[b]thiophene, indan, indole, isoindole, indolizine, 1H-indazole, 2H-indazole, 1H-benzimidazole, 1,3-dihydrobenzimidazole, benzoxazole, dihydro-3H-benzoxazole, benzo[d]isoxazole, benzo[c]isoxazole, benzothiazole, dihydro-3H-benzothiazole, benzo[d]isothiazole, benzo[c]isothiazole, 1H-benzotriazole, benzo[1,2,5]thiadiazole, quinoline, dihydro-1H-quinoline, isoquinoline, dihydro-2H-isoquinoline, cinnoline, quinazoline, quinoxaline, and phthalazine;

the group $Ar^{2a}$ and the group $Ar^{3a}$ may be substituted with 1 or the same or different 2 to 4 of groups $R^{2a}$;

$R^{2a}$ represents (1) an alkyl group having 1 to 4 carbon atoms, (2) an alkoxy group having 1 to 4 carbon atoms, (3) a halogen atom, (4) hydroxyl group, (5) a —N($R^{410}$)($R^{420}$) group, (6) an alkyl group having 1 to 4 carbon atoms substituted with an alkoxy group having 1 to 4 carbon atoms, (7) an alkyl group having 1 to 4 carbon atoms substituted with 1 to 3 halogen atoms, (8) an alkyl group having 1 to 4 carbon atoms substituted with an alkoxy group having 1 to 4 carbon atoms substituted with 1 to 3 halogen atoms, (9) an alkoxy group having 1 to 4 carbon atoms substituted with 1 to 3 halogen atoms, (10) an alkyl group having 1 to 4 carbon atoms substituted with hydroxyl group, (11) a group $Ar^{4a}$, (12) a —O—$Ar^{4a}$ group, (13) an alkyl group having 1 to 4 carbon atoms substituted with a group $Ar^{4a}$, or (14) an alkyl group having 1 to 4 carbon atoms substituted with —O—$Ar^{4a}$ group;

$R^{410}$ and $R^{420}$ independently represent (1) hydrogen atom, (2) methyl group, or (3) ethyl group, or together represent (3) a substituent in which $R^{410}$ and $R^{420}$ bind to each other to form pyrrolidine, piperidine, piperazine, homopiperidine, homopiperazine, or morpholine together with the nitrogen atom to which they bind;

the group $Ar^{4a}$ represents a residue of a cyclic compound selected from the group consisting of cyclopropane, cyclobutane, cyclopentane, cyclohexane, cycloheptane, cyclopentene, cyclohexene, cycloheptene, benzene, aziridine, azetidine, pyrrolidine, pyrroline, imidazoline, imidazolidine, triazoline, triazolidine, pyrazoline, pyrazolidine, piperidine, piperazine, homopiperidine, homopiperazine, azepine, diazepine, morpholine, thiomorpholine, furan, thiophene, pyrrole, oxazole, isoxazole, thiazole, isothiazole, imidazole, pyrazole, triazole, furazan, oxadiazole, thiadiazole, tetrazole, pyran, pyridine, pyridazine, pyrimidine, and pyrazine;

the group $Ar^{4a}$ may be substituted with 1 or the same or different 2 to 4 of groups $R^{3a}$; and $R^{3a}$ represents (1) an alkyl group having 1 to 4 carbon atoms, (2) an alkoxy group having 1 to 4 carbon atoms, (3) a halogen atom, (4) hydroxyl group, (5) an alkyl group having 1 to 4 carbon atoms substituted with 1 to 3 halogen atoms, or (6) an alkoxy group having 1 to 4 carbon atoms substituted with 1 to 3 halogen atoms].

<5> The compound or a salt thereof according to any one of <1> to <4>, which compound is represented by the general formula (I-A-1b):

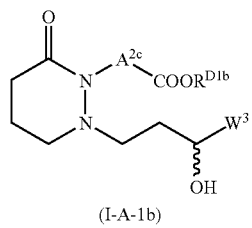

[Formula 9]

(I-A-1b)

[wherein $A^{2c}$ represents (1) a $-G^{1b}-Ar^{1b}-G^{3b}-$ group, (2) a $-G^{1b}-Y^a-Ar^{1b}-G^{3b}-$ group, or (3) a $-G^{1b}-Ar^{1b}-Y^a-G^{3c}-$ group;

the group $Ar^{1b}$ represents a residue of a cyclic compound selected from the group consisting of benzene, furan, thiophene, pyrrole, oxazole, isoxazole, thiazole, isothiazole, imidazole, pyrazole, pyridine, pyridazine, pyrimidine, and pyrazine;

$W^3$ represents (1) a group $Wa^3$ represented by the following formula:

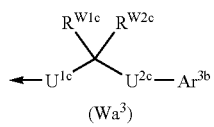

[Formula 10]

$(Wa^3)$ (wherein the arrow indicates a bond with an adjacent carbon atom), or (2) a group $Ar^{2b}$;

$R^{W1c}$ and $R^{W2c}$ independently represent (1) hydrogen atom, or (2) methyl group, or together represent (3) a substituent in which $R^{W1c}$ and $R^{W2c}$ bind to each other to form cyclopropane together with the carbon atom to which they bind;

$U^{1c}$ represents (1) a single bond, (2) methylene group, or (3) ethylene group;

$U^{2c}$ represents (1) a single bond, (2) methylene group, (3) ethylene group, (4) $-O-$ group, or (5) $-S-$ group;

the group $Ar^{2b}$ and the group $Ar^{3b}$ represents a residue of a cyclic compound selected from the group consisting of benzene, naphthalene, furan, thiophene, oxazole, isoxazole, thiazole, isothiazole, imidazole, pyrazole, triazole, pyridine, pyridazine, pyrimidine, pyrazine, benzofuran, benzo[b]thiophene, indan, indole, 1H-indazole, 1H-benzimidazole, benzoxazole, benzo[d]isoxazole, benzo[c]isoxazole, benzothiazole, benzo[d]isothiazole, benzo[c]isothiazole, 1H-benzotriazole, quinoline, isoquinoline, cinnoline, quinazoline, quinoxaline, and phthalazine;

the group $Ar^{2b}$ and the group $Ar^{3b}$ may be substituted with 1 or the same or different 2 to 4 of groups $R^{2b}$;

$R^{2b}$ represents (1) an alkyl group having 1 to 4 carbon atoms, (2) an alkoxy group having 1 to 4 carbon atoms, (3) a halogen atom, (4) an alkyl group having 1 to 4 carbon atoms substituted with an alkoxy group having 1 to 4 carbon atoms, (5) an alkyl group having 1 to 4 carbon atoms substituted with 1 to 3 halogen atoms, (6) an alkoxy group having 1 to 4 carbon atoms substituted with 1 to 3 halogen atoms, (7) an alkyl group having 1 to 4 carbon atoms substituted with hydroxyl group, (8) a group $Ar^{4b}$, (9) a $-O-Ar^{4b}$ group, (10) an alkyl group having 1 to 4 carbon atoms substituted with a group $Ar^{4b}$, or (11) an alkyl group having 1 to 4 carbon atoms substituted with the $-O-Ar^b$ group;

the group $Ar^{4b}$ represents a residue of a cyclic compound selected from the group consisting of benzene, furan, thiophene, pyrrole, oxazole, isoxazole, thiazole, isothiazole, imidazole, pyrazole, pyridine, pyridazine, pyrimidine, and pyrazine;

the group $Ar^{4b}$ may be substituted with 1 or the same or different 2 to 4 of groups $R^{3a}$; and $G^{1b}$, $G^{3b}$, $G^{3c}$, $Y^a$, and $R^{3a}$ have the same meanings as those defined above].

<6> The compound or a salt thereof according to any one of <1> to <5>, which compound is represented by the general formula (I-A-1b1):

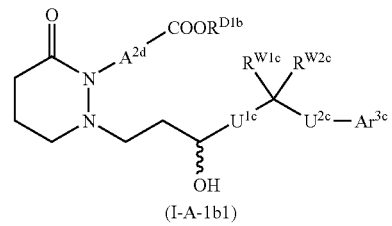

[Formula 11]

(I-A-1b1)

[wherein $A^{2d}$ represents (1) a $-G^{1b}-Ar^{1c}-G^{3b}-$ group, (2) a $-G^{1b}-Y^a-Ar^{1c}-G^{3b}-$ group, or (3) a $-G^{1b}-Ar^{1c}-Y^a-G^{3c}-$ group;

the group $Ar^{1c}$ represents a residue of a cyclic compound selected from the substituents represented by the following formulas:

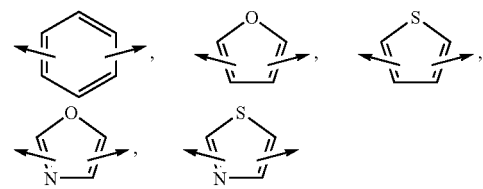

[Formula 12]

(the arrows represent a bond with an adjacent atom, and the bonding position may be any bondable position on a ring-constituting atom);

the group $Ar^{3c}$ represents a residue of a cyclic compound selected from the group consisting of benzene, naphthalene, furan, thiophene, pyridine, benzofuran, benzo[b]thiophene, indan, indole, 1H-indazole, 1H-benzimidazole, benzoxazole, benzothiazole, quinoline, isoquinoline, cinnoline, quinazoline, quinoxaline, and phthalazine;

the group $Ar^{3c}$ may be substituted with 1 or the same or different 2 to 4 of groups $R^{2c}$;

$R^{2c}$ represents methyl group, ethyl group, propyl group, isopropyl group, butyl group, isobutyl group, t-butyl group, methoxy group, ethoxy group, propyloxy group, isopropyloxy group, butoxy group, isobutyloxy group, t-butyloxy group, fluorine atom, chlorine atom, bromine atom, iodine atom, methoxymethyl group, methoxyethyl group, trifluoromethyl group, dichloroethyl group, or hydroxyethyl group, or represents a group $Ar^{4c}$, or a —O—$Ar^{4c}$ group;

the group $Ar^{4c}$ represents phenyl group which may be substituted with 1 or the same or different 2 to 4 of groups $R^{3b}$;

$R^{3b}$ represents methyl group, ethyl group, propyl group, isopropyl group, butyl group, isobutyl group, t-butyl group, methoxy group, ethoxy group, propyloxy group, isopropyloxy group, butoxy group, isobutyloxy group, t-butyloxy group, fluorine atom, chlorine atom, bromine atom, iodine atom, hydroxyl group, trifluoromethyl group, dichloroethyl group, or trifluoromethyloxy group; and $G^{1b}$, $G^{3b}$, $G^{3c}$, $Y^a$, $R^{D1b}$, $U^{1c}$, $U^{2c}$, $R^{W1c}$, and $R^{W2c}$ have the same meanings as those defined above].

<7> The compound or a salt thereof according to any one of <1> to <5>, which compound is represented by the general formula (I-A-1b2):

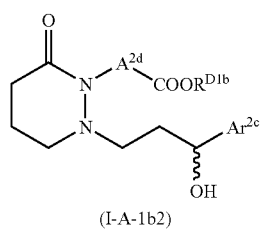

[Formula 13]

(I-A-1b2)

[wherein the group $Ar^{2c}$ represents a residue of a cyclic compound selected from the group consisting of benzene, naphthalene, furan, thiophene, pyridine, benzofuran, benzo[b]thiophene, indan, indole, 1H-indazole, 1H-benzimidazole, benzoxazole, benzothiazole, quinoline, isoquinoline, cinnoline, quinazoline, quinoxaline, and phthalazine;

the group $Ar^{2c}$ may be substituted with 1 or the same or different 2 to 4 of groups $R^{2c}$; and $A^{2d}$, $R^{D1b}$, and $R^{2c}$ have the same meanings as those defined above].

<8> The compound or a salt thereof according to any one of <1> to <6>, which compound is represented by the general formula (I-A-1b3):

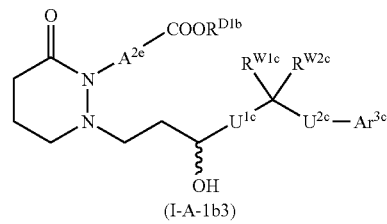

[Formula 14]

(I-A-1b3)

[wherein $A^{2e}$ represents (1) a -$G^{1b}$-$Ar^{1d}$-$G^{3b}$- group, (2) a -$G^{1b}$-$Y^a$—$Ar^{1d}$-$G^{3b}$- group, or (3) a -$G^{1b}$-$Ar^{1d}$—$Y^a$-$G^{3c}$- group;

the group $Ar^{1d}$ represents a residue of a cyclic compound selected from the substituents represented by the following formulas:

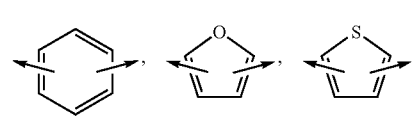

[Formula 15]

(the arrows represent a bond with an adjacent atom, and the bonding position may be any bondable position on a ring-constituting atom); and $G^{1b}$, $G^{3b}$, $G^{3c}$, $Y^a$, $R^{D1b}$, $U^{1c}$, $U^{2c}$, $Ar^{3c}$, $Ar^{4c}$, $R^{W1c}$, and $R^{W2c}$ have the same meanings as those defined above].

<9> The compound or a salt thereof according to any one of <1> to <6>, which compound is represented by the general formula (I-A-1b4):

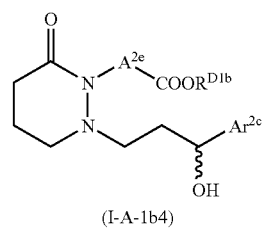

[Formula 16]

(I-A-1b4)

[wherein $A^{2e}$, $Ar^{2c}$, $R^{D1b}$, and $R^{2c}$ have the same meanings as those defined above].

<10> The compound or a salt thereof according to any one of <1> to <4>, which compound is represented by the general formula (Ia-6):

[Formula 17]

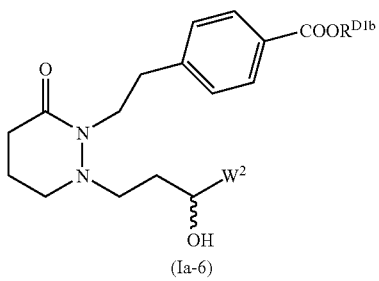
(Ia-6)

(wherein $R^{D1b}$ and $W^2$ have the same meanings as those defined above).

<11> The compound or a salt thereof according to any one of <1> to <4>, which compound is represented by the general formula (Ia-8):

[Formula 18]

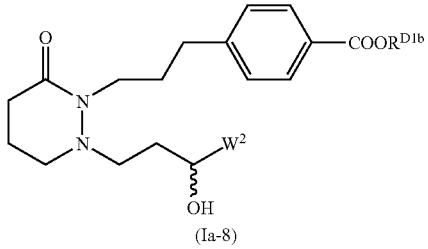
(Ia-8)

(wherein $R^{D1b}$ and $W^2$ have the same meanings as those defined above).

<12> The compound or a salt thereof according to any one of <1> to <4>, which compound is represented by the general formula (Ia-10):

[Formula 19]

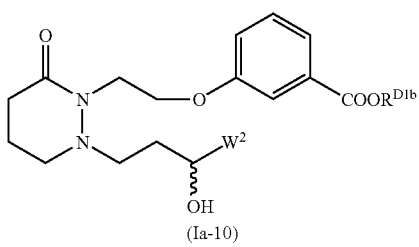
(Ia-10)

(wherein $R^{D1b}$ and $W^2$ have the same meanings as those defined above).

<13> The compound or a salt thereof according to any one of <1> to <4>, which compound is represented by the general formula (Ia-16):

[Formula 20]

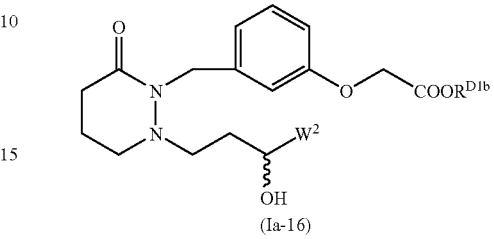
(Ia-16)

(wherein $R^{D1b}$ and $W^2$ have the same meanings as those defined above).

<14> The compound or a salt thereof according to any one of <1> to <5>, which compound is represented by the general formula (Ia1-1):

[Formula 21]

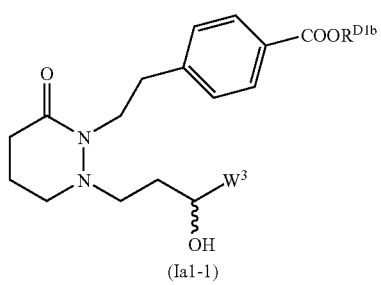
(Ia1-1)

(wherein $R^{D1b}$ and $W^3$ have the same meanings as those defined above).

<15> The compound or a salt thereof according to any one of <1> to <5>, which compound is represented by the general formula (Ia1-2):

[Formula 22]

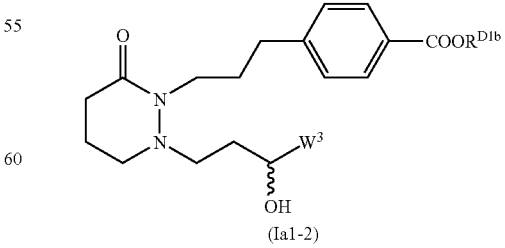
(Ia1-2)

(wherein $R^{D1b}$ and $W^3$ have the same meanings as those defined above).

<16> The compound or a salt thereof according to any one of <1> to <5>, which compound is represented by the general formula (Ia1-7):

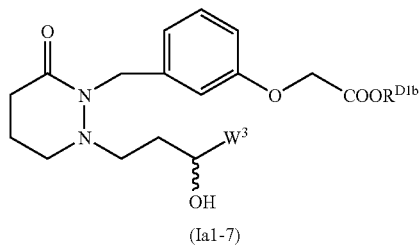

[Formula 23]

(Ia1-7)

(wherein $R^{D1b}$ and $W^3$ have the same meanings as those defined above).

<17> The compound or a salt thereof according to any one of <1> to <6>, which compound is represented by the general formula (Ia2-1):

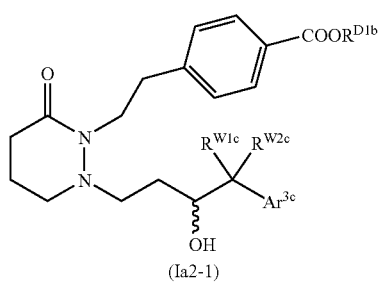

[Formula 24]

(Ia2-1)

(wherein $R^{D1b}$, $R^{W1c}$, $R^{W2c}$, and $Ar^{3c}$ have the same meanings as those defined above).

<18> The compound or a salt thereof according to any one of <1> to <6>, which compound is represented by the general formula (Ia2-2):

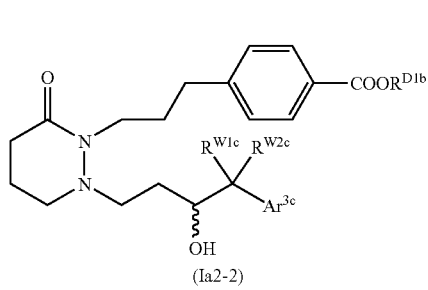

[Formula 25]

(Ia2-2)

(wherein $R^{D1b}$, $R^{W1c}$, $R^{W2c}$ and $Ar^{3c}$ have the same meanings as those defined above).

<19> The compound or a salt thereof according to any one of <1> to <6>, which compound is represented by the general formula (Ia2-3):

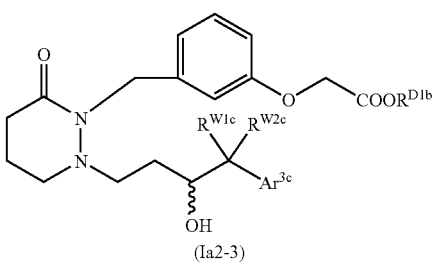

[Formula 26]

(Ia2-3)

(wherein $R^{D1b}$, $R^{W1c}$, $R^{W2c}$, and $Ar^{3c}$ have the same meanings as those defined above).

<20> The compound or a salt thereof according to <1>, which compound is represented by the general formula (I-E):

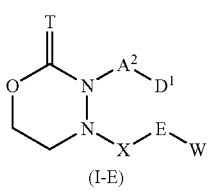

[formula 27]

(I-E)

(wherein T, $A^2$, $D^1$, X, E, and W have the same meanings as those defined above).

<21> The compound or a salt thereof according to <1> or <20>, which compound is represented by the general formula (Ie-1):

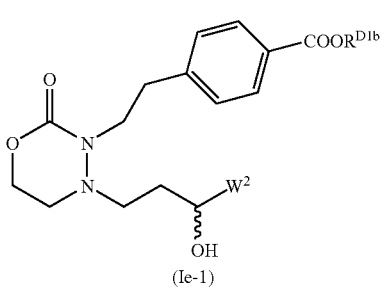

[Formula 28]

(Ie-1)

(wherein $R^{D1b}$ and $W^2$ have the same meanings as those defined above).

<22> The compound or a salt thereof according to any one of <1>, <20> or <21>, which compound is represented by the general formula (Ie1-1):

[Formula 29]

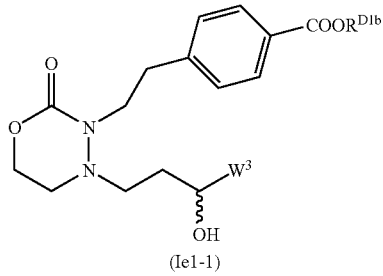

(Ie1-1)

(wherein $R^{D1b}$ and $W^3$ have the same meanings as those defined above).

<23> The compound or a salt thereof according to any one of <1> or <20> to <22>, which compound is represented by the general formula (Ie2-1):

[Formula 30]

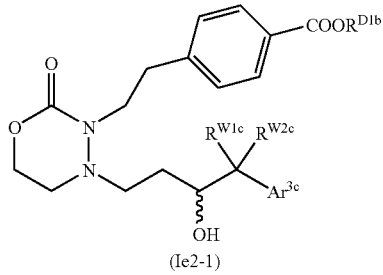

(Ie2-1)

(wherein $R^{D1b}$, $R^{W1c}$, $R^{W2c}$ and $Ar^{3c}$ have the same meanings as those defined above).

<24> The compound or a salt thereof according to <1>, which compound is represented by the general formula (I-F):

[Formula 31]

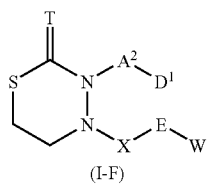

(I-F)

(wherein T, $A^2$, $D^1$, X, E, and W have the same meanings as those defined above).

<24-2> A compound represented by the general formula (I-F) or a salt thereof, wherein T is oxygen atom, $-A^2-D^1$ is $—CH_2CH_2—Ph—CO_2R^{D1b}$, $—X-E-W$ is $—CH_2CH_2—CH(OH)—W^2$, $R^{D1b}$ and $W^2$ have the same meanings as those defined above, and in $—CH_2CH_2—Ph—CO_2R^{D1b}$, $—CH_2CH_2—$ group and the $—CO_2R^{D1b}$ group are at the para-position relative to each other.

<24-3> A compound represented by the general formula (I-F) or a salt thereof, wherein T is oxygen atom, $-A^2-D^1$ is $—CH_2CH_2—Ph—CO_2R^{D1b}$, $—X-E-W$ is $—CH_2CH_2—CH(OH)—W^3$, $R^{D1b}$ and $W^3$ have the same meanings as those defined above, and in $—CH_2CH_2—Ph—CO_2R^{D1b}$, $—CH_2CH_2—$ group and the $—CO_2R^{D1b}$ group are at the para-position relative to each other.

<24-4> A compound represented by the general formula (I-F) or a salt thereof, wherein T is oxygen atom, $-A^2-D^1$ is $—CH_2CH_2—Ph—CO_2R^{D1b}$, $—X-E-W$ is $—CH_2CH_2—CH(OH)—C(R^{W1c})(R^{W2c})(R^{W3c})$, $R^{D1b}$, $R^{W1c}$, $R^{W2c}$ and $R^{W3c}$ have the same meanings as those defined above, and in $—CH_2CH_2—Ph—CO_2R^{D1b}$, $—CH_2CH_2—$ group and the $—CO_2R^{D1b}$ group are at the para-position relative to each other.

<25> The compound or a salt thereof according to <1>, which compound is represented by the general formula (Iae1):

[Formula 32]

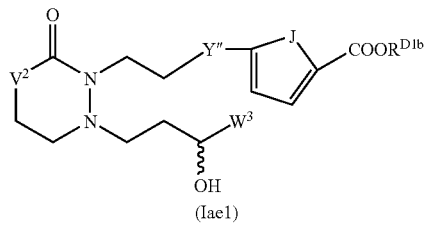

(Iae1)

(wherein $V^2$ represents (1) methylene group, or (2) oxygen atom;
Y" represents (1) a single bond, (2) methylene group, (3) oxygen atom, or (4) sulfur atom;
J represents (1) oxygen atom, or (2) sulfur atom, and
$R^{D1b}$ and $W^3$ have the same meanings as those defined above).

<26> The compound or a salt thereof according to <1>, which is represented by the general formula (Iae2):

[Formula 33]

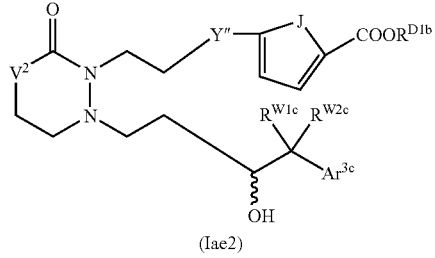

(Iae2)

(wherein $V^2$, Y", J, $R^{D1b}$, $R^{W1c}$, $R^{W2c}$, and $Ar^{3c}$ have the same meanings as those defined above).

From another aspect of the present invention, there is provided:

<27> A medicament containing a compound represented by the with general formula (I) or a pharmaceutically acceptable salt thereof as an active ingredient.

The aforementioned medicament can be used as an osteogenesis promotion agent. The medicament of the present invention can be applied for prophylactic and/or therapeutic treatment of skeletal diseases, and the medicament is useful as a prophylactic and/or therapeutic agent for, for example, osteoporosis, osteomalacia, osteitis fibrosa, aplastic bone, dialytic osteopathia, osteopenia resulting from tumor, osteopenia resulting from medication, osteopenia and arthritis resulting from inflammation, periodontal diseases, cancer bone metastasis, hypercalcemia, Paget's disease of bone, ankylosing spondylitis, bone defects (alveolar bone defect, mandible defect, childhood idiopathic bone defect and the like), fracture, refracture, chronic rheumatoid arthritis, and osteoarthritis, and also useful for prophylactic and/or therapeutic treatment of destruction of joint tissues in similar diseases.

The medicament of the present invention can also be used as an osteoanagenesis promotion agent after a surgical medical treatment, and the medicament can be applied as an osteoanagenesis promotion agent after a medical practice such as joint replacement, repair of vertebral canal (spine fusion surgery, pexis of vertebral canal, posterior lumbar interbody fusion (PLIF)), enlargement of vertebral canal, osteotomy, bone extension, dentistry reconstruction, cranial defect reconstruction, cranioplasty, ilium spacer pexis by bony support, hetero-osteoplasty, bone homograft, bone autograft, alternative therapies for bone graft, bone repair and/or bone reconstruction after surgical extraction of primary malignant tumors or bone metastasis lesions and the like.

The medicament of the present invention can further be applied for various diseases as an $EP_4$ agonist, and thus it is useful as a prophylactic and/or therapeutic agent for, for example, glaucoma, hypertonia oculi, tear gland-associated diseases, myocardial ischemia, hypertension, bronchitis, pulmonary fibrosis, versicular emphysema, chronic obstructive respiratory disease, thrombosis, hepatitis, nephritis (renal failure), stomatitis, alimentary canal ulcers such as gastric ulcer and duodenal ulcer, ulcerative colitis, Crohn's disease, asthma, nerve cell death, arthritis, immune diseases (autoimmune diseases such as rheumatoid arthritis, multiple sclerosis, amyotrophic lateral sclerosis, Sjoegren's syndrome and systemic erythematodes, rejection after organ transplantation and the like), systemic inflammatory response syndrome, sepsis, hemophagocytic syndrome, macrophage activation syndrome, Still disease, Kawasaki disease, thermal burn, systemic granuloma, multiple organ failure, shock, cervical canal obstruction, anomaly in sleep, baldness, psilosis and the like. The medicament is especially useful as a prophylactic and/or therapeutic agent for glaucoma, hypertonia oculi, alimentary canal ulcers such as gastric ulcer and duodenal ulcer, and ulcerative colitis, and is extremely useful as a prophylactic and/or therapeutic agent for glaucoma and ulcerative colitis among others.

From still further aspects of the present invention, there are provided:

<28> Use of a compound represented by the aforementioned general formula (I) or a pharmaceutically acceptable salt thereof for manufacture of the aforementioned medicament;

<29> A method for promoting osteogenesis, which comprises the step of administering an effective amount of a compound represented by the aforementioned general formula (I) or a pharmaceutically acceptable salt thereof to a mammal including human;

<30> A method for prophylactic and/or therapeutic treatment of a skeletal disease such as osteoporosis or fracture, which comprises the step of administering an effective amount of a compound represented by the aforementioned general formula (I) or a pharmaceutically acceptable salt thereof to a mammal including human;

<31> A method for promoting osteoanagenesis after a surgical medical treatment, which comprises the step of administering an effective amount of a compound represented by the aforementioned general formula (I) or a pharmaceutically acceptable salt thereof to a mammal including human;

<32> A method for prophylactic and/or therapeutic treatment of glaucoma, hypertonia oculi, tear gland-associated diseases, myocardial ischemia, hypertension, bronchitis, pulmonary fibrosis, versicular emphysema, chronic obstructive respiratory disease, thrombosis, hepatitis, nephritis (renal failure), stomatitis, alimentary canal ulcers such as gastric ulcer and duodenal ulcer, ulcerative colitis, Crohn's disease, asthma, nerve cell death, arthritis, immune diseases (autoimmune diseases such as rheumatoid arthritis, multiple sclerosis, amyotrophic lateral sclerosis, Sjoegren's syndrome and systemic erythematodes, rejection after organ transplantation and the like), systemic inflammatory response syndrome, sepsis, hemophagocytic syndrome, macrophage activation syndrome, Still disease, Kawasaki disease, thermal burn, systemic granuloma, multiple organ failure, shock, cervical canal obstruction, anomaly in sleep, baldness, psilosis or the like, which comprises the step of administering an effective amount of a compound represented by the aforementioned general formula (I) or a pharmaceutically acceptable salt thereof to a mammal including human;

<33> A method for prophylactic and/or therapeutic treatment of glaucoma, hypertonia oculi, alimentary canal ulcers such as gastric ulcer and duodenal ulcer, or ulcerative colitis, which comprises the step of administering an effective amount of a compound represented by the aforementioned general formula (I) or a pharmaceutically acceptable salt thereof to a mammal including human;

<34> A method for prophylactic and/or therapeutic treatment of glaucoma or ulcerative colitis, which comprises the step of administering an effective amount of a compound represented by the aforementioned general formula (I) or a pharmaceutically acceptable salt thereof to a mammal including human; and <35> The method according to any one of <32> to <34> comprising the step of administering an effective amount of a compound represented by the aforementioned general formula (I) or a pharmaceutically acceptable salt thereof to a mammal including human, wherein the disease is a disease involving $EP_4$.

From a still further aspect of the present invention, there is provided:

<33> A compound represented by the general formula (II) [hereinafter simply referred to as "Compound (II) of the present invention] or a salt thereof:

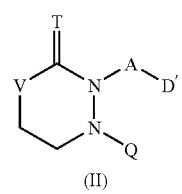

[Formula 34]

(II)

[wherein D' have the same meaning as that of D mentioned above, or when D represents carboxyl group, the carboxyl group may be protected with a group $Rp^1$, when D contains hydroxyl group, the hydroxyl group may be protected with a group $Rp^2$, or when D contains formyl group, the formyl group may be protected with a group $Rp^3$; Q represents hydrogen atom, or a protective group $Rp^4$ of amino group; and T, V and A have the same meanings as those defined above].

BEST MODE FOR CARRYING OUT THE INVENTION

The present invention will be specifically explained.

In the present specification, carbon atom may be simply represented as "C", hydrogen atom as "H", oxygen atom as "O", sulfur atom as "S", and nitrogen atom as "N". Further, carbonyl group may be simply represented as "—C(O)—", carboxyl group as "—COO—", sulfinyl group as "—S(O)—", sulfonyl group as "—S(O)$_2$—", ether bond as "—O—", and thioether bond as "—S—" (each "—" in these groups indicates a bond).

In the specification, the alkyl group having 1 to 4 carbon atoms means methyl group, ethyl group, propyl group, butyl group, or an isomer thereof [normal (n), iso, secondary (sec), tertiary (t) and the like].

Examples of the linear alkylene group having 2 to 8 carbon atoms mentioned in the specification include ethylene group, trimethylene group, tetramethylene group, pentamethylene group, hexamethylene group, heptamethylene group, octamethylene group and the like.

The linear alkenylene group having 2 to 8 carbon atoms mentioned in the specification is not particularly limited so long as it is a linear alkenylene group having one or more double bonds in the group. However, a linear alkenylene group having one or two double bonds in the group is preferred, and examples include, for example, ethenylene group, propenylene group, butenylene group, butadienylene group, pentenylene group, pentadienylene group, hexenylene group, hexadienylene group, heptenylene group, heptadienylene group, octenylene group, octadienylene group and the like.

The linear alkynylene group having 2 to 8 carbon atoms mentioned in the specification is not particularly limited so long as it is a linear alkynylene group having one or more triple bonds in the group. However, a linear alkynylene group having one or two triple bonds in the group is preferred, and examples include, for example, ethynylene group, propynylene group, butynylene group, butadiynylene group, pentynylene group, pentadiynylene group, hexynylene group, hexadiynylene group, heptynylene group, heptadiynylene group, octynylene group, octadiynylene group and the like.

In the specification, the linear alkylene group having 1 to 4 carbon atoms means methylene group, ethylene group, trimethylene group, or tetramethylene group.

In the specification, the linear alkenylene group having 2 to 4 carbon atoms means ethenylene group, propenylene group, butenylene group, or butadienylene group, which has one or two double bonds in the group.

In the specification, the linear alkynylene group having 2 to 4 carbon atoms means ethynylene group, propynylene group, butynylene group, and butadiynylene group, which has one or two triple bonds in the group.

In the specification, the acyl group having 2 to 6 carbon atoms means ethanoyl group, propanoyl group, butanoyl group, pentanoyl group, hexanoyl group, or an isomer thereof.

In the specification, the alkoxy group having 1 to 4 carbon atoms means methoxy group, ethoxy group, propoxy group, butoxy group, or an isomer thereof.

In the specification, the alkylthio group having 1 to 4 carbon atoms means methylthio group, ethylthio group, propylthio group, butylthio group, or an isomer thereof.

In the specification, the halogen atom means fluorine atom, chlorine atom, bromine atom, or iodine atom.

In the specification, the biphenyl group means 2-phenylphenyl group, 3-phenylphenyl group, or 4-phenylphenyl group.

In the specification, M in the —C(O)-$M_m$-OH group and the —O-$M_m$-H group means a divalent residue obtained by eliminating, from a compound having amino group and carboxyl group, hydrogen atom of the amino group and hydroxyl group of the carboxyl group. The amino group in the group M bonds to the adjacent —C(O)— group (or hydrogen atom), and the —C(O)— group in the group M bonds to the adjacent —O— group (or amino group).

The compound having amino group and carboxyl group is not particularly limited, so long as the compound has at least one amino group and at least one carboxyl group in the structural formula thereof. Preferred examples include an amino acid. The amino acid may be a natural amino or abnormal amino acid, and for example, glycine, alanine, valine, leucine, isoleucine, serine, threonine, cysteine, methionine, proline, asparagine, glutamine, phenylalanine, tyrosine, tryptophan, aspartic acid, glutamic acid, lysine, arginine, histidine, β-alanine, cystathionine, cystine, homoserine, norleucine, lanthionine, norvaline, ornithine, sarcosine, thyronine and the like are included. Examples further include those amino acids protected with a protective group.

Examples of the 3- to 7-membered saturated cycloalkane represented by cb mentioned in the specification include cyclopropane, cyclobutane, cyclopentane, cyclohexane, cycloheptane and the like.

Examples of the "residue of a cyclic compound" mentioned in the specification include a monovalent or divalent group and a group of further higher valence. Specific examples include a monovalent or divalent group and a group of further higher valence formed by eliminating, from an arbitrary ring, one or more hydrogen atoms bonding to ring-constituting atoms at arbitrary positions in a number determined by the valence of the group. Specifically, for the monovalent Ar group "Ar—", one hydrogen atom at an arbitrary position on the Ar ring may be eliminated, and for the divalent Ar group "—Ar—", two hydrogen atoms at arbitrary positions on the Ar ring may be eliminated.

Specific examples of the carbocyclic compound constituting the residue of a completely unsaturated, or partially or completely saturated monocyclic compound having 3 to 11 carbon atoms, residue of a condensed bicyclic carbocyclic compound having 7 to 11 carbon atoms, or residue of tricyclic alicyclic hydrocarbon represented by ca1, ca2, ca3 and ca4 mentioned in the specification include, for example, cyclopropane, cyclobutane, cyclopentane, cyclohexane, cycloheptane, cyclooctane, cyclononane, cyclodecane, cycloundecane, cyclopentene, cyclohexene, cycloheptene, cyclooctene, cyclopentadiene, cyclohexadiene, cycloheptadiene, cyclooctadiene, benzene, pentalene, perhydropentalene, indene, perhydroindene, indan, azulene, perhydroazulene, naphthalene, dihydronaphthalene, tetrahydronaphthalene, perhydronaphthalene, spiro[4,4]nonane, spiro[4,5]decane, spiro[5,5]undecane, bicyclo[2,2,1]heptane, bicyclo[2,2,1]hept-2-ene, bicyclo[3,1,1]heptane, bicyclo[3,1,1]hept-2-ene, bicyclo[2,2,2]octane, adamantane, noradamantane and the like.

Specific examples of the heterocyclic compound constituting the residue of a completely unsaturated, or partially or completely saturated monocyclic compound having 3 to 11 ring-constituting atoms containing the same or different 1 to 4 hetero atoms selected from the group consisting of nitrogen atom, oxygen atom and sulfur atom as ring-constituting atoms (the monocyclic compound contains the same or different one or more hetero atoms selected from the group consisting of nitrogen atom, oxygen atom, and sulfur atom as the ring-constituting atoms), residue of a condensed bicyclic heterocyclic compound having 7 to 11 ring-constituting atoms, or residue of a tricyclic heteroalicyclic hydrocarbon represented by qa1, qa2, qa3, and qa4 mentioned in the specification include, for example, aziridine, azetidine, pyrrolidine, pyrroline, imidazoline, imidazolidine, triazoline, triazolidine, tetrazoline, tetrazolidine, pyrazoline, pyrazolidine, piperidine, piperazine, homopiperidine, homopiperazine, azepine, diazepine, morpholine, thiomorpholine, quinuclidine, oxolane, thiolane, oxathiane, furan, thiophene, pyrrole, oxazole, isoxazole, thiazole, isothiazole, imidazole, pyrazole, triazole, furazan, oxadiazole, thiadiazole, tetrazole, pyran, pyridine, pyridazine, pyrimidine, pyrazine, triazine, oxazine, oxadiazine, thiazine, thiadiazine, indoline, isoindoline, dihydrobenzofuran, 1,3-dioxaindan, chroman, 4H-chromene, benzofuran, benzo[b]thiophene, indole, isoindole, indolizine, 1H-indazole, 2H-indazole, 1H-benzimidazole, 1,3-dihydrobenzimidazole, benzoxazole, dihydro-3H-benzoxazole, benzo[d]isoxazole, benzo[c]isoxazole, benzothiazole, dihydro-3H-benzothiazole, benzo[d]isothiazole, benzo[c]isothiazole, 1H-benzotriazole, benzo[1,2,5]thiadiazole, quinoline, dihydro-1H-quinoline, isoquinoline, dihydro-2H-isoquinoline, cinnoline, quinazoline, quinoxaline, phthalazine, imidazo[1,2-a]pyridine, 1H-pyrrolo[2,3-b]pyridine, 1H-pyrrolo[3,2-b]pyridine, 1,3-dihydropyrrolo[2,3-b]pyridine, 1H-pyrrolo[3,2-c]pyridine, 1H-pyrrolo[2,3-c]pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, 1H-pyrazolo[3,4-d]thiazole, [1,2,4]triazolo[1,5-a]pyrimidine, 1H-pyrazolo[3,4-b]pyrazine, 1H-imidazo[4,5-b]pyrazine, 7H-purine, [1,8]naphthalidine, [1,5]naphthalidine and the like.

Specific examples of the heterocyclic compound constituting the residue of a 5- to 7-membered nitrogen-containing saturated monocyclic heterocyclic compound (the heterocyclic ring may further contain one ring-constituting hetero atom selected from the group consisting of nitrogen atom, oxygen atom, and sulfur atom) represented by qb1, qb2, qb3, and qb4 in the specification include, for example, pyrrolidine, piperidine, homopiperidine, imidazolidine, pyrazolidine, piperazine, homopiperazine, morpholine, thiomorpholine and the like. Further, qb1, qb2, qb3, and qb4, which are saturated monocyclic heterocyclic rings, may have 1 or the same or different 2 to 4 alkyl groups having 1 to 4 carbon atoms on a carbon atom constituting the ring and/or a nitrogen atom constituting the ring (limited to a secondary nitrogen atom).

Specific examples of the carbocyclic compound constituting the residue of a completely unsaturated, or partially or completely saturated monocyclic carbocyclic compound having 3 to 7 carbon atoms represented by calm in the specification include, for example, cyclopropane, cyclobutane, cyclopentane, cyclohexane, cycloheptane, cyclopentene, cyclohexene, cycloheptene, benzene and the like.

Specific examples of the heterocyclic compound constituting the residue of a completely unsaturated, or partially or completely saturated monocyclic heterocyclic compound having 3 to 7 ring-constituting atoms and containing the same or different 1 to 3 hetero atoms selected from the group consisting of nitrogen atom, oxygen atom, and sulfur atom as the ring-constituting atoms represented by qa1m in the specification include, for example, aziridine, azetidine, pyrrolidine, pyrroline, imidazoline, imidazolidine, triazoline, triazolidine, pyrazoline, pyrazolidine, piperidine, piperazine, homopiperidine, homopiperazine, azepine, diazepine, morpholine, thiomorpholine, furan, thiophene, pyrrole, oxazole, isoxazole, thiazole, isothiazole, imidazole, pyrazole, triazole, furazan, oxadiazole, thiadiazole, pyran, pyridine, pyridazine, pyrimidine, pyrazine and the like.

In the present invention, all isomers are included, unless specifically indicated. For example, the alkyl group, alkenyl group, alkynyl group, alkoxy group, alkylthio group, alkylene group, alkenylene group, and alkynylene group include linear and branched groups. Further, any of isomers based on a double bond, ring, or condensed ring (E- or Z-isomers, or cis- or trans-isomers), isomers based on the presence of an asymmetric carbon and the like (R- or S-isomer, an isomer based on α- or β-configuration, enantiomers, diastereomers and the like), optically active substances having optical rotation (D- or L-isomers, or d- or l-isomers), isomers based on polarity in chromatographic separation (high polarity isomers or low polarity isomers), equilibrated compounds, rotational isomers, mixtures of these isomers at arbitrary ratios, and racemates fall within the scope of the present invention.

In the present specification, as apparent for those skilled in the art, the symbol:

[Formula 35]

indicates that the bond is on the back of the plane (i.e., α-configuration), the symbol:

[Formula 36]

indicates that the bond is in front of the plane (i.e., β-configuration), the symbol:

[Formula 37]

means α-configuration or β-configuration, or a mixture thereof, and the symbol:

[Formula 38]

means a mixture of α-configuration and β-configuration.

As salts of Compound (I) of the invention, pharmaceutically acceptable salts are preferred. When the compound contains a proton-donating substituent such as carboxyl group, phenolic hydroxyl group or tetrazole group, a salt in which bases in an arbitrary number are added according to the number of the acidic groups can be formed. Examples include, for example, salts with metals such as sodium, inorganic bases such as ammonia, or organic bases such as triethylamine. Further, when the compound contains a substituted or unsubstituted amino group, or a basic cyclic structure such as pyridine ring or quinoline ring, it is meant that a salt, in which acids in an arbitrary number are added according to the number of the basic groups, can be formed. Examples include, for example, salts with inorganic acids such as hydrochloric acid or sulfuric acid, or organic acids such as acetic acid or citric acid.

The general formula (I) will be explained in detail.

T represents (1) oxygen atom, or (2) sulfur atom. Both of the atoms are preferred, and particularly preferred is oxygen atom. Further, sulfur atom is preferred in another embodiment.

V represents (1) $C(R^{O5})(R^{O6})$, (2) oxygen atom, or (3) sulfur atom. Any of these group and atoms are preferred, and particularly preferred is $C(R^{O5})(R^{O6})$. Further, oxygen atom is also particularly preferred.

$R^{O1}$, $R^{O2}$, $R^{O3}$, $R^{O4}$, $R^{O5}$, and $R^{O6}$ independently represent (1) hydrogen atom, or (2) an alkyl group having 1 to 4 carbon atoms. Among them, hydrogen atom, methyl group, and ethyl group are preferred, hydrogen atom, and methyl group are particularly preferred, and hydrogen atom is most preferred.

A represents $A^1$ or $A^2$, and both of them are preferred. $A^1$ represents (1) a linear alkylene group having 2 to 8 carbon atoms which may be substituted with one or two alkyl groups having 1 to 4 carbon atoms, (2) a linear alkenylene group having 2 to 8 carbon atoms which may be substituted with one or two alkyl groups having 1 to 4 carbon atoms, or (3) a linear alkynylene group having 2 to 8 carbon atoms which may be substituted with one or two alkyl groups having 1 to 4 carbon atoms. Preferred examples of $A^1$ include a linear alkylene group having 5 to 7 carbon atoms, and a linear alkenylene group having 5 to 7 carbon atoms, and particularly preferred examples include hexamethylene group, and hexenylene group.

$A^2$ represents a -$G^1$-$G^2$-$G^3$- group.

$G^1$ represents (1) a linear alkylene group having 1 to 4 carbon atoms which may be substituted with one or two alkyl groups having 1 to 4 carbon atoms, (2) a linear alkenylene group having 2 to 4 carbon atoms which may be substituted with one or two alkyl groups having 1 to 4 carbon atoms, or (3) a linear alkynylene group having 2 to 4 carbon atoms which may be substituted with one or two alkyl groups having 1 to 4 carbon atoms. Preferred examples of $G^1$ include a linear alkylene group having 1 to 4 carbon atoms, and particularly preferred examples include methylene group, ethylene group, and trimethylene group.

$G^2$ represents (1) a —$Ar^1$— group, (2) a —Y—$Ar^1$— group, (3) a —$Ar^1$—Y— group, or (4) a —Y— group, and all of these groups are preferred examples. The group $Ar^1$ represents (1) a residue of a carbocyclic compound (ca1), or (2) a residue of a heterocyclic compound (qa1), and all of these groups are preferred examples. Particularly preferred examples include a residue of a completely unsaturated, or partially or completely saturated monocyclic carbocyclic compound having 3 to 7 carbon atoms (ca1m), or a residue of a completely unsaturated, or partially or completely saturated monocyclic heterocyclic compound containing the same or different 1 to 3 hetero atoms selected from the group consisting of nitrogen atom, oxygen atom, and sulfur atom as the ring-constituting atoms and having 3 to 7 ring-constituting atoms (qa1m). Specific examples include, for example, residues of cyclic compounds, cyclopropane, cyclobutane, cyclopentane, cyclohexane, cycloheptane, cyclopentene, cyclohexene, cycloheptene, benzene, aziridine, azetidine, pyrrolidine, pyrroline, imidazoline, imidazolidine, triazoline, triazolidine, pyrazoline, pyrazolidine, piperidine, piperazine, homopiperidine, homopiperazine, azepine, diazepine, morpholine, thiomorpholine, furan, thiophene, pyrrole, oxazole, isoxazole, thiazole, isothiazole, imidazole, pyrazole, triazole, furazan, oxadiazole, thiadiazole, pyran, pyridine, pyridazine, pyrimidine, pyrazine and the like. Further preferred examples of the group $Ar^1$ include residues of cyclic compounds, benzene, furan, pyrrole, oxazole, isoxazole, thiazole, isothiazole, imidazole, pyrazole, pyridine, pyridazine, pyrimidine, pyrazine and the like, and among them, a residue of a cyclic compound, benzene, furan, thiophene, oxazole, or thiazole, is a particularly preferred example. Furthermore, extremely preferred examples include a residue of a cyclic compound, benzene, furan, thiophene or the like, and among them, a residue of benzene is the most preferred example. A residue of furan is the most preferred in another embodiment, and a residue of thiophene is the most preferred in still another embodiment.

The group $Ar^1$ may be substituted with 1 or the same or different 2 to 4 of groups $R^1$. The group $R^1$ represents (1) an alkyl group having 1 to 4 carbon atoms, (2) an alkoxy group having 1 to 4 carbon atoms, or (3) a halogen atom, and any of the groups and atom are preferred examples. When the group $Ar^1$ contains a secondary nitrogen atom as a ring-constituting atoms, the alkyl group as $R^1$ may substitute on the nitrogen atom.

Y represents (1) —S— group, (2) —S(O)— group, (3) —S(O)$_2$— group, (4) —O— group, or (5) a —N($R^{G1}$)— group, and all of these groups are preferred examples. $R^{G1}$ represents (1) hydrogen atom, (2) an alkyl group having 1 to 4 carbon atoms, or (3) an acyl group having 2 to 6 carbon atoms, and all of these groups are preferred examples. Particularly preferred examples of Y include —O—, —S— and the like.

$G^3$ represents (1) a single bond, (2) a linear alkylene group having 1 to 4 carbon atoms which may be substituted with one or two alkyl groups having 1 to 4 carbon atoms, (3) a linear alkenylene group having 2 to 4 carbon atoms which may be substituted with one or two alkyl groups having 1 to 4 carbon atoms, or (4) a linear alkynylene group having 2 to 4 carbon atoms which may be substituted with one or two alkyl groups having 1 to 4 carbon atoms. When $G^2$ to which $G^3$ bonds represents a —$Ar^1$—Y— group, or a —Y— group, that is, when $G^3$ bonds to Y, $G^3$ represents a substituent other than a single bond. Preferred examples of $G^3$ include a single bond, a linear alkylene group having 1 to 4 carbon atoms, a linear alkenylene group having 1 to 4 carbon atoms and the like. When $G^2$ is a —$Ar^1$— group, or a —Y—$Ar^1$— group, particularly preferred examples of $G^3$ are a single bond, methylene group, ethylene group, and ethenylene group, and when $G^2$ is a —$Ar^1$—Y— group, or a —Y— group, particularly preferred examples of $G^3$ are methylene group, ethylene group, and trimethylene group.

D represents $D^1$ or $D^2$, both of them are preferred examples, and particularly preferred is $D^1$. Further, $D^2$ is preferred in another embodiment.

$D^1$ represents (1) a —COO$R^{D1}$ group, (2) tetrazol-5-yl group, or (3) a —C(O)N($R^{D2}$)SO$_2R^{D3}$ group. $R^{D1}$ represents (1) hydrogen atom, (2) an alkyl group having 1 to 4 carbon atoms, (3) phenyl group, (4) an alkyl group having 1 to 4 carbon atoms substituted with phenyl group, or (5) a biphenyl group, and hydrogen atom, an alkyl group having 1 to 4 carbon atoms and the like are preferred.

$R^{D2}$ represents (1) hydrogen atom, or (2) an alkyl group having 1 to 4 carbon atoms, hydrogen atom and methyl group are preferred, and hydrogen atom is particularly preferred.

$R^{D3}$ represents (1) an alkyl group having 1 to 4 carbon atoms, or (2) phenyl group. Methyl group and phenyl group are preferred, and phenyl group is particularly preferred. Further, methyl group is preferred in another embodiment.

$D^1$ is preferably a —COO$R^{D1}$ group, tetrazol-5-yl group or the like, most preferably tetrazol-5-yl group, carboxyl group, carboxymethyl group, carboxyethyl group, carboxypropyl group, carboxybutyl group, or an isomer thereof, further preferably carboxyl group, carboxymethyl group, carboxyethyl group, carboxypropyl group, carboxybutyl group, an isomer thereof or the like.

$D^2$ represents (1) a —$CH_2OR^{D4}$ group, (2) a —$OR^{D4}$ group, (3) formyl group, (4) a —$C(O)NR^{D5}R^{D6}$ group, (5) a —$C(O)N(R^{D5})SO_2R^{D7}$ group, (6) a —$C(O)$-$M_m$-OH group, (7) a —$O$-$M_m$-H group, (8) a —$COOR^{D8}$ group, (9) a —OC(O)—$R^{D9}$ group, (10) a —COO-$Z^1$-$Z^2$-$Z^3$ group, or (11) a substituent selected from the group consisting of the substituents $D^{2a1}$, $D^{2a2}$, $D^{2a3}$, $D^{2a4}$, and $D^{2a5}$ represented by the following formulas:

[Formula 39]

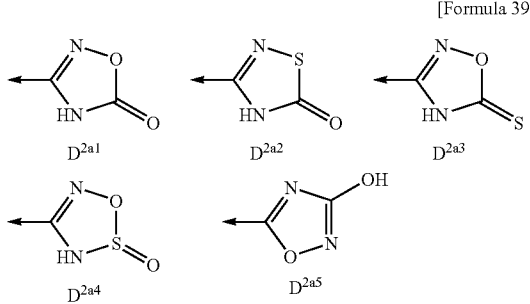

$D^{2a1}$  $D^{2a2}$  $D^{2a3}$ $D^{2a4}$  $D^{2a5}$ (the arrows in the formulas indicate a bond with the group A), $R^{D4}$ represents (1) hydrogen atom, or (2) an alkyl group having 1 to 4 carbon atoms;

$R^{D5}$ and $R^{D6}$ independently represent (1) hydrogen atom, or (2) an alkyl group having 1 to 4 carbon atoms, or (3) $R^{D5}$ and $R^{D6}$ may bind to each other to form a saturated monocyclic heterocyclic ring (qb1) together with the nitrogen atom to which they bind;

$R^{D7}$ represents an alkyl group having 1 to 4 carbon atoms and substituted with phenyl group;

$R^{D8}$ represents (1) an alkyl group having 1 to 4 carbon atoms and substituted with a biphenyl group which may be substituted with 1 to 3 substituents selected from the group consisting of an alkyl group having 1 to 4 carbon atoms, an alkoxy group having 1 to 4 carbon atoms, and a halogen atom, or (2) a biphenyl group which may be substituted with 1 to 3 substituents selected from the group consisting of an alkyl group having 1 to 4 carbon atoms, an alkoxy group having 1 to 4 carbon atoms, and a halogen atom;

$R^{D9}$ represents (1) phenyl group, or (2) an alkyl group having 1 to 4 carbon atoms;

M represents a divalent group obtained by eliminating, from a compound having amino group and carboxyl group, hydrogen atom of the amino group and hydroxyl group of the carboxyl group;

m represents an integer of 1 or 2;

$Z^1$ represents (1) an alkylene group having 1 to 8 carbon atoms, (2) an alkenylene group having 2 to 8 carbon atoms, or (3) an alkynylene group having 2 to 8 carbon atoms;

$Z^2$ represents (1) —C(O)— group, (2) —OC(O)— group, (3) —COO— group, (4) a —C(O)N($R^{Z1}$)— group, (5) a —N($R^{Z2}$)C(O)— group, (6) —O— group, (7) —S— group, (8) —S(O)$_2$— group, (9) a —S(O)$_2$N($R^{Z2}$)— group, (10) a —N($R^{Z2}$)S(O)$_2$— group, (11) a —N($R^{Z3}$)— group, (12) a —N($R^{Z4}$)C(O)N($R^{Z5}$)— group, (13) a —N($R^{Z6}$)C(O)O— group, (14) a —OC(O)N($R^{Z7}$)— group, or (15) —OC(O)O— group;

$Z^3$ represents (1) hydrogen atom, (2) an alkyl group having 1 to 4 carbon atoms, (3) an alkenyl group having 2 to 4 carbon atoms, (4) an alkynyl group having 2 to 4 carbon atoms, (5) a ring Z, or (6) an alkyl group having 1 to 4 carbon atoms substituted with an alkoxy group having 1 to 4 carbon atoms, an alkylthio group having 1 to 4 carbon atoms, a —N($R^{Z8}$)($R^{Z9}$) group, or the ring Z;

the ring Z represents (1) a residue of a carbocyclic compound (ca2), or (2) a residue of a heterocyclic compound (qa2);

$R^{Z1}$, $R^{Z2}$, $R^{Z3}$, $R^{Z4}$, $R^{Z5}$, $R^{Z6}$, $R^{Z7}$, $R^{Z8}$, and $R^{Z9}$ independently represent hydrogen atom, or an alkyl group having 1 to 4 carbon atoms; and further, $R^{Z1}$ and $Z^3$ may form a saturated monocyclic heterocyclic ring (qb2) together with the nitrogen atom to which they bind.

$D^2$ is preferably a —COO-$Z^1$-$Z^2$-$Z^3$ group.

$Z^1$ is preferably an alkylene group having 1 to 8 carbon atoms, most preferably an alkylene group having 1 to 4 carbon atoms.

$Z^2$ is preferably —C(O)— group, —OC(O)— group, —COO— group, a —C(O)N($R^{Z1}$)— group, a —OC(O)N($R^{Z7}$)— group, —OC(O)O— group, most preferably —OC(O)— group, a —OC(O)N($R^{Z7}$)— group, or —OC(O)O— group.

$Z^3$ is preferably an alkyl group having 1 to 4 carbon atoms, a ring Z, or an alkyl group having 1 to 4 carbon atoms substituted with a ring Z, most preferably an alkyl group having 1 to 4 carbon atoms.

$R^{Z1}$ and $R^{Z7}$ independently represent hydrogen atom, or an alkyl group having 1 to 4 carbon atoms, and both of them are preferred examples. $R^{Z1}$ and $Z^3$ may form a saturated monocyclic heterocyclic ring (qb2) together with the nitrogen atom to which they bind, and preferred examples of the heterocyclic ring include pyrrolidine, piperidine, piperazine, homopiperidine, homopiperazine, morpholine and the like. The ring Z represents (1) a residue of a carbocyclic compound (ca2) or (2) a residue of a heterocyclic compound (qa2), and preferred examples of the cyclic compound include benzene, furan, thiophene, pyrrole, oxazole, isoxazole, thiazole, isothiazole, imidazole, pyrazole, pyridine, pyridazine, pyrimidine, pyrazine and the like.

X represents (1) ethylene group, (2) trimethylene group, or (3) —$CH_2CH$=CH— group, any of the groups are preferred examples, and ethylene group is a particularly preferred example.

E represents (1) —CH(OH)— group, or (2) —C(O)— group, both of them are preferred examples, and —CH(OH)— group is a particularly preferred example.

W represents (1) a group Wa represented by the following formula:

[Formula 40]

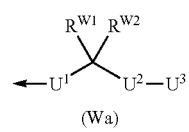

(Wa)

(wherein the arrow indicates a bond with the group E), or (2) a group $Ar^2$, and both of them are preferred examples.

$R^{W1}$ and $R^{W2}$ independently represent (1) hydrogen atom, (2) an alkyl group having 1 to 4 carbon atoms, or (3) fluorine atom, or (4) $R^{W1}$ and $R^{W2}$ may bind to each other to form a 3- to 7-membered saturated cycloalkane (cb) together with the carbon atom to which they bind; and the saturated cycloalkane (cb) may be substituted with 1 or the same or different 2 to 4 alkyl groups having 1 to 4 carbon atoms.

Preferably, $R^{W1}$ and $R^{W2}$ independently represent hydrogen atom, an alkyl group having 1 to 4 carbon atoms, or fluorine atom, most preferably hydrogen atom, or methyl group. Further, it is also preferred that $R^{W1}$ and $R^{W2}$ bind to each other to form a 3- to 7-membered saturated cycloalkane group (cb) together with the carbon atom to which they bind, and particularly preferred examples of the saturated cycloalkane group (cb) include cyclopropane, cyclobutane, cyclopentane, cyclohexane and the like. More preferably, $R^{W1}$ and $R^{W2}$ independently represent hydrogen atom, or methyl group, or $R^{W1}$ and $R^{W2}$ bind to each other to form cyclopropane ring together with the carbon atom to which they bind.

$U^1$ represents (1) a single bond, (2) an alkylene group having 1 to 4 carbon atoms, (3) an alkenylene group having 2 to 4 carbon atoms, or (4) an alkynylene group having 2 to 4 carbon atoms.

$U^1$ is preferably a single bond, or an alkylene group having 1 to 4 carbon atoms, most preferably a single bond, methylene group, ethylene group, or trimethylene group, more preferably a single bond, methylene group, or ethylene group.

$U^2$ represents (1) a single bond, (2) an alkylene group having 1 to 4 carbon atoms, (3) an alkenylene group having 2 to 4 carbon atoms, (4) an alkynylene group having 2 to 4 carbon atoms, (5) —O— group, (6) —S— group, (7) —S(O)— group, (8) —S(O)$_2$— group, (9) a —N($R^{U1}$)— group, (10) —C(O)— group, (11) a —C(O)N($R^{U2}$)— group, (12) a —N($R^{U2}$)C(O)— group, (13) a —S(O)$_2$N($R^{U2}$)— group, or (14) a —N($R^{U2}$)S(O)$_2$— group. $R^{U1}$ represents (1) hydrogen atom, (2) an alkyl group having 1 to 4 carbon atoms, or (3) an acyl group having 2 to 6 carbon atoms, all of these groups are preferred examples, and (1) hydrogen atom, (2) an alkyl group having 1 to 4 carbon atoms and the like are particularly preferred examples.

$R^{U2}$ represents (1) hydrogen atom, or (2) an alkyl group having 1 to 4 carbon atoms.

$U^2$ is preferably a single bond, an alkylene group having 1 to 4 carbon atoms, —O— group, —S— group, —S(O)— group, —S(O)$_2$— group, or —N($R^{U1}$)—, most preferably a single bond, methylene group, ethylene group, trimethylene group, —O— group, —S— group, or —N($R^{U1}$)—, further preferably a single bond, methylene group, ethylene group, —O— group, or —S— group.

$U^3$ represents (1) an alkyl group having 1 to 8 carbon atoms which may be substituted with 1 or the same or different 2 to 4 substituents selected from the group consisting of an alkyl group having 1 to 4 carbon atoms, a halogen atom, hydroxyl group, an alkoxy group having 1 to 4 carbon atoms, an alkylthio group having 1 to 4 carbon atoms, and a —N($R^{U3}$)($R^{U4}$) group, (2) an alkenyl group having 2 to 8 carbon atoms which may be substituted with 1 or the same or different 2 to 4 substituents selected from the group consisting of an alkyl group having 1 to 4 carbon atoms, a halogen atom, hydroxyl group, an alkoxy group having 1 to 4 carbon atoms, an alkylthio group having 1 to 4 carbon atoms, and a —N($R^{U3}$)($R^{U4}$) group, (3) an alkynyl group having 2 to 8 carbon atoms which may be substituted with 1 or the same or different 2 to 4 substituents selected from the group consisting of an alkyl group having 1 to 4 carbon atoms, a halogen atom, hydroxyl group, an alkylthio group having 1 to 4 carbon atoms, and a —N($R^{U3}$)($R^{U4}$) group, (4) an alkyl group having 1 to 8 carbon atoms substituted with a group $Ar^3$, or (5) a group $Ar^3$, preferably an alkyl group having 1 to 8 carbon atoms which may be substituted with 1 or the same or different 2 to 4 substituents selected from the group consisting of an alkyl group having 1 to 4 carbon atoms, a halogen atom, hydroxyl group, an alkoxy group having 1 to 4 carbon atoms, an alkylthio group having 1 to 4 carbon atoms, and a —N($R^{U3}$)($R^{U4}$) group, an alkyl group having 1 to 8 carbon atoms substituted with a group $Ar^3$, or a group $Ar^3$, most preferably a group $Ar^3$.

$R^{U3}$ and $R^{U4}$ independently represent (1) hydrogen atom, or (2) an alkyl group having 1 to 4 carbon atoms, or (3) $R^{U3}$ and $R^{U4}$ may bind to each other to form a saturated monocyclic heterocyclic ring (qb3) together with the nitrogen atom to which they bind, and all of them are preferred examples.

The group $Ar^2$ and group $Ar^3$ independently represent (1) a residue of a carbocyclic compound (ca3) or (2) a residue of a heterocyclic compound (qa3), and both of them are preferred examples. Specific examples of the group $Ar^2$ and group $Ar^3$ include, for example, residues of cyclic compounds such as cyclopropane, cyclobutane, cyclopentane, cyclohexane, cycloheptane, cyclooctane, cyclononane, cyclodecane, cycloundecane, cyclopentene, cyclohexene, cycloheptene, cyclooctene, cyclopentadiene, cyclohexadiene, cycloheptadiene, cyclooctadiene, benzene, pentalene, perhydropentalene, indene, perhydroindene, indan, azulene, perhydroazulene, naphthalene, dihydronaphthalene, tetrahydronaphthalene, perhydronaphthalene, spiro[4,4]nonane, spiro[4,5]decane, spiro[5,5]undecane, bicyclo[2,2,1]heptane, bicyclo[2,2,1]hept-2-ene, bicyclo[3,1,1]heptane, bicyclo[3,1,1]hept-2-ene, bicyclo[2,2,2]octane, adamantane, noradamantane, aziridine, azetidine, pyrrolidine, pyrroline, imidazoline, imidazolidine, triazoline, triazolidine, tetrazoline, tetrazolidine, pyrazoline, pyrazolidine, piperidine, piperazine, homopiperidine, homopiperazine, azepine, diazepine, morpholine, thiomorpholine, quinuclidine, oxolane, thiolane, oxathiane, furan, thiophene, pyrrole, oxazole, isoxazole, thiazole, isothiazole, imidazole, pyrazole, triazole, furazan, oxadiazole, thiadiazole, tetrazole, pyran, pyridine, pyridazine, pyrimidine, pyrazine, triazine, oxazine, oxadiazine, thiazine, thiadiazine, indoline, isoindoline, dihydrobenzofuran, 1,3-dioxaindan, chroman, 4H-chromene, benzofuran, benzo[b]thiophene, indole, isoindole, indolizine, 1H-indazole, 2H-indazole, 1H-benzimidazole, 1,3-dihydrobenzimidazole, benzoxazole, dihydro-3H-benzoxazole, benzo[d]isoxazole, benzo[c]isoxazole, benzothiazole, dihydro-3H-benzothiazole, benzo[d]isothiazole, benzo[c]isothiazole, 1H-benzotriazole, benzo[1,2,5]thiadiazole, quinoline, dihydro-1H-quinoline, isoquinoline, dihydro-2H-isoquinoline, cinnoline, quinazoline, quinoxaline, phthalazine, imidazo[1,2-a]pyridine, 1H-pyrrolo[2,3-b]pyridine, 1H-pyrrolo[3,2-b]pyridine, 1,3-dihydropyrrolo[2,3-b]pyridine, 1H-pyrrolo[3,2-c]pyridine, 1H-pyrrolo[2,3-c]pyridine, 1H-pyrazolo[4,3-b]pyridine, 1H-pyrazolo[4,3-c]pyridine, 1H-pyrazolo[3,4-c]pyridine, 1H-pyrazolo[3,4-b]pyridine, [1,2,4]triazolo[4,3-a]pyridine, thieno[3,2-c]pyridine, thieno[3,2-b]pyridine, 1H-thieno[3,2-c]pyrazole, 1H-pyrazolo[3,4-d]thiazole, [1,2,4]triazolo[1,5-a]pyrimidine, 1H-pyrazolo[3,4-b]pyrazine, 1H-imidazo[4,5-b]pyrazine, 7H-purine, [1,8]naphthalidine, and [1,5]naphthalidine.

Particularly preferred examples include residues of cyclic compounds, cyclopropane, cyclobutane, cyclopentane, cyclohexane, cycloheptane, benzene, azulene, naphthalene, dihydronaphthalene, tetrahydronaphthalene, adamantane, furan, thiophene, pyrrole, oxazole, isoxazole, thiazole, isothiazole, imidazole, pyrazole, triazole, furazan, oxadiazole, thiadiazole, tetrazole, pyridine, pyridazine, pyrimidine, pyrazine, triazine, oxazine, oxadiazine, thiazine, thiadiazine, indoline, isoindoline, dihydrobenzofuran, chroman, 4H-chromene, benzofuran, benzo[b]thiophene, indan, indole, isoindole, indolizine, 1H-indazole, 2H-indazole, 1H-benzimidazole, 1,3-dihydrobenzimidazole, benzoxazole, dihydro-3H-benzoxazole, benzo[d]isoxazole, benzo[c]isoxazole, benzothiazole, dihydro-3H-benzothiazole, benzo[d]isothiazole, benzo[c]isothiazole, 1H-benzotriazole, benzo[1, 2,5]thiadiazole, quinoline, dihydro-1H-quinoline, isoquinoline, dihydro-2H-isoquinoline, cinnoline, quinazoline, quinoxaline, phthalazine and the like, and extremely preferred examples are residues of cyclic compounds, benzene, naphthalene, furan, thiophene, oxazole, isoxazole, thiazole, isothiazole, imidazole, pyrazole, triazole, pyridine, pyridazine, pyrimidine, pyrazine, benzofuran, benzo[b]thiophene, indan, indole, 1H-indazole, 1H-benzimidazole, benzoxazole, benzo[d]isoxazole, benzo[c]isoxazole, benzothiazole, benzo[d]isothiazole, benzo[c]isothiazole, 1H-benzotriazole, quinoline, isoquinoline, cinnoline, quinazoline, quinoxaline, phthalazine and the like. Among them, residues of cyclic compounds, benzene, indan, naphthalene, furan, thiophene, pyridine, benzofuran, benzo[b]thiophene, indole, 1H-indazole, 1H-benzimidazole, benzoxazole, benzothiazole, quinoline, isoquinoline, cinnoline, quinazoline, quinoxaline, phthalazine and the like are particularly preferred examples. Most preferred examples of the group $Ar^3$ include residues of benzene, and naphthalene, and in particular, most preferred example is a residue of benzene.

$R^2$, which may substitute on the group $Ar^2$ and the group $Ar^3$ in a number of 1, or 2 to 4 as the same or different groups $R^2$, represents (1) an alkyl group having 1 to 4 carbon atoms, (2) an alkoxy group having 1 to 4 carbon atoms, (3) an alkylthio group having 1 to 4 carbon atoms, (4) a halogen atom, (5) hydroxyl group, (6) nitro group, (7) a —N($R^{41}$)($R^{42}$) group, (8) an alkyl group having 1 to 4 carbon atoms substituted with an alkoxy group having 1 to 4 carbon atoms, (9) an alkyl group having 1 to 4 carbon atoms substituted with 1 to 3 halogen atoms, (10) an alkyl group having 1 to 4 carbon atoms substituted with an alkoxy group having 1 to 4 carbon atoms substituted with 1 to 3 halogen atoms, (11) an alkyl group having 1 to 4 carbon atoms substituted with a —N($R^{41}$)($R^{42}$) group, (12) a group $Ar^4$, (13) a —O—$Ar^4$ group, (14) an alkyl group having 1 to 4 carbon atoms substituted with a group $Ar^4$, (15) an alkenyl group having 1 to 4 carbon atoms group substituted with a group $Ar^4$, (16) an alkynyl group having 1 to 4 carbon atoms substituted with a group $Ar^4$, (17) an alkoxy group having 1 to 4 carbon atoms substituted with a group $Ar^4$, (18) an alkyl group having 1 to 4 carbon atoms substituted with a —O—$Ar^4$ group, (19) a —COO$R^{43}$ group, (20) an alkoxy group having 1 to 4 carbon atoms substituted with 1 to 3 halogen atoms, (21) formyl group, (22) an alkyl group having 1 to 4 carbon atoms substituted with hydroxyl group, (23) an acyl group having 2 to 6 carbon atoms, (24) oxo group, or (25) thioxo group, and all of them are preferred examples.

Particularly preferred examples of $R^2$ include an alkyl group having 1 to 4 carbon atoms, an alkoxy group having 1 to 4 carbon atoms, a halogen atom, hydroxyl group, a —N($R^{41}$)($R^{42}$) group, an alkyl group having 1 to 4 carbon atoms substituted with an alkoxy group having 1 to 4 carbon atoms, an alkyl group having 1 to 4 carbon atoms substituted with 1 to 3 halogen atoms, an alkyl group having 1 to 4 carbon atoms substituted with an alkoxy group having 1 to 4 carbon atoms substituted with 1 to 3 halogen atoms, an alkoxy group having 1 to 4 carbon atoms substituted with 1 to 3 halogen atoms, an alkyl group having 1 to 4 carbon atoms substituted with hydroxyl group, a group $Ar^4$, a —O—$Ar^4$ group, an alkyl group having 1 to 4 carbon atoms substituted with a group $Ar^4$, an alkyl group having 1 to 4 carbon atoms substituted with a —O—$Ar^4$ group and the like. Further preferred examples of $R^2$ include an alkyl group having 1 to 4 carbon atoms, an alkoxy group having 1 to 4 carbon atoms, a halogen atom, an alkyl group having 1 to 4 carbon atoms substituted with an alkoxy group having 1 to 4 carbon atoms, an alkyl group having 1 to 4 carbon atoms substituted with 1 to 3 halogen atoms, an alkoxy group having 1 to 4 carbon atoms substituted with 1 to 3 halogen atoms, an alkyl group having 1 to 4 carbon atoms substituted with hydroxyl group, a group $Ar^4$, a —O—$Ar^4$ group, an alkyl group having 1 to 4 carbon atoms substituted with a group $Ar^4$, an alkyl group having 1 to 4 carbon atoms and substituted with a —O—Ar group and the like, and among them, methyl group, ethyl group, propyl group, isopropyl group, butyl group, isobutyl group, t-butyl group, methoxy group, ethoxy group, propyloxy group, isopropyloxy group, butoxy group, isobutyloxy group, t-butyloxy group, fluorine atom, chlorine atom, bromine atom, iodine atom, methoxymethyl group, methoxyethyl group, trifluoromethyl group, dichloroethyl group, hydroxyethyl group, a group $Ar^4$, and a —O—$Ar^4$ group are preferred examples.

$R^{41}$ and $R^{42}$ independently represent (1) hydrogen atom, or (2) an alkyl group having 1 to 4 carbon atoms, or (3) $R^{41}$ and $R^{42}$ may bind to each other to form a saturated monocyclic heterocyclic ring (qb4) together with the nitrogen atom to which they bind. All of them are preferred examples. Further, most preferably, they independently represent hydrogen atom, methyl group, or ethyl group, or $R^{41}$ and $R^{42}$ bind to each other to form pyrrolidine, piperidine, piperazine, homopiperidine, homopiperazine, morpholine or the like together with the nitrogen atom to which they bind.

$R^{43}$ represents (1) hydrogen atom, or (2) an alkyl group having 1 to 4 carbon atoms, and both of them are preferred examples.

When a secondary nitrogen atom is present in the group $Ar^2$ or the group $Ar^3$ as the ring-constituting atom, an alkyl group, formyl group, an acyl group, a group $Ar^4$ or the like may substitute on the nitrogen atom as $R^2$.

The group $Ar^4$ represents (1) a residue of a carbocyclic compound (ca4), or (2) a residue of a heterocyclic compound (qa4), and both of them are preferred examples.

The residues of a carbocyclic compound, ca1, ca2, ca3, and ca4, independently represent a residue of a completely unsaturated, or partially or completely saturated monocyclic compound having 3 to 11 carbon atoms, or a residue of condensed bicyclic carbocyclic compound having 8 to 11 carbon atoms.

Particularly preferred examples of the group $Ar^4$ include a residue of a completely unsaturated, or partially or completely saturated monocyclic carbocyclic compound having 3 to 7 carbon atoms, or a residue of a completely unsaturated, or partially or completely saturated monocyclic heterocyclic compound having 3 to 7 ring-constituting atoms and containing the same or different 1 to 4 hetero atoms as the ring-constituting atoms selected from the group consisting of nitrogen atom, oxygen atom, and sulfur atom. Specific examples include, for example, residues of cyclic compounds, cyclopropane, cyclobutane, cyclopentane, cyclohexane, cycloheptane, cyclopentene, cyclohexene, cycloheptene, benzene, aziridine, azetidine, pyrrolidine, pyrroline, imidazoline, imidazolidine, triazoline, triazolidine, pyrazoline, pyrazolidine, piperidine, piperazine, homopiperidine, homopiperazine, azepine, diazepine, morpholine, thiomorpholine, furan, thiophene, pyrrole, oxazole, isoxazole, thiazole, isothiazole, imidazole, pyrazole, triazole, furazan, oxadiazole, thiadiazole, tetrazole, pyran, pyridine, pyridazine, pyrimidine, pyrazine and the like. Further preferred examples of the group $Ar^4$ include residues of cyclic compounds, benzene, furan, thiophene, pyrrole, oxazole, isoxazole, thiazole, isothiazole, imidazole, pyrazole, pyridine, pyridazine, pyrimidine, pyrazine and the like, and among them, phenyl group is a particularly preferred example.

The group $Ar^4$ may be substituted with 1 or the same or different 2 to 4 groups $R^3$. $R^3$ represents (1) an alkyl group having 1 to 4 carbon atoms, (2) an alkenyl group having 2 to 4 carbon atoms, (3) an alkynyl group having 2 to 4 carbon atoms, (4) an alkoxy group having 1 to 4 carbon atoms, (5) an alkyl group having 1 to 4 carbon atoms substituted with an alkoxy group having 1 to 4 carbon atoms, (6) a halogen atom, (7) hydroxyl group, (8) an alkyl group having 1 to 4 carbon atoms substituted with 1 to 3 halogen atoms, or (9) an alkoxy group having 1 to 4 carbon atoms substituted with 1 to 3 halogen atoms, and all of them are preferred examples. Among them, particularly preferred examples are (1) an alkyl group having 1 to 4 carbon atoms, (2) an alkoxy group having 1 to 4 carbon atoms, (3) a halogen atom, (4) hydroxyl group, (5) an alkyl group having 1 to 4 carbon atoms substituted with 1 to 3 halogen atoms, (6) an alkoxy group having 1 to 4 carbon atoms substituted with 1 to 3 halogen atoms and the like, and specific examples are, for example, methyl group, ethyl group, propyl group, isopropyl group, butyl group, isobutyl group, t-butyl group, methoxy group, ethoxy group, propyloxy group, isopropyloxy group, butoxy group, isobutyloxy group, t-butyloxy group, fluorine atom, chlorine atom, bromine atom, iodine atom, hydroxyl group, trifluoromethyl group, dichloroethyl group, trifluoromethyloxy group and the like. When a secondary nitrogen atom is present in the group $Ar^4$ as a ring-constituting atom, an alkyl group, an alkenyl group, an alkynyl group or the like as $R^3$ may substitute on the nitrogen atom.

The residues of a heterocyclic compound, qa1, qa2, qa3, and qa4, independently represent a residue of a completely unsaturated, or partially or completely saturated monocyclic compound having 3 to 11 ring-constituting atoms (the monocyclic compound contains one or more hetero atoms, which may be the same or different, selected from the group consisting of nitrogen atom, oxygen atom, and sulfur atom as the ring-constituting atoms), or a residue of a condensed bicyclic heterocyclic compound (qa) having 7 to 11 ring-constituting atoms, and the heterocyclic compound (qa) contains 1 to 4 hetero atoms, which may be the same or different, selected from the group consisting of nitrogen atom, oxygen atom, and sulfur atom as the ring-constituting atoms.

The residues of a saturated monocyclic heterocyclic compound, qb1, qb2, qb3, and qb4, independently represent a residue of a 5- to 7-membered nitrogen-containing saturated monocyclic heterocyclic compound (qb), and the heterocyclic compound (qb) may further contain one ring-constituting hetero atom selected from the group consisting of nitrogen atom, oxygen atom, and sulfur atom, or may be substituted with 1 or the same or different 2 to 4 alkyl groups having 1 to 4 carbon atoms.

Preferred compounds as Compound (I) of the invention include the compounds represented by the general formula (I-A):

[Formula 41]

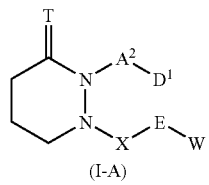

(I-A)

(wherein $A^2$, $D^1$, X, E, W, and T have the same meanings as those defined above), the compounds represented by the general formula (I-B):

[Formula 42]

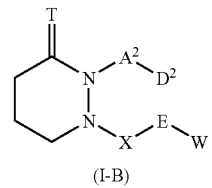

(I-B)

(wherein $A^2$, $D^2$, X, E, W, and T have the same meanings as those defined above), the compounds represented by the general formula (I-C):

[Formula 43]

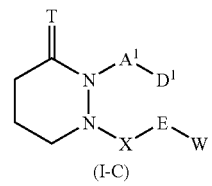

(I-C)

(wherein $A^1$, $D^1$, X, E, W, and T have the same meanings as those defined above), and the compounds represented by the general formula (I-D):

[Formula 44]

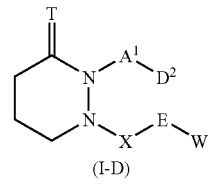

(I-D)

(wherein $A^1$, $D^2$, X, E, W, and T have the same meanings as those defined above).

Preferred compounds as the compounds represented by the general formula (I-A) include the compounds represented by the general formula (I-A-1):

[Formula 45]

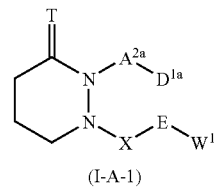

(I-A-1)

(wherein $A^{2a}$ represents (1) a $-G^{1a}-Ar^1-G^{3a}-$ group, (2) a $-G^{1a}-Y-Ar^1-G^{3a}-$ group, (3) a $-G^{1a}-Ar^1-Y-G^{3a}-$ group, or (4) a $-G^{1a}-Y-G^{3a}-$ group;

$G^{1a}$ represents a linear alkylene group having 1 to 4 carbon atoms;

$G^{3a}$ represents (1) a single bond, (2) a linear alkylene group having 1 to 4 carbon atoms, or (3) a linear alkenylene group having 2 to 4 carbon atoms;

$D^{1a}$ represents (1) a $-COOR^{D1}$ group, or (2) tetrazol-5-yl group;

W¹ represents (1) a group Wa¹ represented by the following formula:

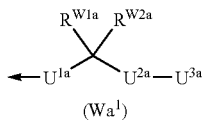

[Formula 46]

(wherein the arrow indicates a bond with the group E), or (2) a group $Ar^2$;

$R^{W1a}$ and $R^{W2a}$ independently represent (1) hydrogen atom, (2) an alkyl group having 1 to 4 carbon atoms, or (3) fluorine atom, or together represent (4) a substituent in which $R^{W1a}$ and $R^{W2a}$ bind to each other to form a 3- to 7-membered saturated cycloalkane group (cb) together with the carbon atom to which they bind;

$U^{1a}$ represents (1) a single bond, or (2) an alkylene group having 1 to 4 carbon atoms;

$U^{2a}$ represents (1) a single bond, (2) an alkylene group having 1 to 4 carbon atoms, (3) —O— group, (4) —S— group, (5) —S(O)— group, (6) —S(O)$_2$— group, or (7) a —N($R^{U1}$)— group;

$U^{3a}$ represents (1) an alkyl group having 1 to 8 carbon atoms which may be substituted with 1 or the same or different 2 to 4 substituents selected from the group consisting of an alkyl group having 1 to 4 carbon atoms, a halogen atom, hydroxyl group, an alkoxy group having 1 to 4 carbon atoms, an alkylthio group having 1 to 4 carbon atoms, and a —N($R^{U3}$)($R^{U4}$) group, (2) an alkyl group having 1 to 8 carbon atoms substituted with a group $Ar^3$, or (3) a group $Ar^3$; and T, $Ar^1$, Y, $R^{D1}$, $Ar^2$, $R^{U1}$, $R^{U3}$, $R^{U4}$, and $Ar^3$ have the same meanings as those defined above].

Particularly preferred compounds as the compounds represented by the general formula (I-A-1) include the compounds represented by the general formula (I-A-1a):

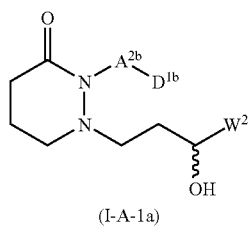

[Formula 47]

(I-A-1a)

[wherein $A^{2b}$ represents (1) a $-G^{1b}-Ar^{1a}-G^{3b}-$ group, (2) a $-G^{1b}-Y^a-Ar^{1a}-G^{3b}-$ group, (3) a $-G^{1b}-Ar^{1a}-Y^a-G^{3c}-$ group, or (4) a $-G^{1b}-Y^a-G^{3c}-$ group;

$G^{1b}$ represents (1) methylene group, (2) ethylene group, or (3) trimethylene group;

the group $Ar^{1a}$ represents (1) a residue of a completely unsaturated, or partially or completely saturated monocyclic carbocyclic compound having 3 to 7 carbon atoms (ca1m), or (2) a residue of a completely unsaturated, or partially or completely saturated monocyclic heterocyclic compound having 3 to 7 carbon atoms as ring-constituting atoms and containing the same or different 1 to 3 hetero atoms selected from the group consisting of nitrogen atom, oxygen atom, and sulfur atom as the ring-constituting atoms (qa1m);

$Y^a$ represents (1) —O— group, or (2) —S— group;

$G^{3b}$ represents (1) a single bond, (2) methylene group, (3) ethylene group, or (4) ethenylene group;

$G^{3c}$ represents (1) methylene group, (2) ethylene group, or (3) ethenylene group;

$D^{1b}$ represents a —COOR$^{D1b}$ group, or tetrazol-5-yl group;

$R^{D1b}$ represents (1) hydrogen atom, or (2) an alkyl group having 1 to 4 carbon atoms;

$W^2$ represents (1) a group $Wa^2$ represented by the following formula:

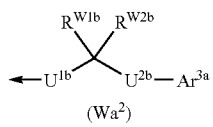

[Formula 48]

(Wa²)

(wherein the arrow indicates a bond with the adjacent carbon atom), or (2) a group $Ar^{2a}$;

$R^{W1b}$ and $R^{W2b}$ independently represent (1) hydrogen atom, or (2) methyl group, or together represents (3) a substituent in which $R^{W1b}$ and $R^{W2b}$ bind to each other to form cyclopropane, cyclobutane, cyclopentane, or cyclohexane together with the carbon atom to which they bind;

$U^{1b}$ represents (1) a single bond, (2) methylene group, (3) ethylene group, or (4) trimethylene group;

$U^{2b}$ represents (1) a single bond, (2) methylene group, (3) ethylene group, (4) trimethylene group, (5) —O— group, (6) —S— group, or (7) —N($R^{U1'}$)—;

$R^{U1'}$ represents (1) hydrogen atom, or (2) an alkyl group having 1 to 4 carbon atoms;

the group $Ar^{2a}$ and the group $Ar^{3a}$ represents residue of a cyclic compound selected from the group consisting of cyclopropane, cyclobutane, cyclopentane, cyclohexane, cycloheptane, benzene, azulene, naphthalene, dihydronaphthalene, tetrahydronaphthalene, adamantane, furan, thiophene, pyrrole, oxazole, isoxazole, thiazole, isothiazole, imidazole, pyrazole, triazole, furazan, oxadiazole, thiadiazole, tetrazole, pyridine, pyridazine, pyrimidine, pyrazine, triazine, oxazine, oxadiazine, thiazine, thiadiazine, indoline, isoindoline, dihydrobenzofuran, chroman, 4H-chromene, benzofuran, benzo[b]thiophene, indan, indole, isoindole, indolizine, 1H-indazole, 2H-indazole, 1H-benzimidazole, 1,3-dihydrobenzimidazole, benzoxazole, dihydro-3H-benzoxazole, benzo[d]isoxazole, benzo[c]isoxazole, benzothiazole, dihydro-3H-benzothiazole, benzo[d]isothiazole, benzo[c]isothiazole, 1H-benzotriazole, benzo[1,2,5]thiadiazole, quinoline, dihydro-1H-quinoline, isoquinoline, dihydro-2H-isoquinoline, cinnoline, quinazoline, quinoxaline, and phthalazinea;

the group $Ar^{2a}$ and the group $Ar^{3a}$ may be substituted with 1 or the same or different 2 to 4 of groups $R^{2a}$;

$R^{2a}$ represents (1) an alkyl group having 1 to 4 carbon atoms, (2) an alkoxy group having 1 to 4 carbon atoms, (3) a halogen atom, (4) hydroxyl group, (5) a —N($R^{410}$)($R^{420}$) group, (6) an alkyl group having 1 to 4 carbon atoms substituted with an alkoxy group having 1 to 4 carbon atoms, (7) an alkyl group having 1 to 4 carbon atoms substituted with 1 to 3 halogen atoms, (8) an alkyl group having 1 to 4 carbon atoms substituted with an alkoxy group having 1 to 4 carbon atoms substituted with 1 to 3 halogen atoms, (9) an alkoxy group having 1 to 4 carbon atoms substituted with 1 to 3 halogen atoms, (10) an alkyl group having 1 to 4 carbon atoms substituted with hydroxyl group, (11) a group $Ar^{4a}$, (12) a —O—$Ar^{4a}$ group, (13) an alkyl group having 1 to 4 carbon atoms and substituted with a group $Ar^{4a}$, or (14) an alkyl group having 1 to 4 carbon atoms substituted with a —O—$Ar^{4a}$ group;

$R^{410}$ and $R^{420}$ independently represent (1) hydrogen atom, (2) methyl group, or (3) ethyl group, or together represent (3) a substituent in which $R^{410}$ and $R^{420}$ bind to each other to form pyrrolidine, piperidine, piperazine, homopiperidine, homopiperazine, or morpholine together with the nitrogen atom to which they bind;

the group $Ar^{4a}$ represents a residue of a cyclic compound selected from the group consisting of cyclopropane, cyclobutane, cyclopentane, cyclohexane, cycloheptane, cyclopentene, cyclohexene, cycloheptene, benzene, aziridine, azetidine, pyrrolidine, pyrroline, imidazoline, imidazolidine, triazoline, triazolidine, pyrazoline, pyrazolidine, piperidine, piperazine, homopiperidine, homopiperazine, azepine, diazepine, morpholine, thiomorpholine, furan, thiophene, pyrrole, oxazole, isoxazole, thiazole, isothiazole, imidazole, pyrazole, triazole, furazan, oxadiazole, thiadiazole, tetrazole, pyran, pyridine, pyridazine, pyrimidine, and pyrazine;

the group $Ar^{4a}$ may be substituted with 1 or the same or different 2 to 4 of $R^{3a}$;

$R^{3a}$ represents (1) an alkyl group having 1 to 4 carbon atoms, (2) an alkoxy group having 1 to 4 carbon atoms, (3) a halogen atom, (4) hydroxyl group, (5) an alkyl group having 1 to 4 carbon atoms substituted with 1 to 3 halogen atoms, or (6) an alkoxy group having 1 to 4 carbon atoms substituted with 1 to 3 halogen atoms].

Further preferred compounds among the compounds represented by the general formula (I-A-1) include the compounds represented by the general formula (I-A-1b):

[Formula 49]

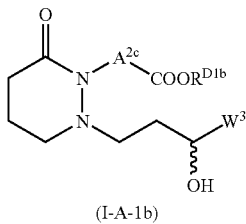

(I-A-1b)

[wherein $A^{2c}$ represents (1) a -$G^{1b}$-$Ar^{1b}$-$G^{3b}$- group, (2) a -$G^{1b}$-$Y^a$—$Ar^{1b}$-$G^{3b}$- group, or (3) a -$G^{1b}$-$Ar^{1b}$—$Y^a$-$G^{3c}$- group;

the group $Ar^{1b}$ represents a residue of a cyclic compound selected from the group consisting of benzene, furan, thiophene, pyrrole, oxazole, isoxazole, thiazole, isothiazole, imidazole, pyrazole, pyridine, pyridazine, pyrimidine, and pyrazine;

$W^3$ represents (1) a group $Wa^3$ represented by the following formula:

[Formula 50]

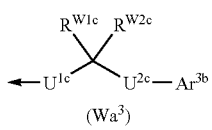

($Wa^3$)

(wherein the arrow indicates a bond with the adjacent carbon atom), or (2) a group $Ar^{2b}$;

$R^{W1c}$ and $R^{W2c}$ independently represent (1) hydrogen atom, or (2) methyl group, or together represent (3) a substituent in which $R^{W1c}$ is $R^{W2c}$ bind to each other to form cyclopropane ring together with the carbon atom to which they bind;

$U^{1c}$ represents (1) a single bond, (2) methylene group, or (3) ethylene group;

$U^{2c}$ represents (1) a single bond, (2) methylene group, (3) ethylene group, (4) —O— group, or (5) —S— group;

the group $Ar^{2b}$ and the group $Ar^{3b}$ represents a residue of a cyclic compound selected from the group consisting of benzene, naphthalene, furan, thiophene, oxazole, isoxazole, thiazole, isothiazole, imidazole, pyrazole, triazole, pyridine, pyridazine, pyrimidine, pyrazine, benzofuran, benzo[b]thiophene, indan, indole, 1H-indazole, 1H-benzimidazole, benzoxazole, benzo[d]isoxazole, benzo[c]isoxazole, benzothiazole, benzo[d]isothiazole, benzo[c]isothiazole, 1H-benzotriazole, quinoline, isoquinoline, cinnoline, quinazoline, quinoxaline, and phthalazine;

the group $Ar^{2b}$ and the group $Ar^{3b}$ may be substituted with 1 or the same or different 2 to 4 of $R^{2b}$;

$R^{2b}$ represents (1) an alkyl group having 1 to 4 carbon atoms, (2) an alkoxy group having 1 to 4 carbon atoms, (3) a halogen atom, (4) an alkyl group having 1 to 4 carbon atoms substituted with an alkoxy group having 1 to 4 carbon atoms, (5) an alkyl group having 1 to 4 carbon atoms substituted with 1 to 3 halogen atoms, (6) an alkoxy group having 1 to 4 carbon atoms substituted with 1 to 3 halogen atoms, (7) an alkyl group having 1 to 4 carbon atoms substituted with hydroxyl group, (8) a group $Ar^{4b}$, (9) a —O—$Ar^{4b}$ group, (10) an alkyl group having 1 to 4 carbon atoms and substituted with a group $Ar^{4b}$, or (11) an alkyl group having 1 to 4 carbon atoms and substituted with a —O—$Ar^b$ group;

the group $Ar^{4b}$ represents a residue of a cyclic compound selected from the group consisting of benzene, furan, thiophene, pyrrole, oxazole, isoxazole, thiazole, isothiazole, imidazole, pyrazole, pyridine, pyridazine, pyrimidine, and pyrazine;

the group $Ar^{4b}$ may be substituted with 1 or the same or different 2 to 4 of $R^{3a}$; and $G^{1b}$, $G^{3b}$, $G^{3c}$, $Y^a$, and $R^{3a}$ have the same meanings as those defined above].

Among them, preferred are the compounds represented by the general formula (I-A-1b1):

[Formula 51]

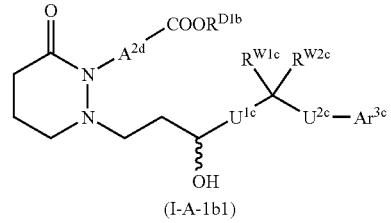

(I-A-1b1)

[wherein $A^{2d}$ represents (1) a -$G^{1b}$-$Ar^{1c}$-$G^{3b}$- group, (2) a -$G^{1b}$-$Y^a$—$Ar^{1c}$-$G^{3b}$- group, or (3) a -$G^{1b}$-$Ar^{1c}$-$Y^a$-$G^{3c}$- group;

the group $Ar^{1c}$ represents a residue of a cyclic compound selected from the substituents represented by the following formulas:

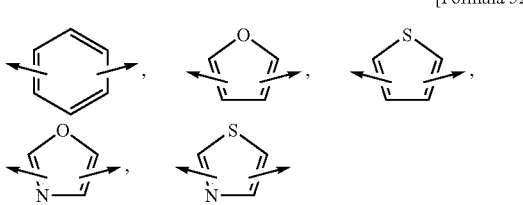

(the arrows represent a bond with the adjacent atom, and the bonding position may be any bondable position on a ring-constituting atom);

the group $Ar^{3c}$ represents a residue of a cyclic compound selected from the group consisting of benzene, naphthalene, furan, thiophene, pyridine, benzofuran, benzo[b]thiophene, indan, indole, 1H-indazole, 1H-benzimidazole, benzoxazole, benzothiazole, quinoline, isoquinoline, cinnoline, quinazoline, quinoxaline, and phthalazine;

the group $Ar^{3c}$ may be substituted with 1 or the same or different 2 to 4 of $R^{2c}$;

$R^{2c}$ represents methyl group, ethyl group, propyl group, isopropyl group, butyl group, isobutyl group, t-butyl group, methoxy group, ethoxy group, propyloxy group, isopropyloxy group, butoxy group, isobutyloxy group, t-butyloxy group, fluorine atom, chlorine atom, bromine atom, iodine atom, methoxymethyl group, methoxyethyl group, trifluoromethyl group, dichloroethyl group, or hydroxyethyl group, or represents a group $Ar^{4c}$, or a —O—$Ar^{4c}$ group;

the group $Ar^{4c}$ represents phenyl group which may be substituted with 1 or the same or different 2 to 4 of $R^{3b}$;

$R^{3b}$ represents methyl group, ethyl group, propyl group, isopropyl group, butyl group, isobutyl group, t-butyl group, methoxy group, ethoxy group, propyloxy group, isopropyloxy group, butoxy group, isobutyloxy group, t-butyloxy group, fluorine atom, chlorine atom, bromine atom, iodine atom, hydroxyl group, trifluoromethyl group, dichloroethyl group, or trifluoromethyloxy group; and $G^{1b}$, $G^{3b}$, $G^{3c}$, $Y^{a}$, $R^{D1b}$, $U^{1c}$, $U^{2c}$, $R^{W1c}$, and $R^{W2c}$ have the same meanings as those defined above].

Further, the compounds represented by the general formula (I-A-1b2):

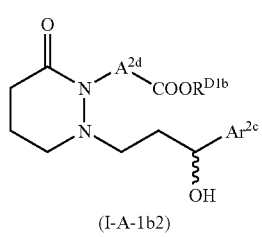

[wherein the group $Ar^{2c}$ represents a residue of a cyclic compound selected from the group consisting of benzene, naphthalene, furan, thiophene, pyridine, benzofuran, benzo[b]thiophene, indan, indole, 1H-indazole, 1H-benzimidazole, benzoxazole, benzothiazole, quinoline, isoquinoline, cinnoline, quinazoline, quinoxaline, and phthalazine;

the group $Ar^{2c}$ may be substituted with 1 or the same or different 2 to 4 of $R^{2c}$; and $A^{2d}$, $R^{D1b}$, and $R^{2c}$ have the same meanings as those defined above] are also preferred examples.

Still further, the compounds represented by the general formula (I-A-1b3):

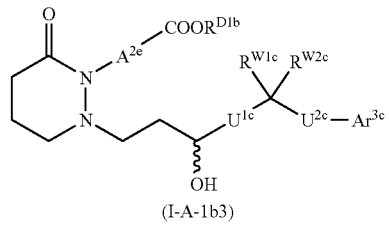

[wherein $A^{2e}$ represents (1) a -$G^{1b}$-$Ar^{1d}$-$G^{3b}$- group, (2) a -$G^{1b}$-$Y^{a}$—$Ar^{1d}$-$G^{3b}$- group, or (3) a -$G^{1b}$-$Ar^{1d}$—$Y^{a}$-$G^{3c}$- group;

the group $Ar^{1d}$ represents a residue of a cyclic compound selected from the substituents represented by the following formulas:

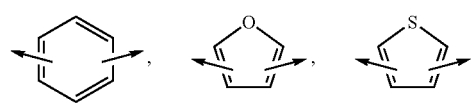

(the arrows represent a bond with an adjacent atom, and the bonding position may be any bondable position on a ring-constituting atom); and $G^{1b}$, $G^{3b}$, $G^{3c}$, $Y^{a}$, $R^{D1b}$, $U^{1c}$, $U^{2c}$, $Ar^{3c}$, $Ar^{4c}$, $R^{W1c}$, and $R^{W2c}$ have the same meanings as those defined above] are particularly preferred examples.

Among the compounds represented by the general formula (I-A-1b3), those wherein the group $Ar^{1d}$ is limited to a residue of benzene are highly preferred examples. As another embodiment, highly preferred examples include those wherein the group $Ar^{1d}$ is limited to a residue of furan. As a still further embodiment, highly preferred examples include those wherein the group $Ar^{1d}$ is limited to a residue of thiophene. Among them, the compounds where $Ar^{3c}$ is a residue of benzene or naphthalene are further preferred, and the compounds where $Ar^{3c}$ is a residue of benzene are particularly preferred.

Further, the compounds represented by the general formula (I-A-1b4):

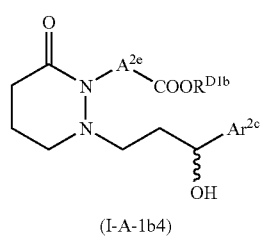

[wherein $A^{2e}$, $Ar^{2c}$, $R^{D1b}$, and $R^{2c}$ have the same meanings as those defined above] are preferred examples.

Among the compounds represented by the general formula (I), particularly preferred compounds include the compounds represented by the general formulas (Ia-1) to (Ia-32) (the symbols $R^{D1b}$ and $W^2$ in the formulas have the same meanings as those defined above) listed in Tables 1 to 3 mentioned below.
TABLE 1
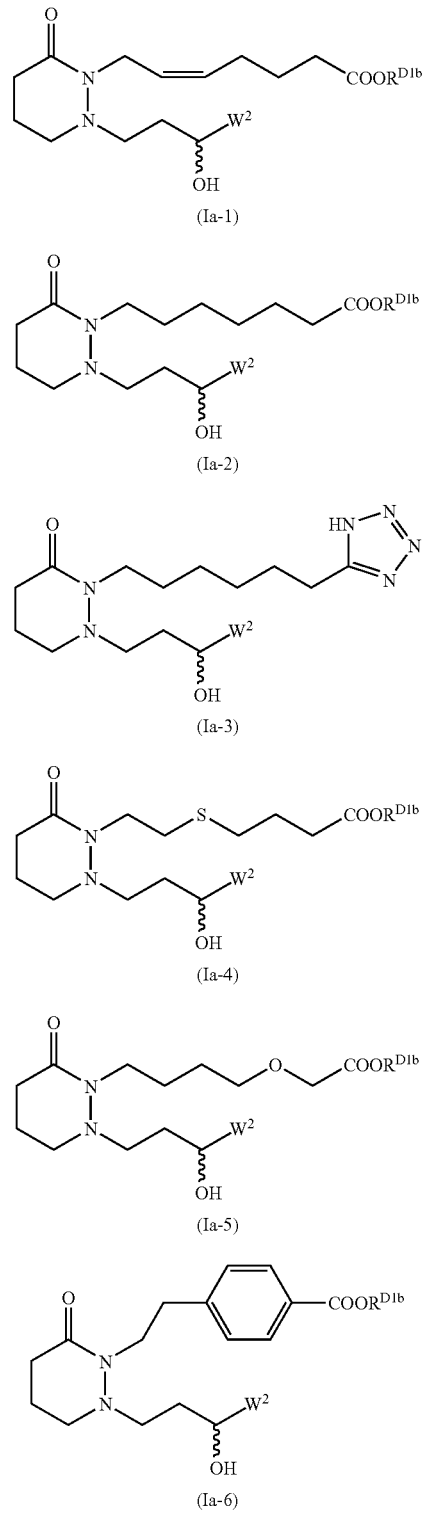
TABLE 1-continued
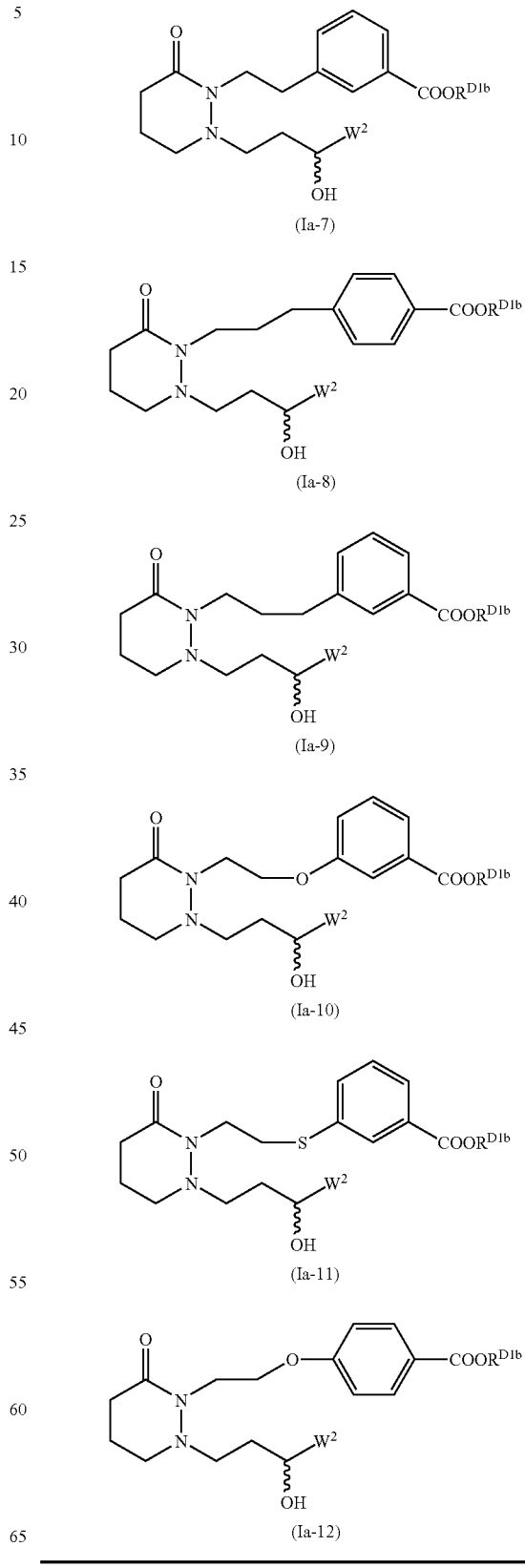

TABLE 2
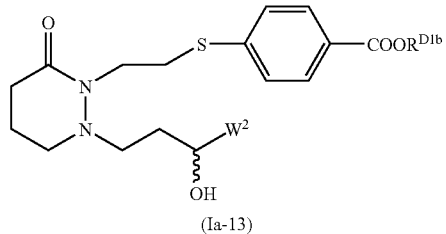
(Ia-13)
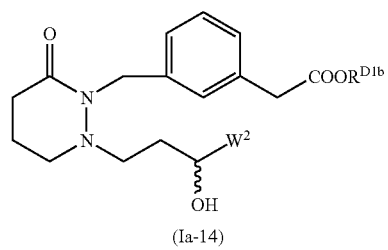
(Ia-14)
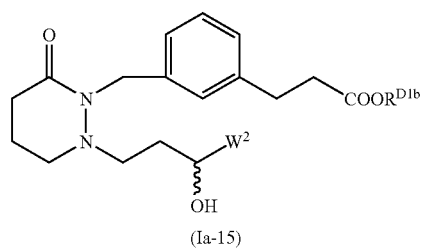
(Ia-15)
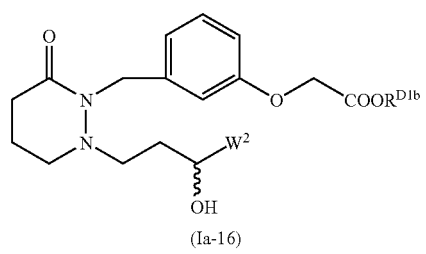
(Ia-16)
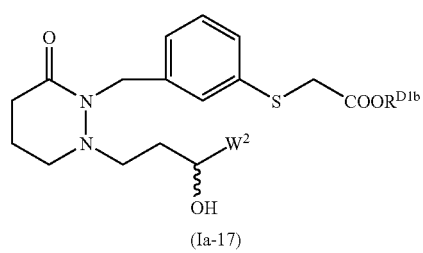
(Ia-17)
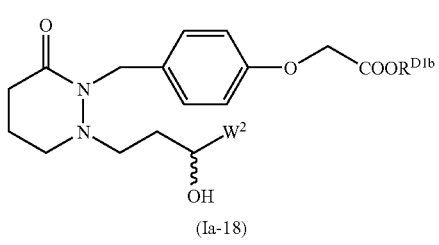
(Ia-18)
TABLE 2-continued
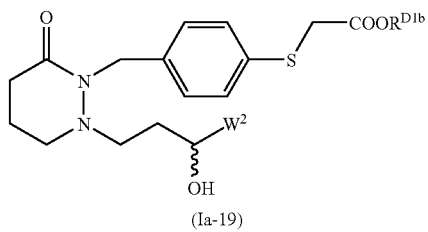
(Ia-19)
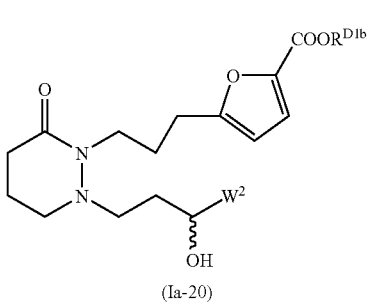
(Ia-20)
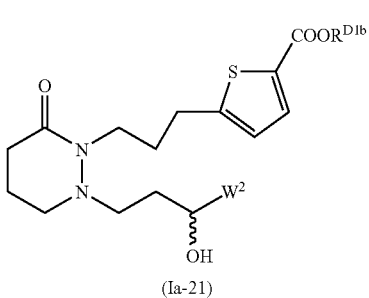
(Ia-21)
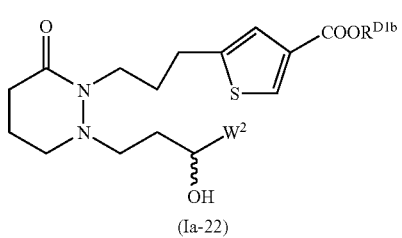
(Ia-22)
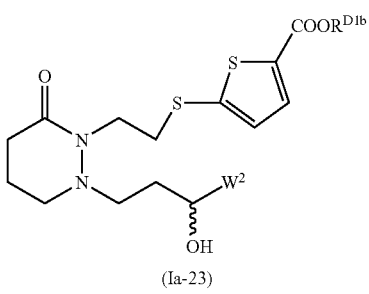
(Ia-23)

TABLE 2-continued
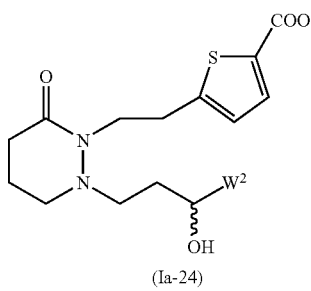
(Ia-24)
TABLE 3
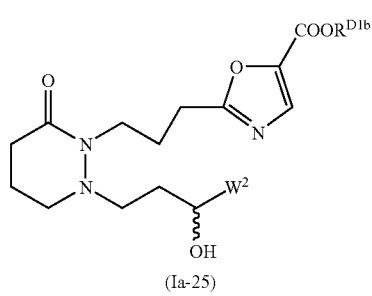
(Ia-25)
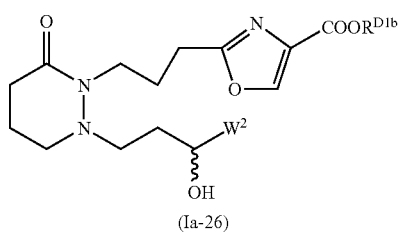
(Ia-26)
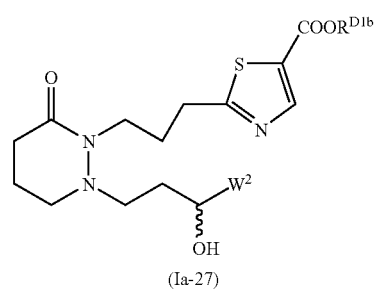
(Ia-27)
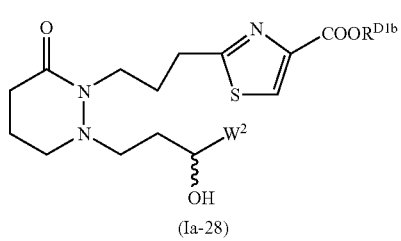
(Ia-28)
TABLE 3-continued
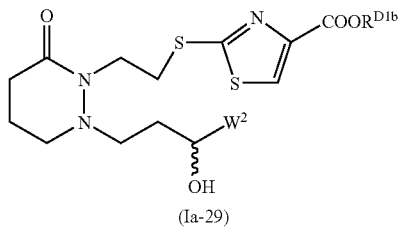
(Ia-29)
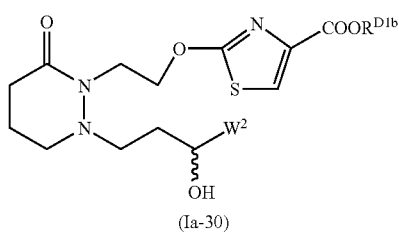
(Ia-30)
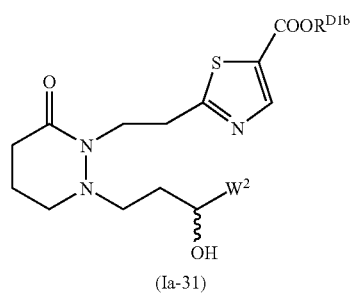
(Ia-31)
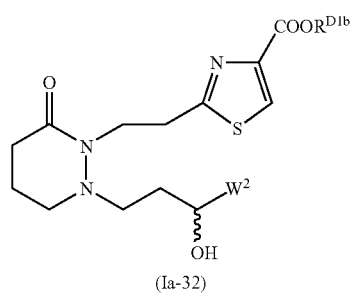
(Ia-32)
Most preferred compounds include those represented by the general formulas (Ia1-1) to (Ia1-10) (the symbols $R^{D1b}$ and $W^3$ in the formulas have the same meanings as those defined above) listed in Table 4 mentioned below.
TABLE 4
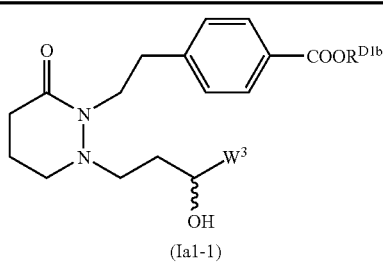
(Ia1-1)

TABLE 4-continued
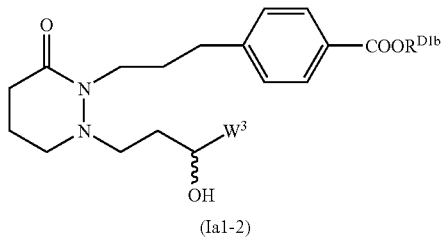
(Ia1-2)
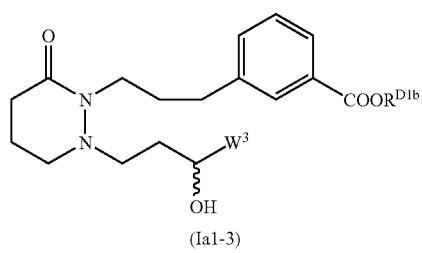
(Ia1-3)
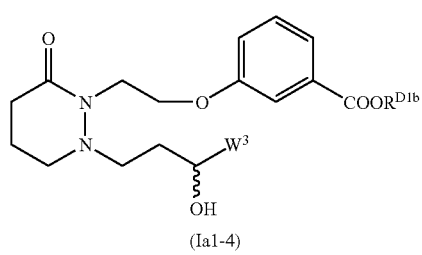
(Ia1-4)
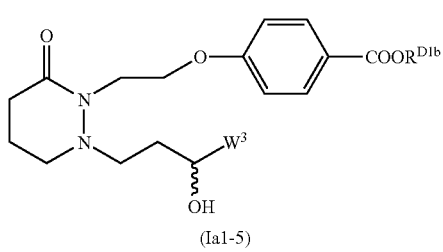
(Ia1-5)
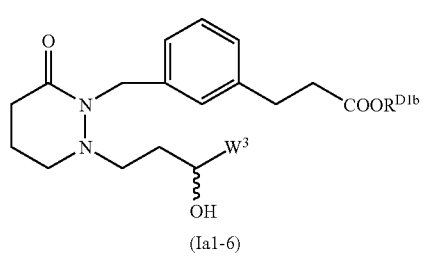
(Ia1-6)
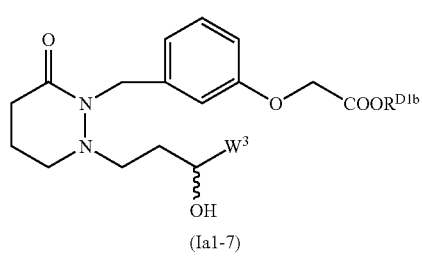
(Ia1-7)
TABLE 4-continued
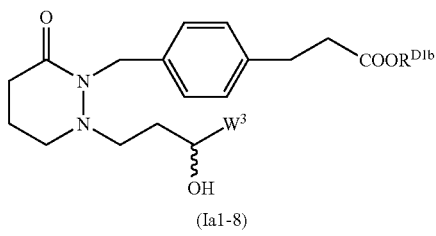
(Ia1-8)
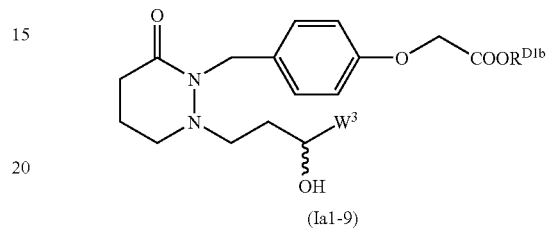
(Ia1-9)
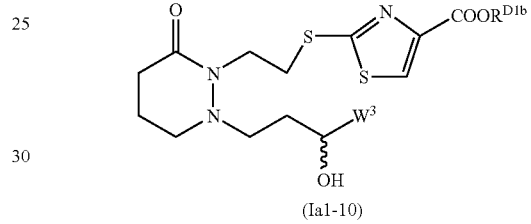
(Ia1-10)
Among the most preferred compounds, the compounds represented by the general formulas (Ia2-1) to (Ia2-5) (the symbols $R^{D1b}$, $R^{W1c}$, $R^{W2c}$ and $Ar^{3c}$ in the formulas have the same meanings as those defined above) listed in Table 5 mentioned below are particularly preferred examples.
TABLE 5
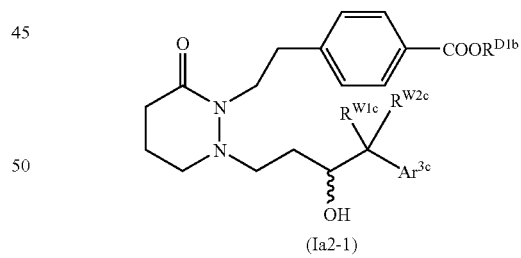
(Ia2-1)
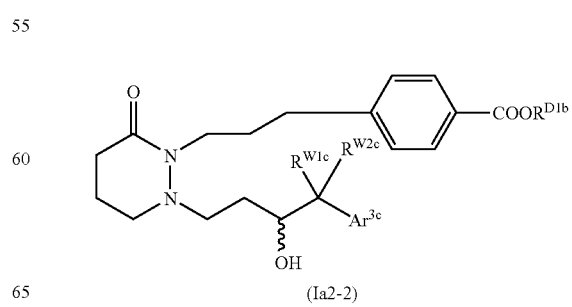
(Ia2-2)

TABLE 5-continued

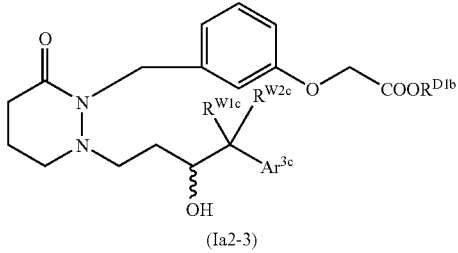

(Ia2-3)

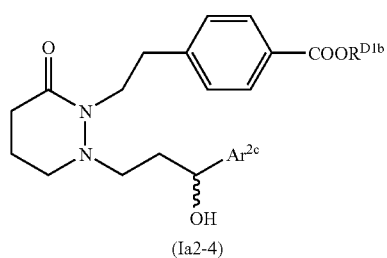

(Ia2-4)

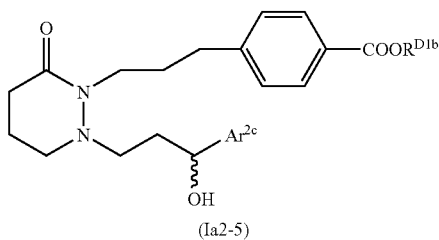

(Ia2-5)

Among the compounds represented by the general formula (I-B), particularly preferred compounds include the compounds represented by the general formula (I-B-1a):

[Formula 57]

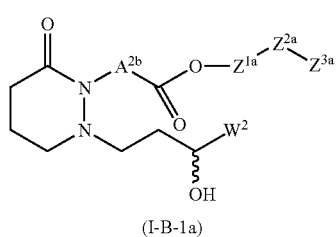

(I-B-1a)

[wherein $Z^{1a}$ represents an alkylene group having 1 to 4 carbon atoms;

$Z^{2a}$ represents (1) —OC(O)— group, (2) a —OC(O)N($R^{Z7}$)— group, or (3) —OC(O)O— group;

$Z^{3a}$ represents an alkyl group having 1 to 4 carbon atoms; and the symbols $A^{2b}$ and $W^2$ have the same meanings as those defined above].

Among the compounds represented by the general formula (I-C), examples of preferred compounds include the compounds represents by the general formula (I-C-1):

[Formula 58]

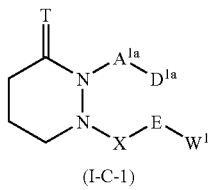

(I-C-1)

[wherein $A^{1a}$ represents (1) a linear alkylene group having 5 to 7 carbon atoms, or (2) a linear alkenylene group having 5 to 7 carbon atoms; and T, $D^{1a}$, and $W^1$ have the same meanings as those defined above].

Among the compounds represented by the general formula (I-C), examples of particularly preferred compounds include the compounds represented by the general formula (I-C-1a):

[Formula 59]

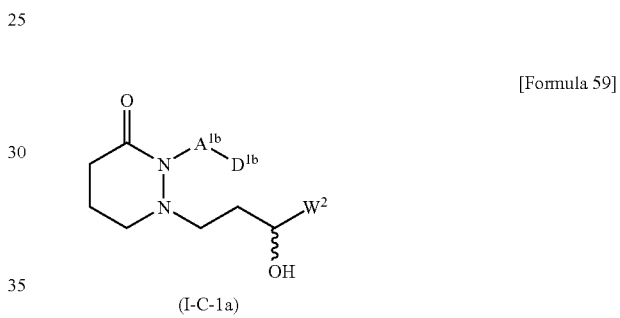

(I-C-1a)

[wherein $A^{1b}$ represents (1) hexamethylene group, or (2) hexenylene group; and $D^{1b}$ and $W^2$ have the same meanings as those defined above].

Among the compounds represented by the general formula (I-D), examples of particularly preferred compounds include the compounds represented by the general formula (I-D-1a):

[Formula 60]

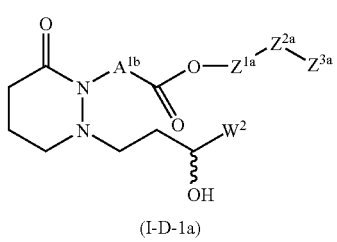

(I-D-1a)

[wherein $A^{1b}$, $Z^{1a}$, $Z^{2a}$, $Z^{3a}$, and $W^2$ have the same meanings as those defined above].

Further, preferred compounds among Compound (I) of the present invention include the compounds represented by the general formula (I-E):

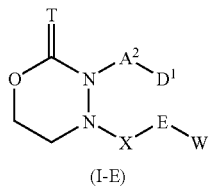

(I-E)

(wherein T, $A^2$, $D^1$, X, E, and W have the same meanings as those defined above), and among them, particularly preferred compounds include those represented by the general formula (I-E-1):

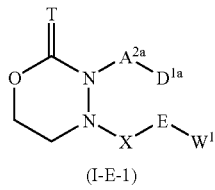

(I-E-1)

(wherein T, $A^{2a}$, $D^{1a}$, X, E, and $W^1$ have the same meanings as those defined above).

Preferred compounds among Compound (I) of the invention include the compounds represented by the general formula (I-F):

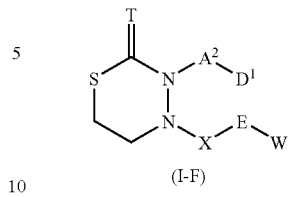

(I-F)

(wherein T, $A^2$, $D^1$, X, E, and W have the same meanings as those defined above), and among them, particularly preferred compounds include the compounds represented by the general formula (I-F-1):

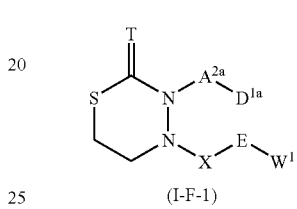

(I-F-1)

(wherein T, $A^{2a}$, $D^{1a}$, X, E, and $W^1$ have the same meanings as those defined above).

Highly preferred compounds among the compounds represented by the general formulas (I-E) and (I-F) include the compounds represented by the general formulas (Ie-1) to (Ie-6) and (If-1) to (If-6) (the symbols $D^{1b}$ and $W^2$ in the formulas have the same meanings as those defined above) listed in Table 6 mentioned below.

TABLE 6

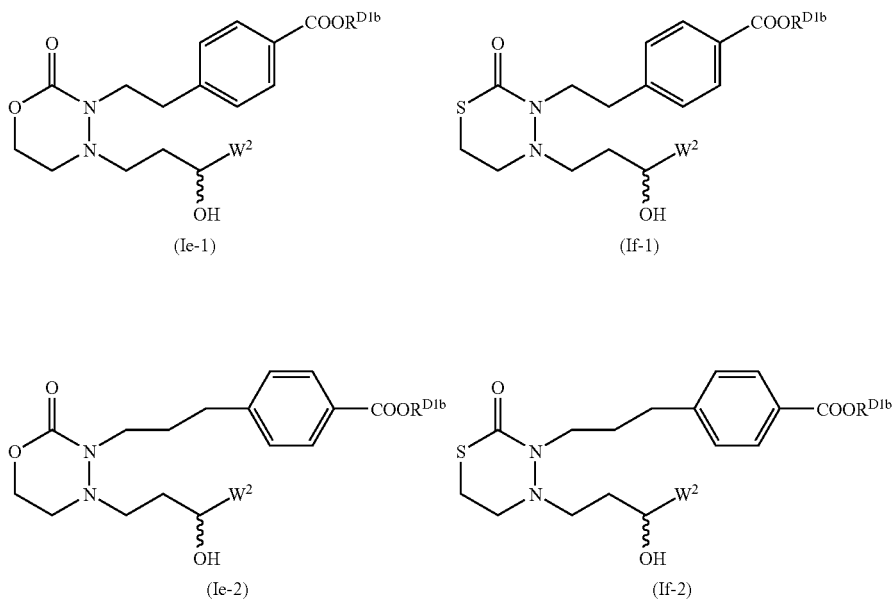

TABLE 6-continued

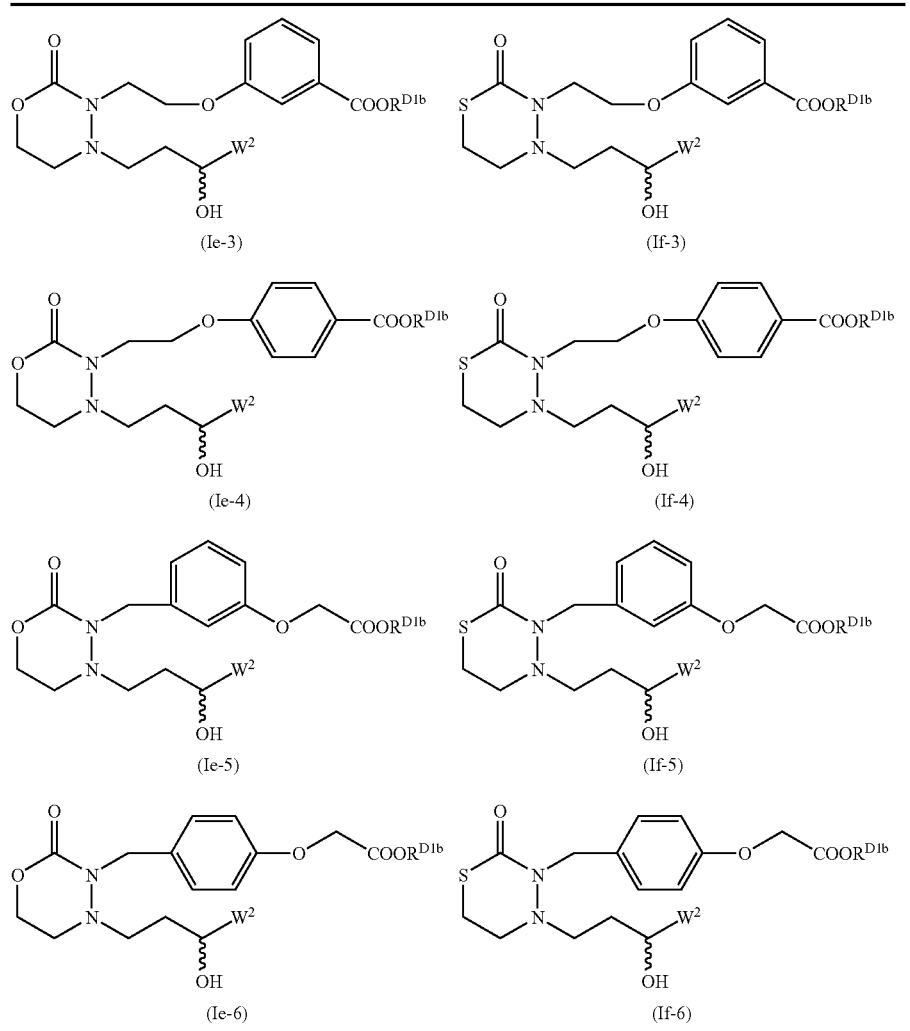

Further, as another embodiment, among the compounds of the present invention, compounds having a particularly preferred combination of substituents include the compounds represented by the general formula (Iae1):

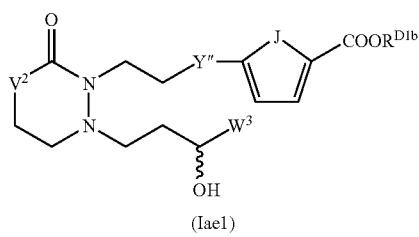

[Formula 65]

(Iae1)

(wherein $V^2$ represents (1) methylene group, or (2) oxygen atom;
Y" represents (1) a single bond, (2) methylene group, (3) oxygen atom, or (4) sulfur atom;
J represents (1) oxygen atom, or (2) sulfur atom, and
$R^{D1b}$ and $W^3$ have the same meanings as those defined above).

Further, among the compounds represented by the general formula (Iae1), compounds having a particularly preferred combination of substituents include the compounds represented by the general formula (Iae2):

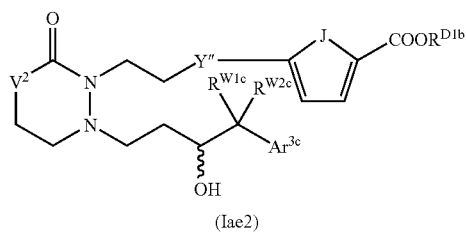

[Formula 66]

(Iae2)

(wherein $V^2$, Y", J, $R^{D1b}$, $R^{W1c}$, $R^{W2c}$, and $Ar^{3c}$ have the same meanings as those defined above).

Among the compounds represented by the general formula (Iae2), highly preferred examples include the compounds wherein J is oxygen atom. Among those, the compounds where $Ar^{3c}$ is a residue of benzene or naphthalene are further preferred, and the compounds where Ar³ᶜ is a residue of benzene are particularly preferred.

Further, the compounds represented by the general formula (I-A-1b3) having the same structure as that of the compounds represented by the general formula (I-A-1b3) except that thioxotetrahydropyridazine ring is used instead of oxotetrahydropyridazine ring are also highly preferred. Further preferred examples of such compounds include those wherein the group Ar¹ᵈ is limited to a residue of benzene, and among them, further extremely preferred examples include the compounds wherein Ar³ᶜ is a residue of benzene.

Specific examples of the compounds according to the present invention include the compounds listed in Tables 7 to 72 mentioned below, the compounds described in the examples, and pharmaceutically acceptable salts thereof.

TABLE 7-continued
(IA1)
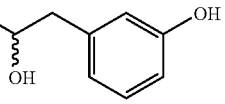
| No. | -X-E-W |
|---|---|
| 18 | 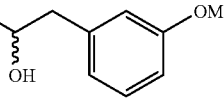 |
| 19 | 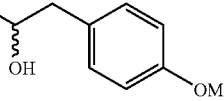 |
| 20 | 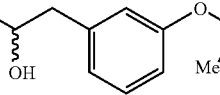 |
| 21 | 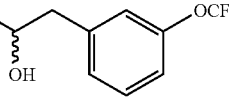 |
| 22 | 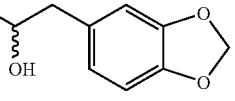 |
| 23 | 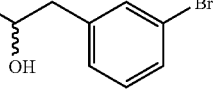 |
| 24 | 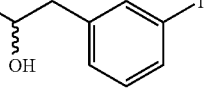 |
| 25 | 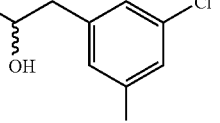 |
| 26 | 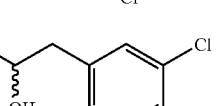 |
| 27 | 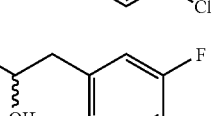 |
| 28 | 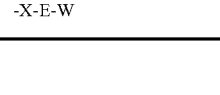 |
TABLE 7-continued
(IA1)
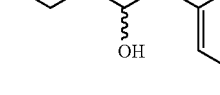
| No. | -X-E-W |
|---|---|
| 29 | 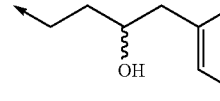 |
| 30 |  |
| 31 | 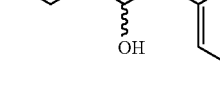 |
| 32 | 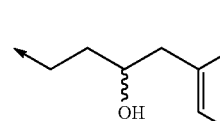 |
| 33 |  |
| 34 | 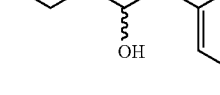 |
| 35 | 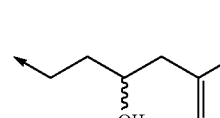 |

TABLE 8

(IA2)

| No. | -X-E-W |
|---|---|
| 1 | 4-hydroxy-5-phenylpentyl |
| 2 | 4-hydroxy-5-phenylhexyl (Me at benzylic C) |
| 3 | 4-hydroxy-5-methyl-5-phenylhexyl (gem-diMe) |
| 4 | 4-hydroxy-4-(1-phenylcyclopropyl)butyl |
| 5 | 4-hydroxy-5-(3-(methoxymethyl)phenyl)pentyl |
| 6 | 4-hydroxy-5-(2-fluorophenyl)pentyl |
| 7 | 4-hydroxy-5-(3-fluorophenyl)pentyl |
| 8 | 4-hydroxy-5-(4-fluorophenyl)pentyl |
| 9 | 4-hydroxy-5-(2-chlorophenyl)pentyl |
| 10 | 4-hydroxy-5-(3-chlorophenyl)pentyl |
| 11 | 4-hydroxy-5-(4-chlorophenyl)pentyl |
| 12 | 4-hydroxy-5-(2-trifluoromethylphenyl)pentyl |
| 13 | 4-hydroxy-5-(3-trifluoromethylphenyl)pentyl |
| 14 | 4-hydroxy-5-(4-trifluoromethylphenyl)pentyl |
| 15 | 4-hydroxy-5-(2-methylphenyl)pentyl |
| 16 | 4-hydroxy-5-(3-methylphenyl)pentyl |
| 17 | 4-hydroxy-5-(4-methylphenyl)pentyl |
| 18 | 4-hydroxy-5-(3-hydroxyphenyl)pentyl |
| 19 | 4-hydroxy-5-(3-methoxyphenyl)pentyl |
| 20 | 4-hydroxy-5-(4-methoxyphenyl)pentyl |
| 21 | 4-hydroxy-5-(3-tert-butoxyphenyl)pentyl |

TABLE 8-continued
(IA2)
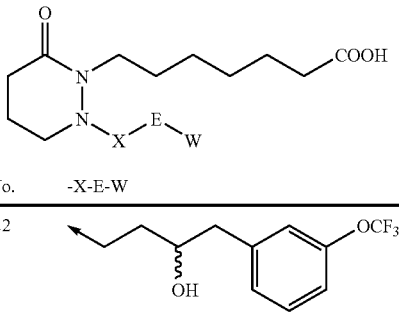
| No. | -X-E-W |
|---|---|
| 22 |  |
| 23 |  |
| 24 | 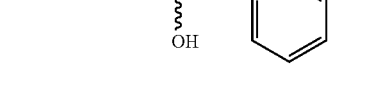 |
| 25 |  |
| 26 |  |
| 27 |  |
| 28 |  |
| 29 | 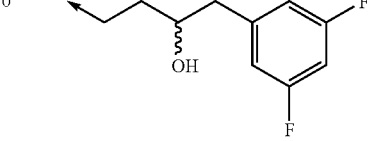 |
| 30 |  |
| 31 | 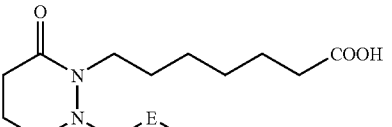 |
TABLE 8-continued
(IA2)
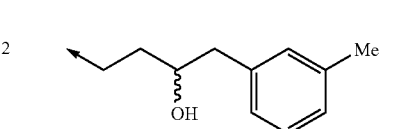
| No. | -X-E-W |
|---|---|
| 32 |  |
| 33 |  |
| 34 |  |
| 35 |  |
TABLE 9
(IA3)
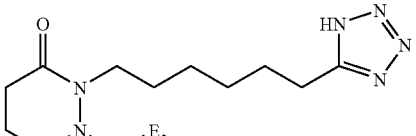
| No. | -X-E-W |
|---|---|
| 1 | 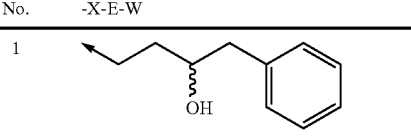 |
| 2 | 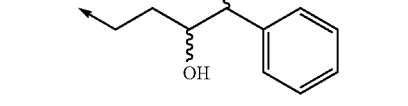 |

TABLE 9-continued (IA3)

| No. | -X-E-W |
|-----|--------|
| 3 | 1-hydroxy-4-methyl-4-phenylpentyl (with Me, Me, phenyl, OH) |
| 4 | 1-hydroxy-4-(1-phenylcyclopropyl)butyl |
| 5 | 2-hydroxy-4-[3-(methoxymethyl)phenyl]butyl |
| 6 | 2-hydroxy-4-(2-fluorophenyl)butyl |
| 7 | 2-hydroxy-4-(3-fluorophenyl)butyl |
| 8 | 2-hydroxy-4-(4-fluorophenyl)butyl |
| 9 | 2-hydroxy-4-(2-chlorophenyl)butyl |
| 10 | 2-hydroxy-4-(3-chlorophenyl)butyl |
| 11 | 2-hydroxy-4-(4-chlorophenyl)butyl |
| 12 | 2-hydroxy-4-(2-trifluoromethylphenyl)butyl |
| 13 | 2-hydroxy-4-(3-trifluoromethylphenyl)butyl |
| 14 | 2-hydroxy-4-(4-trifluoromethylphenyl)butyl |
| 15 | 2-hydroxy-4-(2-methylphenyl)butyl |
| 16 | 2-hydroxy-4-(3-methylphenyl)butyl |
| 17 | 2-hydroxy-4-(4-methylphenyl)butyl |
| 18 | 2-hydroxy-4-(3-hydroxyphenyl)butyl |
| 19 | 2-hydroxy-4-(3-methoxyphenyl)butyl |
| 20 | 2-hydroxy-4-(4-methoxyphenyl)butyl |
| 21 | 2-hydroxy-4-[3-(tert-butoxy)phenyl]butyl |
| 22 | 2-hydroxy-4-(3-trifluoromethoxyphenyl)butyl |
| 23 | 2-hydroxy-4-(1,3-benzodioxol-5-yl)butyl |

TABLE 9-continued
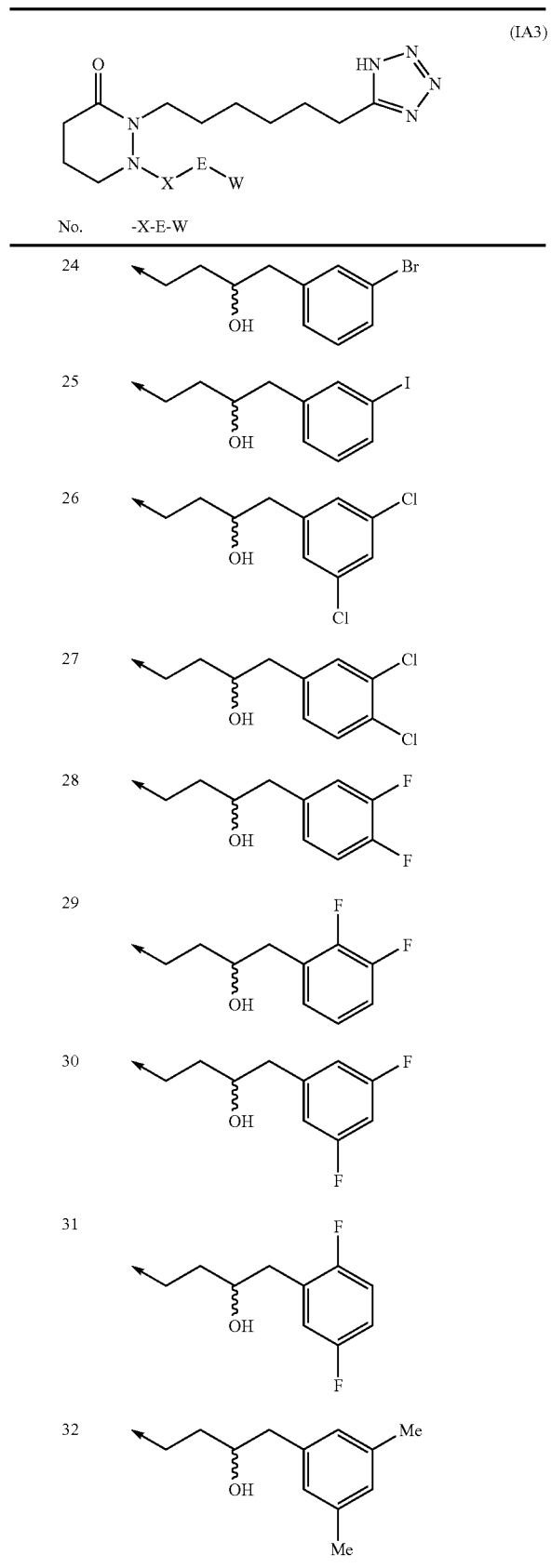
TABLE 9-continued
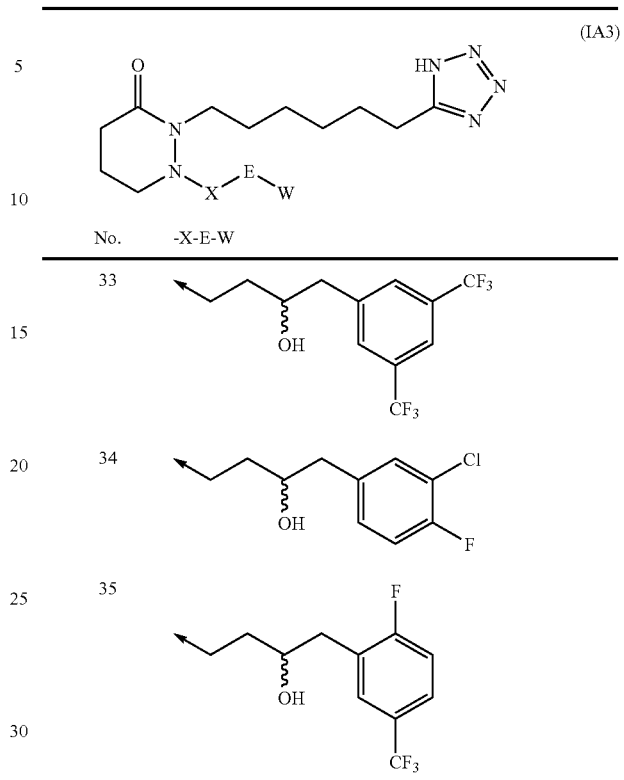
TABLE 10
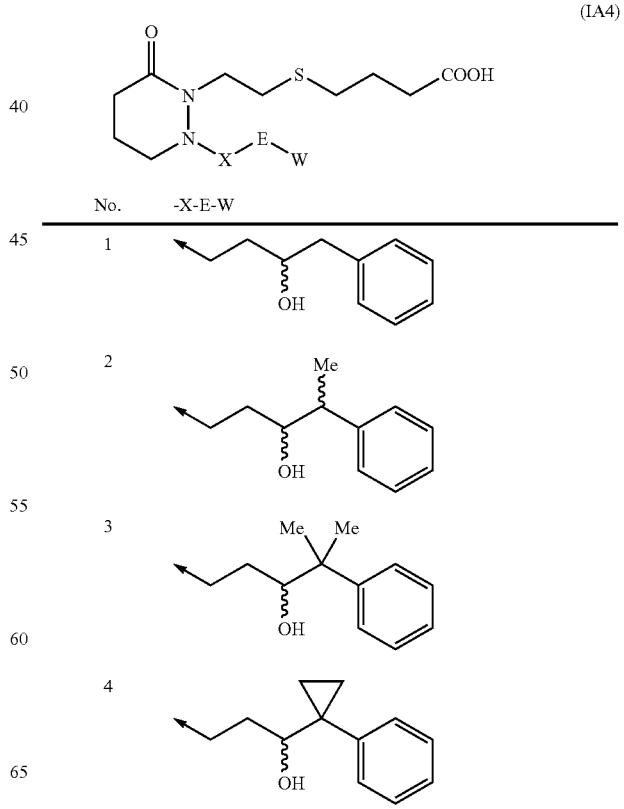

TABLE 10-continued
(IA4)
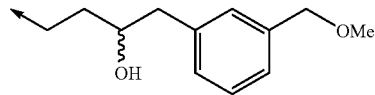
| No. | -X-E-W |
|---|---|
| 5 | 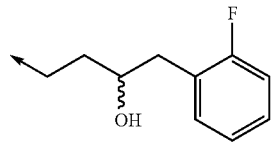 |
| 6 | 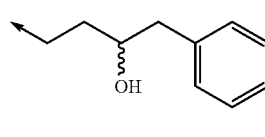 |
| 7 | 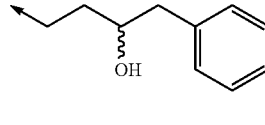 |
| 8 | 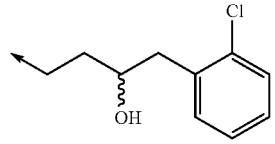 |
| 9 | 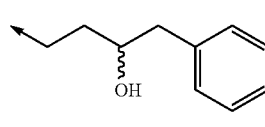 |
| 10 | 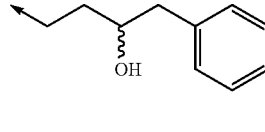 |
| 11 | 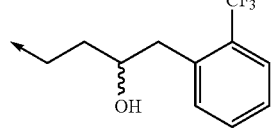 |
| 12 | 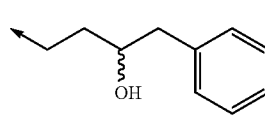 |
| 13 | 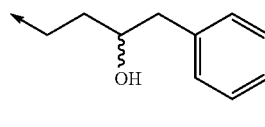 |
| 14 | 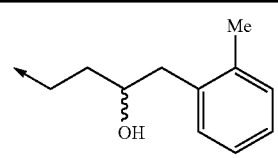 |
TABLE 10-continued
(IA4)
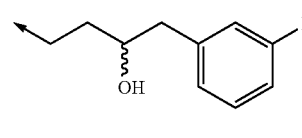
| No. | -X-E-W |
|---|---|
| 15 | 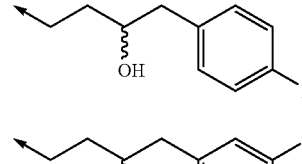 |
| 16 | 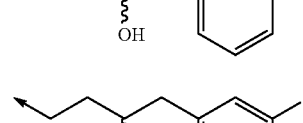 |
| 17 | 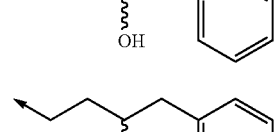 |
| 18 | 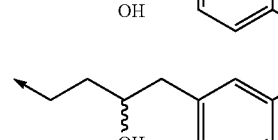 |
| 19 | 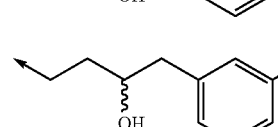 |
| 20 | 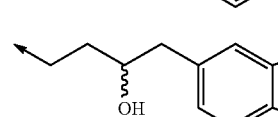 |
| 21 | 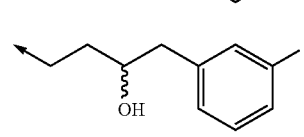 |
| 22 | 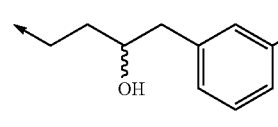 |
| 23 |  |
| 24 | |
| 25 | |

TABLE 10-continued
(IA4)
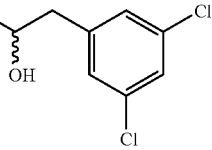
| No. | -X-E-W |
|---|---|
| 26 | 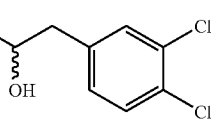 |
| 27 | 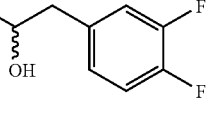 |
| 28 | 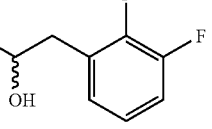 |
| 29 | 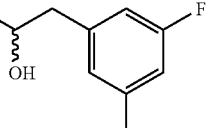 |
| 30 | 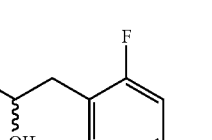 |
| 31 | 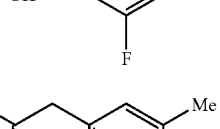 |
| 32 | 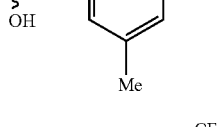 |
| 33 | 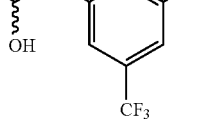 |
| 34 | 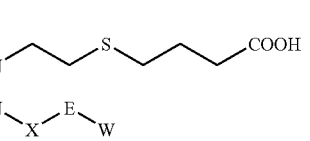 |
TABLE 10-continued
(IA4)
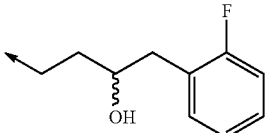
| No. | -X-E-W |
|---|---|
| 35 | 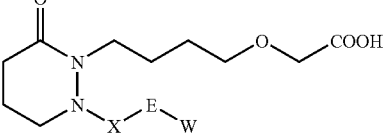 |
TABLE 11
(IA5)
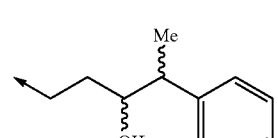
| No. | -X-E-W |
|---|---|
| 1 | 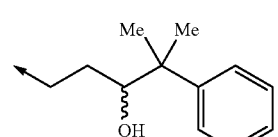 |
| 2 | 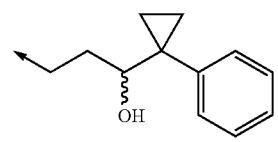 |
| 3 | 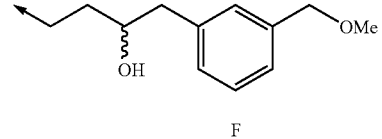 |
| 4 | 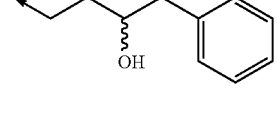 |
| 5 |  |
| 6 |  |

TABLE 11-continued (IA5)

| No. | -X-E-W |
|-----|--------|
| 7 | 4-hydroxy-5-(3-fluorophenyl)pentyl |
| 8 | 4-hydroxy-5-(4-fluorophenyl)pentyl |
| 9 | 4-hydroxy-5-(2-chlorophenyl)pentyl |
| 10 | 4-hydroxy-5-(3-chlorophenyl)pentyl |
| 11 | 4-hydroxy-5-(4-chlorophenyl)pentyl |
| 12 | 4-hydroxy-5-(2-trifluoromethylphenyl)pentyl |
| 13 | 4-hydroxy-5-(3-trifluoromethylphenyl)pentyl |
| 14 | 4-hydroxy-5-(4-trifluoromethylphenyl)pentyl |
| 15 | 4-hydroxy-5-(2-methylphenyl)pentyl |
| 16 | 4-hydroxy-5-(3-methylphenyl)pentyl |
| 17 | 4-hydroxy-5-(4-methylphenyl)pentyl |
| 18 | 4-hydroxy-5-(3-hydroxyphenyl)pentyl |
| 19 | 4-hydroxy-5-(3-methoxyphenyl)pentyl |
| 20 | 4-hydroxy-5-(4-methoxyphenyl)pentyl |
| 21 | 4-hydroxy-5-(3-tert-butoxyphenyl)pentyl |
| 22 | 4-hydroxy-5-(3-trifluoromethoxyphenyl)pentyl |
| 23 | 4-hydroxy-5-(3,4-methylenedioxyphenyl)pentyl |
| 24 | 4-hydroxy-5-(3-bromophenyl)pentyl |
| 25 | 4-hydroxy-5-(3-iodophenyl)pentyl |
| 26 | 4-hydroxy-5-(3,5-dichlorophenyl)pentyl |
| 27 | 4-hydroxy-5-(3,4-dichlorophenyl)pentyl |

TABLE 11-continued
(IA5)
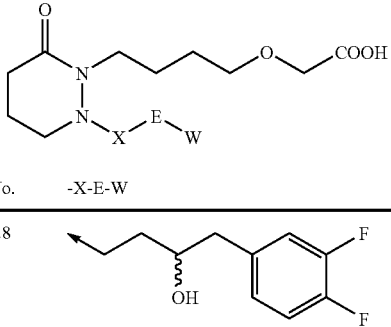
| No. | -X-E-W |
|---|---|
| 28 |  |
| 29 |  |
| 30 |  |
| 31 |  |
| 32 | 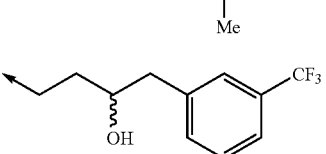 |
| 33 |  |
| 34 |  |
| 35 | 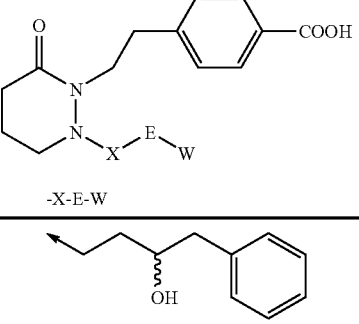 |
TABLE 12
(IA6)

| No. | -X-E-W |
|---|---|
| 1 |  |
| 2 |  |
| 3 | 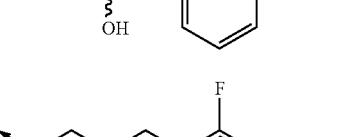 |
| 4 |  |
| 5 |  |
| 6 |  |
| 7 |  |
| 8 | 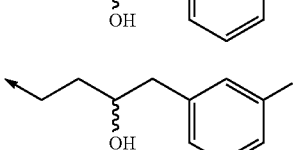 |
| 9 | |
| 10 | |

TABLE 12-continued (IA6)

| No. | -X-E-W |
|-----|--------|
| 11 | 4-Cl-benzyl, CH(OH) linker |
| 12 | 2-CF₃-benzyl, CH(OH) linker |
| 13 | 3-CF₃-benzyl, CH(OH) linker |
| 14 | 4-CF₃-benzyl, CH(OH) linker |
| 15 | 2-Me-benzyl, CH(OH) linker |
| 16 | 3-Me-benzyl, CH(OH) linker |
| 17 | 4-Me-benzyl, CH(OH) linker |
| 18 | 3-OH-benzyl, CH(OH) linker |
| 19 | 3-OMe-benzyl, CH(OH) linker |
| 20 | 4-OMe-benzyl, CH(OH) linker |
| 21 | 3-OtBu-benzyl, CH(OH) linker |
| 22 | 3-OCF₃-benzyl, CH(OH) linker |
| 23 | 3,4-methylenedioxy-benzyl, CH(OH) linker |
| 24 | 3-Br-benzyl, CH(OH) linker |
| 25 | 3-I-benzyl, CH(OH) linker |
| 26 | 3,5-diCl-benzyl, CH(OH) linker |
| 27 | 3,4-diCl-benzyl, CH(OH) linker |
| 28 | 3,4-diF-benzyl, CH(OH) linker |
| 29 | 2,3-diF-benzyl, CH(OH) linker |
| 30 | 3,5-diF-benzyl, CH(OH) linker |

TABLE 12-continued
(IA6)
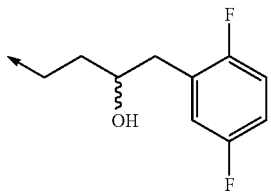
| No. | -X-E-W |
|---|---|
| 31 | 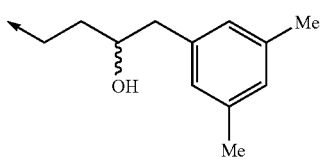 |
| 32 | (3,5-dimethylphenyl) |
| 33 | (3,5-bis-CF3-phenyl) |
| 34 | (3-Cl-4-F-phenyl) |
| 35 | 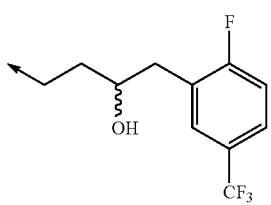 |
TABLE 13
(IA6)
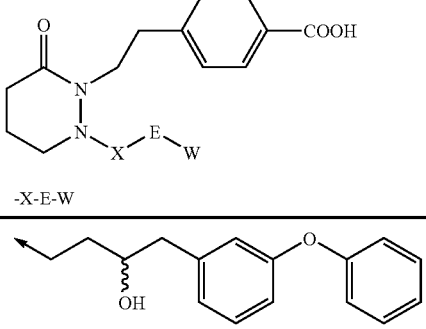
| No. | -X-E-W |
|---|---|
| 36 | (3-phenoxyphenyl) |
TABLE 13-continued
(IA6)
| No. | -X-E-W |
|---|---|
| 37 | (3-phenylphenyl) |
| 38 | (2'-Cl-biphenyl-3-yl) |
| 39 | (naphthalen-2-yl) |
| 40 | (naphthalen-1-yl) |
| 41 | (furan-2-yl) |
| 42 | (thiophen-2-yl) |
| 43 | (5-CF3-thiophen-2-yl) |
| 44 | (pyridin-2-yl) |
| 45 | (benzofuran-5-yl) |
| 46 | (benzothiophen-5-yl) |

TABLE 13-continued
(IA6)
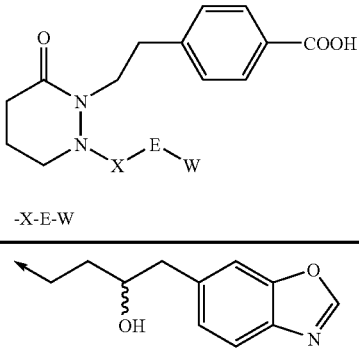
| No. | -X-E-W |
|---|---|
| 47 | 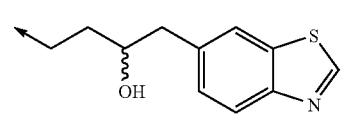 |
| 48 | 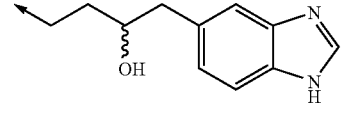 |
| 49 | 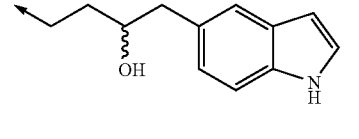 |
| 50 | 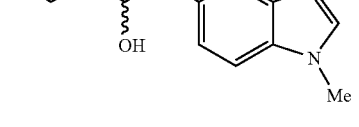 |
| 51 | 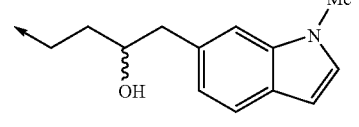 |
| 52 | 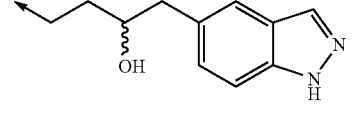 |
| 53 | 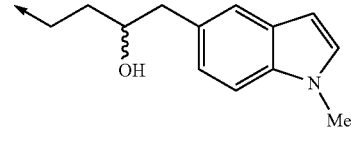 |
| 54 | 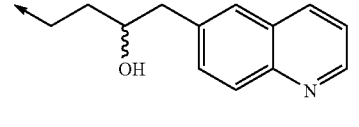 |
| 55 | 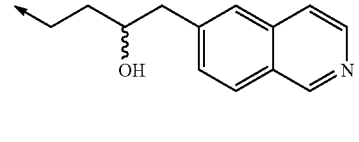 |
| 56 | 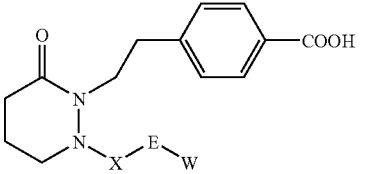 |
TABLE 13-continued
(IA6)
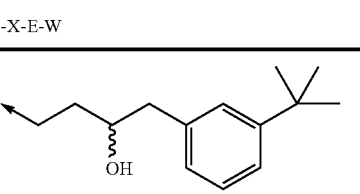
| No. | -X-E-W |
|---|---|
| 57 | 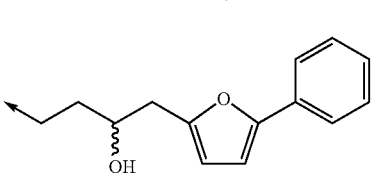 |
| 58 | 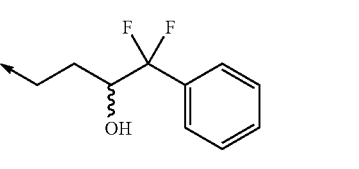 |
| 59 | 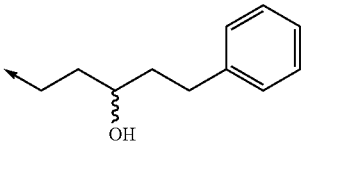 |
| 60 | 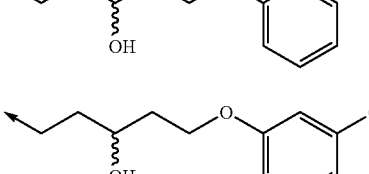 |
| 61 | 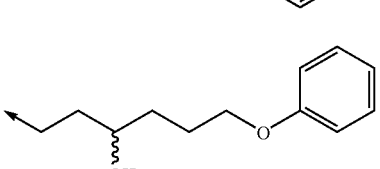 |
| 62 | 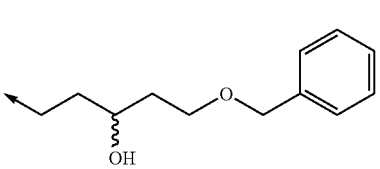 |
| 63 | 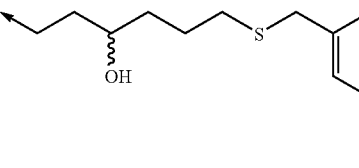 |
| 64 |  |
| 65 | |

TABLE 13-continued
(IA6)
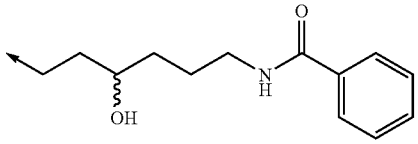
| No. | -X-E-W |
|-----|--------|
| 66 | 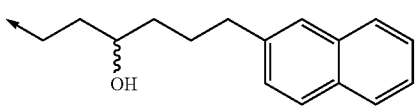 |
| 67 | 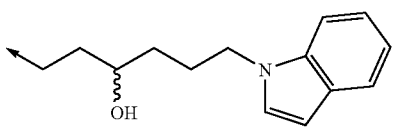 |
| 68 | 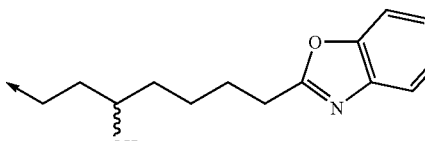 |
| 69 | 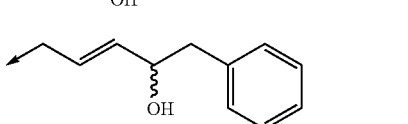 |
| 70 | 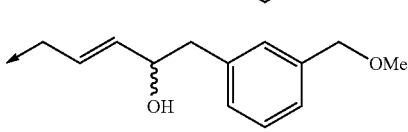 |
| 71 | 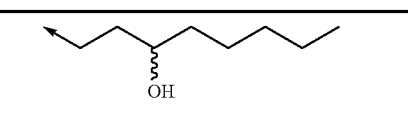 |
TABLE 14
(IA6)
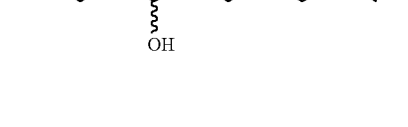
| No. | -X-E-W |
|-----|--------|
| 72 | 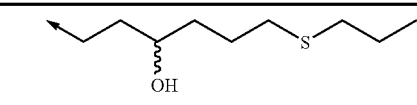 |
| 73 | 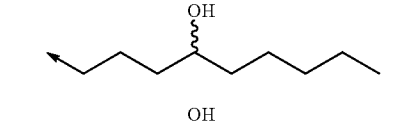 |
TABLE 14-continued
(IA6)
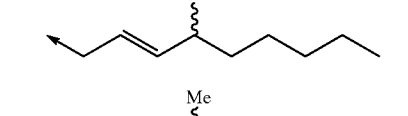
| No. | -X-E-W |
|-----|--------|
| 74 | 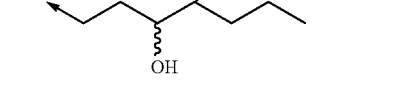 |
| 75 | 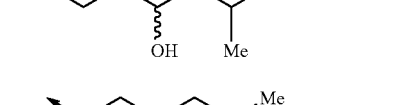 |
| 76 | 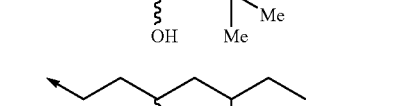 |
| 77 | 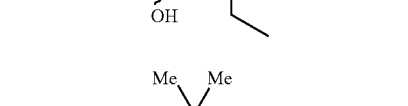 |
| 78 | 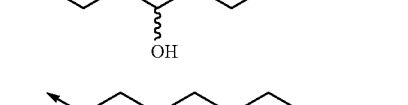 |
| 79 | 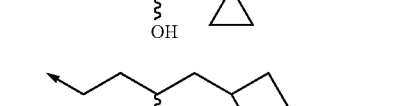 |
| 80 | 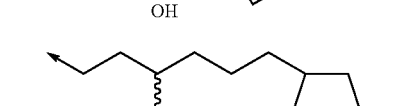 |
| 81 | 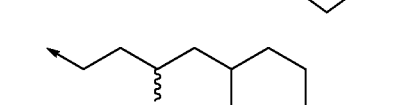 |
| 82 |  |
| 83 |  |
| 84 |  |
| 85 |  |

TABLE 14-continued (IA6)

| No. | -X-E-W |
|---|---|
| 86 | 1-butylcyclobutyl with OH |
| 87 | cyclohexyl with OH |
| 88 | phenyl with OH |
| 89 | 3-methylphenyl with OH |
| 90 | 3-methoxyphenyl with OH |
| 91 | 3-fluorophenyl with OH |
| 92 | 3-chlorophenyl with OH |
| 93 | 3-trifluoromethylphenyl with OH |
| 94 | 3-phenoxyphenyl with OH |
| 95 | 2'-chlorobiphenyl-3-yl with OH |
| 96 | 2-methyl-4-chlorobiphenyl-3-yl with OH |
| 97 | 2-methyl-4-hydroxybiphenyl-3-yl with OH |
| 98 | 5-(trifluoromethyl)furan-2-yl with OH |
| 99 | (S)-3-methylphenyl with OH |
| 100 | (S)-3-fluorophenyl with OH |
| 101 | (S)-3-chlorophenyl with OH |

TABLE 14-continued (IA6)

| No. | -X-E-W |
|---|---|
| 102 | 3-CF₃-phenyl, (R)-OH, propyl linker |
| 103 | 3-Me-phenyl, (R)-OH, propyl linker |
| 104 | 3-F-phenyl, (R)-OH, propyl linker |
| 105 | 3-Cl-phenyl, (R)-OH, propyl linker |
| 106 | 3-CF₃-phenyl, (R)-OH, propyl linker |
| 107 | 3-OMe-phenyl, (R)-OH, propyl linker |
| 108 | 3-OCF₃-phenyl, (R)-OH, propyl linker |

TABLE 15

(IA7)

| No. | -X-E-W |
|---|---|
| 1 | phenyl, OH, propyl linker |
| 2 | α-Me-benzyl, OH, propyl linker |
| 3 | α,α-diMe-benzyl, OH, propyl linker |
| 4 | 1-phenylcyclopropyl, OH, propyl linker |
| 5 | 3-CH₂OMe-phenyl, OH, propyl linker |
| 6 | 2-F-phenyl, OH, propyl linker |
| 7 | 3-F-phenyl, OH, propyl linker |
| 8 | 4-F-phenyl, OH, propyl linker |
| 9 | 2-Cl-phenyl, OH, propyl linker |
| 10 | 3-Cl-phenyl, OH, propyl linker |
| 11 | 4-Cl-phenyl, OH, propyl linker |

TABLE 15-continued
(IA7)
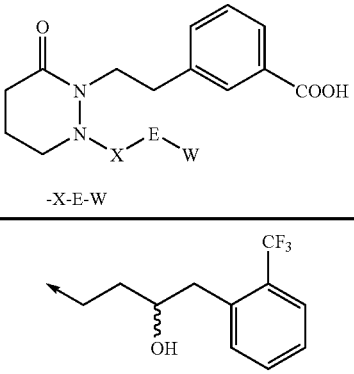
| No. | -X-E-W |
|---|---|
| 12 | 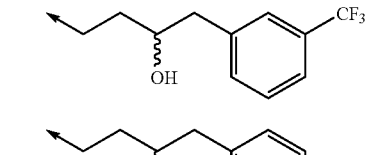 |
| 13 |  |
| 14 | 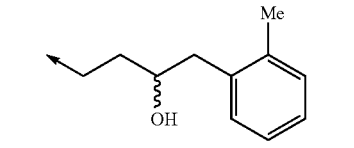 |
| 15 | 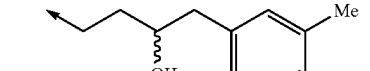 |
| 16 | 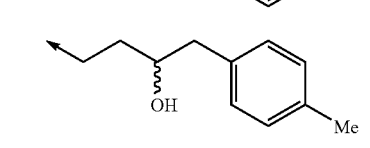 |
| 17 | 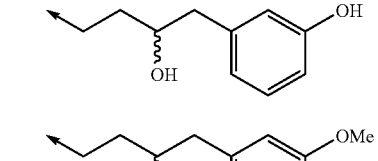 |
| 18 | 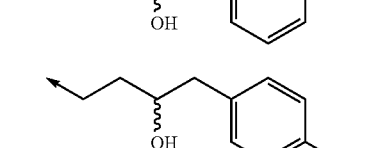 |
| 19 | 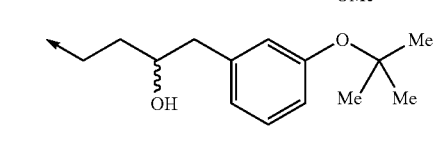 |
| 20 | 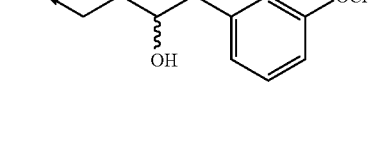 |
| 21 |  |
| 22 | 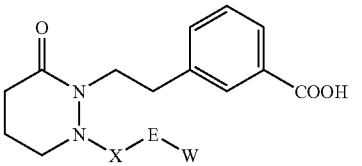 |
TABLE 15-continued
(IA7)
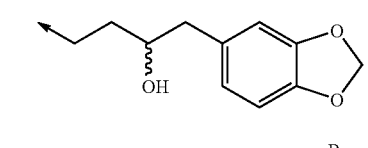
| No. | -X-E-W |
|---|---|
| 23 | 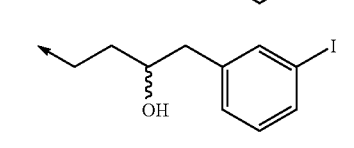 |
| 24 | 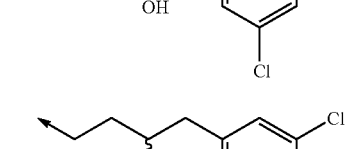 |
| 25 | 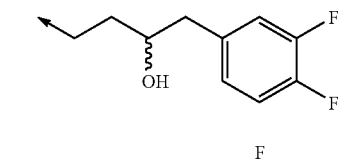 |
| 26 | 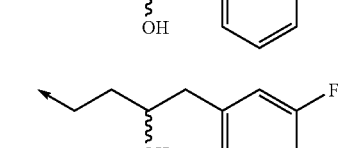 |
| 27 | 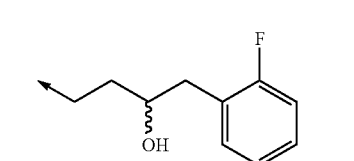 |
| 28 |  |
| 29 |  |
| 30 |  |
| 31 |  |

TABLE 15-continued
(IA7)
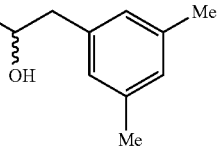
| No. | -X-E-W |
|---|---|
| 32 | 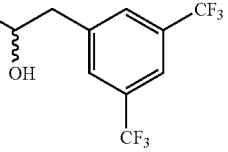 |
| 33 | 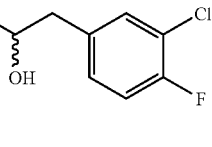 |
| 34 | 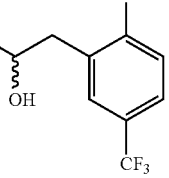 |
| 35 | 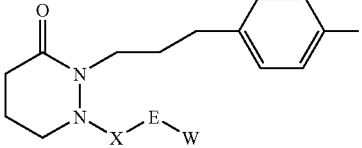 |
TABLE 16
(IA8)
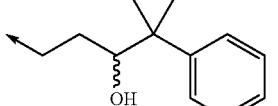
| No. | -X-E-W |
|---|---|
| 1 | 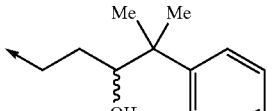 |
| 2 | 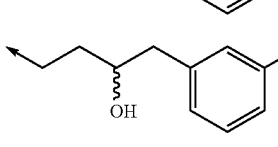 |
TABLE 16-continued
(IA8)
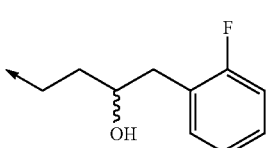
| No. | -X-E-W |
|---|---|
| 3 | 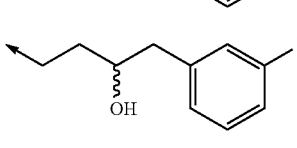 |
| 4 | 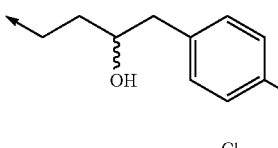 |
| 5 | 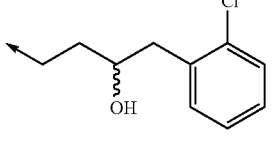 |
| 6 | 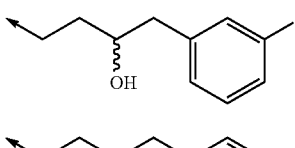 |
| 7 | 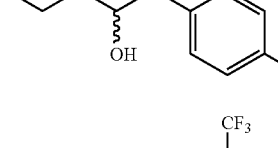 |
| 8 | 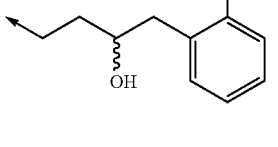 |
| 9 | 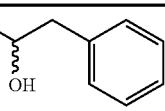 |
| 10 | 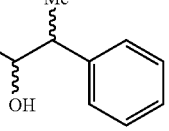 |
| 11 | 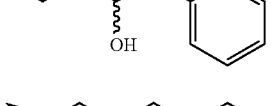 |
| 12 | 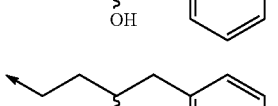 |

TABLE 16-continued (IA8)

| No. | -X-E-W |
|-----|--------|
| 13 | 3-CF₃-benzyl, with -CH₂CH₂CH(OH)- linker |
| 14 | 4-CF₃-benzyl, with -CH₂CH₂CH(OH)- linker |
| 15 | 2-Me-benzyl, with -CH₂CH₂CH(OH)- linker |
| 16 | 3-Me-benzyl, with -CH₂CH₂CH(OH)- linker |
| 17 | 4-Me-benzyl, with -CH₂CH₂CH(OH)- linker |
| 18 | 3-OH-benzyl, with -CH₂CH₂CH(OH)- linker |
| 19 | 3-OMe-benzyl, with -CH₂CH₂CH(OH)- linker |
| 20 | 4-OMe-benzyl, with -CH₂CH₂CH(OH)- linker |
| 21 | 3-OC(Me)₃-benzyl, with -CH₂CH₂CH(OH)- linker |
| 22 | 3-OCF₃-benzyl, with -CH₂CH₂CH(OH)- linker |
| 23 | 3,4-methylenedioxy-benzyl, with -CH₂CH₂CH(OH)- linker |
| 24 | 3-Br-benzyl, with -CH₂CH₂CH(OH)- linker |
| 25 | 3-I-benzyl, with -CH₂CH₂CH(OH)- linker |
| 26 | 3,5-diCl-benzyl, with -CH₂CH₂CH(OH)- linker |
| 27 | 3,4-diCl-benzyl, with -CH₂CH₂CH(OH)- linker |
| 28 | 3,4-diF-benzyl, with -CH₂CH₂CH(OH)- linker |
| 29 | 2,3-diF-benzyl, with -CH₂CH₂CH(OH)- linker |
| 30 | 3,5-diF-benzyl, with -CH₂CH₂CH(OH)- linker |
| 31 | 2,5-diF-benzyl, with -CH₂CH₂CH(OH)- linker |
| 32 | 3,5-diMe-benzyl, with -CH₂CH₂CH(OH)- linker |

TABLE 16-continued (IA8)

| No. | -X-E-W |
|---|---|
| 33 | 3,5-bis(CF₃)phenyl-CH₂-CH(OH)-CH₂-CH₂- |
| 34 | 3-Cl-4-F-phenyl-CH₂-CH(OH)-CH₂-CH₂- |
| 35 | 2-F-5-CF₃-phenyl-CH₂-CH(OH)-CH₂-CH₂- |

TABLE 17

(IA8)

| No. | -X-E-W |
|---|---|
| 36 | 3-phenoxyphenyl-CH₂-CH(OH)-CH₂-CH₂- |
| 37 | 3-biphenyl-CH₂-CH(OH)-CH₂-CH₂- |
| 38 | 2'-Cl-3-biphenyl-CH₂-CH(OH)-CH₂-CH₂- |
| 39 | naphthalen-2-yl-CH₂-CH(OH)-CH₂-CH₂- |
| 40 | naphthalen-1-yl-CH₂-CH(OH)-CH₂-CH₂- |
| 41 | furan-2-yl-CH₂-CH(OH)-CH₂-CH₂- |
| 42 | thiophen-2-yl-CH₂-CH(OH)-CH₂-CH₂- |
| 43 | 5-CF₃-thiophen-2-yl-CH₂-CH(OH)-CH₂-CH₂- |
| 44 | pyridin-2-yl-CH₂-CH(OH)-CH₂-CH₂- |
| 45 | benzofuran-5-yl-CH₂-CH(OH)-CH₂-CH₂- |
| 46 | benzothiophen-5-yl-CH₂-CH(OH)-CH₂-CH₂- |
| 47 | benzoxazol-6-yl-CH₂-CH(OH)-CH₂-CH₂- |
| 48 | benzothiazol-6-yl-CH₂-CH(OH)-CH₂-CH₂- |
| 49 | 1H-benzimidazol-5-yl-CH₂-CH(OH)-CH₂-CH₂- |

TABLE 17-continued (IA8)

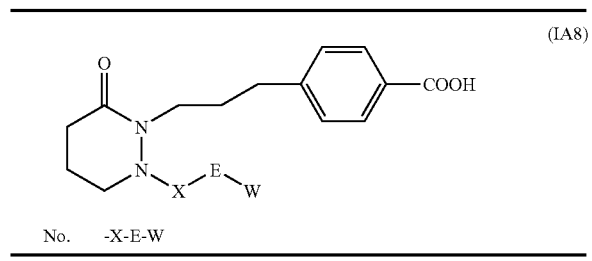

| No. | -X-E-W |
|---|---|
| 50 | 5-(2-hydroxy-indol-5-yl)pentyl |
| 51 | 5-(2-hydroxy-1-methyl-indol-5-yl)pentyl |
| 52 | 5-(2-hydroxy-1-methyl-indol-6-yl)pentyl |
| 53 | 5-(2-hydroxy-1H-indazol-5-yl)pentyl |
| 54 | 5-(2-hydroxy-1-methyl-indol-5-yl)pentyl |
| 55 | 5-(2-hydroxy-quinolin-6-yl)pentyl |
| 56 | 5-(2-hydroxy-isoquinolin-6-yl)pentyl |
| 57 | 5-(2-hydroxy-3-tert-butyl-phenyl)pentyl |
| 58 | 5-(2-hydroxy-5-phenyl-furan-2-yl)pentyl |
| 59 | 4-(difluoro-phenyl-methyl)-2-hydroxy-butyl |

TABLE 17-continued (IA8)

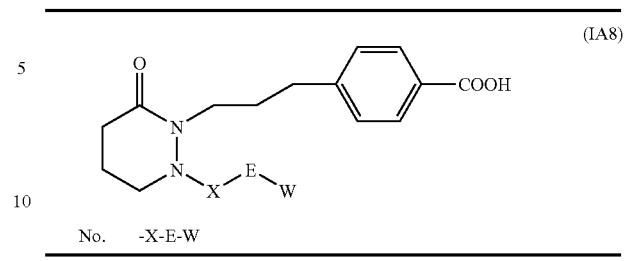

| No. | -X-E-W |
|---|---|
| 60 | 5-phenyl-3-hydroxy-pentyl |
| 61 | 6-phenyl-4-hydroxy-hexyl |
| 62 | 6-(3-chlorophenoxy)-4-hydroxy-hexyl |
| 63 | 7-phenoxy-5-hydroxy-heptyl |
| 64 | 6-benzyloxy-4-hydroxy-hexyl |
| 65 | 6-benzylthio-4-hydroxy-hexyl |
| 66 | 7-benzoylamino-4-hydroxy-heptyl |
| 67 | 7-(naphthalen-2-yl)-4-hydroxy-heptyl |
| 68 | 7-(indol-1-yl)-4-hydroxy-heptyl |
| 69 | 7-(benzoxazol-2-yl)-4-hydroxy-heptyl |

TABLE 17-continued (IA8)

| No. | -X-E-W |
|---|---|
| 70 | (structure: allyl-CH(OH)-CH2-phenyl with trans double bond) |
| 71 | (structure: allyl-CH(OH)-CH2-(3-CH2OMe-phenyl) with trans double bond) |

TABLE 18

(IA8)

| No. | -X-E-W |
|---|---|
| 72 | (structure: CH2CH2-CH(OH)-pentyl branched) |
| 73 | (structure: CH2CH2-CH(OH)-hexyl) |
| 74 | (structure: CH2CH2-CH(OH)-CH2CH2-S-propyl) |
| 75 | (structure: pentyl-CH(OH)-pentyl) |
| 76 | (structure: CH=CH-CH(OH)-pentyl) |
| 77 | (structure: CH2CH2-CH(OH)-CH(Me)-propyl) |
| 78 | (structure: CH2CH2-CH(OH)-CH2-CH(Me)Me) |

TABLE 18-continued (IA8)

| No. | -X-E-W |
|---|---|
| 79 | (structure: CH2CH2-CH(OH)-CH2-C(Me)2Me) |
| 80 | (structure: CH2CH2-CH(OH)-CH(Et)Et) |
| 81 | (structure: CH2CH2-CH(OH)-C(Me)2-Et) |
| 82 | (structure: CH2CH2-CH(OH)-CH2-(1-ethylcyclopropyl)) |
| 83 | (structure: CH2CH2-CH(OH)-CH2-cyclobutyl) |
| 84 | (structure: CH2CH2-CH(OH)-CH2CH2CH2-cyclopentyl) |
| 85 | (structure: CH2CH2-CH(OH)-CH2-cyclohexyl) |
| 86 | (structure: CH2CH2-CH2-C(OH)(butyl)-cyclobutyl) |
| 87 | (structure: CH2CH2-CH(OH)-cyclohexyl) |
| 88 | (structure: CH2CH2-CH(OH)-phenyl) |
| 89 | (structure: CH2CH2-CH(OH)-(3-Me-phenyl)) |

TABLE 18-continued (IA8)

| No. | -X-E-W |
|-----|--------|
| 90  | 3-methoxyphenyl, CH(OH)CH2CH2- |
| 91  | 3-fluorophenyl, CH(OH)CH2CH2- |
| 92  | 3-chlorophenyl, CH(OH)CH2CH2- |
| 93  | 3-(trifluoromethyl)phenyl, CH(OH)CH2CH2- |
| 94  | 3-phenoxyphenyl, CH(OH)CH2CH2- |
| 95  | 2'-chloro-biphenyl-3-yl, CH(OH)CH2CH2- |
| 96  | 4'-chloro-2'-methyl-biphenyl-3-yl, CH(OH)CH2CH2- |
| 97  | 4'-hydroxy-2'-methyl-biphenyl-3-yl, CH(OH)CH2CH2- |
| 98  | 5-(trifluoromethyl)furan-2-yl, CH(OH)CH2CH2- |
| 99  | (S)-3-methylphenyl, CH(OH)CH2CH2- |
| 100 | (S)-3-fluorophenyl, CH(OH)CH2CH2- |
| 101 | (S)-3-chlorophenyl, CH(OH)CH2CH2- |
| 102 | (S)-3-(trifluoromethyl)phenyl, CH(OH)CH2CH2- |
| 103 | (S)-3-methylbenzyl, CH(OH)CH2CH2CH2- |
| 104 | (S)-3-fluorobenzyl, CH(OH)CH2CH2CH2- |
| 105 | (S)-3-chlorobenzyl, CH(OH)CH2CH2CH2- |
| 106 | (S)-3-(trifluoromethyl)benzyl, CH(OH)CH2CH2CH2- |
| 107 | (S)-3-methoxybenzyl, CH(OH)CH2CH2CH2- |

TABLE 18-continued (IA8)

| No. | -X-E-W |
|---|---|
| 108 | 3-OCF3 phenyl, OH (stereo) |

TABLE 19

(IA9)

| No. | -X-E-W |
|---|---|
| 1 | phenyl, OH |
| 2 | α-Me-phenyl, OH |
| 3 | α,α-diMe-phenyl, OH |
| 4 | 1-phenylcyclopropyl, OH |
| 5 | 3-CH2OMe-phenyl, OH |
| 6 | 2-F-phenyl, OH |

TABLE 19-continued (IA9)

| No. | -X-E-W |
|---|---|
| 7 | 3-F-phenyl, OH |
| 8 | 4-F-phenyl, OH |
| 9 | 2-Cl-phenyl, OH |
| 10 | 3-Cl-phenyl, OH |
| 11 | 4-Cl-phenyl, OH |
| 12 | 2-CF3-phenyl, OH |
| 13 | 3-CF3-phenyl, OH |
| 14 | 4-CF3-phenyl, OH |
| 15 | 2-Me-phenyl, OH |
| 16 | 3-Me-phenyl, OH |

TABLE 19-continued (IA9)

| No. | -X-E-W |
|-----|--------|
| 17 | 4-Me-C6H4-CH2-CH(OH)-CH2CH2- |
| 18 | 3-OH-C6H4-CH2-CH(OH)-CH2CH2- |
| 19 | 3-OMe-C6H4-CH2-CH(OH)-CH2CH2- |
| 20 | 4-OMe-C6H4-CH2-CH(OH)-CH2CH2- |
| 21 | 3-OC(Me)3-C6H4-CH2-CH(OH)-CH2CH2- |
| 22 | 3-OCF3-C6H4-CH2-CH(OH)-CH2CH2- |
| 23 | 3,4-methylenedioxy-C6H3-CH2-CH(OH)-CH2CH2- |
| 24 | 3-Br-C6H4-CH2-CH(OH)-CH2CH2- |
| 25 | 3-I-C6H4-CH2-CH(OH)-CH2CH2- |
| 26 | 3,5-Cl2-C6H3-CH2-CH(OH)-CH2CH2- |
| 27 | 3,4-Cl2-C6H3-CH2-CH(OH)-CH2CH2- |
| 28 | 3,4-F2-C6H3-CH2-CH(OH)-CH2CH2- |
| 29 | 2,3-F2-C6H3-CH2-CH(OH)-CH2CH2- |
| 30 | 3,5-F2-C6H3-CH2-CH(OH)-CH2CH2- |
| 31 | 2,5-F2-C6H3-CH2-CH(OH)-CH2CH2- |
| 32 | 3,5-Me2-C6H3-CH2-CH(OH)-CH2CH2- |
| 33 | 3,5-(CF3)2-C6H3-CH2-CH(OH)-CH2CH2- |
| 34 | 3-Cl-4-F-C6H3-CH2-CH(OH)-CH2CH2- |
| 35 | 2-F-5-CF3-C6H3-CH2-CH(OH)-CH2CH2- |

TABLE 20

(IA9)

| No. | -X-E-W |
|---|---|
| 36 | 3-phenoxybenzyl-CH(OH)-CH2CH2- |
| 37 | 3-phenylbenzyl-CH(OH)-CH2CH2- |
| 38 | 2'-chloro-3-biphenyl-CH2-CH(OH)-CH2CH2- |
| 39 | naphthalen-2-ylmethyl-CH(OH)-CH2CH2- |
| 40 | naphthalen-1-ylmethyl-CH(OH)-CH2CH2- |
| 41 | furan-2-ylmethyl-CH(OH)-CH2CH2- |
| 42 | thiophen-2-ylmethyl-CH(OH)-CH2CH2- |
| 43 | (5-CF3-thiophen-2-yl)methyl-CH(OH)-CH2CH2- |
| 44 | pyridin-2-ylmethyl-CH(OH)-CH2CH2- |
| 45 | benzofuran-5-ylmethyl-CH(OH)-CH2CH2- |
| 46 | benzothiophen-5-ylmethyl-CH(OH)-CH2CH2- |
| 47 | benzoxazol-6-ylmethyl-CH(OH)-CH2CH2- |
| 48 | benzothiazol-6-ylmethyl-CH(OH)-CH2CH2- |
| 49 | benzimidazol-5-ylmethyl-CH(OH)-CH2CH2- |
| 50 | indol-5-ylmethyl-CH(OH)-CH2CH2- |
| 51 | (1-Me-indol-5-yl)methyl-CH(OH)-CH2CH2- |
| 52 | (1-Me-indol-6-yl)methyl-CH(OH)-CH2CH2- |
| 53 | indazol-5-ylmethyl-CH(OH)-CH2CH2- |
| 54 | (1-Me-indol-5-yl)methyl-CH(OH)-CH2CH2- |
| 55 | quinolin-6-ylmethyl-CH(OH)-CH2CH2- |
| 56 | isoquinolin-6-ylmethyl-CH(OH)-CH2CH2- |

TABLE 20-continued
(IA9)
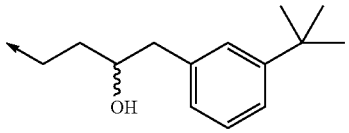
| No. | -X-E-W |
|---|---|
| 57 | 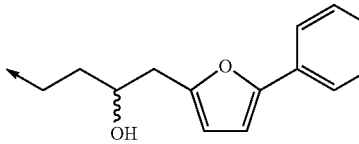 |
| 58 | 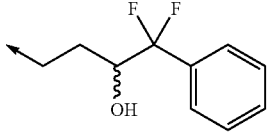 |
| 59 | 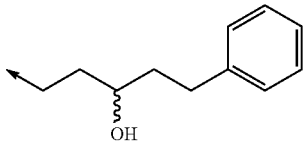 |
| 60 | 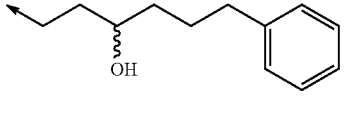 |
| 61 | 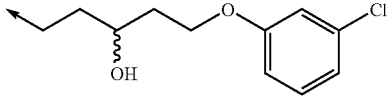 |
| 62 | 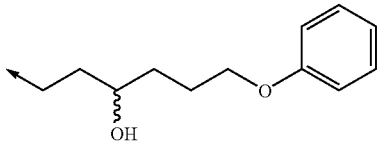 |
| 63 | 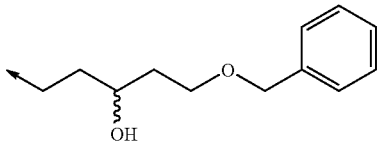 |
| 64 | 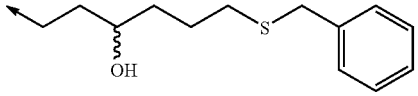 |
| 65 | 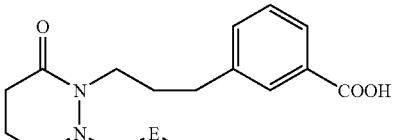 |
TABLE 20-continued
(IA9)
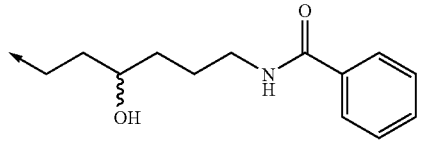
| No. | -X-E-W |
|---|---|
| 66 | 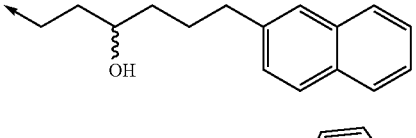 |
| 67 | 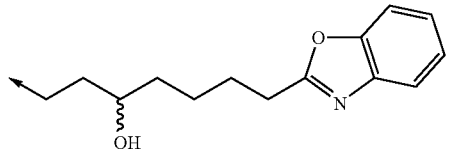 |
| 68 | 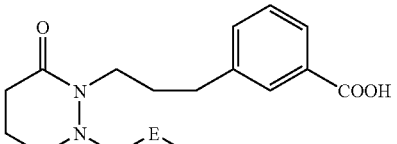 |
| 69 | 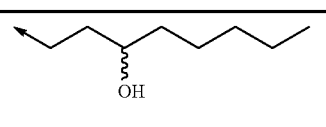 |
| 70 |  |
| 71 | 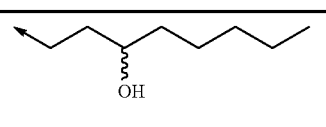 |
TABLE 21
(IA9)
| No. | -X-E-W |
|---|---|
| 72 | |
| 73 | |

TABLE 21-continued
(IA9)
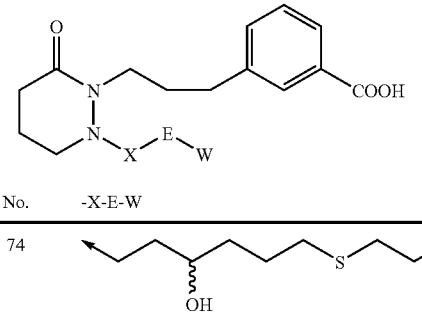
| No. | -X-E-W |
|---|---|
| 74 | 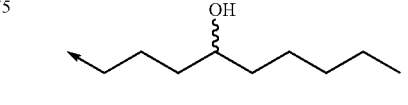 |
| 75 | 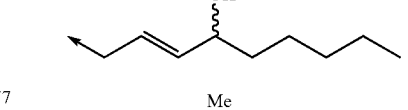 |
| 76 | 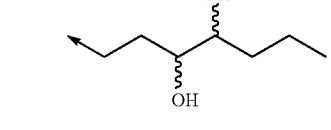 |
| 77 | 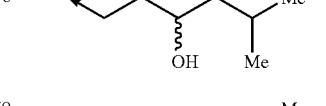 |
| 78 | 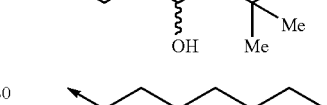 |
| 79 | 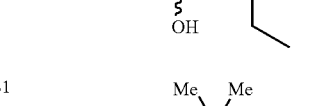 |
| 80 | 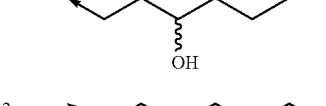 |
| 81 | 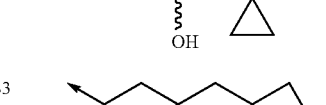 |
| 82 | 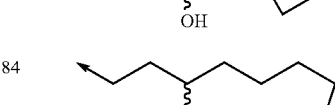 |
| 83 | 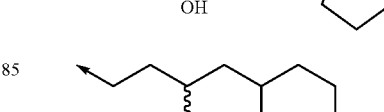 |
| 84 | 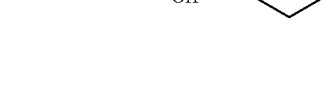 |
| 85 | 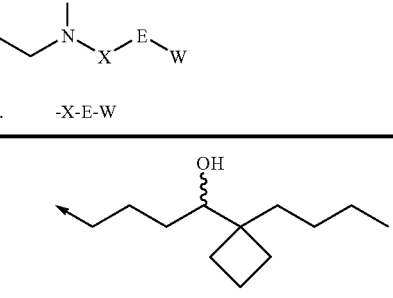 |
TABLE 21-continued
(IA9)
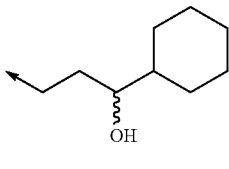
| No. | -X-E-W |
|---|---|
| 86 | 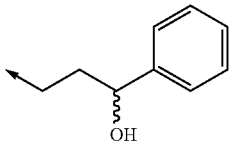 |
| 87 | 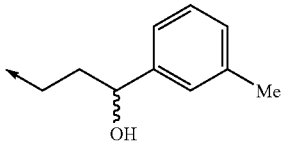 |
| 88 | 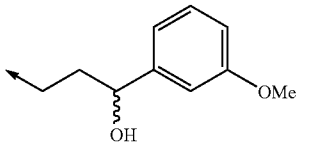 |
| 89 | 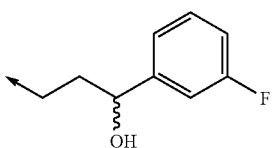 |
| 90 | 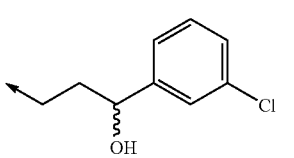 |
| 91 | 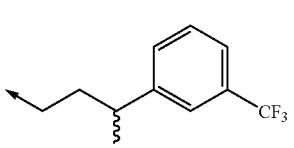 |
| 92 | |
| 93 | |

TABLE 21-continued (IA9)

| No. | -X-E-W |
|---|---|
| 94 | 3-phenoxyphenyl-CH(OH)-CH₂CH₂- |
| 95 | 2'-chloro-biphenyl-3-yl-CH(OH)-CH₂CH₂- |
| 96 | 2-methyl-4-chloro-biphenyl-3-yl-CH(OH)-CH₂CH₂- |
| 97 | 2-methyl-4-hydroxy-biphenyl-3-yl-CH(OH)-CH₂CH₂- |
| 98 | 5-(CF₃)-furan-2-yl-CH(OH)-CH₂CH₂- |
| 99 | 3-methylphenyl-CH(OH)-CH₂CH₂- |
| 100 | 3-fluorophenyl-CH(OH)-CH₂CH₂- |
| 101 | 3-chlorophenyl-CH(OH)-CH₂CH₂- |
| 102 | 3-(CF₃)phenyl-CH(OH)-CH₂CH₂- |
| 103 | 3-methylbenzyl-CH(OH)-CH₂CH₂- |
| 104 | 3-fluorobenzyl-CH(OH)-CH₂CH₂- |
| 105 | 3-chlorobenzyl-CH(OH)-CH₂CH₂- |
| 106 | 3-(CF₃)benzyl-CH(OH)-CH₂CH₂- |
| 107 | 3-methoxybenzyl-CH(OH)-CH₂CH₂- |
| 108 | 3-(OCF₃)benzyl-CH(OH)-CH₂CH₂- |

TABLE 22

(IA10)

| No. | -X-E-W |
|---|---|
| 1 | benzyl-CH(OH)-CH₂CH₂- |

TABLE 22-continued (IA10)

| No. | -X-E-W |
|---|---|
| 2 | 1-phenyl-1-methyl, 2-hydroxy chain |
| 3 | 1-phenyl-1,1-dimethyl, 2-hydroxy chain |
| 4 | 1-phenyl-cyclopropyl, hydroxy chain |
| 5 | 3-(methoxymethyl)phenyl, hydroxy chain |
| 6 | 2-fluorophenyl, hydroxy chain |
| 7 | 3-fluorophenyl, hydroxy chain |
| 8 | 4-fluorophenyl, hydroxy chain |
| 9 | 2-chlorophenyl, hydroxy chain |
| 10 | 3-chlorophenyl, hydroxy chain |
| 11 | 4-chlorophenyl, hydroxy chain |
| 12 | 2-trifluoromethylphenyl, hydroxy chain |
| 13 | 3-trifluoromethylphenyl, hydroxy chain |
| 14 | 4-trifluoromethylphenyl, hydroxy chain |
| 15 | 2-methylphenyl, hydroxy chain |
| 16 | 3-methylphenyl, hydroxy chain |
| 17 | 4-methylphenyl, hydroxy chain |
| 18 | 3-hydroxyphenyl, hydroxy chain |
| 19 | 3-methoxyphenyl, hydroxy chain |
| 20 | 4-methoxyphenyl, hydroxy chain |
| 21 | 3-tert-butoxyphenyl, hydroxy chain |
| 22 | 3-trifluoromethoxyphenyl, hydroxy chain |

TABLE 22-continued (IA10)

| No. | -X-E-W |
|---|---|
| 23 | 3,4-methylenedioxybenzyl, with OH on chain |
| 24 | 3-bromobenzyl, with OH on chain |
| 25 | 3-iodobenzyl, with OH on chain |
| 26 | 3,5-dichlorobenzyl, with OH on chain |
| 27 | 3,4-dichlorobenzyl, with OH on chain |
| 28 | 3,4-difluorobenzyl, with OH on chain |
| 29 | 2,3-difluorobenzyl, with OH on chain |
| 30 | 3,5-difluorobenzyl, with OH on chain |
| 31 | 2,5-difluorobenzyl, with OH on chain |
| 32 | 3,5-dimethylbenzyl, with OH on chain |
| 33 | 3,5-bis(trifluoromethyl)benzyl, with OH on chain |
| 34 | 3-chloro-4-fluorobenzyl, with OH on chain |
| 35 | 2-fluoro-5-(trifluoromethyl)benzyl, with OH on chain |

TABLE 23

(IA10)

| No. | -X-E-W |
|---|---|
| 36 | 3-phenoxybenzyl, with OH on chain |
| 37 | biphenyl-3-ylmethyl, with OH on chain |

TABLE 23-continued (IA10)

| No. | -X-E-W |
|---|---|
| 38 | 2-chlorobiphenyl-3-yl via CH2-CH(OH)-CH2-CH2- |
| 39 | naphthalen-2-yl via CH2-CH(OH)-CH2-CH2- |
| 40 | naphthalen-1-yl via CH2-CH(OH)-CH2-CH2- |
| 41 | furan-2-yl via CH2-CH(OH)-CH2-CH2- |
| 42 | thiophen-2-yl via CH2-CH(OH)-CH2-CH2- |
| 43 | 5-(trifluoromethyl)thiophen-2-yl via CH2-CH(OH)-CH2-CH2- |
| 44 | pyridin-2-yl via CH2-CH(OH)-CH2-CH2- |
| 45 | benzofuran-5-yl via CH2-CH(OH)-CH2-CH2- |
| 46 | benzothiophen-5-yl via CH2-CH(OH)-CH2-CH2- |
| 47 | benzoxazol-6-yl via CH2-CH(OH)-CH2-CH2- |
| 48 | benzothiazol-6-yl via CH2-CH(OH)-CH2-CH2- |
| 49 | 1H-benzimidazol-5-yl via CH2-CH(OH)-CH2-CH2- |
| 50 | 1H-indol-5-yl via CH2-CH(OH)-CH2-CH2- |
| 51 | 1-methyl-1H-indol-5-yl via CH2-CH(OH)-CH2-CH2- |
| 52 | 1-methyl-1H-indol-6-yl via CH2-CH(OH)-CH2-CH2- |
| 53 | 1H-indazol-5-yl via CH2-CH(OH)-CH2-CH2- |
| 54 | 1-methyl-1H-indazol-5-yl via CH2-CH(OH)-CH2-CH2- |
| 55 | quinolin-6-yl via CH2-CH(OH)-CH2-CH2- |
| 56 | isoquinolin-6-yl via CH2-CH(OH)-CH2-CH2- |
| 57 | 3-tert-butylphenyl via CH2-CH(OH)-CH2-CH2- |
| 58 | 5-phenylfuran-2-yl via CH2-CH(OH)-CH2-CH2- |

TABLE 23-continued
(IA10)
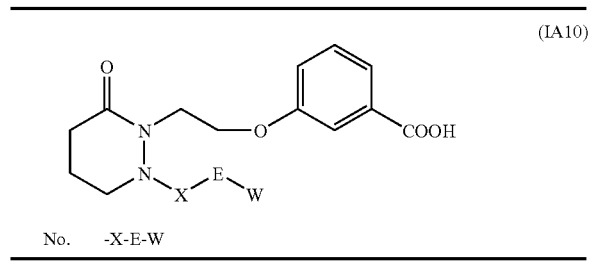
| No. | -X-E-W |
|---|---|
| 59 | 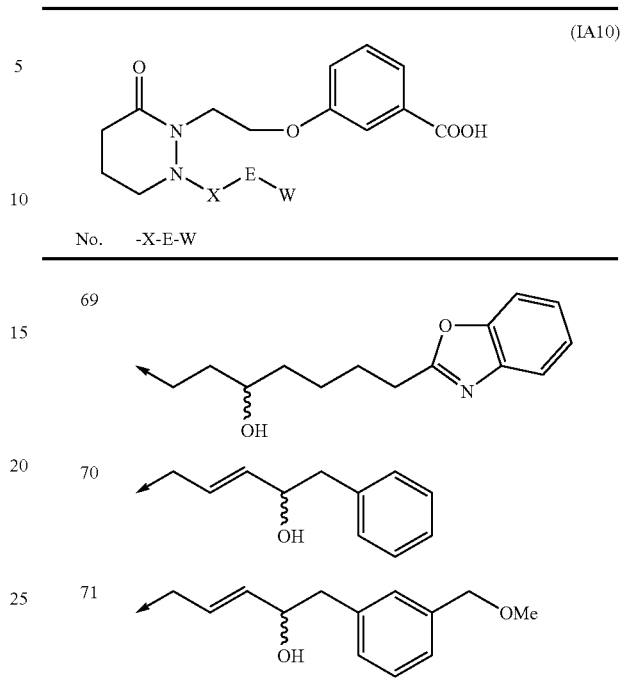 |
| 60 | |
| 61 | |
| 62 | |
| 63 | |
| 64 | |
| 65 | |
| 66 | |
| 67 | |
| 68 | |
TABLE 23-continued
(IA10)
| No. | -X-E-W |
|---|---|
| 69 | 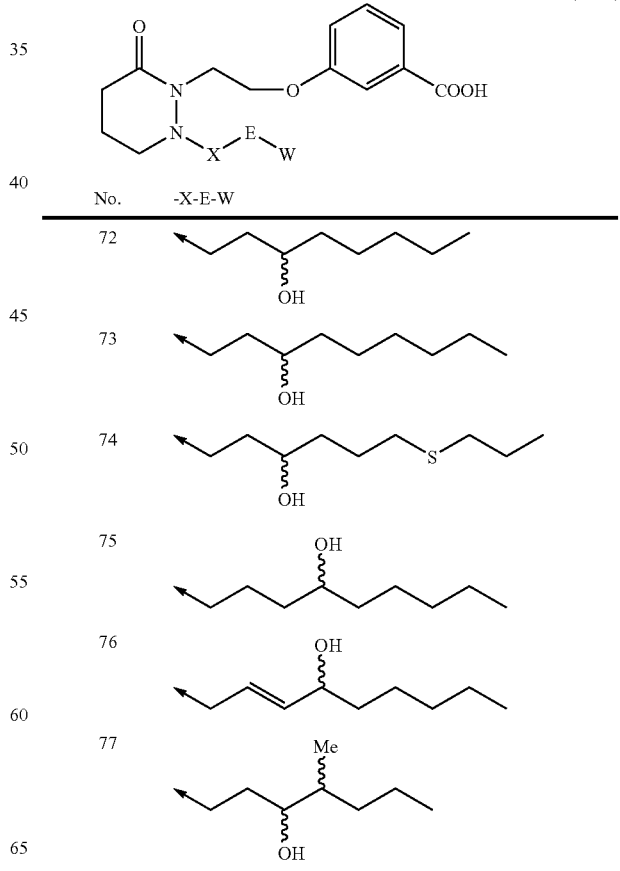 |
| 70 | |
| 71 | |
TABLE 24
(IA10)
| No. | -X-E-W |
|---|---|
| 72 | |
| 73 | |
| 74 | |
| 75 | |
| 76 | |
| 77 | |

TABLE 24-continued
(IA10)
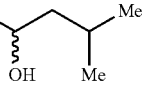
| No. | -X-E-W |
|---|---|
| 78 | 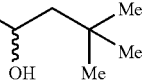 |
| 79 | 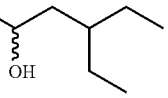 |
| 80 | 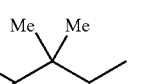 |
| 81 | 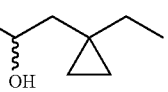 |
| 82 | 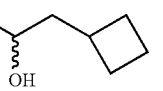 |
| 83 | 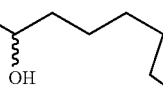 |
| 84 | 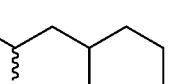 |
| 85 | 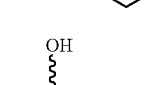 |
| 86 | 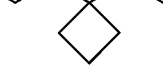 |
| 87 | 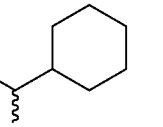 |
| 88 | 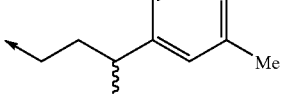 |
TABLE 24-continued
(IA10)
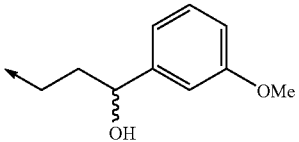
| No. | -X-E-W |
|---|---|
| 89 | 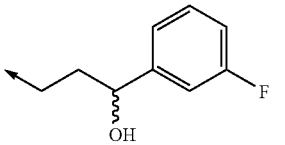 |
| 90 | 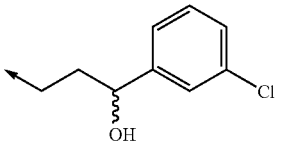 |
| 91 | 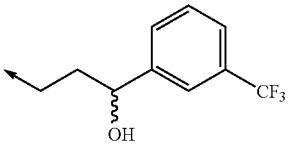 |
| 92 | 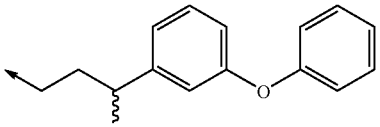 |
| 93 | 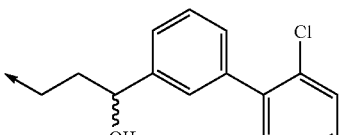 |
| 94 | 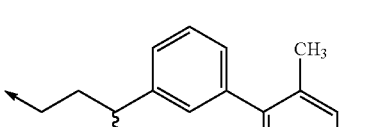 |
| 95 | |
| 96 | |

TABLE 24-continued
(IA10)
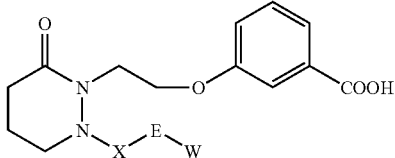
| No. | -X-E-W |
|---|---|
| 97 | 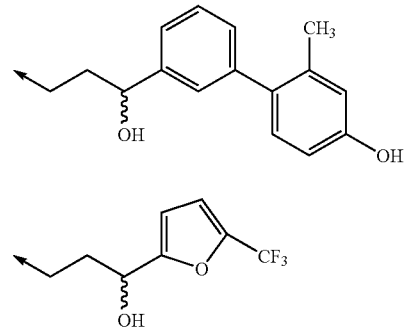 |
| 98 | 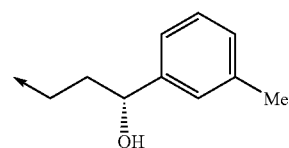 |
| 99 | 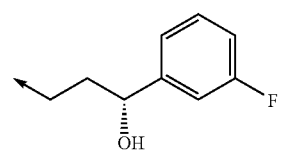 |
| 100 | 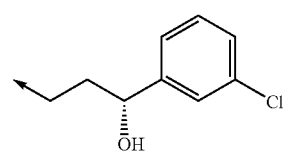 |
| 101 | 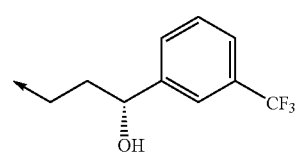 |
| 102 | 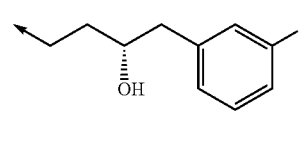 |
| 103 | 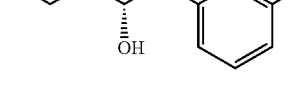 |
| 104 | 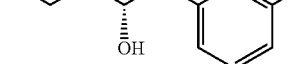 |
| 105 | 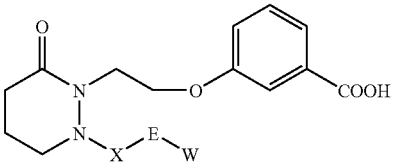 |
TABLE 24-continued
(IA10)
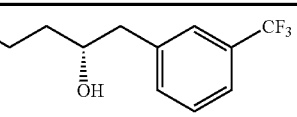
| No. | -X-E-W |
|---|---|
| 106 | 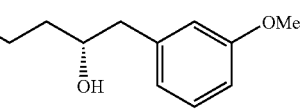 |
| 107 | 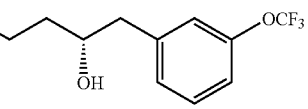 |
| 108 | 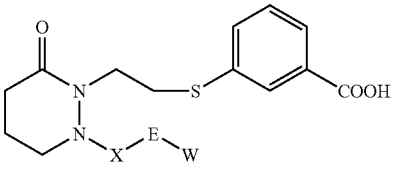 |
TABLE 25
(IA11)
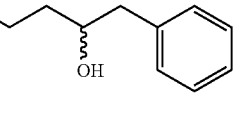
| No. | -X-E-W |
|---|---|
| 1 | 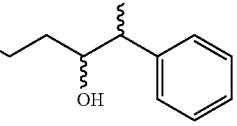 |
| 2 | 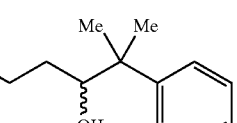 |
| 3 | 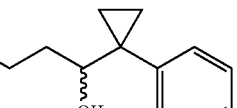 |
| 4 | 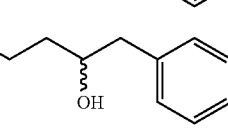 |
| 5 | 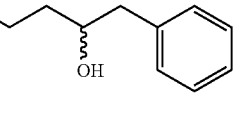 |

TABLE 25-continued (IA11)

[Structure: piperidazinone with N-CH2CH2-S-phenyl-COOH (meta) and N-X-E-W substituent]

| No. | -X-E-W |
|---|---|
| 6 | -CH2CH2-CH(OH)-CH2-(2-F-C6H4) |
| 7 | -CH2CH2-CH(OH)-CH2-(3-F-C6H4) |
| 8 | -CH2CH2-CH(OH)-CH2-(4-F-C6H4) |
| 9 | -CH2CH2-CH(OH)-CH2-(2-Cl-C6H4) |
| 10 | -CH2CH2-CH(OH)-CH2-(3-Cl-C6H4) |
| 11 | -CH2CH2-CH(OH)-CH2-(4-Cl-C6H4) |
| 12 | -CH2CH2-CH(OH)-CH2-(2-CF3-C6H4) |
| 13 | -CH2CH2-CH(OH)-CH2-(3-CF3-C6H4) |
| 14 | -CH2CH2-CH(OH)-CH2-(4-CF3-C6H4) |
| 15 | -CH2CH2-CH(OH)-CH2-(2-Me-C6H4) |
| 16 | -CH2CH2-CH(OH)-CH2-(3-Me-C6H4) |
| 17 | -CH2CH2-CH(OH)-CH2-(4-Me-C6H4) |
| 18 | -CH2CH2-CH(OH)-CH2-(3-OH-C6H4) |
| 19 | -CH2CH2-CH(OH)-CH2-(3-OMe-C6H4) |
| 20 | -CH2CH2-CH(OH)-CH2-(4-OMe-C6H4) |
| 21 | -CH2CH2-CH(OH)-CH2-(3-OC(Me)3-C6H4) |
| 22 | -CH2CH2-CH(OH)-CH2-(3-OCF3-C6H4) |
| 23 | -CH2CH2-CH(OH)-CH2-(3,4-methylenedioxyphenyl) |
| 24 | -CH2CH2-CH(OH)-CH2-(3-Br-C6H4) |
| 25 | -CH2CH2-CH(OH)-CH2-(3-I-C6H4) |
| 26 | -CH2CH2-CH(OH)-CH2-(3,5-diCl-C6H3) |

TABLE 25-continued (IA11)

[Structure: piperidazinone with N-CH2CH2-S-phenyl-COOH and N-X-E-W substituent]

| No. | -X-E-W |
|---|---|
| 27 | 3,4-dichlorobenzyl with CH2CH2CH(OH)- linker |
| 28 | 3,4-difluorobenzyl with CH2CH2CH(OH)- linker |
| 29 | 2,3-difluorobenzyl with CH2CH2CH(OH)- linker |
| 30 | 3,5-difluorobenzyl with CH2CH2CH(OH)- linker |
| 31 | 2,5-difluorobenzyl with CH2CH2CH(OH)- linker |
| 32 | 3,5-dimethylbenzyl with CH2CH2CH(OH)- linker |
| 33 | 3,5-bis(trifluoromethyl)benzyl with CH2CH2CH(OH)- linker |
| 34 | 3-chloro-4-fluorobenzyl with CH2CH2CH(OH)- linker |

TABLE 25-continued (IA11)

[Structure: piperidazinone with N-CH2CH2-S-phenyl-COOH and N-X-E-W substituent]

| No. | -X-E-W |
|---|---|
| 35 | 2-fluoro-5-trifluoromethylbenzyl with CH2CH2CH(OH)- linker |

TABLE 26

(IA12)

[Structure: piperidazinone with N-CH2CH2-O-phenyl-COOH and N-X-E-W substituent]

| No. | -X-E-W |
|---|---|
| 1 | benzyl with CH2CH2CH(OH)- linker |
| 2 | α-methylbenzyl with CH2CH2CH(OH)- linker |
| 3 | α,α-dimethylbenzyl with CH2CH2CH(OH)- linker |
| 4 | 1-phenylcyclopropyl with CH2CH2CH(OH)- linker |
| 5 | 3-(methoxymethyl)benzyl with CH2CH2CH(OH)- linker |
| 6 | 2-fluorobenzyl with CH2CH2CH(OH)- linker |

TABLE 26-continued (IA12)

| No. | -X-E-W |
|---|---|
| 7 | 3-F-benzyl, CH(OH)CH2CH2- |
| 8 | 4-F-benzyl, CH(OH)CH2CH2- |
| 9 | 2-Cl-benzyl, CH(OH)CH2CH2- |
| 10 | 3-Cl-benzyl, CH(OH)CH2CH2- |
| 11 | 4-Cl-benzyl, CH(OH)CH2CH2- |
| 12 | 2-CF3-benzyl, CH(OH)CH2CH2- |
| 13 | 3-CF3-benzyl, CH(OH)CH2CH2- |
| 14 | 4-CF3-benzyl, CH(OH)CH2CH2- |
| 15 | 2-Me-benzyl, CH(OH)CH2CH2- |
| 16 | 3-Me-benzyl, CH(OH)CH2CH2- |
| 17 | 4-Me-benzyl, CH(OH)CH2CH2- |
| 18 | 3-OH-benzyl, CH(OH)CH2CH2- |
| 19 | 3-OMe-benzyl, CH(OH)CH2CH2- |
| 20 | 4-OMe-benzyl, CH(OH)CH2CH2- |
| 21 | 3-OtBu-benzyl, CH(OH)CH2CH2- |
| 22 | 3-OCF3-benzyl, CH(OH)CH2CH2- |
| 23 | 3,4-methylenedioxy-benzyl, CH(OH)CH2CH2- |
| 24 | 3-Br-benzyl, CH(OH)CH2CH2- |
| 25 | 3-I-benzyl, CH(OH)CH2CH2- |
| 26 | 3,5-diCl-benzyl, CH(OH)CH2CH2- |
| 27 | 3,4-diCl-benzyl, CH(OH)CH2CH2- |

TABLE 26-continued (IA12)

| No. | -X-E-W |
|---|---|
| 28 | 3,4-difluorobenzyl with CH(OH) linker |
| 29 | 2,3-difluorobenzyl with CH(OH) linker |
| 30 | 3,5-difluorobenzyl with CH(OH) linker |
| 31 | 2,5-difluorobenzyl with CH(OH) linker |
| 32 | 3,5-dimethylbenzyl with CH(OH) linker |
| 33 | 3,5-bis(trifluoromethyl)benzyl with CH(OH) linker |
| 34 | 3-chloro-4-fluorobenzyl with CH(OH) linker |
| 35 | 2-fluoro-5-(trifluoromethyl)benzyl with CH(OH) linker |

TABLE 27

(IA12)

| No. | -X-E-W |
|---|---|
| 36 | 3-phenoxybenzyl with CH(OH) linker |
| 37 | 3-phenylbenzyl with CH(OH) linker |
| 38 | 2'-chloro-biphenyl-3-yl-methyl with CH(OH) linker |
| 39 | naphthalen-2-ylmethyl with CH(OH) linker |
| 40 | naphthalen-1-ylmethyl with CH(OH) linker |
| 41 | furan-2-ylmethyl with CH(OH) linker |
| 42 | thiophen-2-ylmethyl with CH(OH) linker |
| 43 | 5-(trifluoromethyl)thiophen-2-ylmethyl with CH(OH) linker |
| 44 | pyridin-2-ylmethyl with CH(OH) linker |
| 45 | benzofuran-5-ylmethyl with CH(OH) linker |

TABLE 27-continued (IA12)

| No. | -X-E-W |
|---|---|
| 46 | 5-(2-hydroxybutyl)benzothiophene substituent |
| 47 | 6-(2-hydroxybutyl)benzoxazole substituent |
| 48 | 6-(2-hydroxybutyl)benzothiazole substituent |
| 49 | 5-(2-hydroxybutyl)benzimidazole substituent |
| 50 | 5-(2-hydroxybutyl)indole substituent |
| 51 | 5-(2-hydroxybutyl)-1-methylindole substituent |
| 52 | 6-(2-hydroxybutyl)-1-methylindole substituent |
| 53 | 5-(2-hydroxybutyl)-1H-indazole substituent |
| 54 | 5-(2-hydroxybutyl)-1-methylindazole substituent |
| 55 | 6-(2-hydroxybutyl)quinoline substituent |
| 56 | 6-(2-hydroxybutyl)isoquinoline substituent |

TABLE 27-continued (IA12)

| No. | -X-E-W |
|---|---|
| 57 | 2-hydroxy-4-(3-tert-butylphenyl)butyl |
| 58 | 2-hydroxy-4-(5-phenylfuran-2-yl)butyl |
| 59 | 2-hydroxy-4-(α,α-difluorobenzyl)butyl |
| 60 | 2-hydroxy-4-phenylbutyl |
| 61 | 2-hydroxy-5-phenylpentyl |
| 62 | 3-hydroxy-5-(3-chlorophenoxy)pentyl |
| 63 | 3-hydroxy-6-phenoxyhexyl |
| 64 | 3-hydroxy-5-benzyloxypentyl |
| 65 | 3-hydroxy-5-benzylthiopentyl |

TABLE 27-continued (IA12)

Structure: pyridazinone with N-CH2CH2-O-C6H4-COOH and N-X-E-W substituent

| No. | -X-E-W |
|-----|--------|
| 66 | -CH2CH2CH2-CH(OH)-CH2CH2-NH-C(O)-Ph |
| 67 | -CH2CH2CH2-CH(OH)-CH2CH2-(2-naphthyl) |
| 68 | -CH2CH2CH2-CH(OH)-CH2CH2-(N-indolyl) |
| 69 | -CH2CH2CH2-CH(OH)-CH2CH2CH2-(benzoxazol-2-yl) |
| 70 | -CH2-CH=CH-CH(OH)-CH2-Ph |
| 71 | -CH2-CH=CH-CH(OH)-CH2-(3-CH2OMe-C6H4) |

TABLE 28

(IA12)

Structure: pyridazinone with N-CH2CH2-O-C6H4-COOH and N-X-E-W substituent

| No. | -X-E-W |
|-----|--------|
| 72 | -CH2CH2-CH(OH)-CH2CH2CH2CH2CH3 |
| 73 | -CH2CH2CH2-CH(OH)-CH2CH2CH2CH2CH3 |

TABLE 28-continued (IA12)

| No. | -X-E-W |
|-----|--------|
| 74 | -CH2CH2-CH(OH)-CH2CH2-S-CH2CH2CH3 |
| 75 | -CH2CH2CH2-CH(OH)-CH2CH2CH2CH2CH3 |
| 76 | -CH2-CH=CH-CH(OH)-CH2CH2CH2CH2CH3 |
| 77 | -CH2CH2-CH(OH)-CH(Me)-CH2CH3 |
| 78 | -CH2CH2-CH(OH)-CH2-CH(Me)2 |
| 79 | -CH2CH2-CH(OH)-CH2-C(Me)3 |
| 80 | -CH2CH2-CH(OH)-CH(Et)2 |
| 81 | -CH2CH2-CH(OH)-C(Me)2-CH2CH3 |
| 82 | -CH2CH2-CH(OH)-CH2-(1-ethylcyclopropyl) |
| 83 | -CH2CH2-CH(OH)-CH2-cyclobutyl |
| 84 | -CH2CH2-CH(OH)-CH2CH2-cyclopentyl |
| 85 | -CH2CH2-CH(OH)-CH2-cyclohexyl |

TABLE 28-continued (IA12)

| No. | -X-E-W |
|---|---|
| 86 | 1-butyl-1-(hydroxymethyl-pentyl)cyclobutane chain |
| 87 | 1-cyclohexyl-1-hydroxy chain |
| 88 | 1-phenyl-1-hydroxy chain |
| 89 | 1-(3-methylphenyl)-1-hydroxy chain |
| 90 | 1-(3-methoxyphenyl)-1-hydroxy chain |
| 91 | 1-(3-fluorophenyl)-1-hydroxy chain |
| 92 | 1-(3-chlorophenyl)-1-hydroxy chain |
| 93 | 1-(3-trifluoromethylphenyl)-1-hydroxy chain |
| 94 | 1-(3-phenoxyphenyl)-1-hydroxy chain |
| 95 | 1-(2'-chlorobiphenyl-3-yl)-1-hydroxy chain |
| 96 | 1-(4'-chloro-2'-methylbiphenyl-3-yl)-1-hydroxy chain |
| 97 | 1-(4'-hydroxy-2'-methylbiphenyl-3-yl)-1-hydroxy chain |
| 98 | 1-(5-trifluoromethylfuran-2-yl)-1-hydroxy chain |
| 99 | (S)-1-(3-methylphenyl)-1-hydroxy chain |
| 100 | (S)-1-(3-fluorophenyl)-1-hydroxy chain |
| 101 | (S)-1-(3-chlorophenyl)-1-hydroxy chain |

TABLE 28-continued (IA12)

| No. | -X-E-W |
|---|---|
| 102 | 3-CF₃-phenyl, (R)-OH butyl |
| 103 | 3-Me-phenyl, (R)-OH butyl |
| 104 | 3-F-phenyl, (R)-OH butyl |
| 105 | 3-Cl-phenyl, (R)-OH butyl |
| 106 | 3-CF₃-phenyl, (R)-OH butyl |
| 107 | 3-OMe-phenyl, (R)-OH butyl |
| 108 | 3-OCF₃-phenyl, (R)-OH butyl |

TABLE 29

(IA13)

| No. | -X-E-W |
|---|---|
| 1 | phenyl, OH butyl |
| 2 | α-Me-phenyl, OH butyl |
| 3 | α,α-diMe-phenyl, OH butyl |
| 4 | 1-phenylcyclopropyl, OH butyl |
| 5 | 3-CH₂OMe-phenyl, OH butyl |
| 6 | 2-F-phenyl, OH butyl |
| 7 | 3-F-phenyl, OH butyl |
| 8 | 4-F-phenyl, OH butyl |
| 9 | 2-Cl-phenyl, OH butyl |
| 10 | 3-Cl-phenyl, OH butyl |
| 11 | 4-Cl-phenyl, OH butyl |

TABLE 29-continued
(IA13)
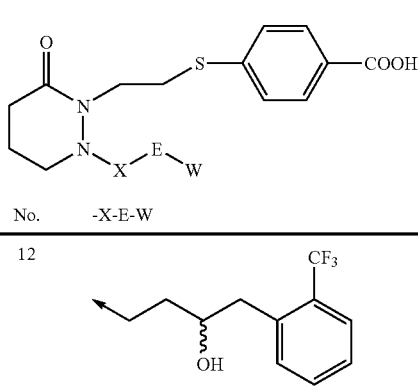
| No. | -X-E-W |
|---|---|
| 12 | 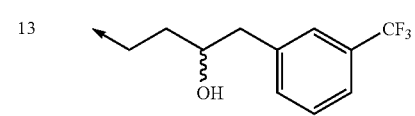 |
| 13 | 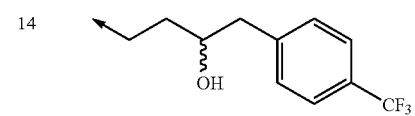 |
| 14 | 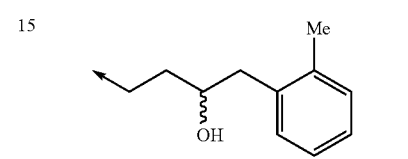 |
| 15 | 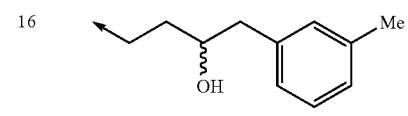 |
| 16 | 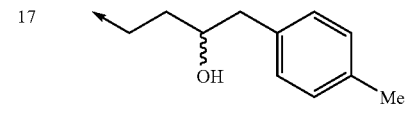 |
| 17 | 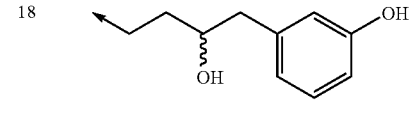 |
| 18 | 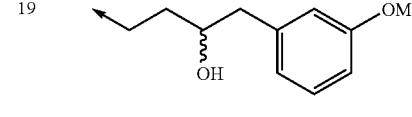 |
| 19 | 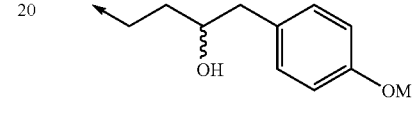 |
| 20 | 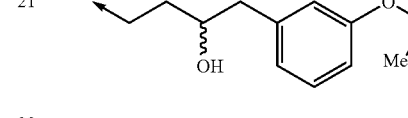 |
| 21 | 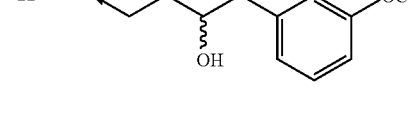 |
| 22 | 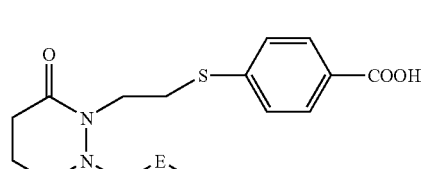 |
TABLE 29-continued
(IA13)
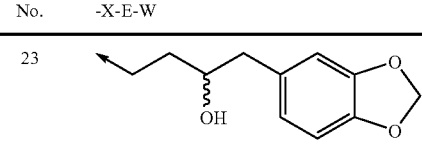
| No. | -X-E-W |
|---|---|
| 23 | 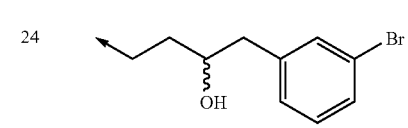 |
| 24 | 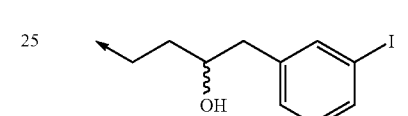 |
| 25 | 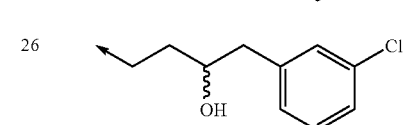 |
| 26 | 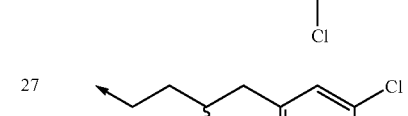 |
| 27 | 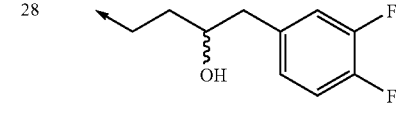 |
| 28 | 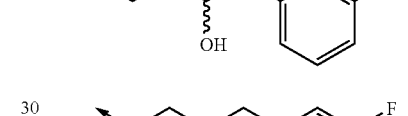 |
| 29 |  |
| 30 | |
| 31 | |

TABLE 29-continued (IA13)

| No. | -X-E-W |
|---|---|
| 32 | 3,5-dimethylbenzyl with OH |
| 33 | 3,5-bis(trifluoromethyl)benzyl with OH |
| 34 | 3-chloro-4-fluorobenzyl with OH |
| 35 | 2-fluoro-5-(trifluoromethyl)benzyl with OH |

TABLE 30

(IA14)

| No. | -X-E-W |
|---|---|
| 1 | benzyl with OH |
| 2 | α-methylbenzyl with OH |

TABLE 30-continued (IA14)

| No. | -X-E-W |
|---|---|
| 3 | α,α-dimethylbenzyl with OH |
| 4 | 1-phenylcyclopropyl with OH |
| 5 | 3-(methoxymethyl)benzyl with OH |
| 6 | 2-fluorobenzyl with OH |
| 7 | 3-fluorobenzyl with OH |
| 8 | 4-fluorobenzyl with OH |
| 9 | 2-chlorobenzyl with OH |
| 10 | 3-chlorobenzyl with OH |
| 11 | 4-chlorobenzyl with OH |
| 12 | 2-(trifluoromethyl)benzyl with OH |

TABLE 30-continued
(IA14)
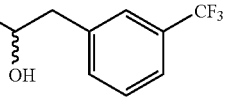
| No. | -X-E-W |
|---|---|
| 13 | 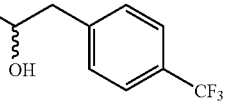 |
| 14 | 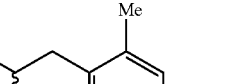 |
| 15 | 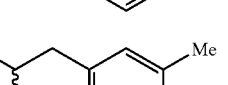 |
| 16 | 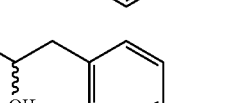 |
| 17 | 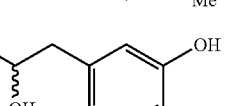 |
| 18 | 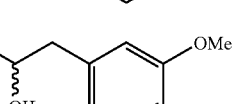 |
| 19 | 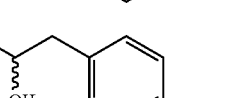 |
| 20 | 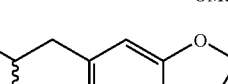 |
| 21 | 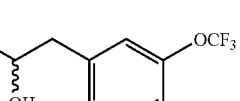 |
| 22 | 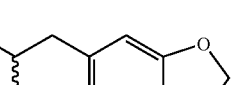 |
| 23 | 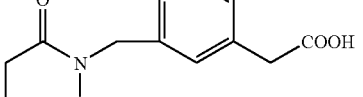 |
TABLE 30-continued
(IA14)
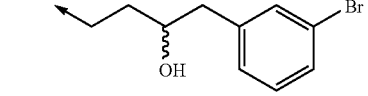
| No. | -X-E-W |
|---|---|
| 24 | 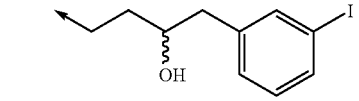 |
| 25 | 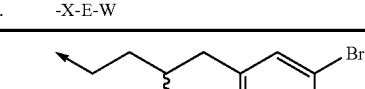 |
| 26 | 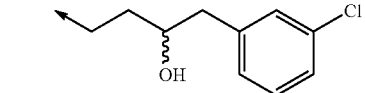 |
| 27 | 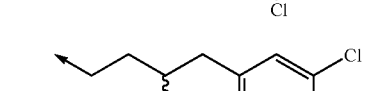 |
| 28 | 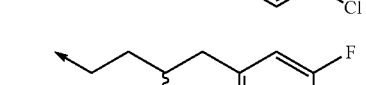 |
| 29 |  |
| 30 | 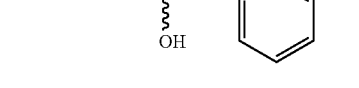 |
| 31 | 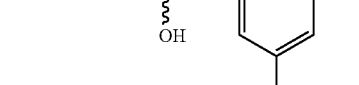 |
| 32 | 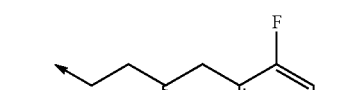 |

TABLE 30-continued (IA14)

| No. | -X-E-W |
|---|---|
| 33 | 3,5-bis(CF₃)benzyl, CH(OH), (CH₂)₃– |
| 34 | 3-Cl-4-F-benzyl, CH(OH), (CH₂)₃– |
| 35 | 2-F-5-CF₃-benzyl, CH(OH), (CH₂)₃– |

TABLE 31

(IA15)

| No. | -X-E-W |
|---|---|
| 1 | benzyl, CH(OH), (CH₂)₃– |
| 2 | α-Me-benzyl, CH(OH), (CH₂)₃– |
| 3 | α,α-diMe-benzyl, CH(OH), (CH₂)₃– |

TABLE 31-continued (IA15)

| No. | -X-E-W |
|---|---|
| 4 | 1-phenylcyclopropyl-CH₂, CH(OH), (CH₂)₃– |
| 5 | 3-(MeOCH₂)benzyl, CH(OH), (CH₂)₃– |
| 6 | 2-F-benzyl, CH(OH), (CH₂)₃– |
| 7 | 3-F-benzyl, CH(OH), (CH₂)₃– |
| 8 | 4-F-benzyl, CH(OH), (CH₂)₃– |
| 9 | 2-Cl-benzyl, CH(OH), (CH₂)₃– |
| 10 | 3-Cl-benzyl, CH(OH), (CH₂)₃– |
| 11 | 4-Cl-benzyl, CH(OH), (CH₂)₃– |
| 12 | 2-CF₃-benzyl, CH(OH), (CH₂)₃– |
| 13 | 3-CF₃-benzyl, CH(OH), (CH₂)₃– |

TABLE 31-continued
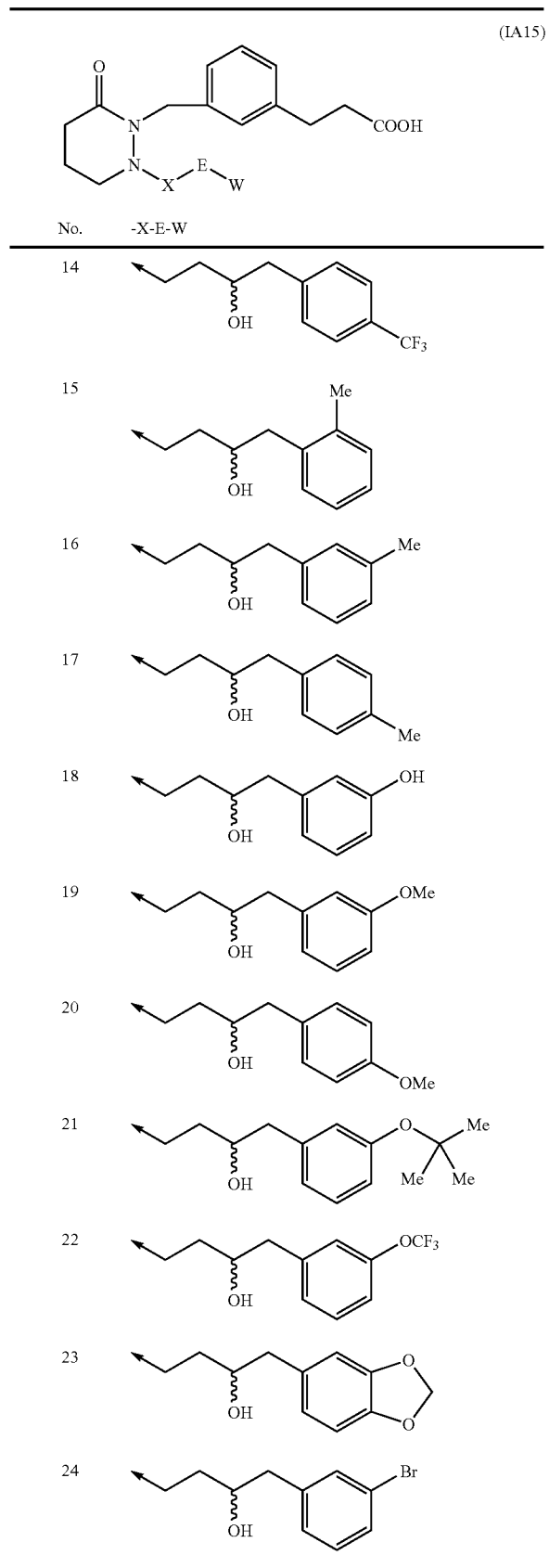
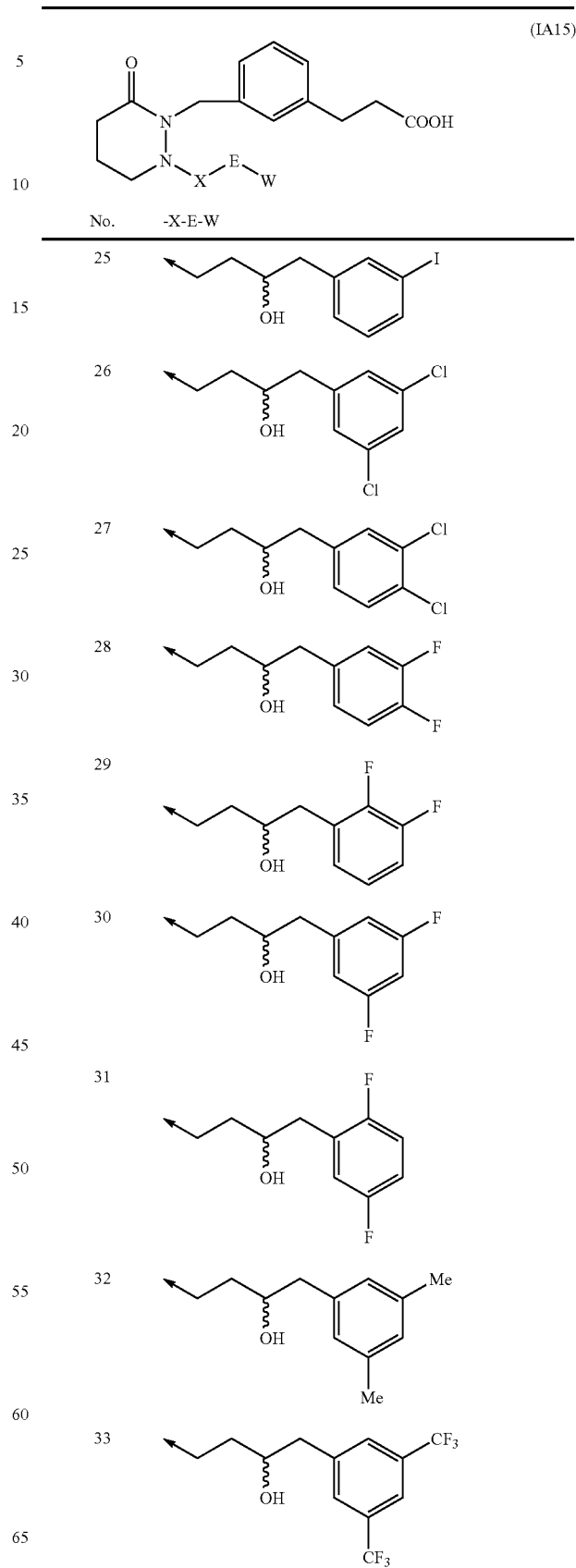

TABLE 31-continued
(IA15)
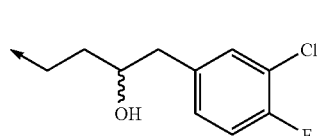
| No. | -X-E-W |
|---|---|
| 34 | 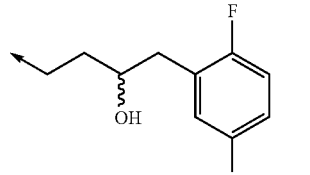 |
| 35 | 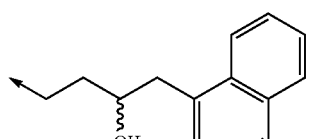 |
TABLE 32
(IA15)
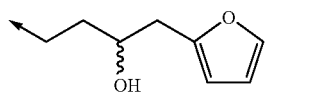
| No. | -X-E-W |
|---|---|
| 36 | 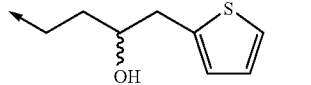 |
| 37 | 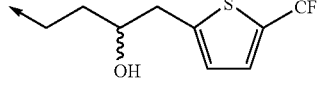 |
| 38 | 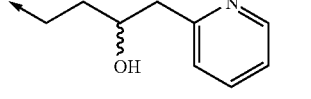 |
| 39 | 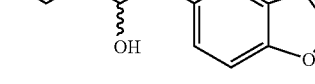 |
TABLE 32-continued
(IA15)
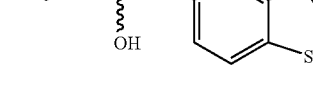
| No. | -X-E-W |
|---|---|
| 40 | 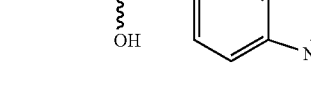 |
| 41 | 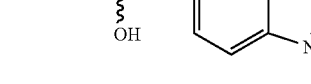 |
| 42 | 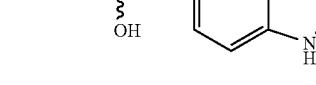 |
| 43 | 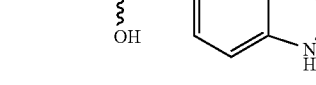 |
| 44 | 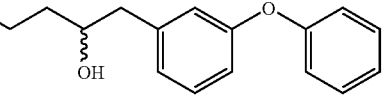 |
| 45 | 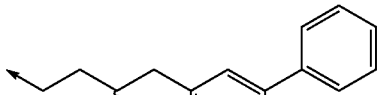 |
| 46 | 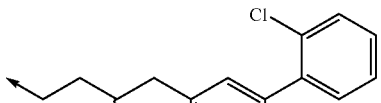 |
| 47 | 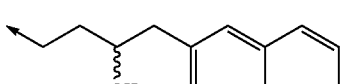 |
| 48 | |
| 49 | |
| 50 | |

TABLE 32-continued
(IA15)
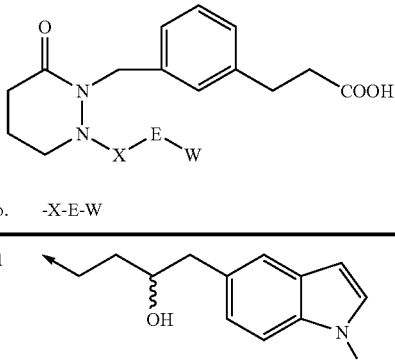
| No. | -X-E-W |
|---|---|
| 51 | 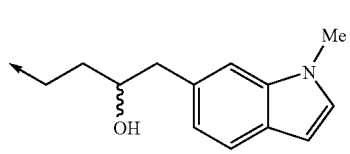 |
| 52 | 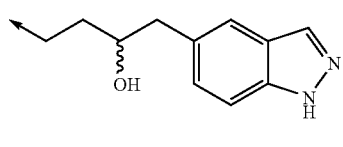 |
| 53 | 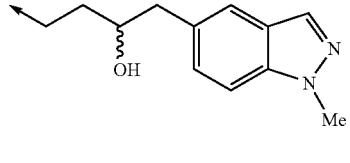 |
| 54 | 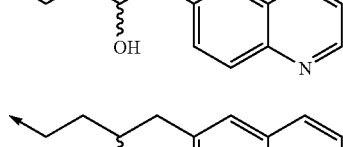 |
| 55 | 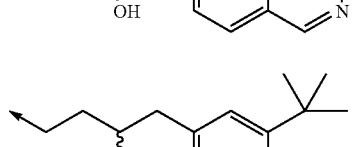 |
| 56 | 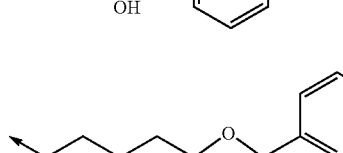 |
| 57 | 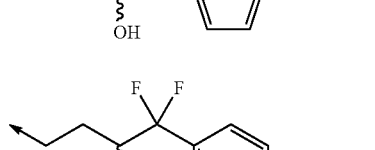 |
| 58 | 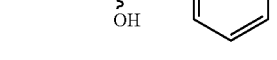 |
| 59 | 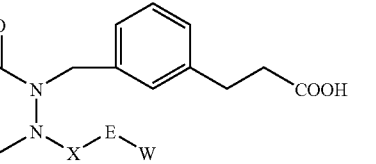 |
| 60 | 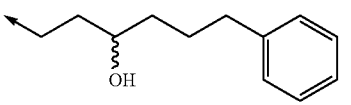 |
| 61 | 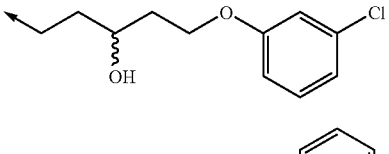 |
| 62 | 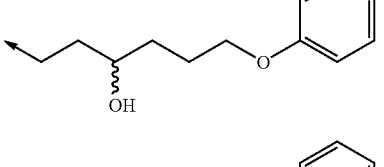 |
| 63 | 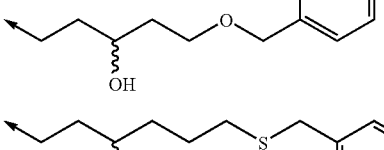 |
| 64 |  |
| 65 | 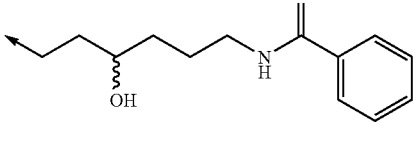 |
| 66 | 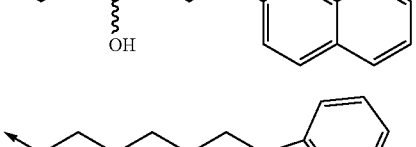 |
| 67 | 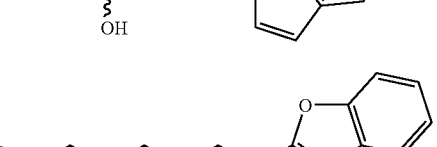 |
| 68 |  |
| 69 | |

TABLE 32-continued
(IA15)
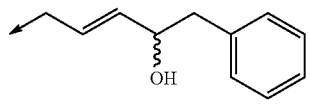
| No. | -X-E-W |
|---|---|
| 70 | 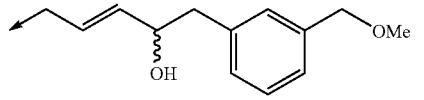 |
| 71 | 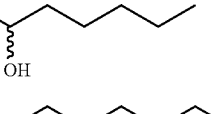 |
TABLE 33
(IA15)
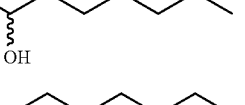
| No. | -X-E-W |
|---|---|
| 72 | 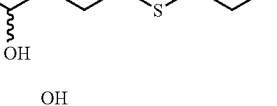 |
| 73 | 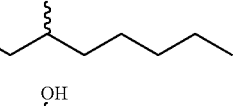 |
| 74 | 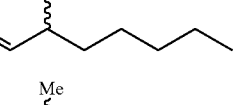 |
| 75 | 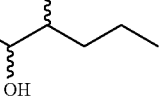 |
| 76 | 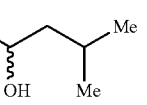 |
| 77 | 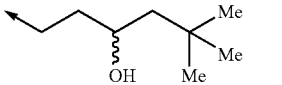 |
| 78 | 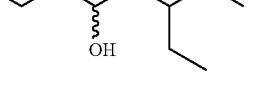 |
TABLE 33-continued
(IA15)
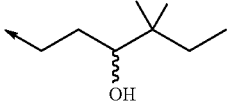
| No. | -X-E-W |
|---|---|
| 79 | 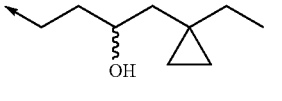 |
| 80 | 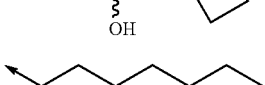 |
| 81 | 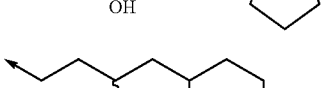 |
| 82 | 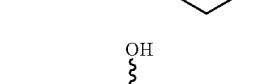 |
| 83 | 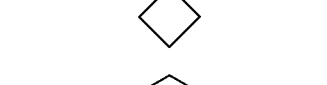 |
| 84 | 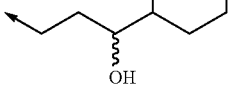 |
| 85 | 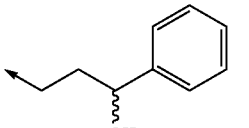 |
| 86 | 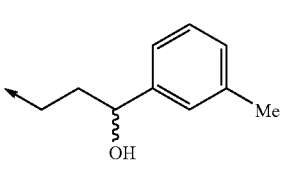 |
| 87 | |
| 88 | |
| 89 | |

TABLE 33-continued
(IA15)
| No. | -X-E-W |
|---|---|
| 90 | 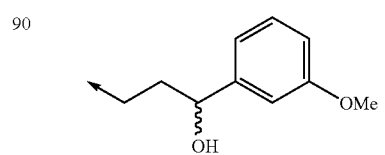 |
| 91 | 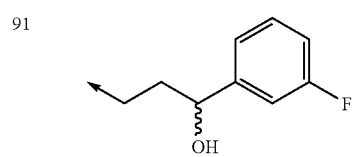 |
| 92 | 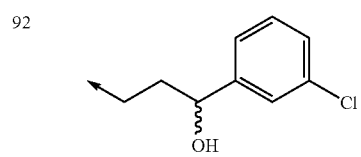 |
| 93 | 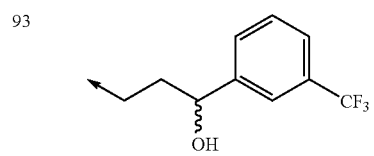 |
| 94 | 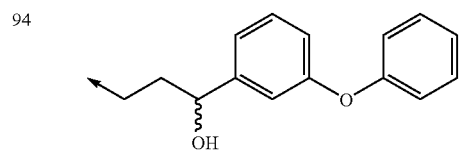 |
| 95 | 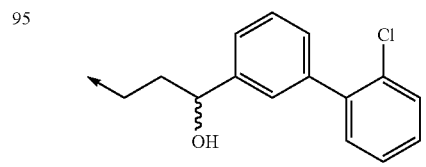 |
| 96 | 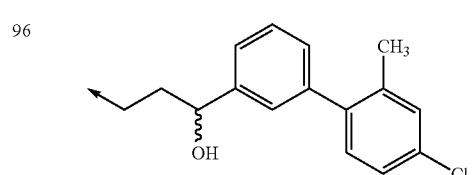 |
| 97 | 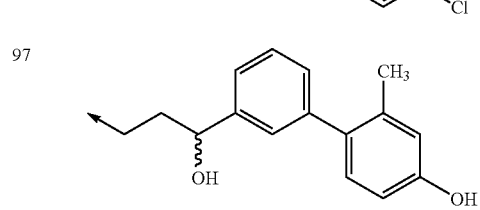 |
TABLE 33-continued
(IA15)
| No. | -X-E-W |
|---|---|
| 98 | 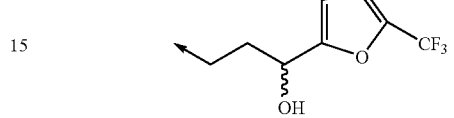 |
| 99 | 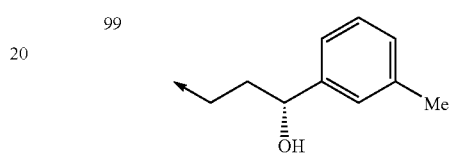 |
| 100 | 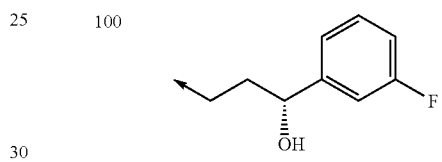 |
| 101 | 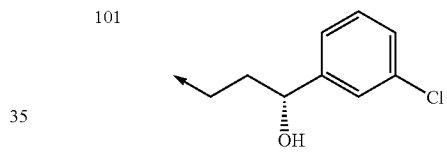 |
| 102 | 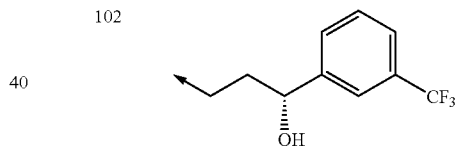 |
| 103 | 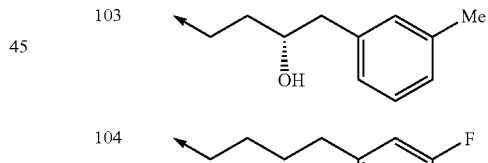 |
| 104 | 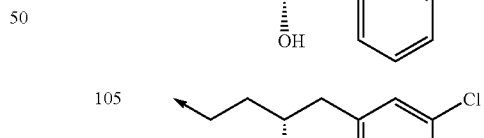 |
| 105 | 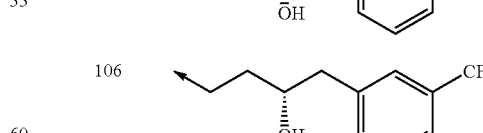 |
| 106 | 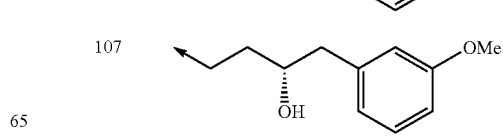 |
| 107 | |

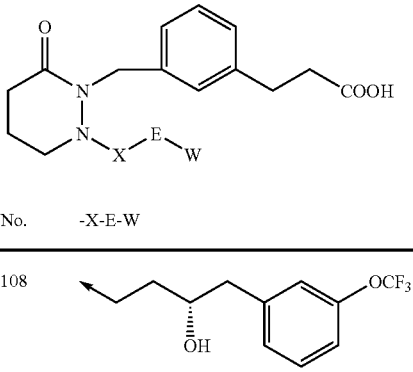

TABLE 34-continued
(IA16)
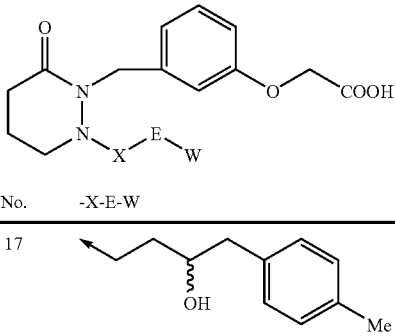
| No. | -X-E-W |
|---|---|
| 17 | 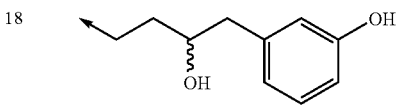 |
| 18 | 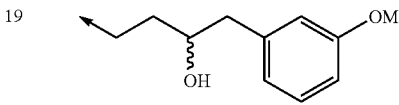 |
| 19 | 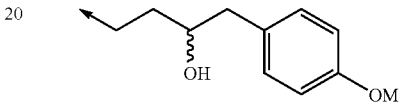 |
| 20 | 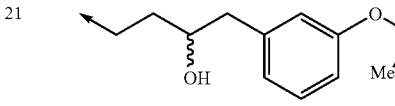 |
| 21 | 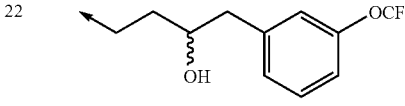 |
| 22 | 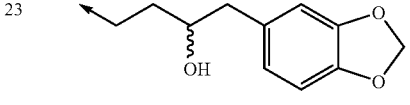 |
| 23 | 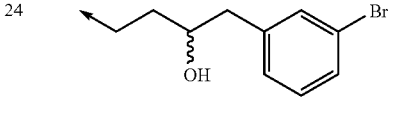 |
| 24 | 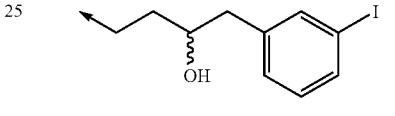 |
| 25 | 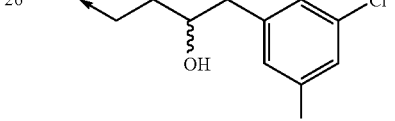 |
| 26 | 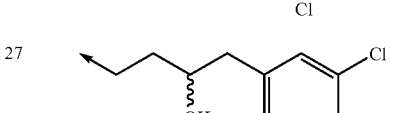 |
| 27 | 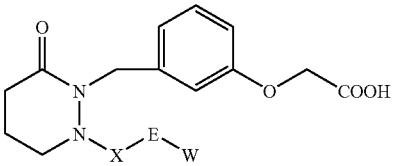 |
TABLE 34-continued
(IA16)
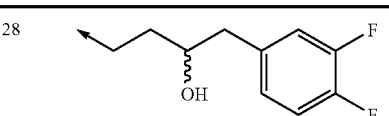
| No. | -X-E-W |
|---|---|
| 28 | 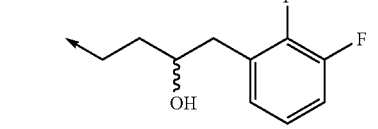 |
| 29 | 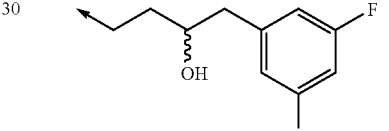 |
| 30 | 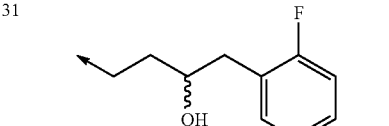 |
| 31 | 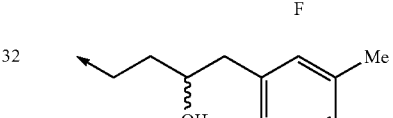 |
| 32 | 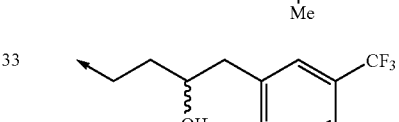 |
| 33 | 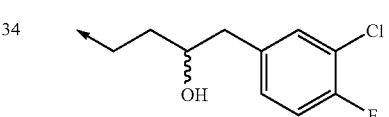 |
| 34 | 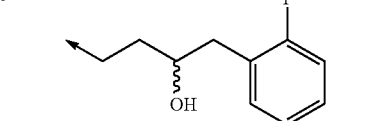 |
| 35 | 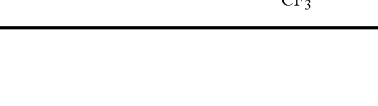 |

TABLE 35 and TABLE 35-continued contain chemical structure entries for formula (IA16), which are not transcribable as text.

TABLE 35-continued
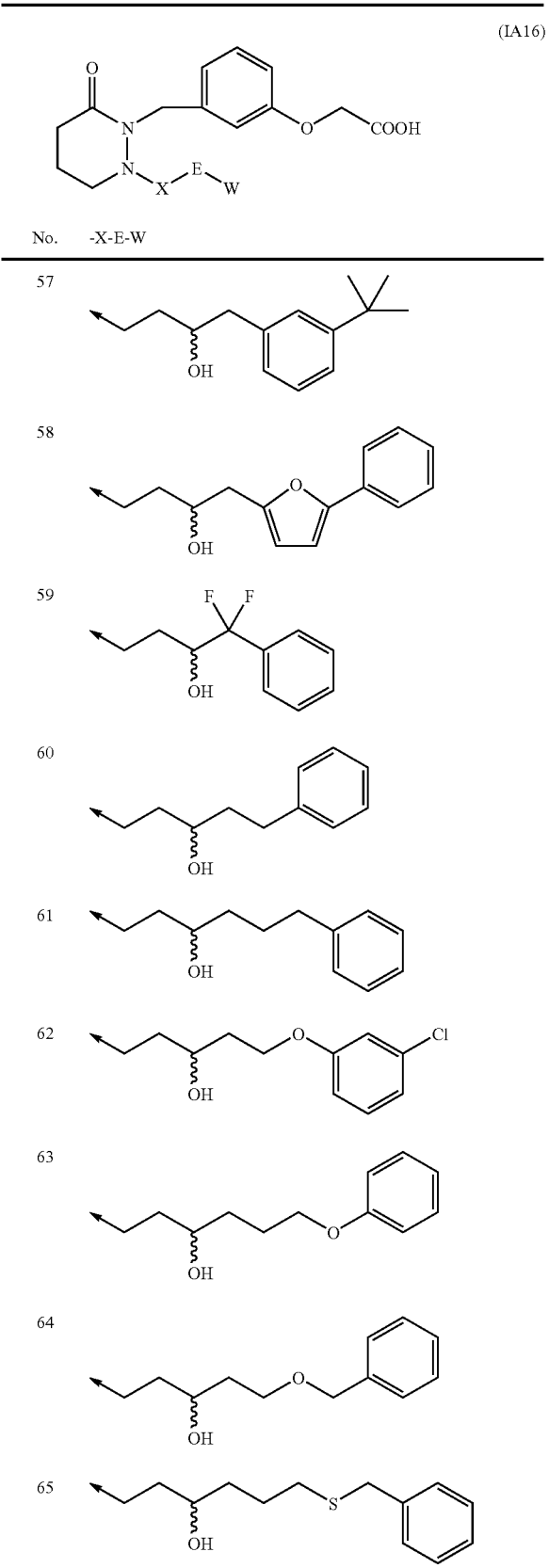
TABLE 35-continued
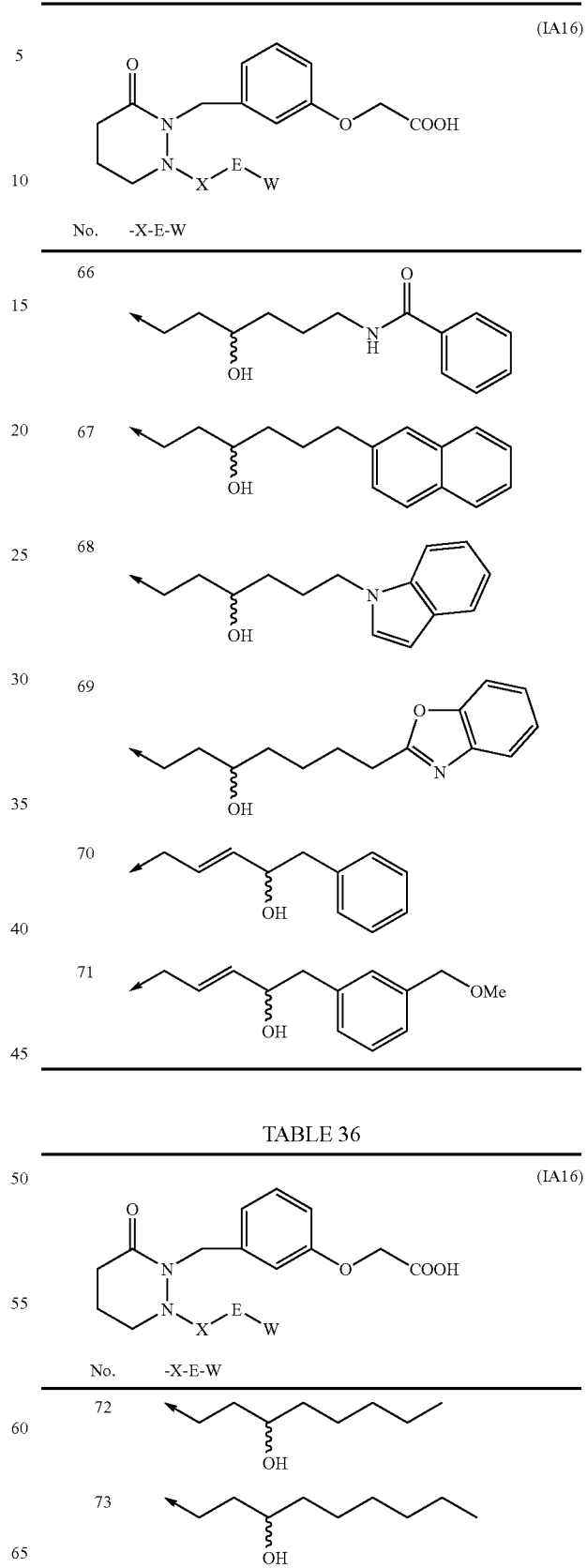
TABLE 36

TABLE 36-continued
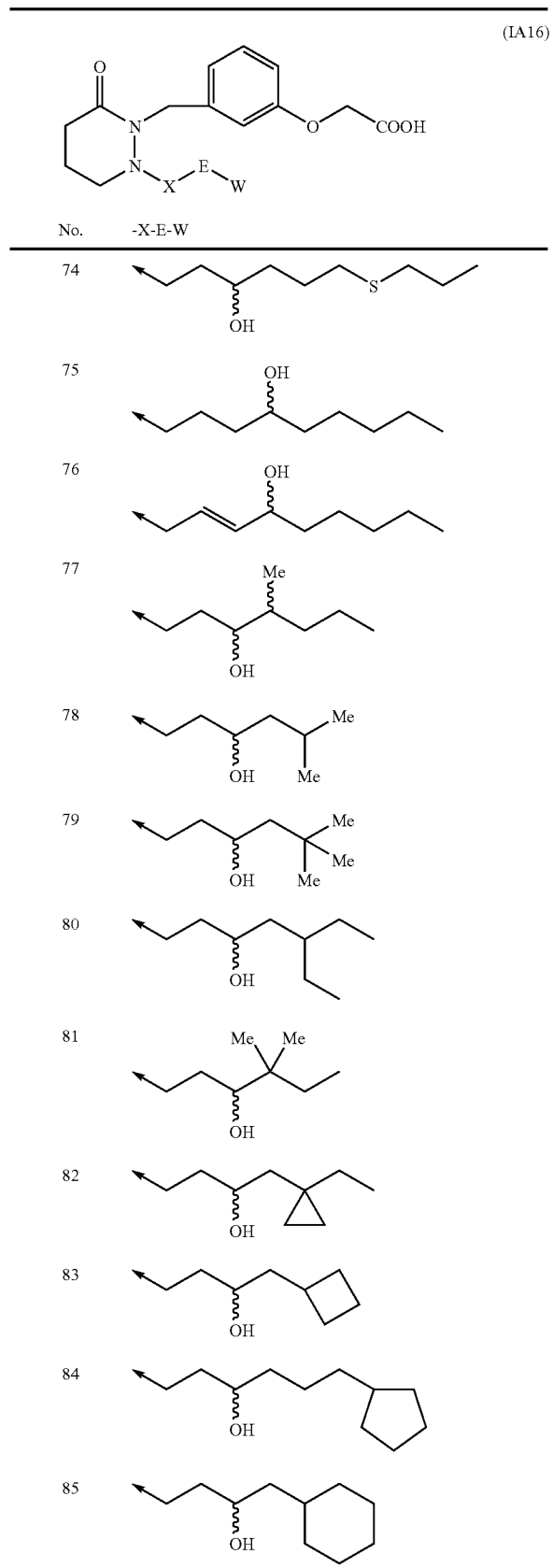
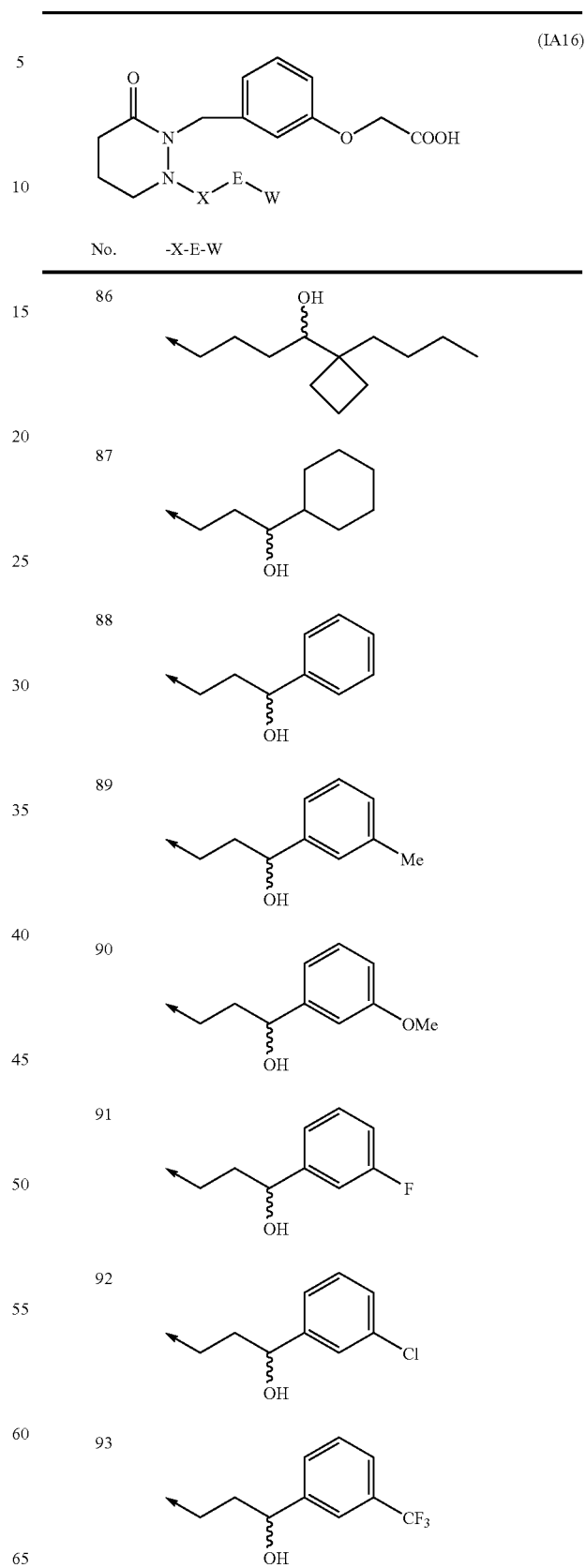

TABLE 36-continued (IA16)

[Structure: piperidazinone with N-benzyl-3-(OCH2COOH)phenyl group and N-X-E-W substituent]

| No. | -X-E-W |
|---|---|
| 94 | 3-phenoxyphenyl-CH(OH)-CH2CH2- |
| 95 | (2'-Cl-biphenyl-3-yl)-CH(OH)-CH2CH2- |
| 96 | (2'-CH3-4'-Cl-biphenyl-3-yl)-CH(OH)-CH2CH2- |
| 97 | (2'-CH3-4'-OH-biphenyl-3-yl)-CH(OH)-CH2CH2- |
| 98 | (5-CF3-furan-2-yl)-CH(OH)-CH2CH2- |
| 99 | (3-Me-phenyl)-CH(OH)-CH2CH2- |
| 100 | (3-F-phenyl)-CH(OH)-CH2CH2- |
| 101 | (3-Cl-phenyl)-CH(OH)-CH2CH2- |

TABLE 36-continued (IA16)

| No. | -X-E-W |
|---|---|
| 102 | (3-CF3-phenyl)-CH(OH)-CH2CH2- |
| 103 | (3-Me-phenyl)-CH2-CH(OH)-CH2CH2- |
| 104 | (3-F-phenyl)-CH2-CH(OH)-CH2CH2- |
| 105 | (3-Cl-phenyl)-CH2-CH(OH)-CH2CH2- |
| 106 | (3-CF3-phenyl)-CH2-CH(OH)-CH2CH2- |
| 107 | (3-OMe-phenyl)-CH2-CH(OH)-CH2CH2- |
| 108 | (3-OCF3-phenyl)-CH2-CH(OH)-CH2CH2- |

TABLE 37

(IA17)

[Structure: piperidazinone with N-benzyl-3-(SCH2COOH)phenyl group and N-X-E-W substituent]

| No. | -X-E-W |
|---|---|
| 1 | phenyl-CH2-CH(OH)-CH2CH2- |

TABLE 37-continued (IA17)

| No. | -X-E-W |
|---|---|
| 2 | -CH₂CH₂CH(OH)-CH(Me)-phenyl |
| 3 | -CH₂CH₂CH(OH)-C(Me)₂-phenyl |
| 4 | -CH₂CH₂CH(OH)-(1-phenylcyclopropyl) |
| 5 | -CH₂CH₂CH(OH)CH₂-(3-CH₂OMe-phenyl) |
| 6 | -CH₂CH₂CH(OH)CH₂-(2-F-phenyl) |
| 7 | -CH₂CH₂CH(OH)CH₂-(3-F-phenyl) |
| 8 | -CH₂CH₂CH(OH)CH₂-(4-F-phenyl) |
| 9 | -CH₂CH₂CH(OH)CH₂-(2-Cl-phenyl) |
| 10 | -CH₂CH₂CH(OH)CH₂-(3-Cl-phenyl) |
| 11 | -CH₂CH₂CH(OH)CH₂-(4-Cl-phenyl) |
| 12 | -CH₂CH₂CH(OH)CH₂-(2-CF₃-phenyl) |
| 13 | -CH₂CH₂CH(OH)CH₂-(3-CF₃-phenyl) |
| 14 | -CH₂CH₂CH(OH)CH₂-(4-CF₃-phenyl) |
| 15 | -CH₂CH₂CH(OH)CH₂-(2-Me-phenyl) |
| 16 | -CH₂CH₂CH(OH)CH₂-(3-Me-phenyl) |
| 17 | -CH₂CH₂CH(OH)CH₂-(4-Me-phenyl) |
| 18 | -CH₂CH₂CH(OH)CH₂-(3-OH-phenyl) |
| 19 | -CH₂CH₂CH(OH)CH₂-(3-OMe-phenyl) |
| 20 | -CH₂CH₂CH(OH)CH₂-(4-OMe-phenyl) |
| 21 | -CH₂CH₂CH(OH)CH₂-(3-OtBu-phenyl) |
| 22 | -CH₂CH₂CH(OH)CH₂-(3-OCF₃-phenyl) |

TABLE 37-continued (IA17)

| No. | -X-E-W |
|---|---|
| 23 | 3,4-methylenedioxybenzyl, β-OH |
| 24 | 3-bromobenzyl, β-OH |
| 25 | 3-iodobenzyl, β-OH |
| 26 | 3,5-dichlorobenzyl, β-OH |
| 27 | 3,4-dichlorobenzyl, β-OH |
| 28 | 3,4-difluorobenzyl, β-OH |
| 29 | 2,3-difluorobenzyl, β-OH |
| 30 | 3,5-difluorobenzyl, β-OH |
| 31 | 2,5-difluorobenzyl, β-OH |

TABLE 37-continued (IA17)

| No. | -X-E-W |
|---|---|
| 32 | 3,5-dimethylbenzyl, β-OH |
| 33 | 3,5-bis(trifluoromethyl)benzyl, β-OH |
| 34 | 3-chloro-4-fluorobenzyl, β-OH |
| 35 | 2-fluoro-5-(trifluoromethyl)benzyl, β-OH |

TABLE 38

(IA18)

| No. | -X-E-W |
|---|---|
| 1 | benzyl, β-OH |
| 2 | α-methylbenzyl, β-OH |

TABLE 38-continued

TABLE 38-continued (IA18)

Structure: cyclic hydrazide with N-CH2-C6H4-O-CH2-COOH and N-X-E-W substituent

| No. | -X-E-W |
|---|---|
| 24 | CH2CH2-CH(OH)-CH2-(3-Br-C6H4) |
| 25 | CH2CH2-CH(OH)-CH2-(3-I-C6H4) |
| 26 | CH2CH2-CH(OH)-CH2-(3,5-Cl2-C6H3) |
| 27 | CH2CH2-CH(OH)-CH2-(3,4-Cl2-C6H3) |
| 28 | CH2CH2-CH(OH)-CH2-(3,4-F2-C6H3) |
| 29 | CH2CH2-CH(OH)-CH2-(2,3-F2-C6H3) |
| 30 | CH2CH2-CH(OH)-CH2-(3,5-F2-C6H3) |
| 31 | CH2CH2-CH(OH)-CH2-(2,6-F2-C6H3) |
| 32 | CH2CH2-CH(OH)-CH2-(3,5-Me2-C6H3) |
| 33 | CH2CH2-CH(OH)-CH2-(3,5-(CF3)2-C6H3) |
| 34 | CH2CH2-CH(OH)-CH2-(3-Cl-4-F-C6H3) |
| 35 | CH2CH2-CH(OH)-CH2-(2-F-5-CF3-C6H3) |

TABLE 39

(IA18)

Structure: cyclic hydrazide with N-CH2-C6H4-O-CH2-COOH and N-X-E-W substituent

| No. | -X-E-W |
|---|---|
| 36 | CH2CH2-CH(OH)-CH2-(3-PhO-C6H4) |
| 37 | CH2CH2-CH(OH)-CH2-(3-Ph-C6H4) |
| 38 | CH2CH2-CH(OH)-CH2-(3-(2-Cl-C6H4)-C6H4) |
| 39 | CH2CH2-CH(OH)-CH2-(2-naphthyl) |

TABLE 39-continued (IA18)

| No. | -X-E-W |
|---|---|
| 40 | 1-naphthyl-CH2-CH(OH)-CH2CH2- |
| 41 | 2-furyl-CH2-CH(OH)-CH2CH2- |
| 42 | 2-thienyl-CH2-CH(OH)-CH2CH2- |
| 43 | 5-(CF3)-2-thienyl-CH2-CH(OH)-CH2CH2- |
| 44 | 2-pyridyl-CH2-CH(OH)-CH2CH2- |
| 45 | 5-benzofuranyl-CH2-CH(OH)-CH2CH2- |
| 46 | 5-benzothienyl-CH2-CH(OH)-CH2CH2- |
| 47 | 6-benzoxazolyl-CH2-CH(OH)-CH2CH2- |
| 48 | 6-benzothiazolyl-CH2-CH(OH)-CH2CH2- |
| 49 | 5-benzimidazolyl-CH2-CH(OH)-CH2CH2- |
| 50 | 5-indolyl-CH2-CH(OH)-CH2CH2- |
| 51 | 5-(1-Me-indolyl)-CH2-CH(OH)-CH2CH2- |
| 52 | 6-(1-Me-indolyl)-CH2-CH(OH)-CH2CH2- |
| 53 | 5-indazolyl-CH2-CH(OH)-CH2CH2- |
| 54 | 5-(1-Me-indazolyl)-CH2-CH(OH)-CH2CH2- |
| 55 | 6-quinolyl-CH2-CH(OH)-CH2CH2- |
| 56 | 6-isoquinolyl-CH2-CH(OH)-CH2CH2- |
| 57 | 3-tBu-phenyl-CH2-CH(OH)-CH2CH2- |
| 58 | 5-phenyl-2-furyl-CH2-CH(OH)-CH2CH2- |
| 59 | Ph-CF2-CH(OH)-CH2CH2- |
| 60 | Ph-CH2-CH(OH)-CH2CH2- |

TABLE 39-continued (IA18)

| No. | -X-E-W |
|---|---|
| 61 | [chain with OH, -(CH2)2-CH(OH)-(CH2)3-phenyl] |
| 62 | [chain with OH, -(CH2)2-CH(OH)-CH2-CH2-O-(3-Cl-phenyl)] |
| 63 | [chain -(CH2)2-CH(OH)-(CH2)3-O-phenyl] |
| 64 | [chain -(CH2)2-CH(OH)-CH2-CH2-O-CH2-phenyl] |
| 65 | [chain -(CH2)2-CH(OH)-(CH2)3-S-CH2-phenyl] |
| 66 | [chain -(CH2)2-CH(OH)-(CH2)3-NH-C(O)-phenyl] |
| 67 | [chain -(CH2)2-CH(OH)-(CH2)3-(2-naphthyl)] |
| 68 | [chain -(CH2)2-CH(OH)-(CH2)3-N(indol-1-yl)] |
| 69 | [chain -(CH2)2-CH(OH)-(CH2)4-(benzoxazol-2-yl)] |
| 70 | [chain -CH2-CH=CH-CH(OH)-CH2-phenyl] |

TABLE 39-continued (IA18)

| No. | -X-E-W |
|---|---|
| 71 | [chain -CH2-CH=CH-CH(OH)-CH2-(3-OMe-phenyl)] |

TABLE 40

(IA18)

| No. | -X-E-W |
|---|---|
| 72 | [chain -(CH2)2-CH(OH)-(CH2)4-CH3] |
| 73 | [chain -(CH2)2-CH(OH)-(CH2)5-CH3] |
| 74 | [chain -(CH2)2-CH(OH)-CH2-CH2-S-CH2-CH2-CH3] |
| 75 | [chain -(CH2)4-C(OH)H-(CH2)4-CH3] |
| 76 | [chain -CH2-CH=CH-CH(OH)-(CH2)4-CH3] |
| 77 | [chain -(CH2)2-CH(OH)-CH(Me)-CH2-CH3] |
| 78 | [chain -(CH2)2-CH(OH)-CH2-CH(Me)2] |
| 79 | [chain -(CH2)2-CH(OH)-CH2-C(Me)3] |
| 80 | [chain -(CH2)2-CH(OH)-CH(Et)-CH2-CH3] |

TABLE 40-continued
(IA18)
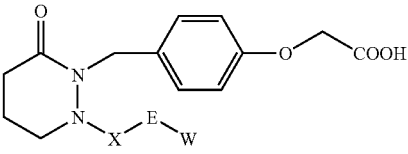
| No. | -X-E-W |
|---|---|
| 81 | 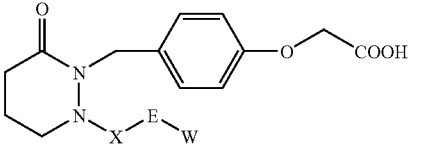 |
| 82 | 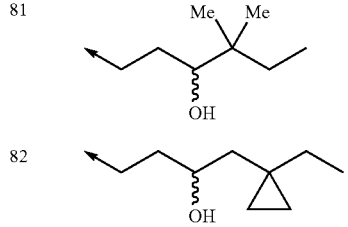 |
| 83 | 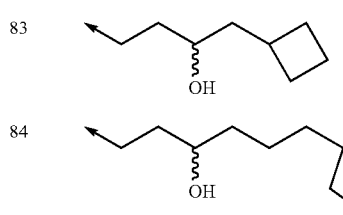 |
| 84 |  |
| 85 | 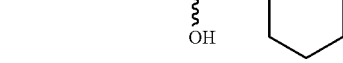 |
| 86 | 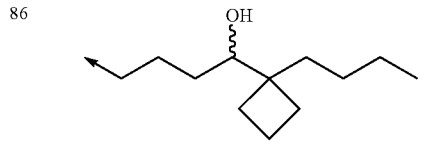 |
| 87 | 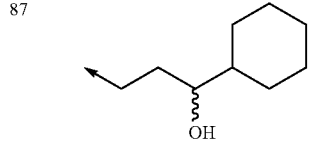 |
| 88 | 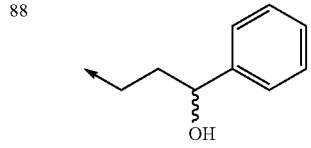 |
| 89 | 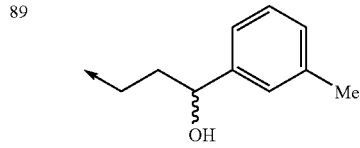 |
| 90 | 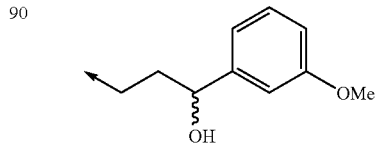 |
TABLE 40-continued
(IA18)

| No. | -X-E-W |
|---|---|
| 91 |  |
| 92 | 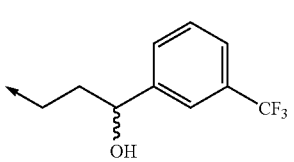 |
| 93 | 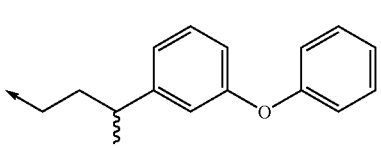 |
| 94 |  |
| 95 |  |
| 96 |  |
| 97 | 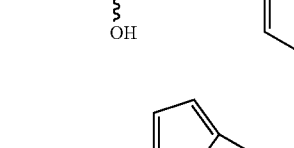 |
| 98 | |

TABLE 40-continued (IA18)

| No. | -X-E-W |
|-----|--------|
| 99 | 3-Me phenyl, (R)-OH butyl |
| 100 | 3-F phenyl, (R)-OH butyl |
| 101 | 3-Cl phenyl, (R)-OH butyl |
| 102 | 3-CF₃ phenyl, (R)-OH butyl |
| 103 | 3-Me benzyl, (R)-OH butyl |
| 104 | 3-F benzyl, (R)-OH butyl |
| 105 | 3-Cl benzyl, (R)-OH butyl |
| 106 | 3-CF₃ benzyl, (R)-OH butyl |
| 107 | 3-OMe benzyl, (R)-OH butyl |
| 108 | 3-OCF₃ benzyl, (R)-OH butyl |

TABLE 41

(IA19)

| No. | -X-E-W |
|-----|--------|
| 1 | benzyl, OH butyl |
| 2 | α-Me benzyl, OH butyl |
| 3 | α,α-diMe benzyl, OH butyl |
| 4 | 1-phenylcyclopropyl, OH butyl |
| 5 | 3-CH₂OMe benzyl, OH butyl |
| 6 | 2-F benzyl, OH butyl |
| 7 | 3-F benzyl, OH butyl |
| 8 | 4-F benzyl, OH butyl |
| 9 | 2-Cl benzyl, OH butyl |
| 10 | 3-Cl benzyl, OH butyl |

TABLE 41-continued (IA19)

| No. | -X-E-W |
|---|---|
| 11 | 4-Cl-C6H4, OH |
| 12 | 2-CF3-C6H4, OH |
| 13 | 3-CF3-C6H4, OH |
| 14 | 4-CF3-C6H4, OH |
| 15 | 2-Me-C6H4, OH |
| 16 | 3-Me-C6H4, OH |
| 17 | 4-Me-C6H4, OH |
| 18 | 3-OH-C6H4, OH |
| 19 | 3-OMe-C6H4, OH |
| 20 | 4-OMe-C6H4, OH |
| 21 | 3-OtBu-C6H4, OH |
| 22 | 3-OCF3-C6H4, OH |
| 23 | 3,4-methylenedioxy-C6H3, OH |
| 24 | 3-Br-C6H4, OH |
| 25 | 3-I-C6H4, OH |
| 26 | 3,5-Cl2-C6H3, OH |
| 27 | 3,4-Cl2-C6H3, OH |
| 28 | 3,4-F2-C6H3, OH |
| 29 | 2,3-F2-C6H3, OH |
| 30 | 3,5-F2-C6H3, OH |
| 31 | 2,5-F2-C6H3, OH |

TABLE 41-continued (IA19)

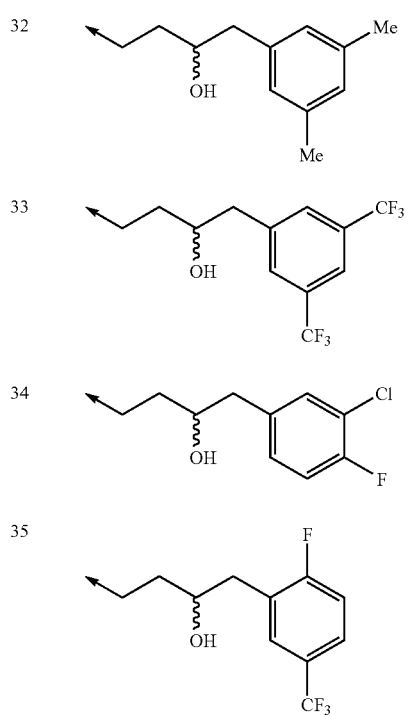

| No. | -X-E-W |
|---|---|
| 32 | 3,5-dimethylbenzyl-CH(OH)-CH2CH2- |
| 33 | 3,5-bis(CF3)benzyl-CH(OH)-CH2CH2- |
| 34 | 3-Cl-4-F-benzyl-CH(OH)-CH2CH2- |
| 35 | 2-F-5-CF3-benzyl-CH(OH)-CH2CH2- |

TABLE 42

(IA20)

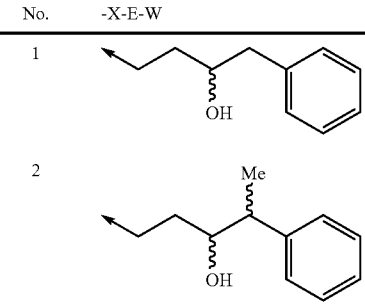

| No. | -X-E-W |
|---|---|
| 1 | benzyl-CH(OH)-CH2CH2- |
| 2 | α-methylbenzyl-CH(OH)-CH2CH2- |

TABLE 42-continued (IA20)

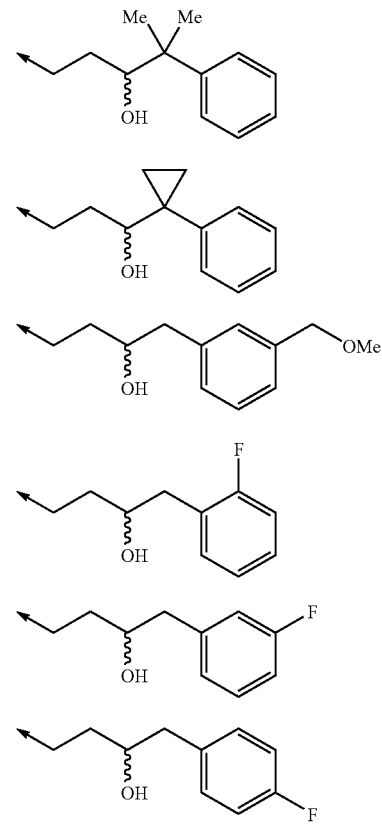

| No. | -X-E-W |
|---|---|
| 3 | α,α-dimethylbenzyl-CH(OH)-CH2CH2- |
| 4 | 1-phenylcyclopropyl-CH(OH)-CH2CH2- |
| 5 | 3-(methoxymethyl)benzyl-CH(OH)-CH2CH2- |
| 6 | 2-F-benzyl-CH(OH)-CH2CH2- |
| 7 | 3-F-benzyl-CH(OH)-CH2CH2- |
| 8 | 4-F-benzyl-CH(OH)-CH2CH2- |
| 9 | 2-Cl-benzyl-CH(OH)-CH2CH2- |
| 10 | 3-Cl-benzyl-CH(OH)-CH2CH2- |
| 11 | 4-Cl-benzyl-CH(OH)-CH2CH2- |
| 12 | 2-CF3-benzyl-CH(OH)-CH2CH2- |

TABLE 42-continued (IA20)

| No. | -X-E-W |
|---|---|
| 13 | 3-CF₃-C₆H₄-CH₂-CH(OH)-CH₂-CH₂- |
| 14 | 4-CF₃-C₆H₄-CH₂-CH(OH)-CH₂-CH₂- |
| 15 | 2-Me-C₆H₄-CH₂-CH(OH)-CH₂-CH₂- |
| 16 | 3-Me-C₆H₄-CH₂-CH(OH)-CH₂-CH₂- |
| 17 | 4-Me-C₆H₄-CH₂-CH(OH)-CH₂-CH₂- |
| 18 | 3-OH-C₆H₄-CH₂-CH(OH)-CH₂-CH₂- |
| 19 | 3-OMe-C₆H₄-CH₂-CH(OH)-CH₂-CH₂- |
| 20 | 4-OMe-C₆H₄-CH₂-CH(OH)-CH₂-CH₂- |
| 21 | 3-OC(Me)₃-C₆H₄-CH₂-CH(OH)-CH₂-CH₂- |
| 22 | 3-OCF₃-C₆H₄-CH₂-CH(OH)-CH₂-CH₂- |
| 23 | 3,4-(methylenedioxy)-C₆H₃-CH₂-CH(OH)-CH₂-CH₂- |

TABLE 42-continued (IA20)

| No. | -X-E-W |
|---|---|
| 24 | 3-Br-C₆H₄-CH₂-CH(OH)-CH₂-CH₂- |
| 25 | 3-I-C₆H₄-CH₂-CH(OH)-CH₂-CH₂- |
| 26 | 3,5-Cl₂-C₆H₃-CH₂-CH(OH)-CH₂-CH₂- |
| 27 | 3,4-Cl₂-C₆H₃-CH₂-CH(OH)-CH₂-CH₂- |
| 28 | 3,4-F₂-C₆H₃-CH₂-CH(OH)-CH₂-CH₂- |
| 29 | 2,3-F₂-C₆H₃-CH₂-CH(OH)-CH₂-CH₂- |
| 30 | 3,5-F₂-C₆H₃-CH₂-CH(OH)-CH₂-CH₂- |
| 31 | 2,5-F₂-C₆H₃-CH₂-CH(OH)-CH₂-CH₂- |
| 32 | 3,5-Me₂-C₆H₃-CH₂-CH(OH)-CH₂-CH₂- |

TABLE 42-continued (IA20)

| No. | -X-E-W |
|---|---|
| 33 | 3,5-bis(CF₃)-phenyl-CH₂-CH(OH)-CH₂-CH₂- |
| 34 | 3-Cl,4-F-phenyl-CH₂-CH(OH)-CH₂-CH₂- |
| 35 | 2-F,5-CF₃-phenyl-CH₂-CH(OH)-CH₂-CH₂- |

TABLE 43

(IA21)

| No. | -X-E-W |
|---|---|
| 1 | phenyl-CH₂-CH(OH)-CH₂-CH₂- |
| 2 | phenyl-CH(Me)-CH(OH)-CH₂-CH₂- |
| 3 | phenyl-C(Me)₂-CH(OH)-CH₂-CH₂- |

TABLE 43-continued (IA21)

| No. | -X-E-W |
|---|---|
| 4 | phenyl-C(cyclopropyl)-CH(OH)-CH₂-CH₂- |
| 5 | 3-(CH₂OMe)-phenyl-CH₂-CH(OH)-CH₂-CH₂- |
| 6 | 2-F-phenyl-CH₂-CH(OH)-CH₂-CH₂- |
| 7 | 3-F-phenyl-CH₂-CH(OH)-CH₂-CH₂- |
| 8 | 4-F-phenyl-CH₂-CH(OH)-CH₂-CH₂- |
| 9 | 2-Cl-phenyl-CH₂-CH(OH)-CH₂-CH₂- |
| 10 | 3-Cl-phenyl-CH₂-CH(OH)-CH₂-CH₂- |
| 11 | 4-Cl-phenyl-CH₂-CH(OH)-CH₂-CH₂- |
| 12 | 2-CF₃-phenyl-CH₂-CH(OH)-CH₂-CH₂- |
| 13 | 3-CF₃-phenyl-CH₂-CH(OH)-CH₂-CH₂- |

TABLE 43-continued (IA21)

| No. | -X-E-W |
|---|---|
| 14 | 4-CF3-benzyl, with OH on middle carbon |
| 15 | 2-Me-benzyl, with OH |
| 16 | 3-Me-benzyl, with OH |
| 17 | 4-Me-benzyl, with OH |
| 18 | 3-OH-benzyl, with OH |
| 19 | 3-OMe-benzyl, with OH |
| 20 | 4-OMe-benzyl, with OH |
| 21 | 3-OC(Me)3-benzyl, with OH |
| 22 | 3-OCF3-benzyl, with OH |
| 23 | 3,4-methylenedioxy-benzyl, with OH |
| 24 | 3-Br-benzyl, with OH |
| 25 | 3-I-benzyl, with OH |
| 26 | 3,5-diCl-benzyl, with OH |
| 27 | 3,4-diCl-benzyl, with OH |
| 28 | 3,4-diF-benzyl, with OH |
| 29 | 2,3-diF-benzyl, with OH |
| 30 | 3,5-diF-benzyl, with OH |
| 31 | 2,5-diF-benzyl, with OH |
| 32 | 3,5-diMe-benzyl, with OH |

TABLE 43-continued (IA21)

| No. | -X-E-W |
|---|---|
| 33 | 3,5-bis(CF₃)-benzyl, with -CH₂CH₂CH(OH)- linker |
| 34 | 3-Cl-4-F-benzyl, with -CH₂CH₂CH(OH)- linker |
| 35 | 2-F-5-CF₃-benzyl, with -CH₂CH₂CH(OH)- linker |

TABLE 44

(IA22)

| No. | -X-E-W |
|---|---|
| 1 | benzyl, with -CH₂CH₂CH(OH)- linker |
| 2 | α-methylbenzyl, with -CH₂CH₂CH(OH)- linker |
| 3 | α,α-dimethylbenzyl, with -CH₂CH₂CH(OH)- linker |

TABLE 44-continued (IA22)

| No. | -X-E-W |
|---|---|
| 4 | 1-phenylcyclopropylmethyl, with -CH₂CH₂CH(OH)- linker |
| 5 | 3-(methoxymethyl)benzyl, with -CH₂CH₂CH(OH)- linker |
| 6 | 2-F-benzyl, with -CH₂CH₂CH(OH)- linker |
| 7 | 3-F-benzyl, with -CH₂CH₂CH(OH)- linker |
| 8 | 4-F-benzyl, with -CH₂CH₂CH(OH)- linker |
| 9 | 2-Cl-benzyl, with -CH₂CH₂CH(OH)- linker |
| 10 | 3-Cl-benzyl, with -CH₂CH₂CH(OH)- linker |
| 11 | 4-Cl-benzyl, with -CH₂CH₂CH(OH)- linker |
| 12 | 2-CF₃-benzyl, with -CH₂CH₂CH(OH)- linker |
| 13 | 3-CF₃-benzyl, with -CH₂CH₂CH(OH)- linker |

TABLE 44-continued (IA22)

| No. | -X-E-W |
|-----|--------|
| 14  | 4-CF3-phenyl, with OH on chain |
| 15  | 2-Me-phenyl, with OH |
| 16  | 3-Me-phenyl, with OH |
| 17  | 4-Me-phenyl, with OH |
| 18  | 3-OH-phenyl, with OH |
| 19  | 3-OMe-phenyl, with OH |
| 20  | 4-OMe-phenyl, with OH |
| 21  | 3-OC(Me)3-phenyl, with OH |
| 22  | 3-OCF3-phenyl, with OH |
| 23  | benzo[1,3]dioxol-5-yl, with OH |
| 24  | 3-Br-phenyl, with OH |
| 25  | 3-I-phenyl, with OH |
| 26  | 3,5-diCl-phenyl, with OH |
| 27  | 3,4-diCl-phenyl, with OH |
| 28  | 3,4-diF-phenyl, with OH |
| 29  | 2,3-diF-phenyl, with OH |
| 30  | 3,5-diF-phenyl, with OH |
| 31  | 2,5-diF-phenyl, with OH |
| 32  | 3,5-diMe-phenyl, with OH |
| 33  | 3,5-di(CF3)-phenyl, with OH |

TABLE 44-continued
(IA22)
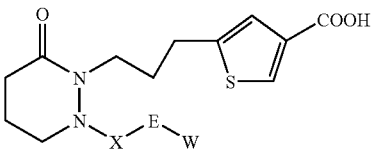
| No. | -X-E-W |
|---|---|
| 34 | 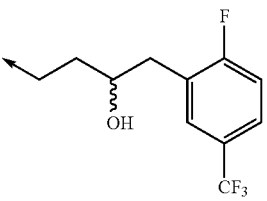 |
| 35 | 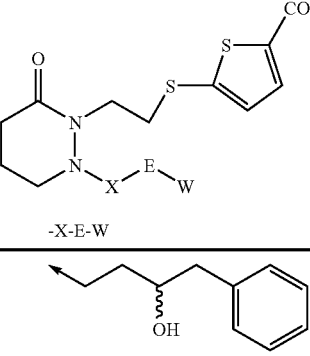 |
TABLE 45
(IA23)
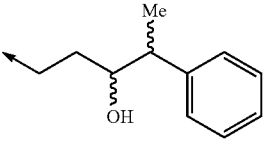
| No. | -X-E-W |
|---|---|
| 1 | 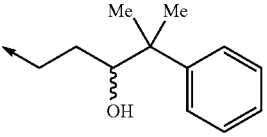 |
| 2 | 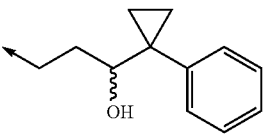 |
| 3 | 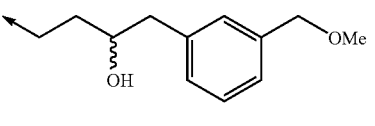 |
| 4 | 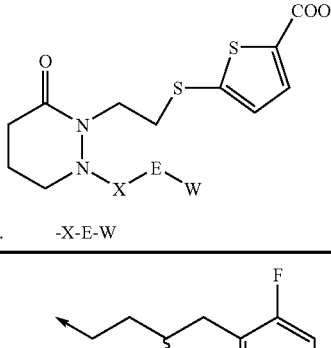 |
| 5 | 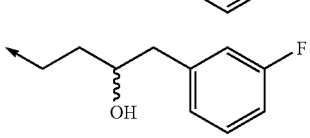 |
TABLE 45-continued
(IA23)
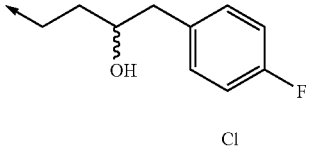
| No. | -X-E-W |
|---|---|
| 6 | 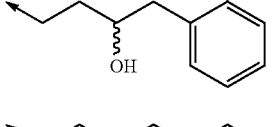 |
| 7 | 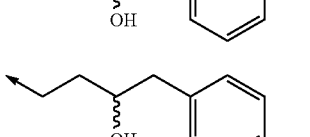 |
| 8 | 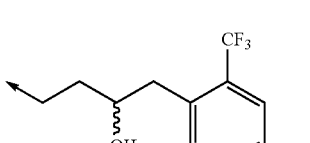 |
| 9 | 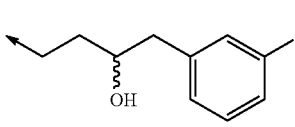 |
| 10 | 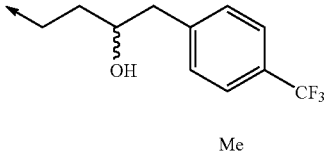 |
| 11 | 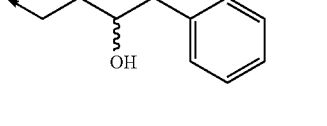 |
| 12 |  |
| 13 | |
| 14 | |
| 15 | |

TABLE 45-continued (IA23)

| No. | -X-E-W |
|---|---|
| 16 | 3-methylbenzyl, CH(OH) |
| 17 | 4-methylbenzyl, CH(OH) |
| 18 | 3-hydroxybenzyl, CH(OH) |
| 19 | 3-methoxybenzyl, CH(OH) |
| 20 | 4-methoxybenzyl, CH(OH) |
| 21 | 3-tert-butoxybenzyl, CH(OH) |
| 22 | 3-trifluoromethoxybenzyl, CH(OH) |
| 23 | 3,4-methylenedioxybenzyl, CH(OH) |
| 24 | 3-bromobenzyl, CH(OH) |
| 25 | 3-iodobenzyl, CH(OH) |
| 26 | 3,5-dichlorobenzyl, CH(OH) |

TABLE 45-continued (IA23)

| No. | -X-E-W |
|---|---|
| 27 | 3,4-dichlorobenzyl, CH(OH) |
| 28 | 3,4-difluorobenzyl, CH(OH) |
| 29 | 2,3-difluorobenzyl, CH(OH) |
| 30 | 3,5-difluorobenzyl, CH(OH) |
| 31 | 2,5-difluorobenzyl, CH(OH) |
| 32 | 3,5-dimethylbenzyl, CH(OH) |
| 33 | 3,5-bis(trifluoromethyl)benzyl, CH(OH) |
| 34 | 3-chloro-4-fluorobenzyl, CH(OH) |

TABLE 45-continued
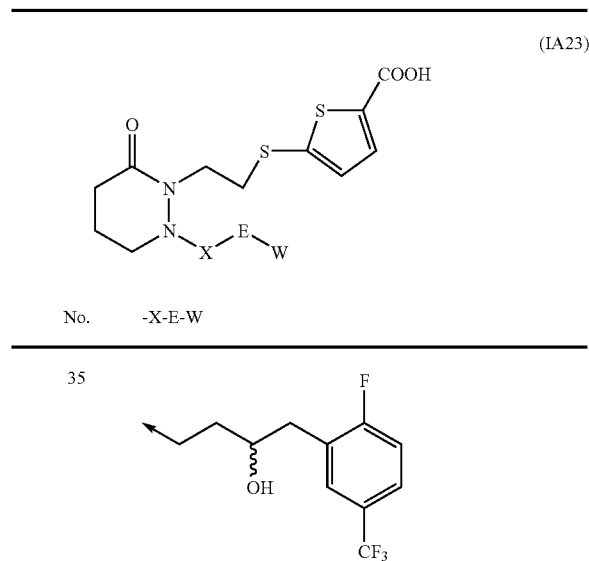
| No. | -X-E-W |
|---|---|
| 35 |  |
TABLE 46
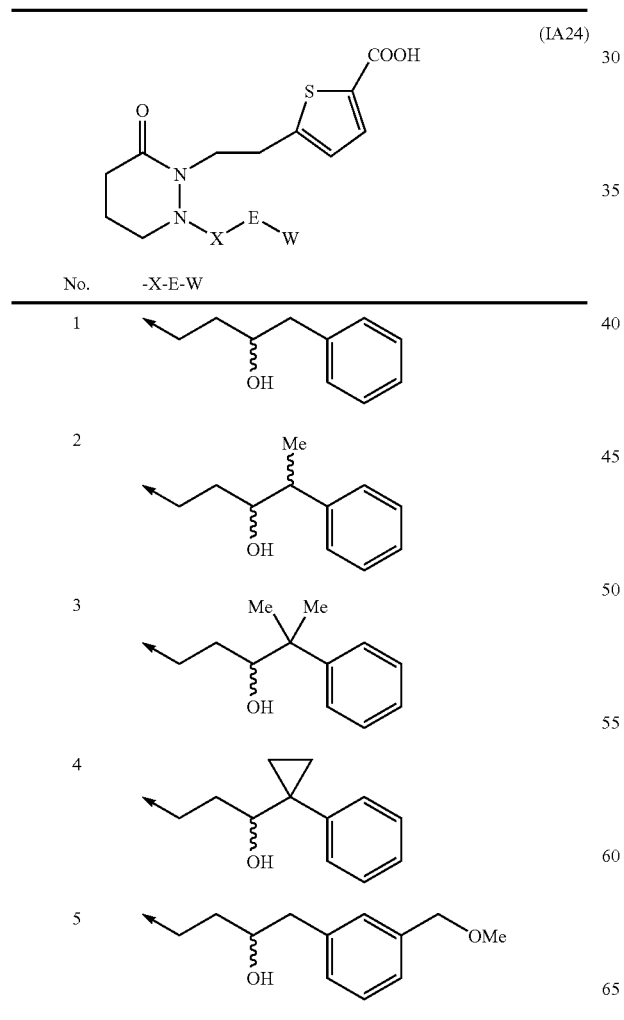
| No. | -X-E-W |
|---|---|
| 1 | 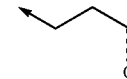 |
| 2 | 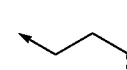 |
| 3 |  |
| 4 | 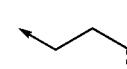 |
| 5 | 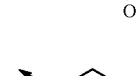 |
TABLE 46-continued
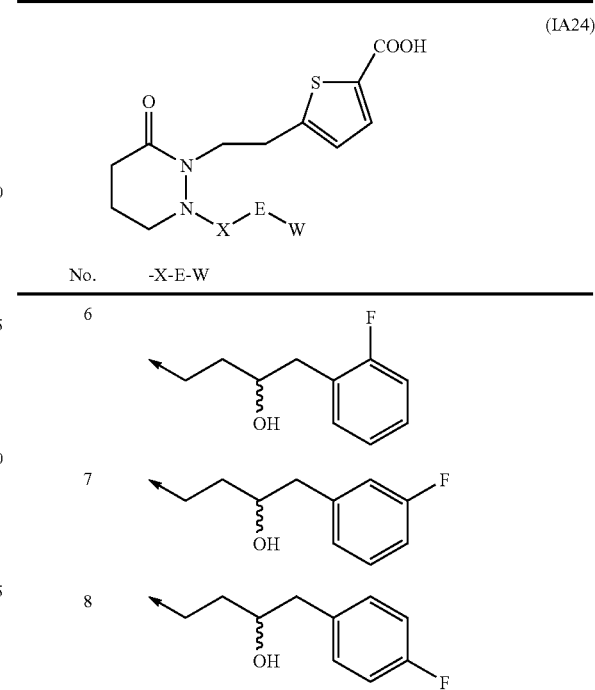
| No. | -X-E-W |
|---|---|
| 6 | |
| 7 | |
| 8 | |
| 9 | |
| 10 | |
| 11 | |
| 12 | |
| 13 | |
| 14 | |
| 15 | |

TABLE 46-continued (IA24)

| No. | -X-E-W |
|---|---|
| 16 | 3-Me-C6H4-CH2-CH(OH)-CH2CH2- |
| 17 | 4-Me-C6H4-CH2-CH(OH)-CH2CH2- |
| 18 | 3-OH-C6H4-CH2-CH(OH)-CH2CH2- |
| 19 | 3-OMe-C6H4-CH2-CH(OH)-CH2CH2- |
| 20 | 4-OMe-C6H4-CH2-CH(OH)-CH2CH2- |
| 21 | 3-OC(Me)3-C6H4-CH2-CH(OH)-CH2CH2- |
| 22 | 3-OCF3-C6H4-CH2-CH(OH)-CH2CH2- |
| 23 | 3,4-methylenedioxy-C6H3-CH2-CH(OH)-CH2CH2- |
| 24 | 3-Br-C6H4-CH2-CH(OH)-CH2CH2- |
| 25 | 3-I-C6H4-CH2-CH(OH)-CH2CH2- |
| 26 | 3,5-Cl2-C6H3-CH2-CH(OH)-CH2CH2- |
| 27 | 3,4-Cl2-C6H3-CH2-CH(OH)-CH2CH2- |
| 28 | 3,4-F2-C6H3-CH2-CH(OH)-CH2CH2- |
| 29 | 2,3-F2-C6H3-CH2-CH(OH)-CH2CH2- |
| 30 | 3,5-F2-C6H3-CH2-CH(OH)-CH2CH2- |
| 31 | 2,5-F2-C6H3-CH2-CH(OH)-CH2CH2- |
| 32 | 3,5-Me2-C6H3-CH2-CH(OH)-CH2CH2- |
| 33 | 3,5-(CF3)2-C6H3-CH2-CH(OH)-CH2CH2- |
| 34 | 3-Cl-4-F-C6H3-CH2-CH(OH)-CH2CH2- |

TABLE 46-continued (IA24)

| No. | -X-E-W |
|---|---|
| 35 | 2-fluoro-5-trifluoromethylbenzyl with OH |

TABLE 47

(IA25)

| No. | -X-E-W |
|---|---|
| 1 | phenyl with OH |
| 2 | phenyl with Me, OH |
| 3 | phenyl with Me, Me, OH |
| 4 | 1-phenylcyclopropyl with OH |
| 5 | 3-(methoxymethyl)phenyl with OH |

TABLE 47-continued (IA25)

| No. | -X-E-W |
|---|---|
| 6 | 2-fluorobenzyl with OH |
| 7 | 3-fluorobenzyl with OH |
| 8 | 4-fluorobenzyl with OH |
| 9 | 2-chlorobenzyl with OH |
| 10 | 3-chlorobenzyl with OH |
| 11 | 4-chlorobenzyl with OH |
| 12 | 2-trifluoromethylbenzyl with OH |
| 13 | 3-trifluoromethylbenzyl with OH |
| 14 | 4-trifluoromethylbenzyl with OH |
| 15 | 2-methylbenzyl with OH |

TABLE 47-continued
(IA25)
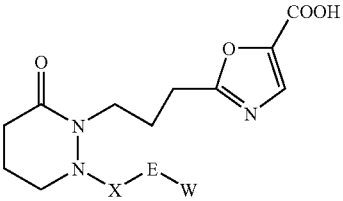
| No. | -X-E-W |
|---|---|
| 16 | 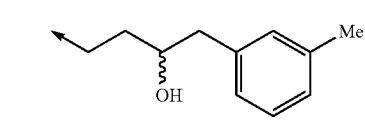 |
| 17 | 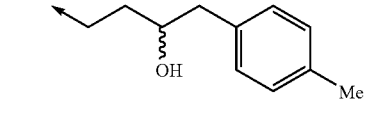 |
| 18 | 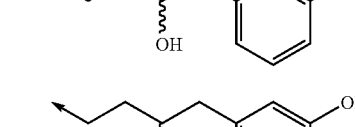 |
| 19 | 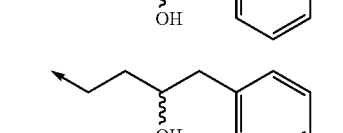 |
| 20 | 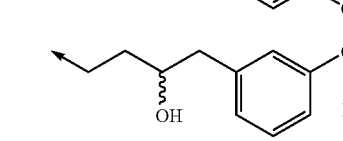 |
| 21 | 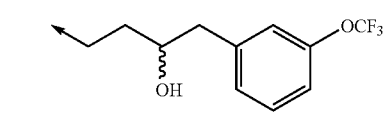 |
| 22 | 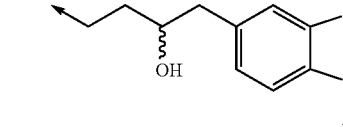 |
| 23 | 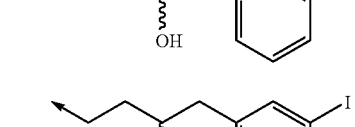 |
| 24 | 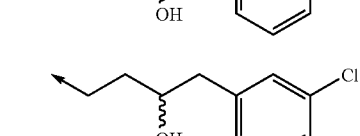 |
| 25 |  |
| 26 |  |
TABLE 47-continued
(IA25)
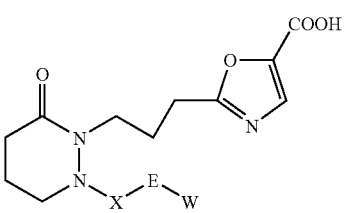
| No. | -X-E-W |
|---|---|
| 27 | 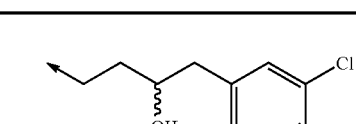 |
| 28 | 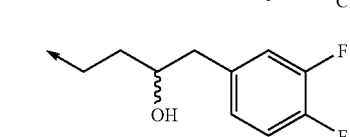 |
| 29 | 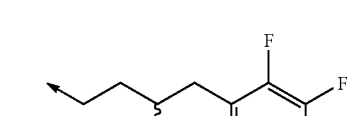 |
| 30 | 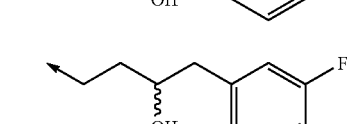 |
| 31 |  |
| 32 | 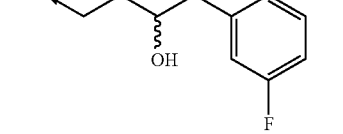 |
| 33 | 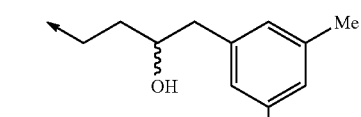 |
| 34 | 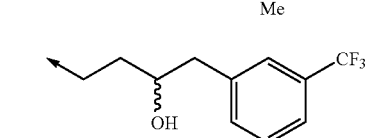 |

TABLE 47-continued (IA25)

| No. | -X-E-W |
|---|---|
| 35 | (2-F, 5-CF₃ benzyl with CH₂CH₂CH(OH)– linker) |

TABLE 48

(IA26)

| No. | -X-E-W |
|---|---|
| 1 | CH₂CH₂CH(OH)CH₂-phenyl |
| 2 | CH₂CH₂CH(OH)CH(Me)-phenyl |
| 3 | CH₂CH₂CH(OH)C(Me)₂-phenyl |
| 4 | CH₂CH₂CH(OH)-(1-phenylcyclopropyl) |
| 5 | CH₂CH₂CH(OH)CH₂-(3-OMe-benzyl) phenyl with 3-CH₂OMe |

TABLE 48-continued (IA26)

| No. | -X-E-W |
|---|---|
| 6 | CH₂CH₂CH(OH)CH₂-(2-F-phenyl) |
| 7 | CH₂CH₂CH(OH)CH₂-(3-F-phenyl) |
| 8 | CH₂CH₂CH(OH)CH₂-(4-F-phenyl) |
| 9 | CH₂CH₂CH(OH)CH₂-(2-Cl-phenyl) |
| 10 | CH₂CH₂CH(OH)CH₂-(3-Cl-phenyl) |
| 11 | CH₂CH₂CH(OH)CH₂-(4-Cl-phenyl) |
| 12 | CH₂CH₂CH(OH)CH₂-(2-CF₃-phenyl) |
| 13 | CH₂CH₂CH(OH)CH₂-(3-CF₃-phenyl) |
| 14 | CH₂CH₂CH(OH)CH₂-(4-CF₃-phenyl) |
| 15 | CH₂CH₂CH(OH)CH₂-(2-Me-phenyl) |

TABLE 48-continued (IA26)

| No. | -X-E-W |
|---|---|
| 16 | 3-Me-benzyl with OH |
| 17 | 4-Me-benzyl with OH |
| 18 | 3-OH-benzyl with OH |
| 19 | 3-OMe-benzyl with OH |
| 20 | 4-OMe-benzyl with OH |
| 21 | 3-OtBu-benzyl with OH |
| 22 | 3-OCF$_3$-benzyl with OH |
| 23 | 3,4-methylenedioxy-benzyl with OH |
| 24 | 3-Br-benzyl with OH |
| 25 | 3-I-benzyl with OH |
| 26 | 3,5-diCl-benzyl with OH |
| 27 | 3,4-diCl-benzyl with OH |
| 28 | 3,4-diF-benzyl with OH |
| 29 | 2,3-diF-benzyl with OH |
| 30 | 3,5-diF-benzyl with OH |
| 31 | 2,5-diF-benzyl with OH |
| 32 | 3,5-diMe-benzyl with OH |
| 33 | 3,5-di(CF$_3$)-benzyl with OH |
| 34 | 3-Cl-4-F-benzyl with OH |

TABLE 48-continued (IA26)

| No. | -X-E-W |
|---|---|
| 35 | 2-fluoro-5-(trifluoromethyl)benzyl with OH |

TABLE 49

(IA27)

| No. | -X-E-W |
|---|---|
| 1 | benzyl with OH |
| 2 | α-methylbenzyl with OH |
| 3 | α,α-dimethylbenzyl with OH |
| 4 | 1-phenylcyclopropyl with OH |
| 5 | 3-(methoxymethyl)benzyl with OH |

TABLE 49-continued (IA27)

| No. | -X-E-W |
|---|---|
| 6 | 2-fluorobenzyl with OH |
| 7 | 3-fluorobenzyl with OH |
| 8 | 4-fluorobenzyl with OH |
| 9 | 2-chlorobenzyl with OH |
| 10 | 3-chlorobenzyl with OH |
| 11 | 4-chlorobenzyl with OH |
| 12 | 2-(trifluoromethyl)benzyl with OH |
| 13 | 3-(trifluoromethyl)benzyl with OH |
| 14 | 4-(trifluoromethyl)benzyl with OH |
| 15 | 2-methylbenzyl with OH |

TABLE 49-continued (IA27)

| No. | -X-E-W |
|---|---|
| 16 | 3-methylbenzyl with OH |
| 17 | 4-methylbenzyl with OH |
| 18 | 3-hydroxybenzyl with OH |
| 19 | 3-methoxybenzyl with OH |
| 20 | 4-methoxybenzyl with OH |
| 21 | 3-tert-butoxybenzyl with OH |
| 22 | 3-trifluoromethoxybenzyl with OH |
| 23 | benzo[1,3]dioxol-5-ylmethyl with OH |
| 24 | 3-bromobenzyl with OH |
| 25 | 3-iodobenzyl with OH |
| 26 | 3,5-dichlorobenzyl with OH |

TABLE 49-continued (IA27)

| No. | -X-E-W |
|---|---|
| 27 | 3,4-dichlorobenzyl with OH |
| 28 | 3,4-difluorobenzyl with OH |
| 29 | 2,3-difluorobenzyl with OH |
| 30 | 3,5-difluorobenzyl with OH |
| 31 | 2,5-difluorobenzyl with OH |
| 32 | 3,5-dimethylbenzyl with OH |
| 33 | 3,5-bis(trifluoromethyl)benzyl with OH |
| 34 | 3-chloro-4-fluorobenzyl with OH |

TABLE 49-continued (IA27)

| No. | -X-E-W |
|---|---|
| 35 | (2-F, 5-CF₃ benzyl, OH chain) |

TABLE 50

(IA28)

| No. | -X-E-W |
|---|---|
| 1 | benzyl, OH chain |
| 2 | α-Me benzyl, OH chain |
| 3 | α,α-diMe benzyl, OH chain |
| 4 | 1-phenylcyclopropyl, OH chain |
| 5 | 3-(OMe-methyl)benzyl, OH chain |

TABLE 50-continued (IA28)

| No. | -X-E-W |
|---|---|
| 6 | 2-F benzyl, OH chain |
| 7 | 3-F benzyl, OH chain |
| 8 | 4-F benzyl, OH chain |
| 9 | 2-Cl benzyl, OH chain |
| 10 | 3-Cl benzyl, OH chain |
| 11 | 4-Cl benzyl, OH chain |
| 12 | 2-CF₃ benzyl, OH chain |
| 13 | 3-CF₃ benzyl, OH chain |
| 14 | 4-CF₃ benzyl, OH chain |
| 15 | 2-Me benzyl, OH chain |

TABLE 50-continued (IA28)

| No. | -X-E-W |
|---|---|
| 16 | 3-methylbenzyl with OH |
| 17 | 4-methylbenzyl with OH |
| 18 | 3-hydroxybenzyl with OH |
| 19 | 3-methoxybenzyl with OH |
| 20 | 4-methoxybenzyl with OH |
| 21 | 3-(tert-butoxy)benzyl with OH |
| 22 | 3-(trifluoromethoxy)benzyl with OH |
| 23 | benzo[1,3]dioxol-5-ylmethyl with OH |
| 24 | 3-bromobenzyl with OH |
| 25 | 3-iodobenzyl with OH |
| 26 | 3,5-dichlorobenzyl with OH |

TABLE 50-continued (IA28)

| No. | -X-E-W |
|---|---|
| 27 | 3,4-dichlorobenzyl with OH |
| 28 | 3,4-difluorobenzyl with OH |
| 29 | 2,3-difluorobenzyl with OH |
| 30 | 3,5-difluorobenzyl with OH |
| 31 | 2,5-difluorobenzyl with OH |
| 32 | 3,5-dimethylbenzyl with OH |
| 33 | 3,5-bis(trifluoromethyl)benzyl with OH |
| 34 | 3-chloro-4-fluorobenzyl with OH |

TABLE 50-continued (IA28)

| No. | -X-E-W |
|---|---|
| 35 | 2-F, 5-CF₃ benzyl, CH(OH), propyl linker |

TABLE 51

(IA29)

| No. | -X-E-W |
|---|---|
| 1 | benzyl, CH(OH), propyl linker |
| 2 | α-methylbenzyl, CH(OH), propyl linker |
| 3 | α,α-dimethylbenzyl, CH(OH), propyl linker |
| 4 | 1-phenylcyclopropyl, CH(OH), propyl linker |
| 5 | 3-(CH₂OMe)benzyl, CH(OH), propyl linker |
| 6 | 2-F benzyl, CH(OH), propyl linker |

TABLE 51-continued (IA29)

| No. | -X-E-W |
|---|---|
| 7 | 3-F benzyl, CH(OH), propyl linker |
| 8 | 4-F benzyl, CH(OH), propyl linker |
| 9 | 2-Cl benzyl, CH(OH), propyl linker |
| 10 | 3-Cl benzyl, CH(OH), propyl linker |
| 11 | 4-Cl benzyl, CH(OH), propyl linker |
| 12 | 2-CF₃ benzyl, CH(OH), propyl linker |
| 13 | 3-CF₃ benzyl, CH(OH), propyl linker |
| 14 | 4-CF₃ benzyl, CH(OH), propyl linker |
| 15 | 2-Me benzyl, CH(OH), propyl linker |
| 16 | 3-Me benzyl, CH(OH), propyl linker |

TABLE 51-continued (IA29)

| No. | -X-E-W |
|---|---|
| 17 | 4-methylbenzyl, with OH on chain |
| 18 | 3-hydroxybenzyl, with OH on chain |
| 19 | 3-methoxybenzyl, with OH on chain |
| 20 | 4-methoxybenzyl, with OH on chain |
| 21 | 3-(tert-butoxy)benzyl, with OH on chain |
| 22 | 3-(trifluoromethoxy)benzyl, with OH on chain |
| 23 | benzo[1,3]dioxol-5-ylmethyl, with OH on chain |
| 24 | 3-bromobenzyl, with OH on chain |
| 25 | 3-iodobenzyl, with OH on chain |
| 26 | 3,5-dichlorobenzyl, with OH on chain |
| 27 | 3,4-dichlorobenzyl, with OH on chain |

TABLE 51-continued (IA29)

| No. | -X-E-W |
|---|---|
| 28 | 3,4-difluorobenzyl, with OH on chain |
| 29 | 2,3-difluorobenzyl, with OH on chain |
| 30 | 3,5-difluorobenzyl, with OH on chain |
| 31 | 2,5-difluorobenzyl, with OH on chain |
| 32 | 3,5-dimethylbenzyl, with OH on chain |
| 33 | 3,5-bis(trifluoromethyl)benzyl, with OH on chain |
| 34 | 3-chloro-4-fluorobenzyl, with OH on chain |
| 35 | 2-fluoro-5-(trifluoromethyl)benzyl, with OH on chain |

TABLE 52

TABLE 52-continued
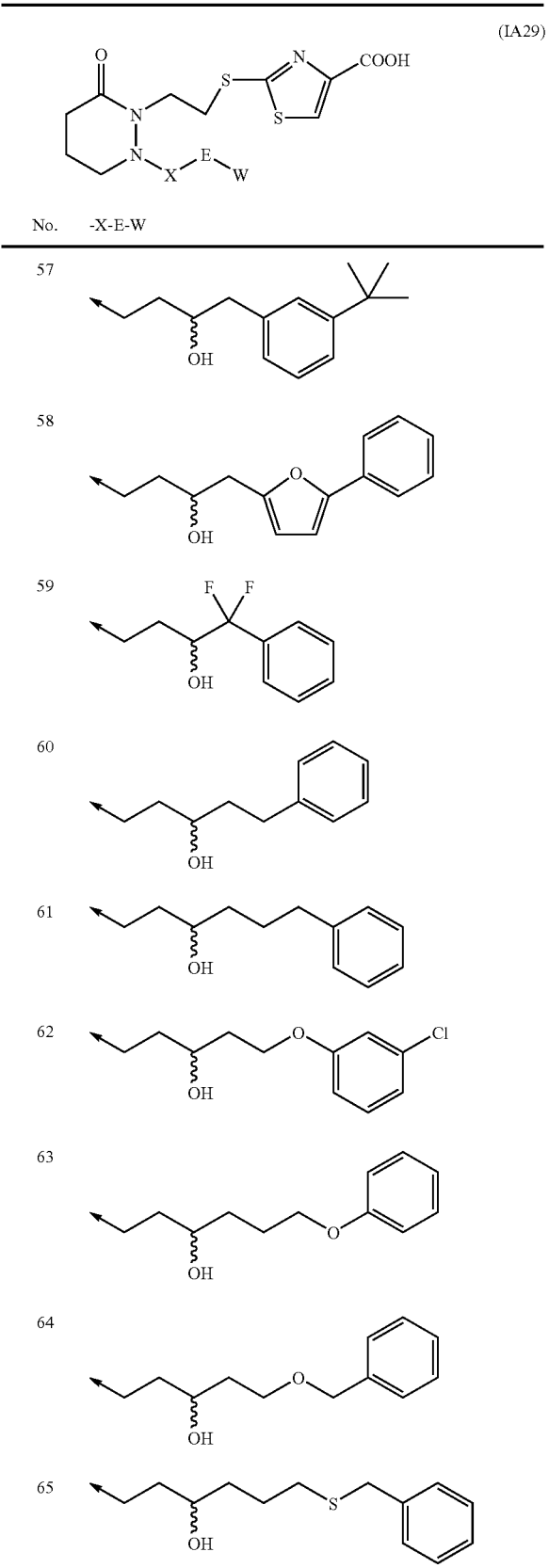
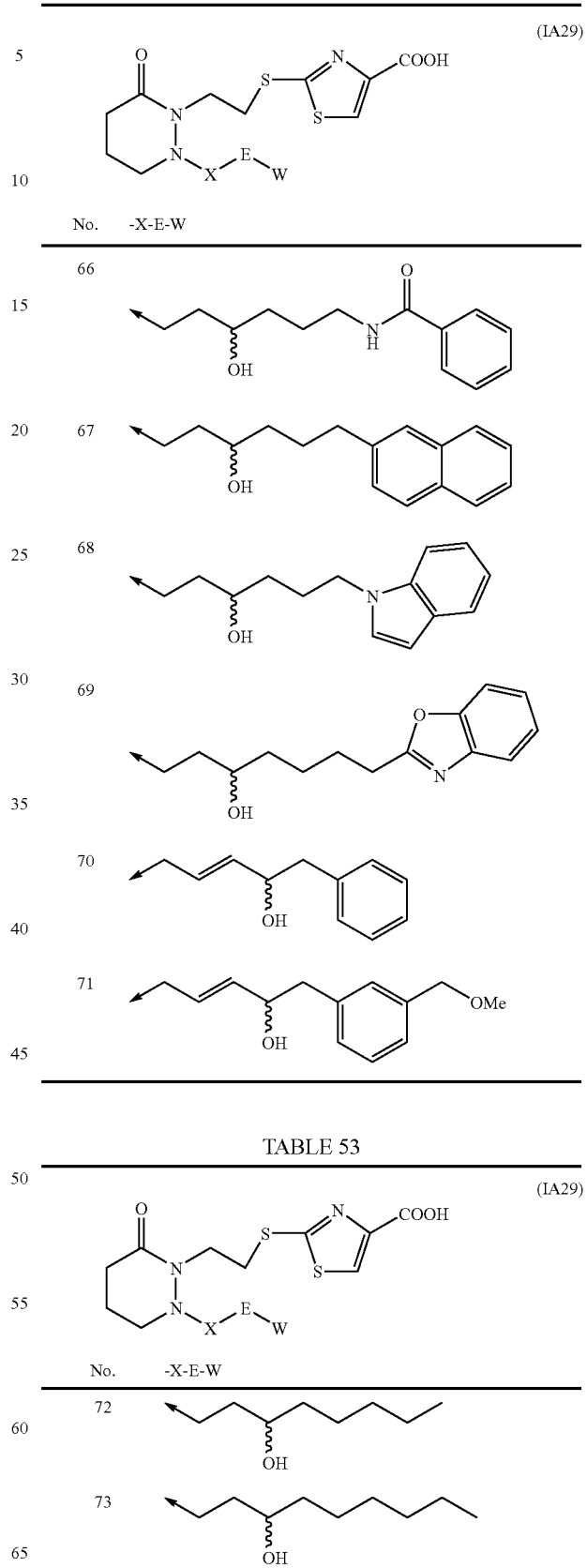
TABLE 53
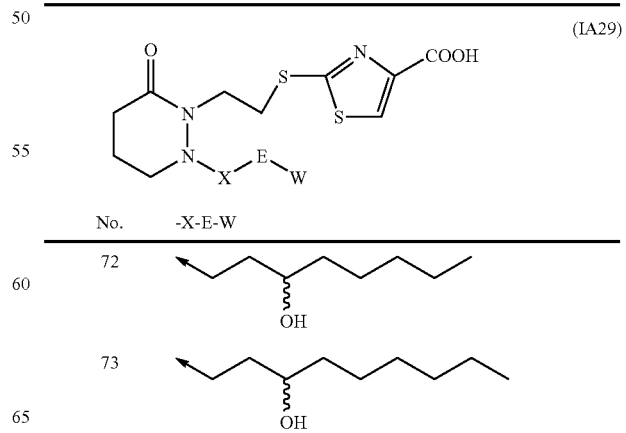

TABLE 53-continued
(IA29)
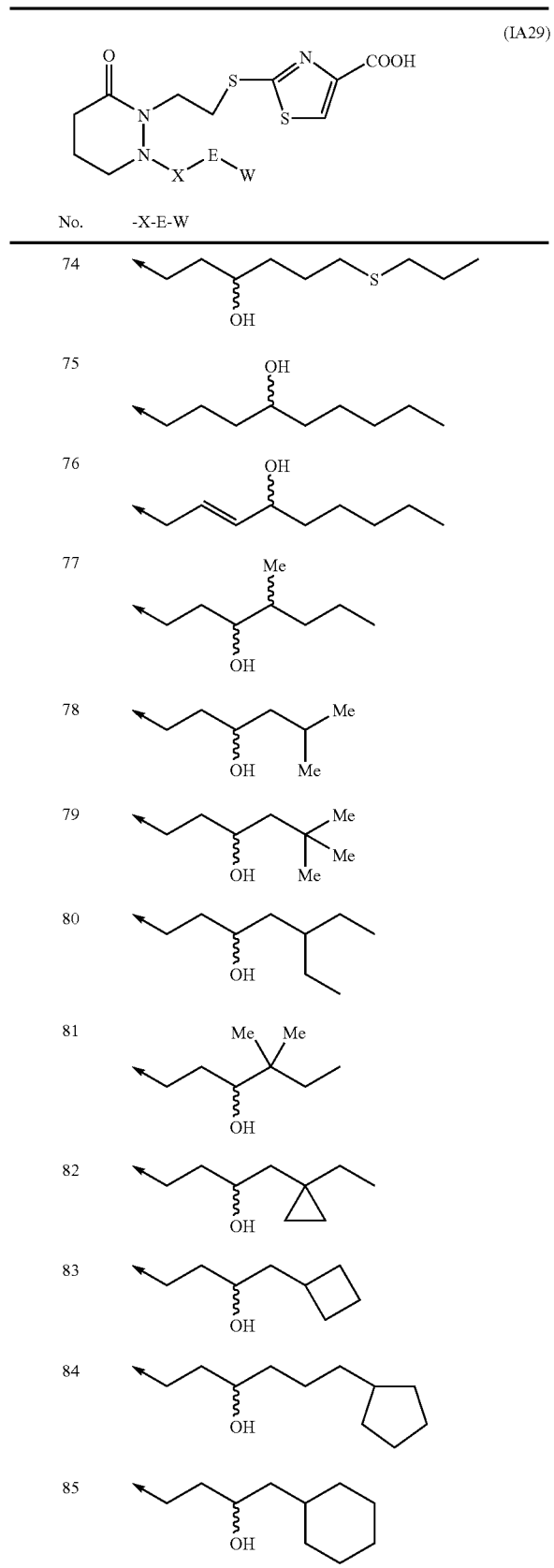
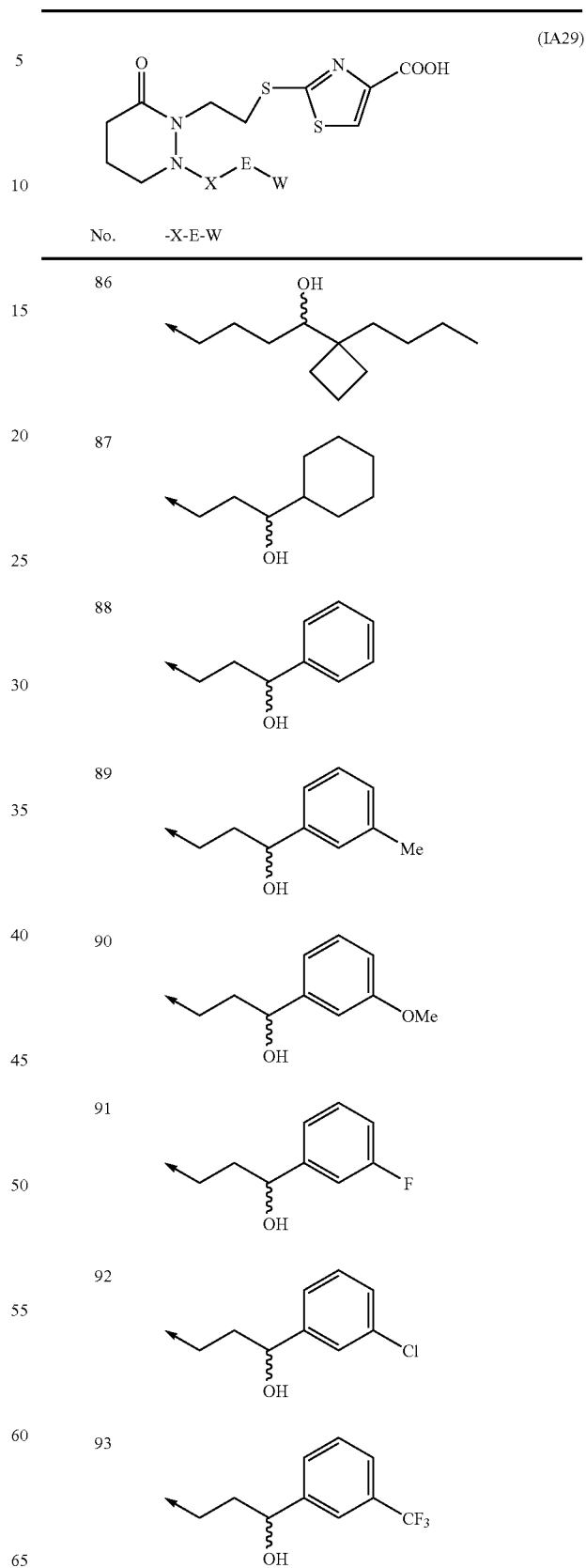

TABLE 53-continued (IA29)

No. -X-E-W

| No. | -X-E-W |
|-----|--------|
| 94  | 3-phenoxyphenyl, CH(OH)CH₂CH₂- |
| 95  | 2'-chloro-biphenyl-3-yl, CH(OH)CH₂CH₂- |
| 96  | 4'-chloro-2'-methyl-biphenyl-3-yl, CH(OH)CH₂CH₂- |
| 97  | 4'-hydroxy-2'-methyl-biphenyl-3-yl, CH(OH)CH₂CH₂- |
| 98  | 5-(trifluoromethyl)furan-2-yl, CH(OH)CH₂CH₂- |
| 99  | 3-methylphenyl, CH(OH)CH₂CH₂- |
| 100 | 3-fluorophenyl, CH(OH)CH₂CH₂- |
| 101 | 3-chlorophenyl, CH(OH)CH₂CH₂- |

TABLE 53-continued (IA29)

| No. | -X-E-W |
|-----|--------|
| 102 | 3-(trifluoromethyl)phenyl, CH(OH)CH₂CH₂- |
| 103 | 3-methylbenzyl, CH(OH)CH₂CH₂CH₂- |
| 104 | 3-fluorobenzyl, CH(OH)CH₂CH₂CH₂- |
| 105 | 3-chlorobenzyl, CH(OH)CH₂CH₂CH₂- |
| 106 | 3-(trifluoromethyl)benzyl, CH(OH)CH₂CH₂CH₂- |
| 107 | 3-methoxybenzyl, CH(OH)CH₂CH₂CH₂- |
| 108 | 3-(trifluoromethoxy)benzyl, CH(OH)CH₂CH₂CH₂- |

TABLE 54

(IA30)

| No. | -X-E-W |
|-----|--------|
| 1   | benzyl, CH(OH)CH₂CH₂- |

TABLE 54-continued (IA30)

| No. | -X-E-W |
|---|---|
| 2 | 4-hydroxy-5-phenylhexyl (with α-Me) |
| 3 | 4-hydroxy-5-methyl-5-phenylhexyl (gem-diMe) |
| 4 | 3-(1-phenylcyclopropyl)-2-hydroxypropyl |
| 5 | 2-hydroxy-4-[3-(methoxymethyl)phenyl]butyl |
| 6 | 2-hydroxy-4-(2-fluorophenyl)butyl |
| 7 | 2-hydroxy-4-(3-fluorophenyl)butyl |
| 8 | 2-hydroxy-4-(4-fluorophenyl)butyl |
| 9 | 2-hydroxy-4-(2-chlorophenyl)butyl |
| 10 | 2-hydroxy-4-(3-chlorophenyl)butyl |
| 11 | 2-hydroxy-4-(4-chlorophenyl)butyl |

TABLE 54-continued (IA30)

| No. | -X-E-W |
|---|---|
| 12 | 2-hydroxy-4-(2-trifluoromethylphenyl)butyl |
| 13 | 2-hydroxy-4-(3-trifluoromethylphenyl)butyl |
| 14 | 2-hydroxy-4-(4-trifluoromethylphenyl)butyl |
| 15 | 2-hydroxy-4-(2-methylphenyl)butyl |
| 16 | 2-hydroxy-4-(3-methylphenyl)butyl |
| 17 | 2-hydroxy-4-(4-methylphenyl)butyl |
| 18 | 2-hydroxy-4-(3-hydroxyphenyl)butyl |
| 19 | 2-hydroxy-4-(3-methoxyphenyl)butyl |
| 20 | 2-hydroxy-4-(4-methoxyphenyl)butyl |
| 21 | 2-hydroxy-4-[3-(tert-butoxy)phenyl]butyl |
| 22 | 2-hydroxy-4-(3-trifluoromethoxyphenyl)butyl |

TABLE 54-continued (IA30)

No. -X-E-W

| No. | -X-E-W |
|---|---|
| 23 | 3,4-methylenedioxybenzyl, CH(OH) |
| 24 | 3-Br-benzyl, CH(OH) |
| 25 | 3-I-benzyl, CH(OH) |
| 26 | 3,5-diCl-benzyl, CH(OH) |
| 27 | 3,4-diCl-benzyl, CH(OH) |
| 28 | 3,4-diF-benzyl, CH(OH) |
| 29 | 2,3-diF-benzyl, CH(OH) |
| 30 | 3,5-diF-benzyl, CH(OH) |
| 31 | 2,5-diF-benzyl, CH(OH) |

TABLE 54-continued (IA30)

| No. | -X-E-W |
|---|---|
| 32 | 3,5-diMe-benzyl, CH(OH) |
| 33 | 3,5-di(CF3)-benzyl, CH(OH) |
| 34 | 3-Cl-4-F-benzyl, CH(OH) |
| 35 | 2-F-5-CF3-benzyl, CH(OH) |

TABLE 55

(IA31)

| No. | -X-E-W |
|---|---|
| 1 | benzyl, CH(OH) |
| 2 | α-methylbenzyl, CH(OH) |

TABLE 55-continued (IA31)

| No. | -X-E-W |
|---|---|
| 3 | 1-hydroxy-3-methyl-3-phenylbutyl (Me, Me, OH, phenyl) |
| 4 | 1-hydroxy-3-(1-phenylcyclopropyl)propyl |
| 5 | 1-hydroxy-3-(3-(methoxymethyl)phenyl)propyl |
| 6 | 1-hydroxy-3-(2-fluorophenyl)propyl |
| 7 | 1-hydroxy-3-(3-fluorophenyl)propyl |
| 8 | 1-hydroxy-3-(4-fluorophenyl)propyl |
| 9 | 1-hydroxy-3-(2-chlorophenyl)propyl |
| 10 | 1-hydroxy-3-(3-chlorophenyl)propyl |
| 11 | 1-hydroxy-3-(4-chlorophenyl)propyl |

TABLE 55-continued (IA31)

| No. | -X-E-W |
|---|---|
| 12 | 1-hydroxy-3-(2-(trifluoromethyl)phenyl)propyl |
| 13 | 1-hydroxy-3-(3-(trifluoromethyl)phenyl)propyl |
| 14 | 1-hydroxy-3-(4-(trifluoromethyl)phenyl)propyl |
| 15 | 1-hydroxy-3-(2-methylphenyl)propyl |
| 16 | 1-hydroxy-3-(3-methylphenyl)propyl |
| 17 | 1-hydroxy-3-(4-methylphenyl)propyl |
| 18 | 1-hydroxy-3-(3-hydroxyphenyl)propyl |
| 19 | 1-hydroxy-3-(3-methoxyphenyl)propyl |
| 20 | 1-hydroxy-3-(4-methoxyphenyl)propyl |
| 21 | 1-hydroxy-3-(3-tert-butoxyphenyl)propyl |

TABLE 55-continued
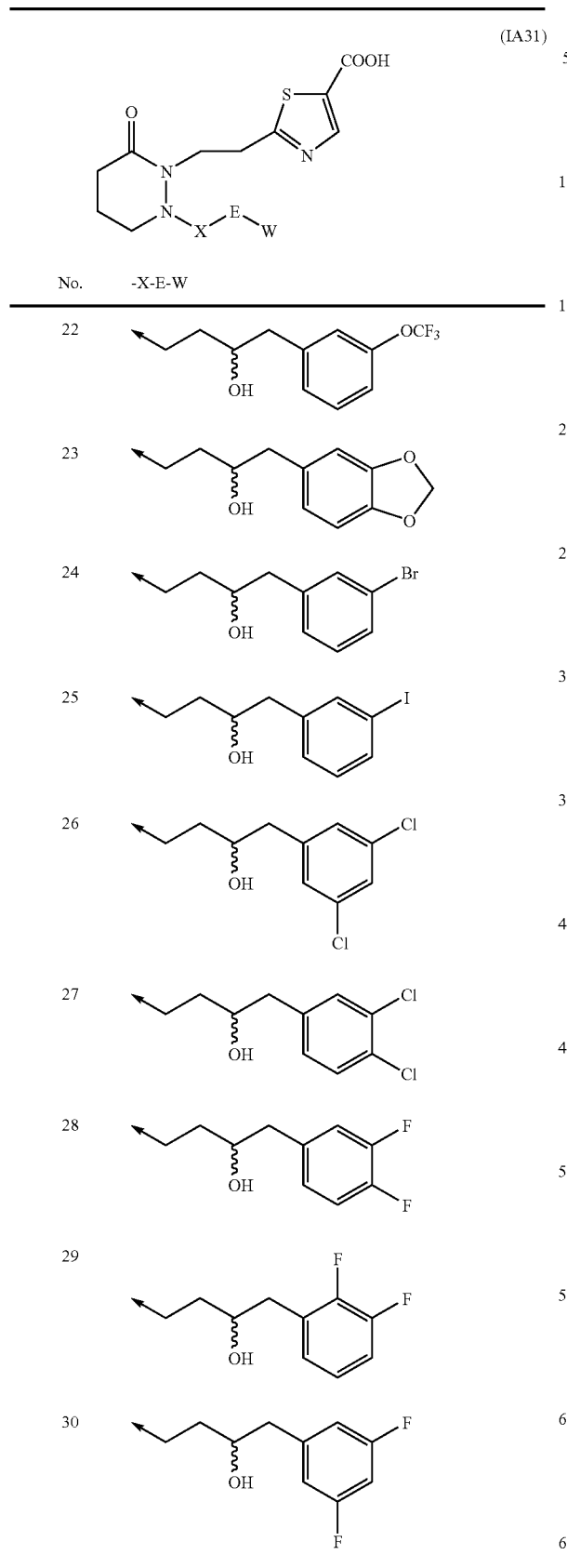
TABLE 55-continued
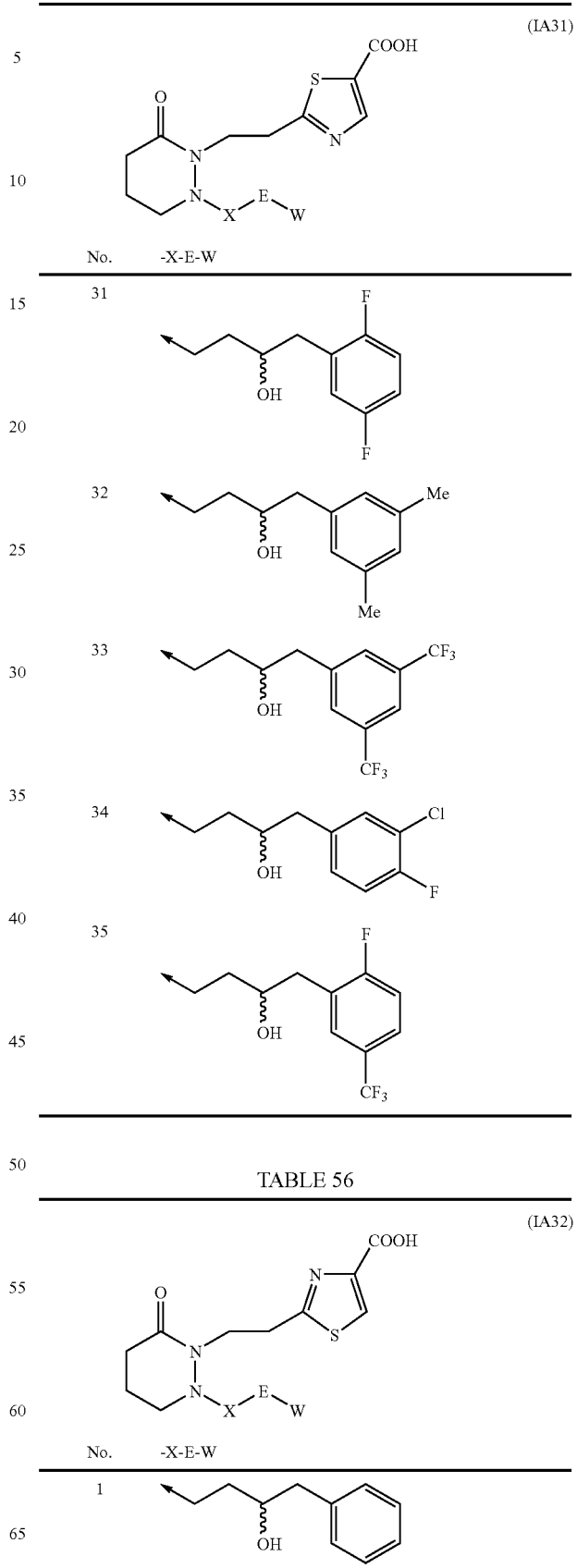

TABLE 56-continued (IA32)

| No. | -X-E-W |
|---|---|
| 2 | -CH2CH2CH(OH)CH(Me)-phenyl |
| 3 | -CH2CH2CH(OH)C(Me)2-phenyl |
| 4 | -CH2CH2CH(OH)-(1-phenylcyclopropyl) |
| 5 | -CH2CH2CH(OH)CH2-(3-CH2OMe-phenyl) |
| 6 | -CH2CH2CH(OH)CH2-(2-F-phenyl) |
| 7 | -CH2CH2CH(OH)CH2-(3-F-phenyl) |
| 8 | -CH2CH2CH(OH)CH2-(4-F-phenyl) |
| 9 | -CH2CH2CH(OH)CH2-(2-Cl-phenyl) |
| 10 | -CH2CH2CH(OH)CH2-(3-Cl-phenyl) |
| 11 | -CH2CH2CH(OH)CH2-(4-Cl-phenyl) |
| 12 | -CH2CH2CH(OH)CH2-(2-CF3-phenyl) |
| 13 | -CH2CH2CH(OH)CH2-(3-CF3-phenyl) |
| 14 | -CH2CH2CH(OH)CH2-(4-CF3-phenyl) |
| 15 | -CH2CH2CH(OH)CH2-(2-Me-phenyl) |
| 16 | -CH2CH2CH(OH)CH2-(3-Me-phenyl) |
| 17 | -CH2CH2CH(OH)CH2-(4-Me-phenyl) |
| 18 | -CH2CH2CH(OH)CH2-(3-OH-phenyl) |
| 19 | -CH2CH2CH(OH)CH2-(3-OMe-phenyl) |
| 20 | -CH2CH2CH(OH)CH2-(4-OMe-phenyl) |

TABLE 56-continued (IA32)

| No. | -X-E-W |
|---|---|
| 21 | 3-(tert-butoxy)benzyl with OH on chain |
| 22 | 3-(OCF₃)benzyl with OH on chain |
| 23 | benzo[1,3]dioxol-5-ylmethyl with OH on chain |
| 24 | 3-bromobenzyl with OH on chain |
| 25 | 3-iodobenzyl with OH on chain |
| 26 | 3,5-dichlorobenzyl with OH on chain |
| 27 | 3,4-dichlorobenzyl with OH on chain |
| 28 | 3,4-difluorobenzyl with OH on chain |
| 29 | 2,3-difluorobenzyl with OH on chain |
| 30 | 3,5-difluorobenzyl with OH on chain |

TABLE 56-continued (IA32)

| No. | -X-E-W |
|---|---|
| 31 | 2,5-difluorobenzyl with OH on chain |
| 32 | 3,5-dimethylbenzyl with OH on chain |
| 33 | 3,5-bis(CF₃)benzyl with OH on chain |
| 34 | 3-chloro-4-fluorobenzyl with OH on chain |
| 35 | 2-fluoro-5-(CF₃)benzyl with OH on chain |

TABLE 57

(IE1)

| No. | -X-E-W |
|---|---|
| 1 | benzyl with OH on chain |

TABLE 57-continued (IE1)

| No. | -X-E-W |
|---|---|
| 2 | CH(Me)Ph with CH₂CH₂CH(OH) linker |
| 3 | C(Me)₂Ph with CH₂CH₂CH(OH) linker |
| 4 | 1-phenylcyclopropyl with CH₂CH₂CH(OH) linker |
| 5 | 3-(MeOCH₂)phenyl-CH₂- with CH₂CH₂CH(OH) linker |
| 6 | 2-F-C₆H₄-CH₂- with CH₂CH₂CH(OH) linker |
| 7 | 3-F-C₆H₄-CH₂- with CH₂CH₂CH(OH) linker |
| 8 | 4-F-C₆H₄-CH₂- with CH₂CH₂CH(OH) linker |
| 9 | 2-Cl-C₆H₄-CH₂- with CH₂CH₂CH(OH) linker |
| 10 | 3-Cl-C₆H₄-CH₂- with CH₂CH₂CH(OH) linker |
| 11 | 4-Cl-C₆H₄-CH₂- with CH₂CH₂CH(OH) linker |

TABLE 57-continued (IE1)

| No. | -X-E-W |
|---|---|
| 12 | 2-CF₃-C₆H₄-CH₂- with CH₂CH₂CH(OH) linker |
| 13 | 3-CF₃-C₆H₄-CH₂- with CH₂CH₂CH(OH) linker |
| 14 | 4-CF₃-C₆H₄-CH₂- with CH₂CH₂CH(OH) linker |
| 15 | 2-Me-C₆H₄-CH₂- with CH₂CH₂CH(OH) linker |
| 16 | 3-Me-C₆H₄-CH₂- with CH₂CH₂CH(OH) linker |
| 17 | 4-Me-C₆H₄-CH₂- with CH₂CH₂CH(OH) linker |
| 18 | 3-OH-C₆H₄-CH₂- with CH₂CH₂CH(OH) linker |
| 19 | 3-OMe-C₆H₄-CH₂- with CH₂CH₂CH(OH) linker |
| 20 | 4-OMe-C₆H₄-CH₂- with CH₂CH₂CH(OH) linker |
| 21 | 3-OC(Me)₃-C₆H₄-CH₂- with CH₂CH₂CH(OH) linker |
| 22 | 3-OCF₃-C₆H₄-CH₂- with CH₂CH₂CH(OH) linker |

TABLE 57-continued (IE1)

| No. | -X-E-W |
|-----|--------|
| 23 | 3,4-methylenedioxybenzyl, CH(OH)CH2CH2– |
| 24 | 3-bromobenzyl, CH(OH)CH2CH2– |
| 25 | 3-iodobenzyl, CH(OH)CH2CH2– |
| 26 | 3,5-dichlorobenzyl, CH(OH)CH2CH2– |
| 27 | 3,4-dichlorobenzyl, CH(OH)CH2CH2– |
| 28 | 3,4-difluorobenzyl, CH(OH)CH2CH2– |
| 29 | 2,3-difluorobenzyl, CH(OH)CH2CH2– |
| 30 | 3,5-difluorobenzyl, CH(OH)CH2CH2– |
| 31 | 2,5-difluorobenzyl, CH(OH)CH2CH2– |

TABLE 57-continued (IE1)

| No. | -X-E-W |
|-----|--------|
| 32 | 3,5-dimethylbenzyl, CH(OH)CH2CH2– |
| 33 | 3,5-bis(trifluoromethyl)benzyl, CH(OH)CH2CH2– |
| 34 | 3-chloro-4-fluorobenzyl, CH(OH)CH2CH2– |
| 35 | 2-fluoro-5-(trifluoromethyl)benzyl, CH(OH)CH2CH2– |

TABLE 58

(IE1)

| No. | -X-E-W |
|-----|--------|
| 36 | 3-phenoxybenzyl, CH(OH)CH2CH2– |
| 37 | biphenyl-3-ylmethyl, CH(OH)CH2CH2– |

TABLE 58-continued (IE1)

| No. | -X-E-W |
|-----|--------|
| 38 | 2-chlorobiphenyl-3-yl with CH(OH) linker |
| 39 | naphthalen-2-yl with CH(OH) linker |
| 40 | naphthalen-1-yl with CH(OH) linker |
| 41 | furan-2-yl with CH(OH) linker |
| 42 | thiophen-2-yl with CH(OH) linker |
| 43 | 5-(trifluoromethyl)thiophen-2-yl with CH(OH) linker |
| 44 | pyridin-2-yl with CH(OH) linker |
| 45 | benzofuran-5-yl with CH(OH) linker |
| 46 | benzothiophen-5-yl with CH(OH) linker |
| 47 | benzoxazol-6-yl with CH(OH) linker |
| 48 | benzothiazol-6-yl with CH(OH) linker |

TABLE 58-continued (IE1)

| No. | -X-E-W |
|-----|--------|
| 49 | 1H-benzimidazol-5-yl with CH(OH) linker |
| 50 | 1H-indol-5-yl with CH(OH) linker |
| 51 | 1-methyl-1H-indol-5-yl with CH(OH) linker |
| 52 | 1-methyl-1H-indol-6-yl with CH(OH) linker |
| 53 | 1H-indazol-5-yl with CH(OH) linker |
| 54 | 1-methyl-1H-indazol-5-yl with CH(OH) linker |
| 55 | quinolin-6-yl with CH(OH) linker |
| 56 | isoquinolin-6-yl with CH(OH) linker |
| 57 | 3-tert-butylphenyl with CH(OH) linker |
| 58 | 5-phenylfuran-2-yl with CH(OH) linker |

TABLE 58-continued
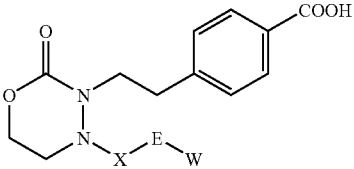
| No. | -X-E-W |
|---|---|
| 59 | |
| 60 | |
| 61 | |
| 62 | |
| 63 | |
| 64 | |
| 65 | |
| 66 | |
| 67 | |
| 68 | |
TABLE 58-continued
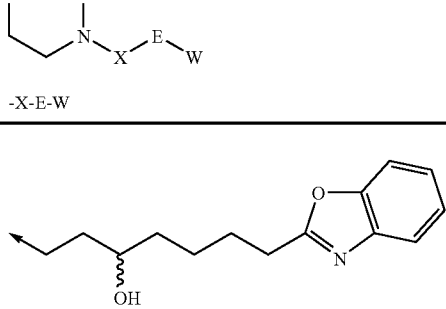
| No. | -X-E-W |
|---|---|
| 69 | |
| 70 | |
| 71 | |
TABLE 59
| No. | -X-E-W |
|---|---|
| 72 | |
| 73 | |
| 74 | |
| 75 | |
| 76 | |
| 77 | |

TABLE 59-continued

| No. | -X-E-W |
|---|---|
| 78 | CH2CH2CH(OH)CH2CH(Me)2 |
| 79 | CH2CH2CH(OH)CH2C(Me)3 |
| 80 | CH2CH2CH(OH)CH(Et)2 |
| 81 | CH2CH2CH(OH)C(Me)2Et |
| 82 | CH2CH2CH(OH)CH2-(1-ethylcyclopropyl) |
| 83 | CH2CH2CH(OH)CH2-cyclobutyl |
| 84 | CH2CH2CH(OH)CH2CH2-cyclopentyl |
| 85 | CH2CH2CH(OH)CH2-cyclohexyl |
| 86 | CH2CH2CH2-C(OH)(Bu)-cyclobutyl |
| 87 | CH2CH2CH(OH)-cyclohexyl |
| 88 | CH2CH2CH(OH)-phenyl |
| 89 | CH2CH2CH(OH)-(3-methylphenyl) |
| 90 | CH2CH2CH(OH)-(3-methoxyphenyl) |
| 91 | CH2CH2CH(OH)-(3-fluorophenyl) |
| 92 | CH2CH2CH(OH)-(3-chlorophenyl) |
| 93 | CH2CH2CH(OH)-(3-trifluoromethylphenyl) |
| 94 | CH2CH2CH(OH)-(3-phenoxyphenyl) |
| 95 | CH2CH2CH(OH)-(2'-chlorobiphenyl-3-yl) |
| 96 | CH2CH2CH(OH)-(2'-methyl-4'-chlorobiphenyl-3-yl) |

TABLE 59-continued (IE1)

| No. | -X-E-W |
|---|---|
| 97 | 3-(2-methyl-4-hydroxyphenyl)phenyl CH(OH)CH2CH2- |
| 98 | 5-(CF3)furan-2-yl CH(OH)CH2CH2- |
| 99 | (S)-3-Me-C6H4-CH(OH)CH2CH2- |
| 100 | (S)-3-F-C6H4-CH(OH)CH2CH2- |
| 101 | (S)-3-Cl-C6H4-CH(OH)CH2CH2- |
| 102 | (S)-3-CF3-C6H4-CH(OH)CH2CH2- |
| 103 | (S)-3-Me-C6H4-CH2-CH(OH)CH2CH2- |
| 104 | (S)-3-F-C6H4-CH2-CH(OH)CH2CH2- |
| 105 | (S)-3-Cl-C6H4-CH2-CH(OH)CH2CH2- |

TABLE 59-continued (IE1)

| No. | -X-E-W |
|---|---|
| 106 | (S)-3-CF3-C6H4-CH2-CH(OH)CH2CH2- |
| 107 | (S)-3-OMe-C6H4-CH2-CH(OH)CH2CH2- |
| 108 | (S)-3-OCF3-C6H4-CH2-CH(OH)CH2CH2- |

TABLE 60

(IE2)

| No. | -X-E-W |
|---|---|
| 1 | (S)-PhCH2-CH(OH)CH2CH2- |
| 2 | Ph-CH(Me)-CH(OH)CH2CH2- |
| 3 | Ph-C(Me)2-CH(OH)CH2CH2- |
| 4 | Ph-C(cyclopropyl)-CH(OH)CH2CH2- |
| 5 | (S)-3-(CH2OMe)-C6H4-CH2-CH(OH)CH2CH2- |

TABLE 60-continued
(IE2)
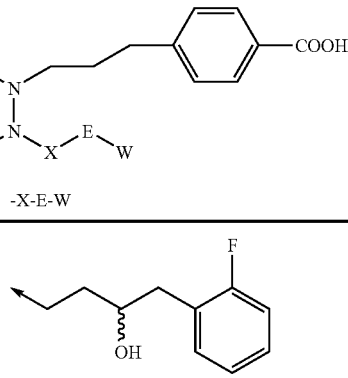
| No. | -X-E-W |
|---|---|
| 6 | 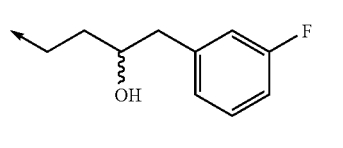 |
| 7 | 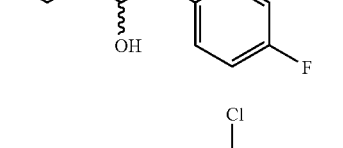 |
| 8 | 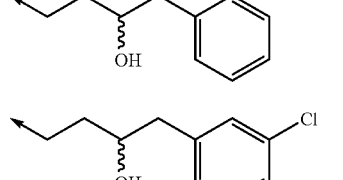 |
| 9 | 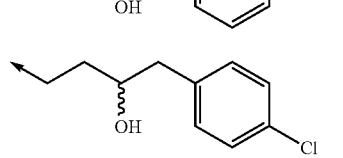 |
| 10 | 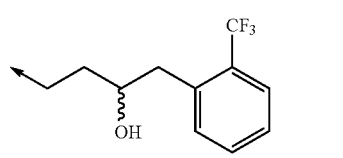 |
| 11 | 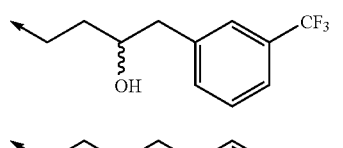 |
| 12 | 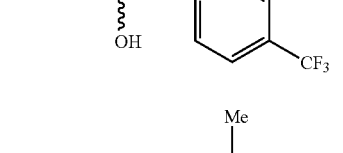 |
| 13 | 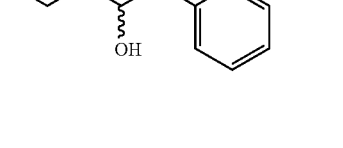 |
| 14 |  |
| 15 | 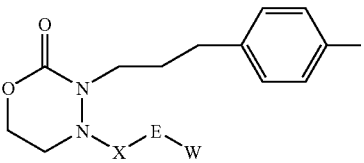 |
TABLE 60-continued
(IE2)
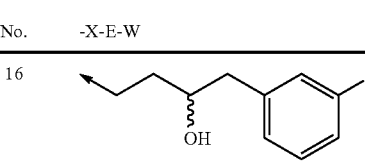
| No. | -X-E-W |
|---|---|
| 16 | 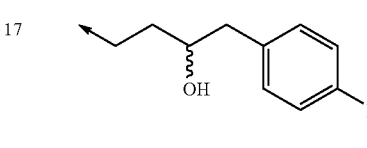 |
| 17 | 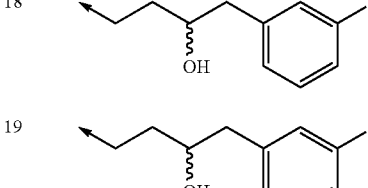 |
| 18 | 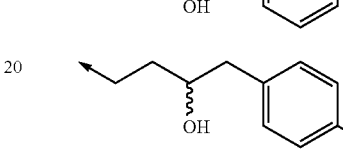 |
| 19 | 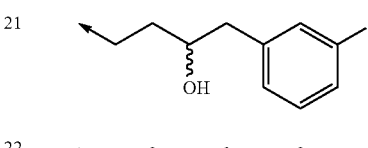 |
| 20 | 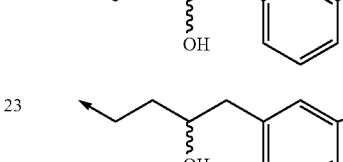 |
| 21 | 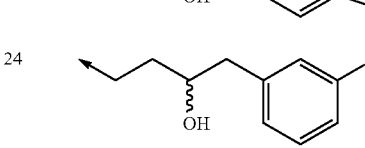 |
| 22 | 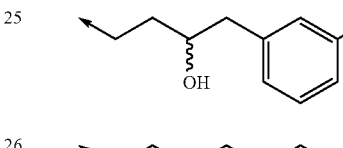 |
| 23 | 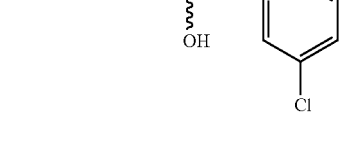 |
| 24 |  |
| 25 | |
| 26 | |

TABLE 60-continued (IE2)

| No. | -X-E-W |
|---|---|
| 27 | 3,4-dichlorophenyl, CH₂CH₂CH(OH)CH₂- |
| 28 | 3,4-difluorophenyl, CH₂CH₂CH(OH)CH₂- |
| 29 | 2,3-difluorophenyl, CH₂CH₂CH(OH)CH₂- |
| 30 | 3,5-difluorophenyl, CH₂CH₂CH(OH)CH₂- |
| 31 | 2,5-difluorophenyl, CH₂CH₂CH(OH)CH₂- |
| 32 | 3,5-dimethylphenyl, CH₂CH₂CH(OH)CH₂- |
| 33 | 3,5-bis(CF₃)phenyl, CH₂CH₂CH(OH)CH₂- |
| 34 | 3-Cl-4-F-phenyl, CH₂CH₂CH(OH)CH₂- |

TABLE 60-continued (IE2)

| No. | -X-E-W |
|---|---|
| 35 | 2-F-5-CF₃-phenyl, CH₂CH₂CH(OH)CH₂- |

TABLE 61

(IE3)

| No. | -X-E-W |
|---|---|
| 1 | phenyl, CH₂CH₂CH(OH)CH₂- |
| 2 | phenyl, CH₂CH₂CH(OH)CH(Me)- |
| 3 | phenyl, CH₂CH₂CH(OH)C(Me)₂- |
| 4 | 1-phenylcyclopropyl, CH₂CH₂CH(OH)- |
| 5 | 3-(CH₂OMe)phenyl, CH₂CH₂CH(OH)CH₂- |
| 6 | 2-fluorophenyl, CH₂CH₂CH(OH)CH₂- |

TABLE 61-continued
(IE3)
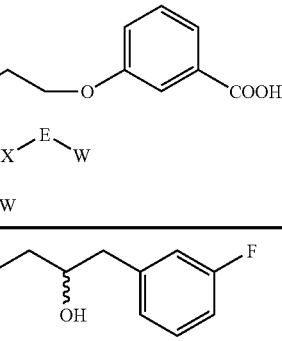
| No. | -X-E-W |
|---|---|
| 7 | 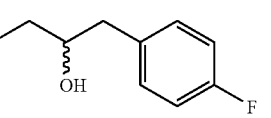 |
| 8 | 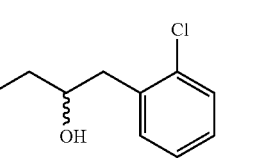 |
| 9 | 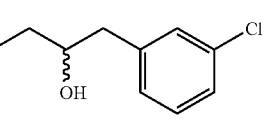 |
| 10 | 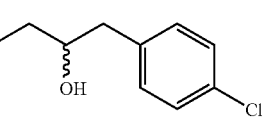 |
| 11 | 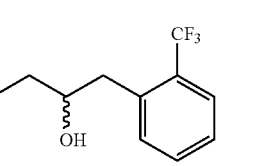 |
| 12 | 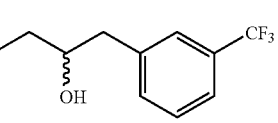 |
| 13 | 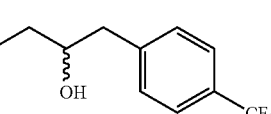 |
| 14 | 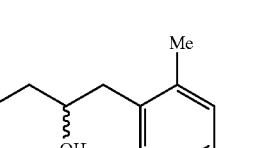 |
| 15 | 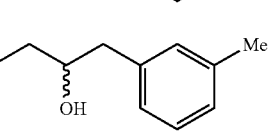 |
| 16 | 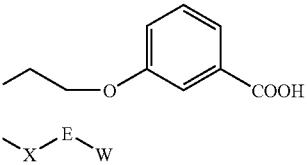 |
TABLE 61-continued
(IE3)
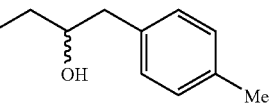
| No. | -X-E-W |
|---|---|
| 17 | 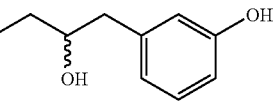 |
| 18 | 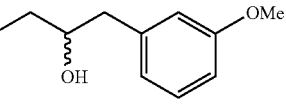 |
| 19 | 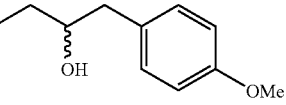 |
| 20 | 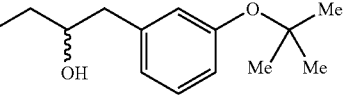 |
| 21 | 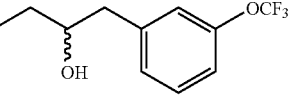 |
| 22 | 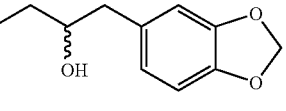 |
| 23 | 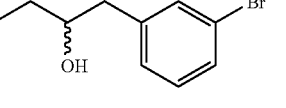 |
| 24 | 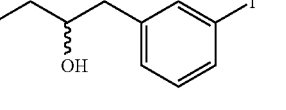 |
| 25 | 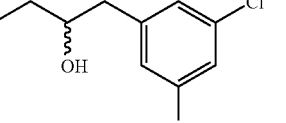 |
| 26 | 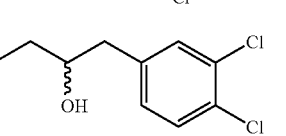 |
| 27 |  |

TABLE 61-continued (IE3)

Structure: cyclic carbamate-hydrazine linked via ethylene-O to 3-carboxyphenyl; N-X-E-W substituent.

| No. | -X-E-W |
|---|---|
| 28 | -CH2CH2CH(OH)-CH2-(3,4-difluorophenyl) |
| 29 | -CH2CH2CH(OH)-CH2-(2,3-difluorophenyl) |
| 30 | -CH2CH2CH(OH)-CH2-(3,5-difluorophenyl) |
| 31 | -CH2CH2CH(OH)-CH2-(2,5-difluorophenyl) |
| 32 | -CH2CH2CH(OH)-CH2-(3,5-dimethylphenyl) |
| 33 | -CH2CH2CH(OH)-CH2-(3,5-bis(trifluoromethyl)phenyl) |
| 34 | -CH2CH2CH(OH)-CH2-(3-chloro-4-fluorophenyl) |
| 35 | -CH2CH2CH(OH)-CH2-(2-fluoro-5-trifluoromethylphenyl) |

TABLE 62

(IE4)

Structure: cyclic carbamate-hydrazine linked via ethylene-O to 4-carboxyphenyl; N-X-E-W substituent.

| No. | -X-E-W |
|---|---|
| 1 | -CH2CH2CH(OH)-CH2-phenyl |
| 2 | -CH2CH2CH(OH)-CH(Me)-phenyl |
| 3 | -CH2CH2CH(OH)-C(Me)2-phenyl |
| 4 | -CH2CH2CH(OH)-(1-phenylcyclopropyl) |
| 5 | -CH2CH2CH(OH)-CH2-(3-methoxymethylphenyl) |
| 6 | -CH2CH2CH(OH)-CH2-(2-fluorophenyl) |
| 7 | -CH2CH2CH(OH)-CH2-(3-fluorophenyl) |
| 8 | -CH2CH2CH(OH)-CH2-(4-fluorophenyl) |
| 9 | -CH2CH2CH(OH)-CH2-(2-chlorophenyl) |
| 10 | -CH2CH2CH(OH)-CH2-(3-chlorophenyl) |

TABLE 62-continued (IE4)

Structure: cyclic carbamate-N-N(-X-E-W) with ethylene linker to O-C6H4-COOH

| No. | -X-E-W |
|-----|--------|
| 11 | -CH2CH2-CH(OH)-CH2-(4-Cl-C6H4) |
| 12 | -CH2CH2-CH(OH)-CH2-(2-CF3-C6H4) |
| 13 | -CH2CH2-CH(OH)-CH2-(3-CF3-C6H4) |
| 14 | -CH2CH2-CH(OH)-CH2-(4-CF3-C6H4) |
| 15 | -CH2CH2-CH(OH)-CH2-(2-Me-C6H4) |
| 16 | -CH2CH2-CH(OH)-CH2-(3-Me-C6H4) |
| 17 | -CH2CH2-CH(OH)-CH2-(4-Me-C6H4) |
| 18 | -CH2CH2-CH(OH)-CH2-(3-OH-C6H4) |
| 19 | -CH2CH2-CH(OH)-CH2-(3-OMe-C6H4) |
| 20 | -CH2CH2-CH(OH)-CH2-(4-OMe-C6H4) |
| 21 | -CH2CH2-CH(OH)-CH2-(3-OC(Me)3-C6H4) |

TABLE 62-continued (IE4)

| No. | -X-E-W |
|-----|--------|
| 22 | -CH2CH2-CH(OH)-CH2-(3-OCF3-C6H4) |
| 23 | -CH2CH2-CH(OH)-CH2-(3,4-methylenedioxyphenyl) |
| 24 | -CH2CH2-CH(OH)-CH2-(3-Br-C6H4) |
| 25 | -CH2CH2-CH(OH)-CH2-(3-I-C6H4) |
| 26 | -CH2CH2-CH(OH)-CH2-(3,5-Cl2-C6H3) |
| 27 | -CH2CH2-CH(OH)-CH2-(3,4-Cl2-C6H3) |
| 28 | -CH2CH2-CH(OH)-CH2-(3,4-F2-C6H3) |
| 29 | -CH2CH2-CH(OH)-CH2-(2,3-F2-C6H3) |
| 30 | -CH2CH2-CH(OH)-CH2-(3,5-F2-C6H3) |

TABLE 62-continued (IE4)

| No. | -X-E-W |
|---|---|
| 31 | 2-F, 5-F benzyl with CH(OH)CH2CH2- linker |
| 32 | 3,5-diMe benzyl with CH(OH)CH2CH2- linker |
| 33 | 3,5-bis(CF3) benzyl with CH(OH)CH2CH2- linker |
| 34 | 3-Cl, 4-F benzyl with CH(OH)CH2CH2- linker |
| 35 | 2-F, 5-CF3 benzyl with CH(OH)CH2CH2- linker |

TABLE 63

(IE5)

| No. | -X-E-W |
|---|---|
| 1 | benzyl with CH(OH)CH2CH2- linker |

TABLE 63-continued (IE5)

| No. | -X-E-W |
|---|---|
| 2 | α-Me benzyl with CH(OH)CH2CH2- linker |
| 3 | α,α-diMe benzyl with CH(OH)CH2CH2- linker |
| 4 | 1-phenylcyclopropyl with CH(OH)CH2CH2- linker |
| 5 | 3-(CH2OMe) benzyl with CH(OH)CH2CH2- linker |
| 6 | 2-F benzyl with CH(OH)CH2CH2- linker |
| 7 | 3-F benzyl with CH(OH)CH2CH2- linker |
| 8 | 4-F benzyl with CH(OH)CH2CH2- linker |
| 9 | 2-Cl benzyl with CH(OH)CH2CH2- linker |
| 10 | 3-Cl benzyl with CH(OH)CH2CH2- linker |
| 11 | 4-Cl benzyl with CH(OH)CH2CH2- linker |

TABLE 63-continued
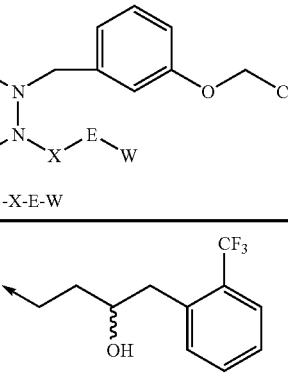
(IE5)
| No. | -X-E-W |
|---|---|
| 12 | 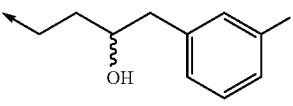 |
| 13 | 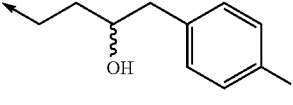 |
| 14 | 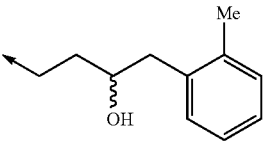 |
| 15 | 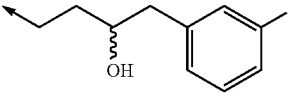 |
| 16 | 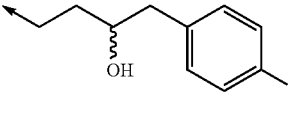 |
| 17 | 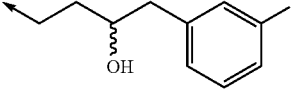 |
| 18 | 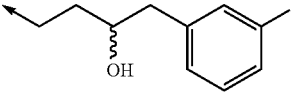 |
| 19 | 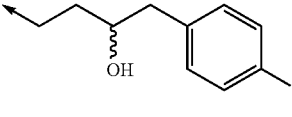 |
| 20 | 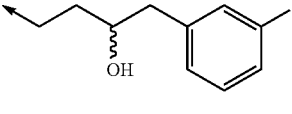 |
| 21 | 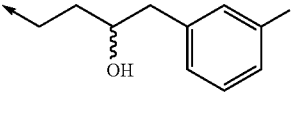 |
| 22 | 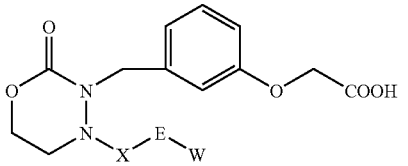 |
TABLE 63-continued
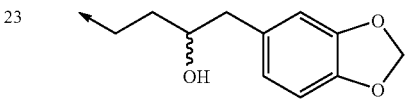
(IE5)
| No. | -X-E-W |
|---|---|
| 23 | 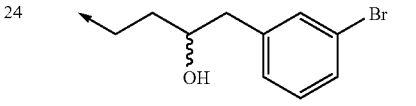 |
| 24 | 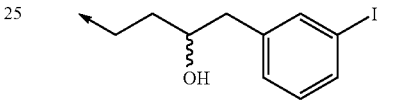 |
| 25 | 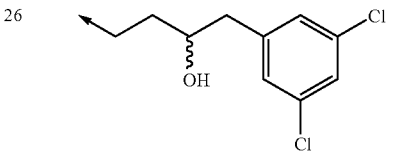 |
| 26 | 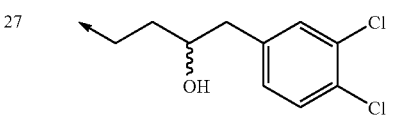 |
| 27 | 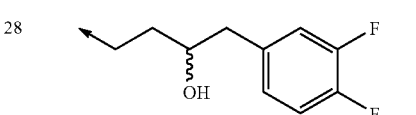 |
| 28 | 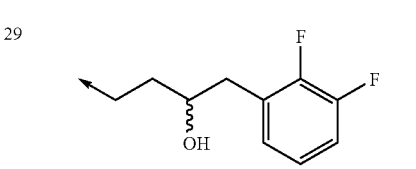 |
| 29 | 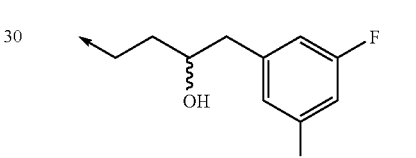 |
| 30 | |
| 31 | |

TABLE 63-continued (IE5)

| No. | -X-E-W |
|---|---|
| 32 | 3,5-dimethylbenzyl CH(OH)CH2CH2– |
| 33 | 3,5-bis(trifluoromethyl)benzyl CH(OH)CH2CH2– |
| 34 | 3-chloro-4-fluorobenzyl CH(OH)CH2CH2– |
| 35 | 2-fluoro-5-(trifluoromethyl)benzyl CH(OH)CH2CH2– |

TABLE 64

(IE6)

| No. | -X-E-W |
|---|---|
| 1 | benzyl CH(OH)CH2CH2– |
| 2 | 1-phenylethyl-CH(OH)CH2CH2– |

TABLE 64-continued (IE6)

| No. | -X-E-W |
|---|---|
| 3 | 2-methyl-2-phenyl, C(OH) CH2CH2– |
| 4 | 1-phenylcyclopropyl C(OH)CH2CH2– |
| 5 | 3-(methoxymethyl)benzyl CH(OH)CH2CH2– |
| 6 | 2-fluorobenzyl CH(OH)CH2CH2– |
| 7 | 3-fluorobenzyl CH(OH)CH2CH2– |
| 8 | 4-fluorobenzyl CH(OH)CH2CH2– |
| 9 | 2-chlorobenzyl CH(OH)CH2CH2– |
| 10 | 3-chlorobenzyl CH(OH)CH2CH2– |
| 11 | 4-chlorobenzyl CH(OH)CH2CH2– |
| 12 | 2-(trifluoromethyl)benzyl CH(OH)CH2CH2– |

TABLE 64-continued (IE6)

| No. | -X-E-W |
|---|---|
| 13 | 3-(CF₃)-benzyl, CH(OH) |
| 14 | 4-(CF₃)-benzyl, CH(OH) |
| 15 | 2-Me-benzyl, CH(OH) |
| 16 | 3-Me-benzyl, CH(OH) |
| 17 | 4-Me-benzyl, CH(OH) |
| 18 | 3-OH-benzyl, CH(OH) |
| 19 | 3-OMe-benzyl, CH(OH) |
| 20 | 4-OMe-benzyl, CH(OH) |
| 21 | 3-OC(Me)₃-benzyl, CH(OH) |
| 22 | 3-OCF₃-benzyl, CH(OH) |
| 23 | 3,4-methylenedioxybenzyl, CH(OH) |

TABLE 64-continued (IE6)

| No. | -X-E-W |
|---|---|
| 24 | 3-Br-benzyl, CH(OH) |
| 25 | 3-I-benzyl, CH(OH) |
| 26 | 3,5-diCl-benzyl, CH(OH) |
| 27 | 3,4-diCl-benzyl, CH(OH) |
| 28 | 3,4-diF-benzyl, CH(OH) |
| 29 | 2,3-diF-benzyl, CH(OH) |
| 30 | 3,5-diF-benzyl, CH(OH) |
| 31 | 2,5-diF-benzyl, CH(OH) |
| 32 | 3,5-diMe-benzyl, CH(OH) |

TABLE 64-continued (IE6)

| No. | -X-E-W |
|---|---|
| 33 | 3,5-bis(CF$_3$)-benzyl, CH(OH), (CH$_2$)$_2$- |
| 34 | 3-Cl-4-F-benzyl, CH(OH), (CH$_2$)$_2$- |
| 35 | 2-F-5-CF$_3$-benzyl, CH(OH), (CH$_2$)$_2$- |

TABLE 65

(IF1)

| No. | -X-E-W |
|---|---|
| 1 | benzyl, CH(OH), (CH$_2$)$_2$- |
| 2 | α-methylbenzyl, CH(OH), (CH$_2$)$_2$- |
| 3 | α,α-dimethylbenzyl, CH(OH), (CH$_2$)$_2$- |
| 4 | 1-phenylcyclopropyl, CH(OH), (CH$_2$)$_2$- |

TABLE 65-continued (IF1)

| No. | -X-E-W |
|---|---|
| 5 | 3-(OMe-CH$_2$)-benzyl, CH(OH), (CH$_2$)$_2$- |
| 6 | 2-F-benzyl, CH(OH), (CH$_2$)$_2$- |
| 7 | 3-F-benzyl, CH(OH), (CH$_2$)$_2$- |
| 8 | 4-F-benzyl, CH(OH), (CH$_2$)$_2$- |
| 9 | 2-Cl-benzyl, CH(OH), (CH$_2$)$_2$- |
| 10 | 3-Cl-benzyl, CH(OH), (CH$_2$)$_2$- |
| 11 | 4-Cl-benzyl, CH(OH), (CH$_2$)$_2$- |
| 12 | 2-CF$_3$-benzyl, CH(OH), (CH$_2$)$_2$- |
| 13 | 3-CF$_3$-benzyl, CH(OH), (CH$_2$)$_2$- |
| 14 | 4-CF$_3$-benzyl, CH(OH), (CH$_2$)$_2$- |

TABLE 65-continued (IF1)

[Structure: thiadiazinone ring with S-CH2-CH2-N-N(X-E-W)-C(=O)-N-CH2CH2-C6H4-COOH]

| No. | -X-E-W |
|---|---|
| 15 | -CH2CH2-CH(OH)-CH2-(2-Me-C6H4) |
| 16 | -CH2CH2-CH(OH)-CH2-(3-Me-C6H4) |
| 17 | -CH2CH2-CH(OH)-CH2-(4-Me-C6H4) |
| 18 | -CH2CH2-CH(OH)-CH2-(3-OH-C6H4) |
| 19 | -CH2CH2-CH(OH)-CH2-(3-OMe-C6H4) |
| 20 | -CH2CH2-CH(OH)-CH2-(4-OMe-C6H4) |
| 21 | -CH2CH2-CH(OH)-CH2-(3-OC(Me)3-C6H4) |
| 22 | -CH2CH2-CH(OH)-CH2-(3-OCF3-C6H4) |
| 23 | -CH2CH2-CH(OH)-CH2-(3,4-methylenedioxyphenyl) |
| 24 | -CH2CH2-CH(OH)-CH2-(3-Br-C6H4) |
| 25 | -CH2CH2-CH(OH)-CH2-(3-I-C6H4) |

TABLE 65-continued (IF1)

[Same core structure]

| No. | -X-E-W |
|---|---|
| 26 | -CH2CH2-CH(OH)-CH2-(3,5-Cl2-C6H3) |
| 27 | -CH2CH2-CH(OH)-CH2-(3,4-Cl2-C6H3) |
| 28 | -CH2CH2-CH(OH)-CH2-(3,4-F2-C6H3) |
| 29 | -CH2CH2-CH(OH)-CH2-(2,3-F2-C6H3) |
| 30 | -CH2CH2-CH(OH)-CH2-(3,5-F2-C6H3) |
| 31 | -CH2CH2-CH(OH)-CH2-(2,5-F2-C6H3) |
| 32 | -CH2CH2-CH(OH)-CH2-(3,5-Me2-C6H3) |
| 33 | -CH2CH2-CH(OH)-CH2-(3,5-(CF3)2-C6H3) |

TABLE 65-continued (IF1)

| No. | -X-E-W |
|---|---|
| 34 | (2-chloro-4-fluorobenzyl, OH) |
| 35 | (2-fluoro-5-trifluoromethylbenzyl, OH) |

TABLE 66

(IF1)

| No. | -X-E-W |
|---|---|
| 36 | (3-phenoxybenzyl, OH) |
| 37 | (biphenyl-3-yl-methyl, OH) |
| 38 | (2'-chlorobiphenyl-3-yl-methyl, OH) |
| 39 | (naphthalen-2-yl-methyl, OH) |

TABLE 66-continued (IF1)

| No. | -X-E-W |
|---|---|
| 40 | (naphthalen-1-yl-methyl, OH) |
| 41 | (furan-2-yl-methyl, OH) |
| 42 | (thiophen-2-yl-methyl, OH) |
| 43 | (5-trifluoromethylthiophen-2-yl-methyl, OH) |
| 44 | (pyridin-2-yl-methyl, OH) |
| 45 | (benzofuran-5-yl-methyl, OH) |
| 46 | (benzothiophen-5-yl-methyl, OH) |
| 47 | (benzoxazol-6-yl-methyl, OH) |
| 48 | (benzothiazol-6-yl-methyl, OH) |
| 49 | (1H-benzimidazol-5-yl-methyl, OH) |
| 50 | (1H-indol-5-yl-methyl, OH) |

TABLE 66-continued
(IF1)
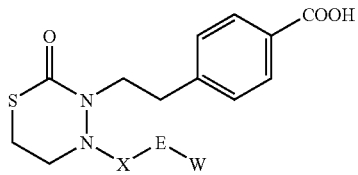
| No. | -X-E-W |
|-----|--------|
| 51 | 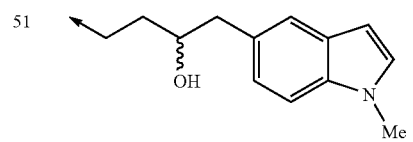 |
| 52 | |
| 53 |  |
| 54 |  |
| 55 | |
| 56 | |
| 57 | |
| 58 | |
| 59 |  |
TABLE 66-continued
(IF1)
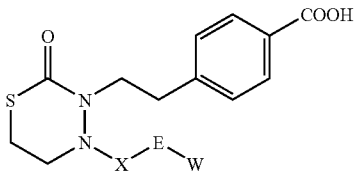
| No. | -X-E-W |
|-----|--------|
| 60 | 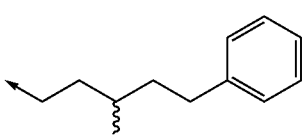 |
| 61 |  |
| 62 | |
| 63 | |
| 64 | |
| 65 | |
| 66 | |
| 67 | |
| 68 | |

TABLE 66-continued
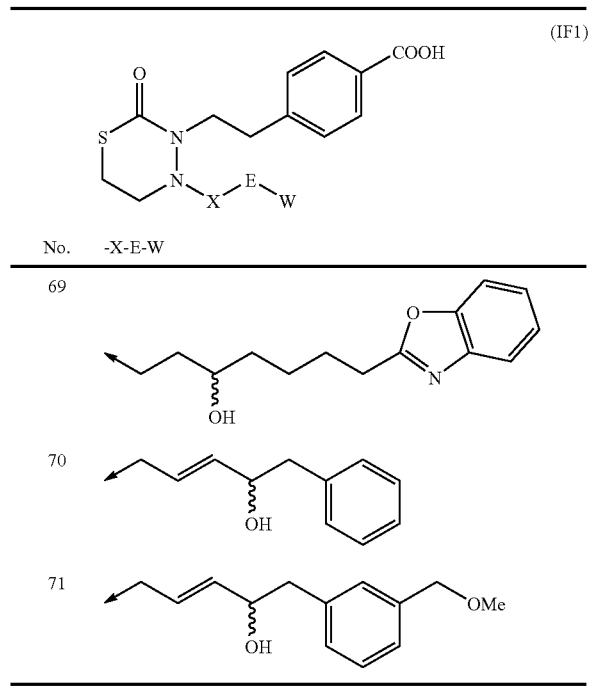
| No. | -X-E-W |
|-----|--------|
| 69  | |
| 70  | |
| 71  | |
TABLE 67
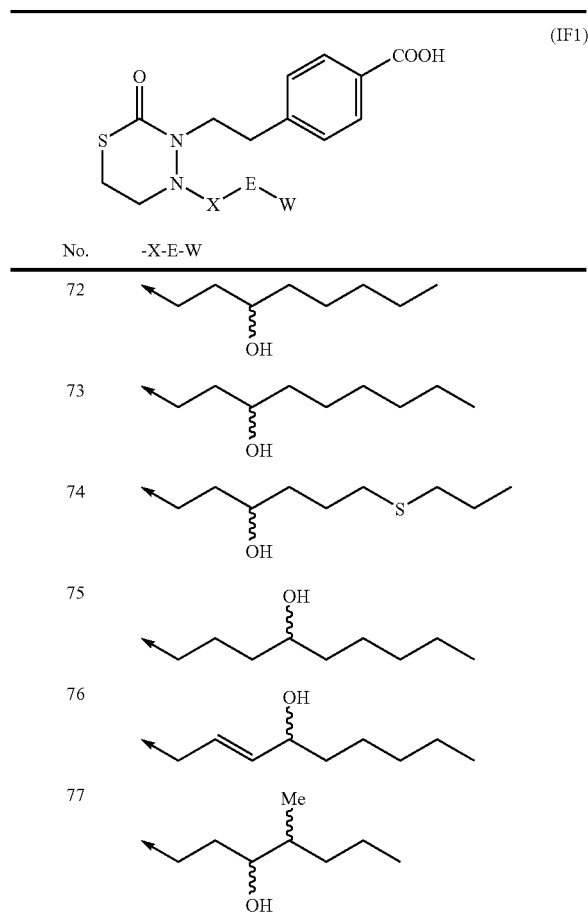
| No. | -X-E-W |
|-----|--------|
| 72 | |
| 73 | |
| 74 | |
| 75 | |
| 76 | |
| 77 | |
TABLE 67-continued
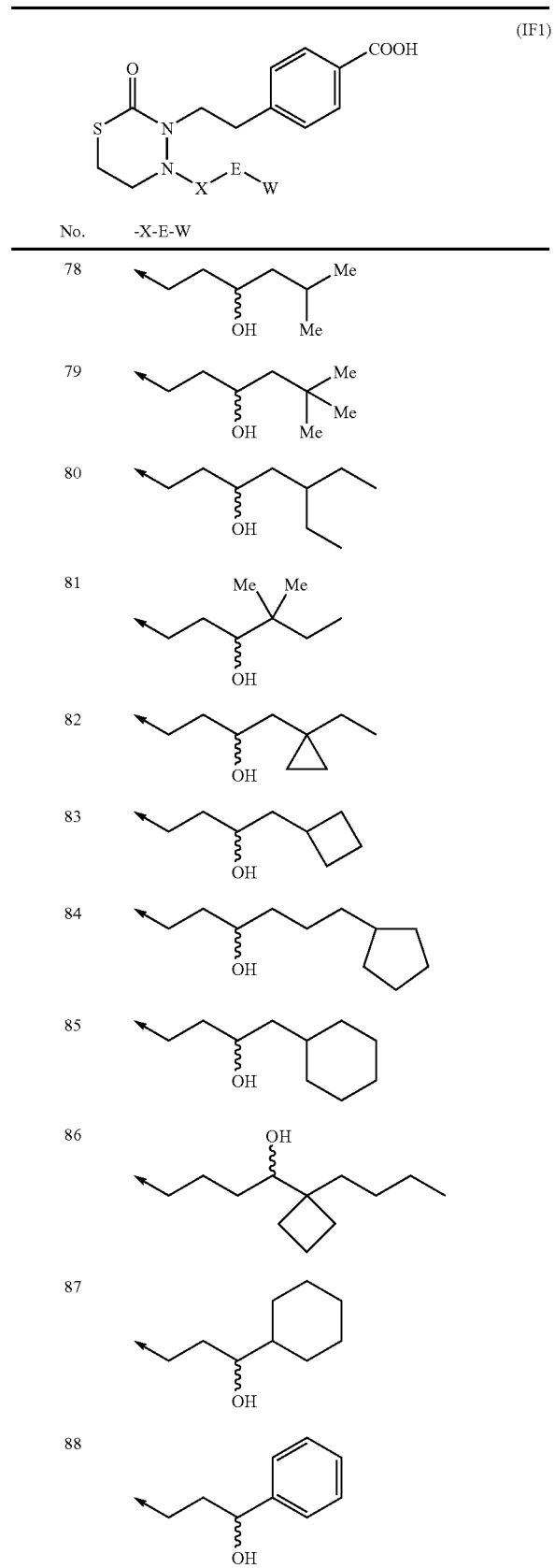
| No. | -X-E-W |
|-----|--------|
| 78 | |
| 79 | |
| 80 | |
| 81 | |
| 82 | |
| 83 | |
| 84 | |
| 85 | |
| 86 | |
| 87 | |
| 88 | |

TABLE 67-continued (IF1)

| No. | -X-E-W |
|---|---|
| 89 | 3-Me-phenyl-CH(OH)-CH2CH2- |
| 90 | 3-OMe-phenyl-CH(OH)-CH2CH2- |
| 91 | 3-F-phenyl-CH(OH)-CH2CH2- |
| 92 | 3-Cl-phenyl-CH(OH)-CH2CH2- |
| 93 | 3-CF3-phenyl-CH(OH)-CH2CH2- |
| 94 | 3-phenoxy-phenyl-CH(OH)-CH2CH2- |
| 95 | 2'-Cl-biphenyl-3-yl-CH(OH)-CH2CH2- |
| 96 | 4'-Cl-2'-Me-biphenyl-3-yl-CH(OH)-CH2CH2- |
| 97 | 4'-OH-2'-Me-biphenyl-3-yl-CH(OH)-CH2CH2- |
| 98 | 5-CF3-furan-2-yl-CH(OH)-CH2CH2- |
| 99 | (S)-3-Me-phenyl-CH(OH)-CH2CH2- |
| 100 | (S)-3-F-phenyl-CH(OH)-CH2CH2- |
| 101 | (S)-3-Cl-phenyl-CH(OH)-CH2CH2- |
| 102 | (S)-3-CF3-phenyl-CH(OH)-CH2CH2- |
| 103 | (S)-3-Me-benzyl-CH(OH)-CH2CH2- |
| 104 | (S)-3-F-benzyl-CH(OH)-CH2CH2- |
| 105 | (S)-3-Cl-benzyl-CH(OH)-CH2CH2- |

TABLE 67-continued (IF1)

| No. | -X-E-W |
|---|---|
| 106 | 3-CF₃-phenyl, (S)-OH chain |
| 107 | 3-OMe-phenyl, (S)-OH chain |
| 108 | 3-OCF₃-phenyl, (S)-OH chain |

TABLE 68

(IF2)

| No. | -X-E-W |
|---|---|
| 1 | phenyl, OH chain |
| 2 | phenyl with Me, OH chain |
| 3 | phenyl with Me, Me, OH chain |
| 4 | cyclopropyl-phenyl, OH chain |
| 5 | 3-CH₂OMe-phenyl, OH chain |

TABLE 68-continued (IF2)

| No. | -X-E-W |
|---|---|
| 6 | 2-F-phenyl, OH chain |
| 7 | 3-F-phenyl, OH chain |
| 8 | 4-F-phenyl, OH chain |
| 9 | 2-Cl-phenyl, OH chain |
| 10 | 3-Cl-phenyl, OH chain |
| 11 | 4-Cl-phenyl, OH chain |
| 12 | 2-CF₃-phenyl, OH chain |
| 13 | 3-CF₃-phenyl, OH chain |
| 14 | 4-CF₃-phenyl, OH chain |
| 15 | 2-Me-phenyl, OH chain |

TABLE 68-continued (IF2)

| No. | -X-E-W |
|---|---|
| 16 | 3-Me-benzyl, CH(OH)CH2CH2- |
| 17 | 4-Me-benzyl, CH(OH)CH2CH2- |
| 18 | 3-OH-benzyl, CH(OH)CH2CH2- |
| 19 | 3-OMe-benzyl, CH(OH)CH2CH2- |
| 20 | 4-OMe-benzyl, CH(OH)CH2CH2- |
| 21 | 3-OC(Me)3-benzyl, CH(OH)CH2CH2- |
| 22 | 3-OCF3-benzyl, CH(OH)CH2CH2- |
| 23 | 3,4-methylenedioxybenzyl, CH(OH)CH2CH2- |
| 24 | 3-Br-benzyl, CH(OH)CH2CH2- |
| 25 | 3-I-benzyl, CH(OH)CH2CH2- |
| 26 | 3,5-diCl-benzyl, CH(OH)CH2CH2- |

TABLE 68-continued (IF2)

| No. | -X-E-W |
|---|---|
| 27 | 3,4-diCl-benzyl, CH(OH)CH2CH2- |
| 28 | 3,4-diF-benzyl, CH(OH)CH2CH2- |
| 29 | 2,3-diF-benzyl, CH(OH)CH2CH2- |
| 30 | 3,5-diF-benzyl, CH(OH)CH2CH2- |
| 31 | 2,5-diF-benzyl, CH(OH)CH2CH2- |
| 32 | 3,5-diMe-benzyl, CH(OH)CH2CH2- |
| 33 | 3,5-di(CF3)-benzyl, CH(OH)CH2CH2- |
| 34 | 3-Cl-4-F-benzyl, CH(OH)CH2CH2- |

TABLE 68-continued (IF2)

| No. | -X-E-W |
|---|---|
| 35 | (2-fluoro-5-trifluoromethylbenzyl, hydroxy, propyl chain) |

TABLE 69

(IF3)

| No. | -X-E-W |
|---|---|
| 1 | (benzyl, OH, propyl) |
| 2 | (α-methylbenzyl, OH, propyl) |
| 3 | (α,α-dimethylbenzyl, OH, propyl) |
| 4 | (1-phenylcyclopropyl, OH, propyl) |
| 5 | (3-methoxymethylbenzyl, OH, propyl) |
| 6 | (2-fluorobenzyl, OH, propyl) |

TABLE 69-continued (IF3)

| No. | -X-E-W |
|---|---|
| 7 | (3-fluorobenzyl, OH, propyl) |
| 8 | (4-fluorobenzyl, OH, propyl) |
| 9 | (2-chlorobenzyl, OH, propyl) |
| 10 | (3-chlorobenzyl, OH, propyl) |
| 11 | (4-chlorobenzyl, OH, propyl) |
| 12 | (2-trifluoromethylbenzyl, OH, propyl) |
| 13 | (3-trifluoromethylbenzyl, OH, propyl) |
| 14 | (4-trifluoromethylbenzyl, OH, propyl) |
| 15 | (2-methylbenzyl, OH, propyl) |
| 16 | (3-methylbenzyl, OH, propyl) |

TABLE 69-continued
(IF3)
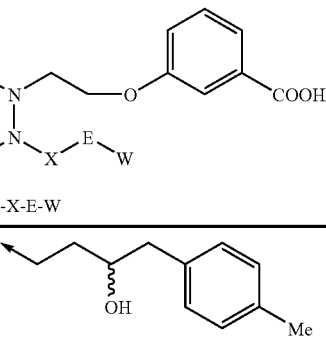
| No. | -X-E-W |
|---|---|
| 17 | 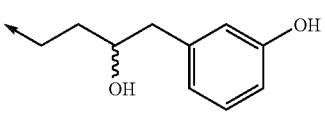 |
| 18 | 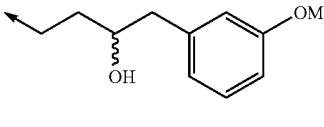 |
| 19 | 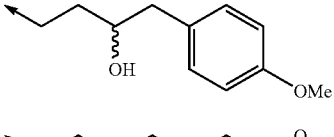 |
| 20 | 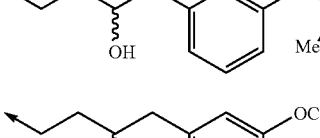 |
| 21 | 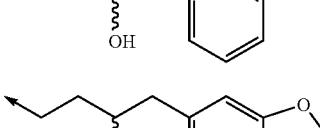 |
| 22 | 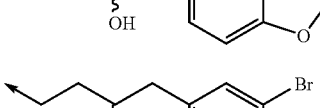 |
| 23 | 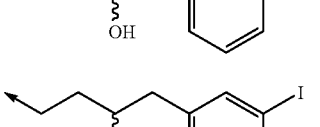 |
| 24 | 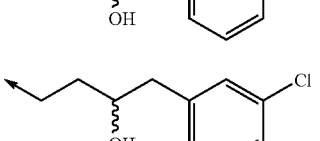 |
| 25 | 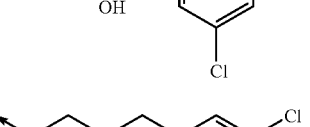 |
| 26 | 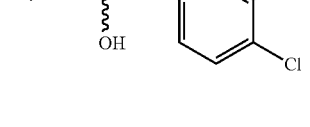 |
| 27 | 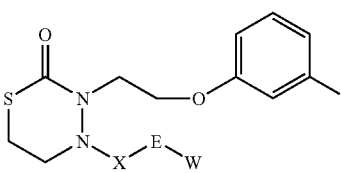 |
TABLE 69-continued
(IF3)
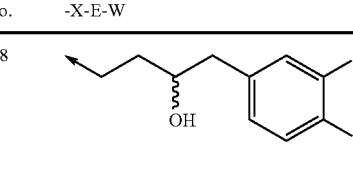
| No. | -X-E-W |
|---|---|
| 28 | 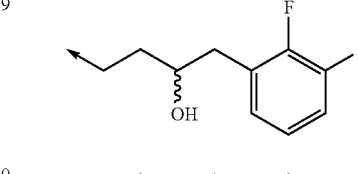 |
| 29 | 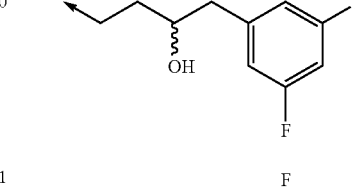 |
| 30 | 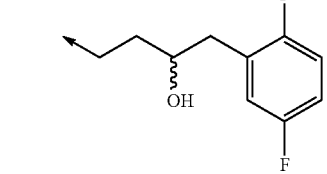 |
| 31 | 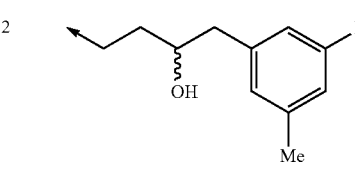 |
| 32 | 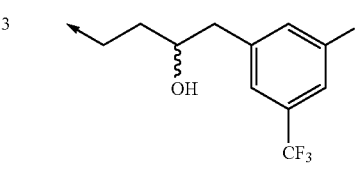 |
| 33 | 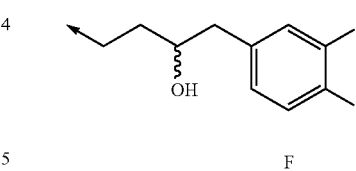 |
| 34 | 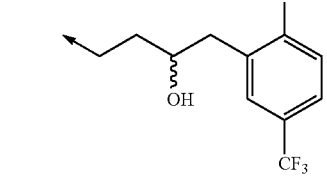 |
| 35 | |

TABLE 70

(IF4)

Structure: thiadiazinanone with S-CH2-CH2-N-C(=O)-N(CH2CH2-O-C6H4-COOH)-N-X-E-W

| No. | -X-E-W |
|---|---|
| 1 | -CH2CH2-CH(OH)-CH2-Ph |
| 2 | -CH2CH2-CH(OH)-CH(Me)-Ph |
| 3 | -CH2CH2-CH(OH)-C(Me)2-Ph |
| 4 | -CH2CH2-C(OH)(cyclopropyl-Ph) |
| 5 | -CH2CH2-CH(OH)-CH2-(3-CH2OMe-C6H4) |
| 6 | -CH2CH2-CH(OH)-CH2-(2-F-C6H4) |
| 7 | -CH2CH2-CH(OH)-CH2-(3-F-C6H4) |
| 8 | -CH2CH2-CH(OH)-CH2-(4-F-C6H4) |
| 9 | -CH2CH2-CH(OH)-CH2-(2-Cl-C6H4) |
| 10 | -CH2CH2-CH(OH)-CH2-(3-Cl-C6H4) |

TABLE 70-continued (IF4)

| No. | -X-E-W |
|---|---|
| 11 | -CH2CH2-CH(OH)-CH2-(4-Cl-C6H4) |
| 12 | -CH2CH2-CH(OH)-CH2-(2-CF3-C6H4) |
| 13 | -CH2CH2-CH(OH)-CH2-(3-CF3-C6H4) |
| 14 | -CH2CH2-CH(OH)-CH2-(4-CF3-C6H4) |
| 15 | -CH2CH2-CH(OH)-CH2-(2-Me-C6H4) |
| 16 | -CH2CH2-CH(OH)-CH2-(3-Me-C6H4) |
| 17 | -CH2CH2-CH(OH)-CH2-(4-Me-C6H4) |
| 18 | -CH2CH2-CH(OH)-CH2-(3-OH-C6H4) |
| 19 | -CH2CH2-CH(OH)-CH2-(3-OMe-C6H4) |
| 20 | -CH2CH2-CH(OH)-CH2-(4-OMe-C6H4) |
| 21 | -CH2CH2-CH(OH)-CH2-(3-OC(Me)3-C6H4) |

TABLE 70-continued (IF4)

| No. | -X-E-W |
|---|---|
| 22 | 3-OCF₃ benzyl, CH(OH) |
| 23 | 3,4-methylenedioxybenzyl, CH(OH) |
| 24 | 3-Br benzyl, CH(OH) |
| 25 | 3-I benzyl, CH(OH) |
| 26 | 3,5-diCl benzyl, CH(OH) |
| 27 | 3,4-diCl benzyl, CH(OH) |
| 28 | 3,4-diF benzyl, CH(OH) |
| 29 | 2,3-diF benzyl, CH(OH) |
| 30 | 3,5-diF benzyl, CH(OH) |

TABLE 70-continued (IF4)

| No. | -X-E-W |
|---|---|
| 31 | 2,5-diF benzyl, CH(OH) |
| 32 | 3,5-diMe benzyl, CH(OH) |
| 33 | 3,5-diCF₃ benzyl, CH(OH) |
| 34 | 3-Cl, 4-F benzyl, CH(OH) |
| 35 | 2-F, 5-CF₃ benzyl, CH(OH) |

TABLE 71

(IF5)

| No. | -X-E-W |
|---|---|
| 1 | benzyl, CH(OH) |

TABLE 71-continued
(IF5)
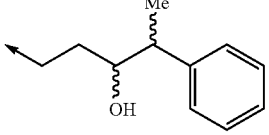
| No. | -X-E-W |
|---|---|
| 2 | 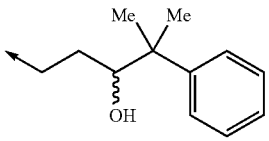 |
| 3 | 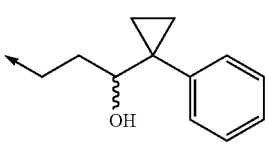 |
| 4 | 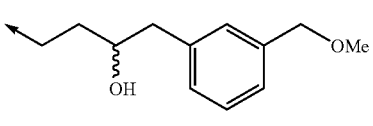 |
| 5 | 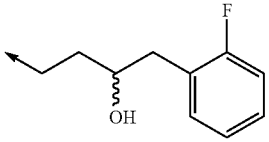 |
| 6 | 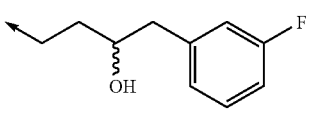 |
| 7 | 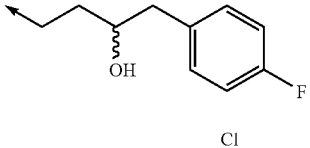 |
| 8 | 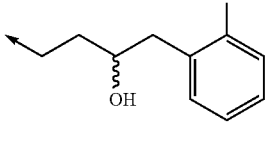 |
| 9 | 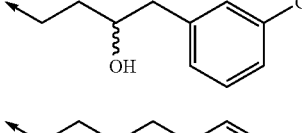 |
| 10 | 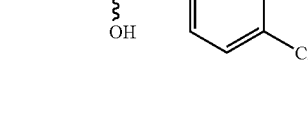 |
| 11 | 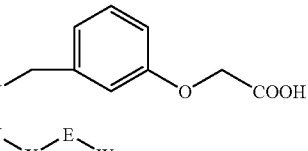 |
TABLE 71-continued
(IF5)
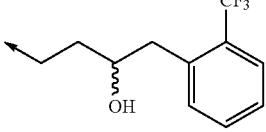
| No. | -X-E-W |
|---|---|
| 12 | 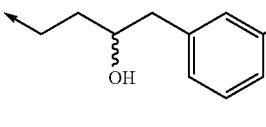 |
| 13 | 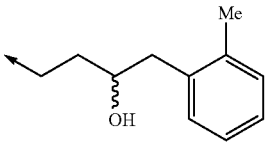 |
| 14 | 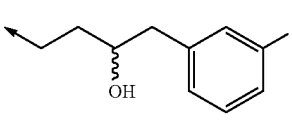 |
| 15 | 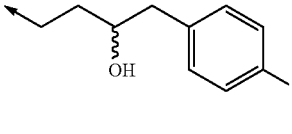 |
| 16 | 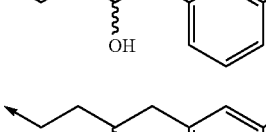 |
| 17 | 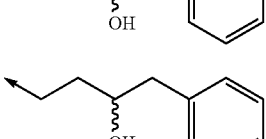 |
| 18 | 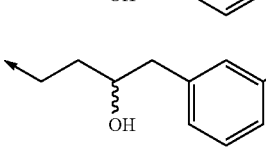 |
| 19 | 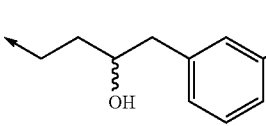 |
| 20 |  |
| 21 |  |
| 22 |  |

TABLE 71-continued
(IF5)
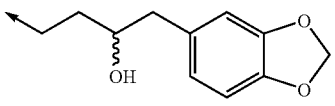
| No. | -X-E-W |
|---|---|
| 23 | 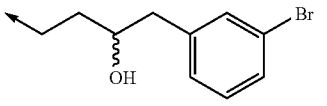 |
| 24 | 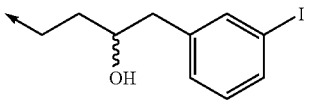 |
| 25 | 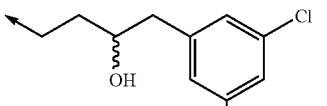 |
| 26 | 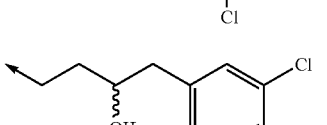 |
| 27 | 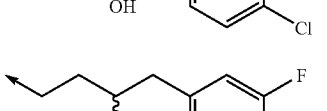 |
| 28 | 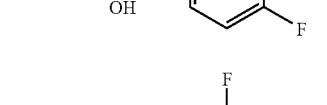 |
| 29 | 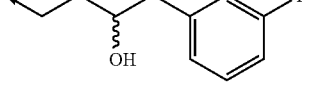 |
| 30 | 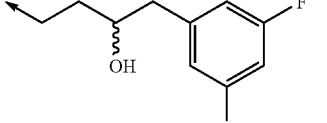 |
| 31 | 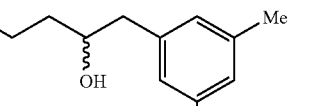 |
TABLE 71-continued
(IF5)
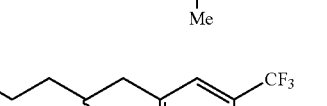
| No. | -X-E-W |
|---|---|
| 32 | 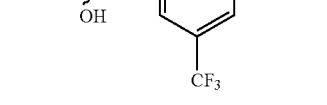 |
| 33 | 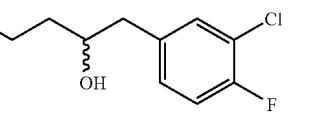 |
| 34 | 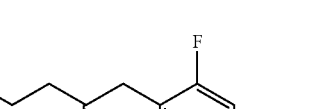 |
| 35 | 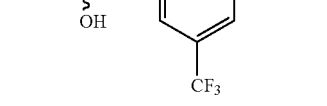 |
TABLE 72
(IF6)
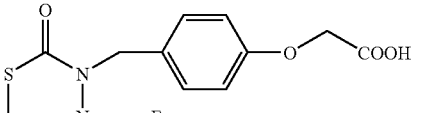
| No. | -X-E-W |
|---|---|
| 1 | 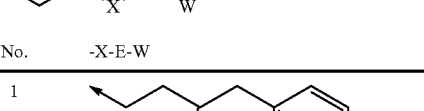 |
| 2 | 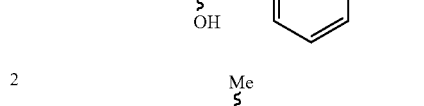 |

TABLE 72-continued (IF6)

| No. | -X-E-W |
|---|---|
| 3 | 4-hydroxy-5-methyl-5-phenylhexyl |
| 4 | 4-hydroxy-4-(1-phenylcyclopropyl)butyl |
| 5 | 4-hydroxy-5-(3-methoxymethylphenyl)pentyl |
| 6 | 4-hydroxy-5-(2-fluorophenyl)pentyl |
| 7 | 4-hydroxy-5-(3-fluorophenyl)pentyl |
| 8 | 4-hydroxy-5-(4-fluorophenyl)pentyl |
| 9 | 4-hydroxy-5-(2-chlorophenyl)pentyl |
| 10 | 4-hydroxy-5-(3-chlorophenyl)pentyl |
| 11 | 4-hydroxy-5-(4-chlorophenyl)pentyl |
| 12 | 4-hydroxy-5-(2-trifluoromethylphenyl)pentyl |
| 13 | 4-hydroxy-5-(3-trifluoromethylphenyl)pentyl |
| 14 | 4-hydroxy-5-(4-trifluoromethylphenyl)pentyl |
| 15 | 4-hydroxy-5-(2-methylphenyl)pentyl |
| 16 | 4-hydroxy-5-(3-methylphenyl)pentyl |
| 17 | 4-hydroxy-5-(4-methylphenyl)pentyl |
| 18 | 4-hydroxy-5-(3-hydroxyphenyl)pentyl |
| 19 | 4-hydroxy-5-(3-methoxyphenyl)pentyl |
| 20 | 4-hydroxy-5-(4-methoxyphenyl)pentyl |
| 21 | 4-hydroxy-5-(3-tert-butoxyphenyl)pentyl |
| 22 | 4-hydroxy-5-(3-trifluoromethoxyphenyl)pentyl |
| 23 | 4-hydroxy-5-(3,4-methylenedioxyphenyl)pentyl |

TABLE 72-continued (IF6)

| No. | -X-E-W |
|---|---|
| 24 | 3-Br-benzyl, CH(OH)CH₂CH₂- |
| 25 | 3-I-benzyl, CH(OH)CH₂CH₂- |
| 26 | 3,5-diCl-benzyl, CH(OH)CH₂CH₂- |
| 27 | 3,4-diCl-benzyl, CH(OH)CH₂CH₂- |
| 28 | 3,4-diF-benzyl, CH(OH)CH₂CH₂- |
| 29 | 2,3-diF-benzyl, CH(OH)CH₂CH₂- |
| 30 | 3,5-diF-benzyl, CH(OH)CH₂CH₂- |
| 31 | 2,5-diF-benzyl, CH(OH)CH₂CH₂- |
| 32 | 3,5-diMe-benzyl, CH(OH)CH₂CH₂- |
| 33 | 3,5-diCF₃-benzyl, CH(OH)CH₂CH₂- |
| 34 | 3-Cl-4-F-benzyl, CH(OH)CH₂CH₂- |
| 35 | 2-F-5-CF₃-benzyl, CH(OH)CH₂CH₂- |

In the general formula (II), D' has the same meaning as that of D mentioned above, or when D is carboxyl (COOH) group, the carboxyl group may be protected with a group $Rp^1$, when D contains hydroxyl (OH) group, the hydroxyl group may be protected with a group $Rp^2$, and when D contains formyl (CHO) group, the formyl group may be protected with a group $Rp^3$.

Q represents hydrogen atom, or a protective group $Rp^4$ for amino group (NH), and both of them are preferred examples. Hydrogen atom may sometimes be preferred, or $Rp^4$ may alternatively be preferred.

Examples of $Rp^1$ include, for example, an alkyl group having 1 to 4 carbon atoms, an alkenyl group having 2 to 4 carbon atoms, an alkyl group having 1 to 4 carbon atoms substituted with an alkoxy group having 1 to 4 carbon atoms, an alkyl group having 1 to 4 carbon atoms substituted with 1 to 3 halogen atoms and the like, and specific examples include methyl group, ethyl group, t-butyl group, allyl group, methoxyethyl group, trichloroethyl group and the like. Further, examples of $Rp^1$ also include, for example, a group $-Ap^1-Rp^5$ and the like. $Ap^1$ in the group $-Ap^1-Rp^5$ represents a single bond, methylene group, or —CH₂C(O)—, $Rp^5$ represents phenyl group which may be substituted with 1 or the same or different 2 or more of Xp. The substituent Xp represents an alkyl group having 1 to 4 carbon atoms, hydroxyl group, a halogen atom, trifluoromethyl group, nitro group, an alkoxy group having 1 to 4 carbon atoms, or a mono- or dialkylamino group having 1 to 4 carbon atoms in each alkyl group. Specific examples of $-Ap^1-Rp^5$ include phenyl group, methylphenyl group, chlorophenyl group, benzyl (Bn) group, methylbenzyl group, chlorobenzyl group, dichlorobenzyl group, fluorobenzyl group, trifluoromethylbenzyl group, nitrobenzyl group, methoxyphenyl group, N-methylaminobenzyl group, N,N-dimethylaminobenzyl group, phenacyl group and the like.

Among them, an alkyl group having 1 to 4 carbon atoms and the like are particularly preferred examples.

$Rp^2$ represents, for example, an alkyl group having 1 to 4 carbon atoms, an alkenyl group having 2 to 4 carbon atoms, an alkyl group having 1 to 4 carbon atoms substituted with an alkoxy group having 1 to 4 carbon atoms, an alkyl group having 1 to 4 carbon atoms substituted with 1 to 3 halogen atoms, a silyl group substituted with the same or different 3 of alkyl groups having 1 to 4 carbon atoms or phenyl groups, tetrahydropyranyl group, tetrahydrofuryl group, propargyl group, a group -$Ap^1$-$Rp^5$, a group —$CH_2$-$Ap^2$-$Rp^6$, a group —$C(O)Rp^6$, a group —$COORp^6$ or the like. $Ap^2$ represents oxygen atom, or sulfur atom, $Rp^6$ represents hydrogen atom, an alkyl group having 1 to 4 carbon atoms, trimethylsilylethyl group, chloromethyl group, trichloromethyl group, trifluoromethyl group, 9-fluorenylmethyl group, adamantyl group, allyl group, a group -$Ap^1$-$Rp^5$ or the like. Specific examples of $Rp^2$ include methyl group, ethyl group, t-butyl group, allyl group, methoxymethyl (MOM) group, methoxyethyl (MEM) group, trichloroethyl group, phenyl group, methylphenyl group, chlorophenyl group, benzyl group, methylbenzyl group, chlorobenzyl group, dichlorobenzyl group, fluorobenzyl group, trifluoromethylbenzyl group, nitrobenzyl group, methoxyphenyl group, N-methylaminobenzyl group, N,N-dimethylaminobenzyl group, phenacyl group, trityl group, 1-ethoxyethyl (EE) group, tetrahydropyranyl (THP) group, tetrahydrofuryl group, propargyl group, trimethylsilyl (TMS) group, triethylsilyl(TES) group, t-butyldimethylsilyl (TBDMS) group, t-butyldiphenylsilyl (TBDPS) group, acetyl (Ac) group, pivaloyl group, benzoyl group, allyloxycarbonyl (Alloc) group, 2,2,2-trichloroethoxycarbonyl (Troc) group and the like.

$Rp^3$ represents, for example, acetal group or the like, and specific examples include dimethylacetal and the like.

$Rp^4$ represents, for example, 1 or the same or different 2 or more of the groups -$Ap^1$-$Rp^5$, groups —$C(O)Rp^6$, groups —$COORp^6$ and the like. Specific examples include benzyl group, methylbenzyl group, chlorobenzyl group, dichlorobenzyl group, fluorobenzyl group, trifluoromethylbenzyl group, nitrobenzyl group, methoxyphenyl group, N-methylaminobenzyl group, N,N-dimethylaminobenzyl group, phenacyl group, acetyl group, trifluoroacetyl group, pivaloyl group, benzoyl group, allyloxycarbonyl group, 2,2,2-trichloroethoxycarbonyl group, benzyloxycarbonyl group, t-butoxycarbonyl (Boc) group, 1-methyl-1-(4-biphenyl)ethoxycarbonyl (Bpoc) group, 9-fluorenylmethoxycarbonyl group, benzyloxymethyl (BOM) group, 2-(trimethylsilyl)ethoxymethyl (SEM) group and the like.

However, the protective groups of carboxyl group, hydroxyl group, formyl group, and amino group are not limited to these examples, and they can be selected by referring to and examining methods for introduction of protective groups and deprotection described in commonly available chemical articles, for example, Protective Groups In Organic Synthesis, THIRD EDITION, John Wiley & Sons, or references cited therein and the like.

As Compound (II), the compounds represented by the general formulas (IIa-1) to (IIa-10) ($R^{10}$ in the formulas represents an alkyl group having 1 to 4 carbon atoms) listed in Table 73 mentioned below can be exemplified as particularly preferred compounds.

TABLE 73

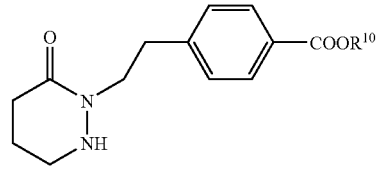

(IIa-1)

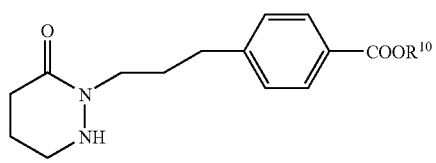

(IIa-2)

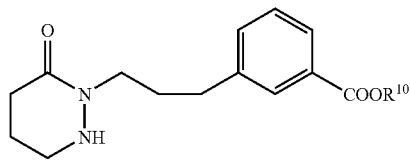

(IIa-3)

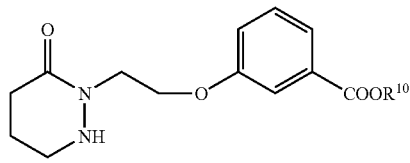

(IIa-4)

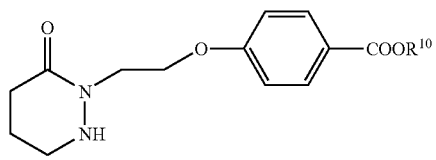

(IIa-5)

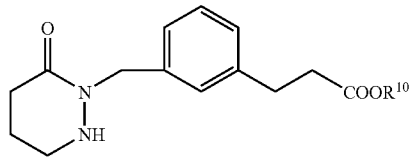

(IIa-6)

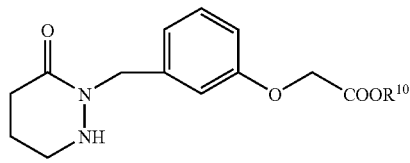

(IIa-7)

TABLE 73-continued

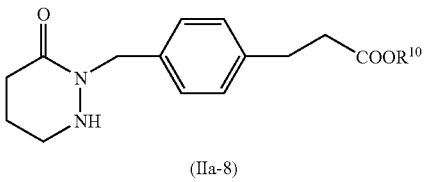

(IIa-8)

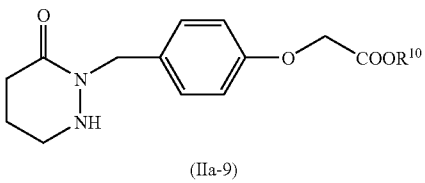

(IIa-9)

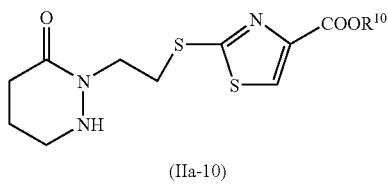

(IIa-10)

<Method for Preparing Compounds of the Present Invention>

Compound (I) and Compound (II) of the present invention can be prepared by, for example, using reactions according to the various methods mentioned below. When carboxyl (COOH) group, hydroxyl (OH) group, thiol (SH) group, carbonyl (C(O)) group or ketone containing formyl (CHO) group, or amino (NH) group is contained in the structures of the compounds of the present invention or synthetic intermediates thereof, those substituents may be protected with a protective group as required. When a heterocyclic ring containing NH in the ring such as indole ring and indazole ring is contained in the structures of the compounds of the present invention or synthetic intermediates thereof, that NH is amino group which may also be protected.

As for types of the protective groups, examples include those mentioned above, for example. However, protective groups are not limited to these examples, and types of protective groups, selection and introduction thereof can be achieved by referring to and reviewing commonly available chemical articles, for example, Protective Groups In Organic Synthesis mentioned above, references cited therein and the like. Further, by removing these protective groups simultaneously with the preparation of desired compounds or stepwise during the preparation process or at the final step, protected compounds can be converted into target compounds. Deprotection reactions for carboxyl group, hydroxyl group, thiol group, ketone or carbonyl group containing formyl group, and amino group are well known, and examples include, for example, (1) alkali hydrolysis, (2) deprotection reaction under an acidic condition, (3) deprotection reaction by hydrogenolysis, (4) deprotection reaction of silyl group, (5) deprotection reaction using a metal, (6) deprotection reaction using a metal complex and the like.

These methods are specifically performed as follows.
(1) The deprotection reaction by alkali hydrolysis is performed by, for example, reacting a protected compound with a base in a polar solvent. Examples of the base used in this reaction include, for example, alkali metal bases such as sodium hydroxide, potassium hydroxide, lithium hydroxide, barium hydroxide, calcium hydroxide, sodium carbonate, potassium carbonate, sodium methoxide, and potassium t-butoxide, and organic bases such as triethylamine. They are usually used in an amount of 1 to 20 fold moles, preferably 1 to 10 fold moles, based on the reactant when an alkali metal base is used, or 1 fold mole to largely excess amount when an organic base is used. As for a reaction solvent, it is usually preferred that the reaction is performed in an inactive medium that does not inhibit the reaction, preferably in a polar solvent. Examples of the polar solvent include water, methanol, ethanol, tetrahydrofuran, dioxane and the like, and these solvents can be used as a mixture as required. As for a reaction temperature, a suitable temperature, for example, from −10° C. to the reflux temperature of the solvent is chosen. The reaction time is, for example, usually 0.5 to 72 hours, preferably 1 to 48 hours when an alkali metal base is used, or 5 hours to 14 days when an organic base is used. However, since the progress of the reaction can be monitored by thin layer chromatography (TLC), high performance liquid chromatography (HPLC) or the like, it is usually preferred that the reaction is terminated when a maximum yield of the target compound is obtained.
(2) The deprotection reaction under an acidic condition is performed, for example, in an organic solvent (dichloromethane, chloroform, dioxane, ethyl acetate, anisole and the like) in the presence of an organic acid (acetic acid, trifluoroacetic acid, methanesulfonic acid, p-toluenesulfonic acid and the like), an inorganic acid (hydrochloric acid, sulfuric acid and the like), or a mixture thereof (hydrogen bromide/acetic acid and the like) at a temperature of −10 to 100° C.
(3) The deprotection reaction by hydrogenolysis is performed, for example, in a solvent [ether type solvents (tetrahydrofuran, dioxane, dimethoxyethane, diethyl ether and the like), alcohol type solvents (methanol, ethanol and the like), benzene type solvent (benzene, toluene and the like), ketone type solvents (acetone, methyl ethyl ketone and the like), nitrile type solvents (acetonitrile and the like), amide type solvents (dimethylformamide and the like), ester type solvents (ethyl acetate and the like), water, acetic acid, mixtures of two or more types of those solvents and the like] in the presence of a catalyst (palladium/carbon powder, platinum oxide ($PtO_2$), activated nickel and the like) and a hydrogen source such as hydrogen gas of ordinary pressure or under pressurization, ammonium formate, or hydrazine hydrate at a temperature of −10 to 60° C.
(4) The deprotection reaction of silyl group is performed, for example, by using tetra-n-butylammonium fluoride or the like in a water-miscible organic solvent (tetrahydrofuran, acetonitrile and the like) at a temperature of −10 to 60° C.
(5) The deprotection reaction using a metal is performed, for example, in an acidic solvent (acetic acid, buffer of pH 4.2 to 7.2, a mixture of such a solution and an organic solvent such as tetrahydrofuran) in the presence of zinc powder with or without ultrasonication at a temperature of −10 to 60° C.
(6) The deprotection reaction using a metal complex is performed, for example, in an organic solvent (dichloromethane, dimethylformamide, tetrahydrofuran, ethyl acetate, acetonitrile, dioxane, ethanol and the like), water, or a mixture thereof in the presence of a trap reagent (tributyltin hydride, triethylsilane, dimedone, morpholine, diethylamine, pyrrolidine and the like), an organic acid (acetic acid, formic acid, 2-ethylhexanoic acid and the like) and/or an organic acid salt (sodium 2-ethylhexanoate, potassium 2-ethylhexanoate and the like) in the presence or absence of a phosphine type regent (triphenylphosphine and the like) by using a metal complex [tetrakistriphenylphosphine palladium(0), bis(triphenylphosphine) palladium(II) dichloride, palladium(II) acetate, tris(triphenylphosphine) rhodium(I) chloride and the like] at a temperature of −10 to 60° C.

Further, according to methods other than the aforementioned methods, the deprotection reaction can be performed by referring to and examining ordinary chemical articles, for example, Protective Groups In Organic Synthesis, mentioned above, references cited therein and the like.

As readily understood by those skilled in the art, conversion to the compounds of the present invention can be easily conducted by combining these protection/deprotection reactions, or selecting suitable method therefrom.

[Preparation Method 1]

(Scheme 1)

[Formula 67]

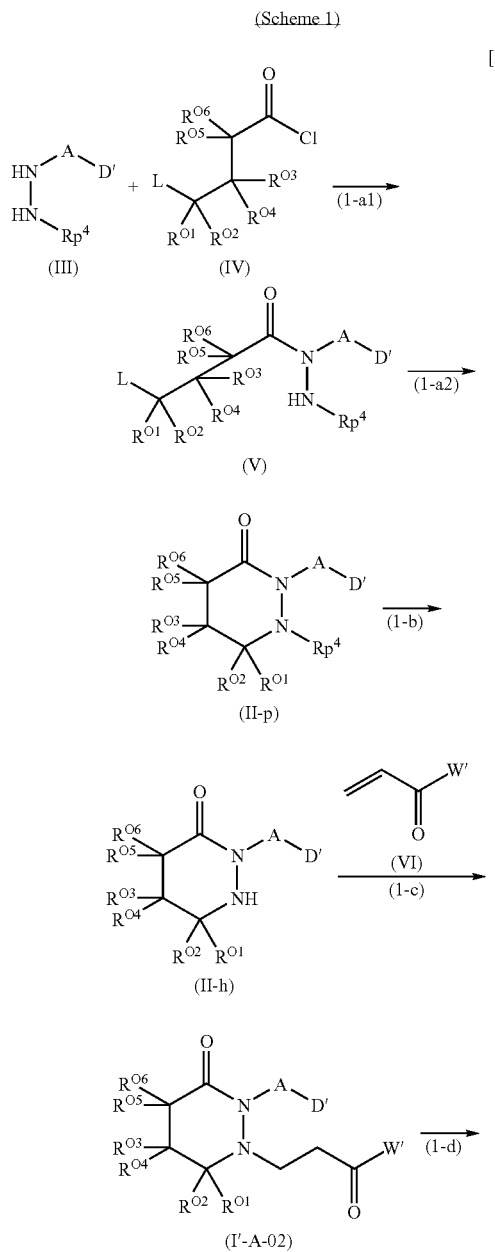

-continued

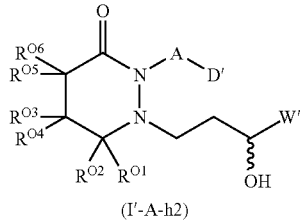

Examples of the methods for preparing the compounds represented by the general formula (I'-A-o2) or the general formula (I'-A-h2) [henceforth simply referred to as "compound (I'-A-o2)" and "compound (I'-A-h2)", respectively], which constitute a part of Compound (I) of the invention, of which substituent D and/or W may be protected, and the compounds represented by the general formula (II-p) or the general formula (II-h) [henceforth simply referred to as "compound (II-p)" and "compound (II-h)", respectively], which constitute a part of Compound (II) of the present invention, of which substituent D may be protected, include, for example, a method of performing the reaction steps described below according to Scheme 1. Although these compound (I'-A-o2) and compound (I'-A-h2), per se, may sometimes be Compound (I) of the invention, when they contain a protective group, they can be converted into Compound (I) of the invention by deprotection. Similarly, the compound (II-p) and compound (II-h), per se, may be occasionally Compound (II) of the present invention, when they contain a protective group, they can be converted into Compound (II) of the invention by deprotection. In Scheme 1, W' has the same meaning as that of W mentioned above, or when W is carboxyl group, the carboxyl group may be protected with the group $Rp^1$, when W contains hydroxyl group, the hydroxyl group may be protected with the group $Rp^2$, when W contains formyl group, the formyl group may be protected with the group $Rp^3$, further, when W contains amino group, the amino group may be protected with the group $Rp^4$, L represents chlorine atom, bromine atom, iodine atom, mesylate group, triflate group, or an arenesulfonate group of which aromatic ring moiety may be substituted with 1 or the same or different 2 or more alkyl groups, a halogen atom and the like, and $R^{O1}$ to $R^{O6}$, A, D', $Rp^1$, $Rp^2$, $Rp^3$, and $Rp^4$ have the same meanings as those defined above.

Step (1-a1):

Examples of the methods for preparing the compounds represented by the general formula (V) [henceforth simply referred to as "compound (V)"], which are intermediates of the target compounds, include a method of condensing a compound represented by the general formula (III) [henceforth simply referred to as "compound (III)"] with a compound represented by the general formula (IV) [henceforth simply referred to as "compound (IV)"] in an inert solvent in the presence of a base, if needed. The compound (IV) is used, for example, usually in an amount of 0.9 to 10 fold moles, preferably 1 to 3 fold moles, based on the compound (III). Examples of the inert solvent used for this method include, for example, halogenated hydrocarbons such as dichloromethane and chloroform, ethers such as tetrahydrofuran, dioxane, and diethyl ether, dimethyl sulfoxide, N,N-dimethylformamide, acetonitrile and the like. These solvents can be used alone or a mixed solvent. Examples of the base used for the aforementioned reaction include, for example, alkali metal compounds such as sodium hydrogencarbonate, sodium hydroxide, sodium hydride, potassium carbonate, sodium carbonate, potassium hydroxide, and sodium methylate, and organic tertiary amines such as pyridine, trimethylamine, triethylamine, diisopropylethylamine, and N-methylmorpholine. These bases are used in an amount of, for example, usually 1 to 20 fold moles, preferably 1 to 10 fold moles, based on the compound (III). The reaction temperature is, for example, generally −30 to 120° C., preferably −20 to 50° C. The reaction time is generally 0.5 to 72 hours, preferably 0.5 to 48 hours. However, since the progress of the reaction can be monitored by thin layer chromatography (TLC), high performance liquid chromatography (HPLC) or the like, it is usually preferred that the reaction is terminated when a maximum yield of the compound (V) is obtained.

Step (1-a2):

Examples of the methods for preparing the compound (II-p) include a method of reacting a compound (V) in an inert solvent in the presence of base, if needed. As the inert solvent and base used in this method, those similarly used in Step (1-a1) can be used. The reaction temperature is, for example, generally 0 to 120° C., preferably 20 to 80° C. The reaction time is generally 1 to 72 hours, preferably 1 to 48 hours. However, since the progress of the reaction can be monitored by thin layer chromatography (TLC), high performance liquid chromatography (HPLC) or the like, it is usually preferred that the reaction is terminated when a maximum yield of the compound (II-p) is obtained. Although this reaction may be performed after isolating the compound (V) obtained in Step (1-a1), the reaction may be performed under the same condition or with elevating the reaction temperature, or/and further adding the base, and prolonging the reaction time.

Step (1-b):

Examples of the methods for preparing the compound (II-h) include a method of removing the protective group $Rp^4$ of the amino group in the compound (II-p). Examples of the deprotection method include, for example, the aforementioned examples. For example, when $Rp^4$ is t-butoxycarbonyl (Boc) group, the compound (II-p) can be reacted with trifluoroacetic acid in an inert solvent such as dichloromethane to obtain the compound (II-h). Trifluoroacetic acid is used in an amount of, for example, usually 0.1 fold mole to largely excessive amount, preferably 1 to 20 fold moles, based on the compound (II-p). The reaction temperature is, for example, generally −30° C. to room temperature. The reaction time is generally 0.2 to 24 hours, preferably 0.5 to 1 hour. However, since the progress of the reaction can be monitored by thin layer chromatography (TLC), high performance liquid chromatography (HPLC) or the like, it is usually preferred that the reaction is terminated when a maximum yield of the compound (II-h) is obtained.

Step (1-c):

Examples of the methods for preparing the compound (I'-A-o2) include a method of reacting a compound (II-h) with a compound represented by the general formula (VI) [henceforth simply referred to as "compound (VI)"] in an inert solvent in the presence of a base or an acid, if needed. The compound (VI) is used in an amount of, for example, usually 1 to 20 fold moles, preferably 1 to 10 fold moles, based on the compound (II-h). Examples of the inert solvent used for this method include, for example, halogenated hydrocarbons such as dichloromethane and chloroform, alcohol type solvents such as methanol and ethanol, ethers such as tetrahydrofuran, dioxane, and diethyl ether, dimethyl sulfoxide, N,N-dimethylformamide, acetonitrile, water and the like. These solvents can be used alone or a mixed solvent. When a base is used in the aforementioned reaction, examples of the base include, for example, alkali metal compounds such as sodium hydrogencarbonate, sodium hydroxide, potassium carbonate, sodium carbonate, potassium hydroxide and sodium methylate, and organic tertiary amines such as pyridine, trimethylamine, triethylamine, diisopropylethylamine, and N-methylmorpholine. Further, when an acid is used, examples of the acid include, for example, acetic acid, and Lewis acids such as copper(II) acetate and ferric chloride. These acids are used in an amount of, for example, usually a catalytic amount to 20 fold moles, preferably 1 to 10 fold moles, based on the compound (II-h). The reaction temperature is, for example, generally −30 to 120° C., preferably −20 to 50° C. The reaction time is generally 0.5 to 72 hours, preferably 1 to 48 hours. However, since the progress of the reaction can be monitored by thin layer chromatography (TLC), high performance liquid chromatography (HPLC) or the like, it is usually preferred that the reaction is terminated when a maximum yield of the compound (I'-A-o2) is obtained.

Step (1-d):

Examples of the methods for preparing the compound (I'-A-h2) include a method of reducing the ketone or carbonyl group of the compound (I'-A-o2) in a polar solvent by using an appropriate reducing agent. Examples of the polar solvent include water, methanol, ethanol, tetrahydrofuran, dioxane and the like, and if needed, these solvents can be used as a mixture. Examples of the reducing agent used in the aforementioned reaction include, for example, sodium borohydride, zinc borohydride, triethyllithium borohydride and the like. The reducing agent is used in an amount of, for example, usually a catalytic amount to 10 fold moles, preferably 0.5 to 3 fold moles, based on the compound (I'-A-o2). The reaction temperature is, for example, generally −50 to 50° C., preferably −20° C. to room temperature. The reaction time is generally 0.5 to 72 hours, preferably 1 to 24 hours. However, since the progress of the reaction can be monitored by thin layer chromatography (TLC), high performance liquid chromatography (HPLC) or the like, it is usually preferred that the reaction is terminated when a maximum yield of the compound (I'-A-h2) is obtained.

When the desired compound as the compound (I'-A-h2) is an optically active isomer, the target substance can be obtained by subjecting the ketone or carbonyl group in the compound (I'-A-o2) to asymmetric reduction. Asymmetric reduction reactions are well known, and examples include, for example, (1) a method of using an optically active phosphine ligand-rhodium complex, (2) a method of using a BINAP-ruthenium complex, (3) a method of using asymmetric hydrosilylation, (4) a method of using asymmetrically modified lithium aluminum hydride, (5) a method of using a borate and borane, (6) a method of using an enzyme or microorganism and the like.

Specific examples include a method of reducing a compound (I'-A-o2) with $BH_3$ in an inert solvent in the presence of an oxaborolidine [e.g., (R)-2-methyl-CBS-oxaborolidine regent, (S)-isomer thereof and the like], which is commercially available or can be obtained by a known method. Examples of the inert solvent used for this method include, for example, tetrahydrofuran, dioxane, diethyl ether, toluene and the like, and these solvents can be used alone or a mixed solvent. The oxaborolidine is used in an amount of, for example, ordinarily a catalytic amount to 2 fold moles, preferably 0.01 to 1 fold mole, most preferably 0.02 to 0.1 fold mole, based on the compound (I'-A-o2). Preferred examples of BH$_3$ used for the reaction include boron-THF complex, boron-dimethyl sulfide complex and the like, and the reagent is used in an amount of, for example, usually 0.8 to 10 fold moles, preferably 1 to 2 fold moles. The reaction temperature is, for example, generally −100 to 50° C., preferably −100 to 0° C., most preferably −70 to −10° C. The reaction time is generally 0.5 to 72 hours, preferably 1 to 48 hours. However, since the progress of the reaction can be monitored by thin layer chromatography (TLC), high performance liquid chromatography (HPLC) or the like, and the optical purity of the product can be confirmed by HPLC using an asymmetric column or the like, it is usually preferred that the reaction is terminated when a maximum yield and optical purity of the compound (I'-A-h2) are obtained.

The methods of the asymmetric reduction are not limited to these methods, and the preparation can be attained according to the methods described in ordinary literature of chemistry, for example Jikken Kagaku Koza (Lecture of Experiment Chemistry), 4th-edition, Ed. by the Chemical Society of Japan, Vol. 26, pp. 23-26, Maruzen, references cited therein and the like.

The compounds (III), (IV) and (VI) are commercially available, or can be synthesized by known methods or similar methods.

[Preparation Method 2]

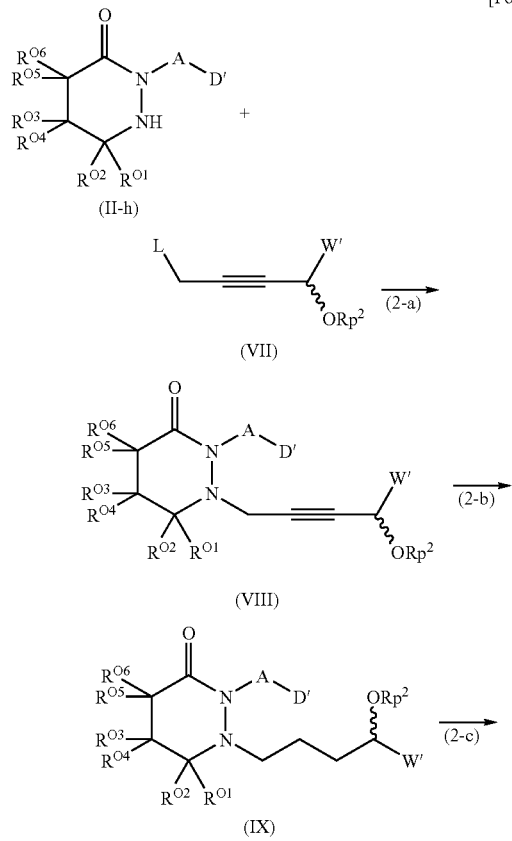

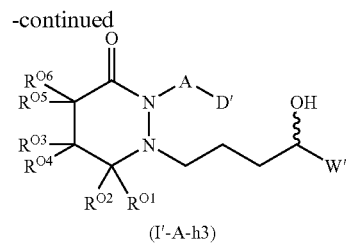

Examples of the method for preparing the compounds represented by the general formula (I'-A-h3) [henceforth simply referred to as "compound (I'-A-h3)"], which constitute a part of Compound (I) of the invention, of which substituent D and/or W may be protected, include, for example, a method of performing the reaction steps described below in accordance with Scheme 2. Although the compound (I'-A-h3), per se, may occasionally be Compound (I) of the invention, when the compound contains a protective group, it can be subjected to deprotection and thereby converted into Compound (I) of the invention. In Scheme 2, $R^{O1}$ to $R^{O6}$, A, D', L, Rp$^2$, and W' have the same meanings as those defined above.

Step (2-a):

Examples of the methods for preparing the compounds represented by the general formula (VIII) [henceforth simply referred to as "compound (VIII)"], which are intermediates of the target compounds, include a method of condensing the aforementioned compound (II-h) with a compound represented by the general formula (VII) [henceforth simply referred to as "compound (VII)"] in an inert solvent in the presence of a base, if needed. Examples of the method of the condensation reaction include a method similar to the method of Preparation method 1, Step (1-a1) mentioned above.

The compound (VII) is commercially available, or can be synthesized by known methods or similar methods.

Step (2-b):

Examples of the methods for preparing the compounds represented by the general formula (IX) [henceforth simply referred to as "compound (IX)"] include a method of converting the triple bond of the compound (VIII) into a single bond, for example, by performing a reduction reaction described in ordinary chemical articles. Examples include, for example, a method of converting the triple bond of the compound (VIII) into a single bond by hydrogenation using a hydrogen source such as hydrogen gas, ammonium formate, and hydrazine hydrate in a single or mixed solvent of alcohol type solvents such as methanol, and ester type solvents such as ethyl acetate in the presence of a catalyst such as palladium/carbon powder, platinum oxide (PtO$_2$), and activated nickel and the like.

Step (2-c):

Examples of the methods for preparing the compound (I'-A-h3) include a method of removing the Rp$^2$ group of the compound (IX) as a protective group of hydroxyl group. Examples of the deprotection method include methods similar to the methods described above.

[Preparation Method 3]

(Scheme 3)

[Formula 69]

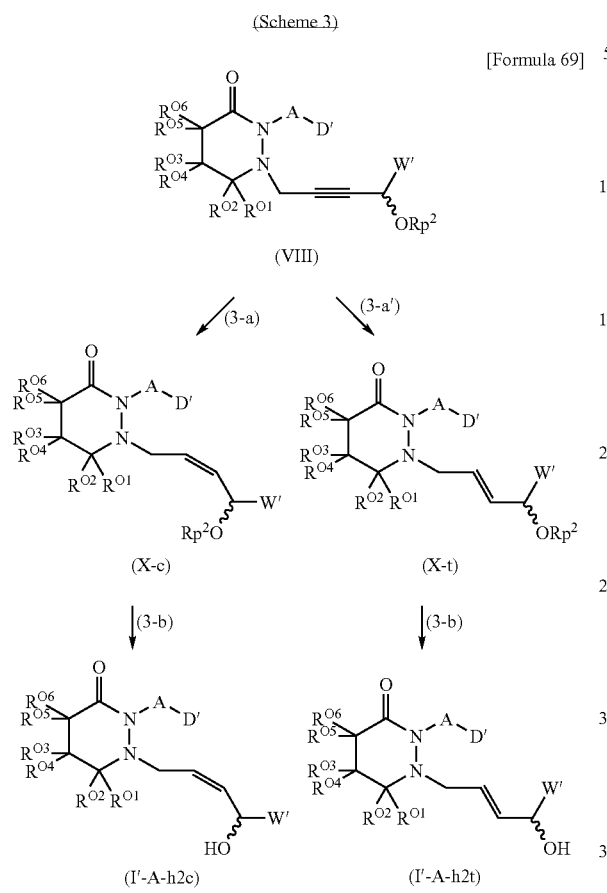

Examples of the method for preparing the compounds represented by the general formula (I'-A-h2c) or (I'-A-h2t) [henceforth simply referred to as "compound (I'-A-h2c)" and "compound (I'-A-h2t)", respectively], which constitute a part of Compound (I) of the invention, of which substituent D and/or W may be protected, include, for example, a method of performing the reaction steps described below in accordance with Scheme 3. Although the compound (I'-A-h2c) or (I'-A-h2t), per se, may occasionally be Compound (I) of the invention, when the compound contains a protective group, it can be subjected to deprotection and thereby converted into Compound (I) of the invention. In Scheme 3, $R^{O1}$ to $R^{O6}$, A, D', $Rp^2$, and W' have the same meanings as those defined above.

Step (3-a):

Examples of the methods for preparing the compounds represented by the general formula (X-c) [henceforth simply referred to as "compound (X-c)"], which are intermediates of the target compounds, include a method of converting the triple bond of the aforementioned compound (VIII) into a double bond in cis-configuration, for example, by performing a reduction reaction described in ordinary chemical articles. Examples include, for example, a method of converting the triple bond of the compound (VIII) into a double bond in cis-configuration by hydrogenation using a hydrogen source such as hydrogen gas, ammonium formate, and hydrazine hydrate in a single or mixed solvent of alcohol type solvents such as methanol, and ester type solvents such as ethyl acetate in the presence of a catalyst such as palladium/barium carbonate, palladium/calcium carbonate, palladium/calcium carbonate-lead acetate (Lindler catalyst), and palladium/barium carbonate-quinoline and the like.

Step (3-a'):

Examples of the methods for preparing the compounds represented by the general formula (X-t) [henceforth simply referred to as "compound (X-t)"] include a method of converting the triple bond of the aforementioned compound (VIII) into a double bond in trans-configuration, for example, by performing a reduction reaction described in ordinary chemical articles. Examples include, for example, a method of converting the triple bond of the compound (VIII) into a double bond in trans-configuration by performing a reaction with sodium bis(2-methoxyethoxy)aluminum hydride (Red-Al) or the like in a single or mixed solvent of tetrahydrofuran, dioxane, diethyl ether, toluene or the like.

Step (3-b):

Examples of the methods for preparing the compounds (I'-A-h2c) or (I'-A-h2t) include a method of removing the $Rp^2$ group of the compound (X-c) or (X-t) as a protective group of hydroxyl group by a method similar to the method of Preparation method 2, Step (2-c).

[Preparation Method 4]

(Scheme 4)

[Formula 70]

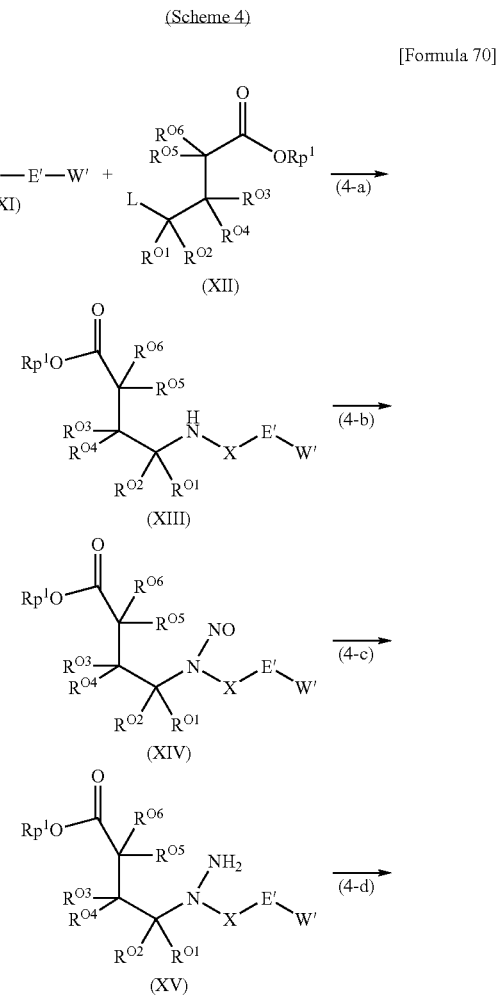

-continued

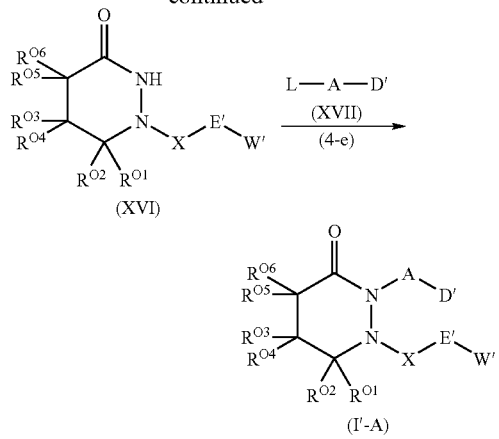

Examples of the method for preparing the compounds represented by the general formula (I'-A) [henceforth simply referred to as "compound (I'-A)"], which constitute a part of Compound (I) of the invention, of which substituent D, E and/or W may be protected, include, for example, a method of performing the reaction steps described below in accordance with Scheme 4. Although the compound (I'-A), per se, may occasionally be Compound (I) of the invention, when the compound contains a protective group, it can be subjected to deprotection and thereby converted into Compound (I) of the invention. In Scheme 4, E' has the same meaning as that of E mentioned above, and when E contains hydroxyl group, the hydroxyl group may be protected with the group $Rp^2$. $R^{O1}$ to $R^{O6}$, A, D', $Rp^1$, X, W', and L have the same meanings as those defined above.

Step (4-a):

Examples of the methods for preparing the compounds represented by the general formula (XIII) [henceforth simply referred to as "compound (XIII)"], which are intermediates of the target compounds, include a method of condensing the aforementioned compound (XI) with a compound represented by the general formula (XII) [henceforth simply referred to as "compound (XII)"] in an inert solvent in the presence of a base, if needed. Examples of the method of the condensation reaction include a method similar to the method of Preparation method 1, Step (1-a1) mentioned above.

Step (4-b):

Examples of the methods for preparing the compounds represented by the general formula (XIV) [henceforth simply referred to as "compound (XIV)"] include a method of performing a nitrosation reaction described in ordinary chemical articles for the amino group of the compound (XIII). Examples of the methods for the nitrosation reaction include, for example, a method of reacting the compound (XIII) with sodium nitrite or the like in a single or mixed solvent of acetic acid, water, methanol, ethanol, tetrahydrofuran, and dioxane in the presence of an acid such as acetic acid, sulfuric acid, nitric acid, and hydrochloric acid.

Step (4-c):

Examples of the methods for preparing the compounds represented by the general formula (XV) [henceforth simply referred to as "compound (XV)"] include a method of performing a reduction reaction described in ordinary chemical articles for the nitroso group of the compound (XIV). Examples of the methods for the reduction reaction for the nitroso group include, for example, a method of reduction with zinc powder in acetic acid or a mixed solvent of acetic acid and a polar solvent such as water and methanol.

Step (4-d):

Examples of the methods for preparing the compounds represented by the general formula (XVI) [henceforth simply referred to as "compound (XVI)"] include a method of cyclizing the compound (XV) in a polar solvent in the presence of a base. Examples of the polar solvent include methanol, ethanol, tetrahydrofuran, dioxane, dimethyl sulfoxide, N,N-dimethylformamide, acetonitrile and the like, and if needed, these solvents can be used as a mixture. Examples of the base used include alkali metal alkoxides and the like, and preferred examples include, for example, sodium methylate, sodium ethylate, magnesium ethylate, potassium t-butoxide and the like. These bases are used in an amount of, for example, usually 0.5 to 10 fold moles, preferably 1 to 5 fold moles, based on the compound (XV). The reaction temperature is, for example, generally −30 to 100° C., preferably 0 to 50° C. The reaction time is generally 0.5 to 72 hours, preferably 1 to 48 hours. However, since the progress of the reaction can be monitored by thin layer chromatography (TLC), high performance liquid chromatography (HPLC) or the like, it is usually preferred that the reaction is terminated when a maximum yield of the compound (XVI) is obtained.

Step (4-e):

Examples of the methods for preparing the compound (I'-A) include a method of condensing the compound (XVI) with a compound represented by the general formula (XVII) [henceforth simply referred to as "compound (XVII)"] in an organic solvent in the presence of a base. The compound (XVII) is used in an amount of, for example, usually 1 to 20 fold moles, preferably 1 to 5 fold moles, based on the compound (XVI). Examples of the organic solvent used include tetrahydrofuran, dioxane, dimethyl sulfoxide, N,N-dimethylformamide, acetonitrile and the like, and these solvents can be used as a mixture, if needed. Examples of the base used include, for example, sodium hydride, potassium hydride, sodium methylate, sodium ethylate, potassium t-butoxide and the like. These bases are used in an amount of, for example, usually 1 to 10 fold moles, preferably 1 to 3 fold moles, based on the compound (XVI). The reaction temperature is, for example, generally −30 to 100° C., preferably 0 to 50° C. The reaction time is generally 0.5 to 72 hours, preferably 1 to 48 hours. However, since the progress of the reaction can be monitored by thin layer chromatography (TLC), high performance liquid chromatography (HPLC) or the like, it is usually preferred that the reaction is terminated when a maximum yield of the compound (I'-A) is obtained.

The compounds (XI), (XII), and (XVII) are commercially available, or can be synthesized by known methods or similar methods.

[Preparation Method 5]

(Scheme 5)

[Formula 71]

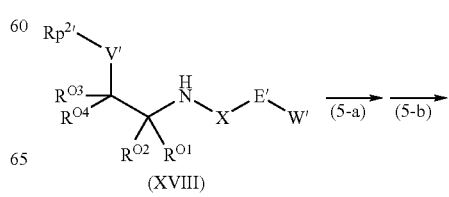

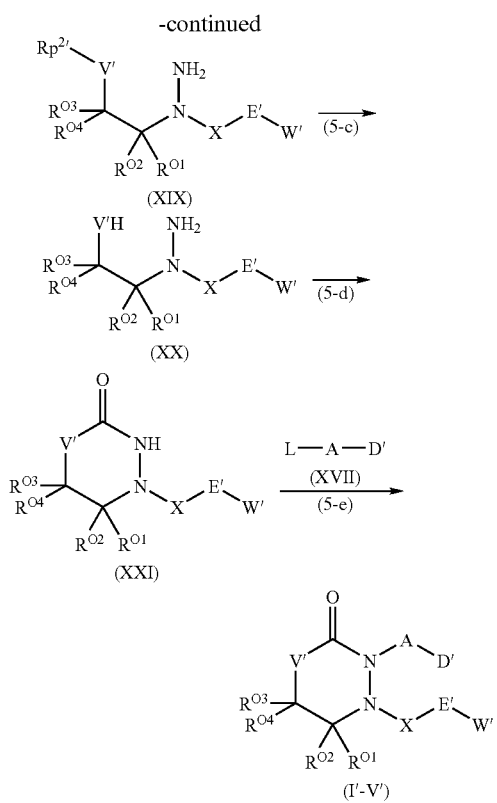

Examples of the method for preparing the compounds represented by the general formula (I'-V') [henceforth simply referred to as "compound (I'-V')"], which constitute a part of Compound (I) of the invention, of which substituent D, E and/or W may be protected, include, for example, a method of performing the reaction steps described below in accordance with Scheme 5. Although the compound (I'-V'), per se, may be Compound (I) of the invention, when the compound contains a protective group, it can be subjected to deprotection and thereby converted into Compound (I) of the invention. In Scheme 5, V' represents oxygen atom, or sulfur atom, $Rp^{2'}$ represents a protective group of hydroxyl group or thiol group, and $R^{O1}$ to $R^{O4}$, X, W', and L have the same meanings as those defined above.

Steps (5-a) and (5-b):

Examples of the methods for preparing the compounds represented by the general formula (XIX) [henceforth simply referred to as "compound (XIX)"], which are intermediates of the target compounds, include a method of nitrosating a compound represented by the general formula (XVIII) [henceforth simply referred to as "compound (XVIII)"] by a method similar to that of Preparation method 4, Step (4-b) mentioned above and then reducing the nitroso group by a method similar to that of Preparation method 4, Step (4-c).

The compound (XVIII) can be synthesized by known methods or similar methods.

Step (5-c):

Examples of the methods for preparing the compounds represented by the general formula (XX) [henceforth simply referred to as "compound (XX)"] include a method of subjecting the protective group of the hydroxyl group or thiol group of the compound (XIX), $Rp^{2'}$, to the aforementioned deprotection reaction.

Step (5-d):

Examples of the methods for preparing the compounds represented by the general formula (XXI) [henceforth simply referred to as "compound (XXI)"] include a method of treating the compound (XX) with a carbonylation agent in an organic solvent in the presence of a base to cyclize the compound (XX). Examples of the organic solvent used include dichloromethane, tetrahydrofuran, dimethoxyethane, diethyl ether, dimethylformamide and the like, and these solvents can be used as a mixture, if needed. Examples of the base used include, for example, sodium hydrogencarbonate, potassium carbonate, triethylamine, pyridine and the like. These bases are used in an amount of, for example, usually 1 to 10 fold moles, preferably 1 to 3 fold moles, based on the compound (XX). Examples of the carbonylation agent include triphosgene, 1,1'-carbonyldiimidazole (CDI), phosgene and the like, and these solvents are used in an amount of, for example, usually 1 to 10 fold moles, preferably 1 to 3 fold moles, based on the compound (XX). The reaction temperature is, for example, generally −30 to 100° C., preferably 0 to 50° C. The reaction time is generally 0.5 to 72 hours, preferably 1 to 48 hours. However, since the progress of the reaction can be monitored by thin layer chromatography (TLC), high performance liquid chromatography (HPLC) or the like, it is usually preferred that the reaction is terminated when a maximum yield of the compound (XXI) is obtained.

Step (5-e):

Examples of the methods for preparing the compound (I'-V') include a method of condensing the compound (XXI) with the compound (XVII) by a method similar to that of Preparation method 4, Step (4-e).

[Preparation Method 6]

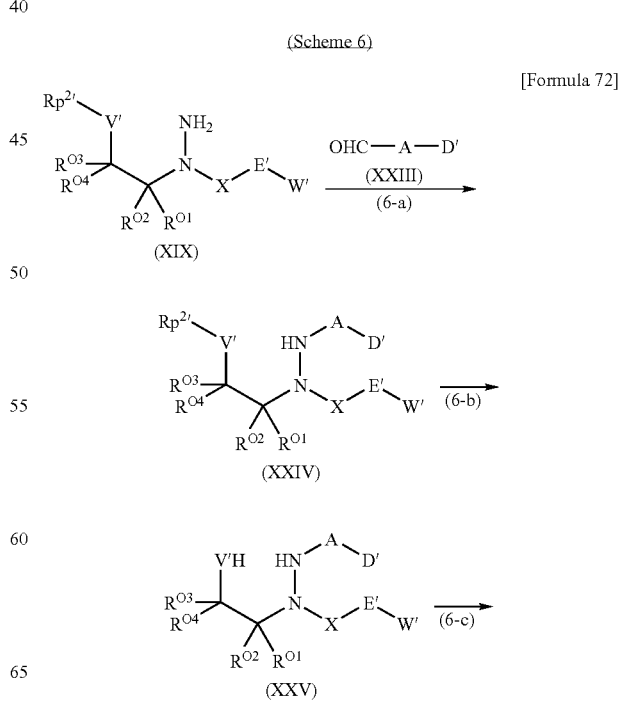

-continued

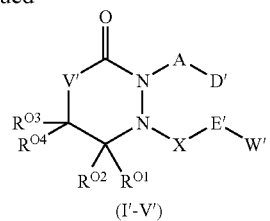

(I'-V')

Examples of the methods for preparing the compound (I'-V') include, besides the method shown in Preparation method 5 mentioned above, for example, a method of performing the reaction steps described below in accordance with Scheme 6. Although the compound (I'-V') obtained by Preparation method 6, per se, may be Compound (I) of the invention, when the compound contains a protective group, it can be subjected to deprotection and thereby converted into Compound (I) of the invention. In Scheme 6, V', $R^{O1}$ to $R^{O4}$, A, D', X, E', W', and $Rp^{2'}$ have the same meanings as those defined above.

Step (6-a):

Examples of the methods for preparing the compounds represented by the general formula (XXIV) [henceforth simply referred to as "compound (XXIV)"], which are intermediates of the target compounds, include a method of subjecting the aforementioned compound (XIX) and a compound represented by the general formula (XXIII) [henceforth simply referred to as "compound (XXIII)"] to a reductive amination reaction in an organic solvent. The compound (XXIII) is used in an amount of, for example, usually 0.5 to 10 fold moles, preferably 0.9 to 2 fold moles, based on the compound (XIX). Examples of the organic solvent used include dichloromethane, tetrahydrofuran, dimethoxyethane, diethyl ether and the like, and these solvents can be used as a mixture, if needed. Examples of the reducing agent used include, for example, sodium cyanoborohydride, sodium borohydride, sodium triacetoxyborohydride, pyridine borane and the like. These agents are used in an amount of, for example, usually 1 to 5 fold moles, preferably 1 to 3 fold moles, based on the compound (XIX). The reaction temperature is, for example, generally –10 to 100° C., preferably 0 to 50° C. The reaction time is generally 0.5 to 72 hours, preferably 1 to 48 hours. However, since the progress of the reaction can be monitored by thin layer chromatography (TLC), high performance liquid chromatography (HPLC) or the like, it is usually preferred that the reaction is terminated when a maximum yield of the compound (XXIV) is obtained.

The compound (XXIII) is commercially available, or can be synthesized by known methods or similar methods.

Step (6-b):

Examples of the methods for preparing the compounds represented by the general formula (XXV) [henceforth simply referred to as "compound (XXV)"] include a method of subjecting the protective group of the hydroxyl group or thiol group of the compound (XXIV), $Rp^{2'}$, to the aforementioned deprotection reaction.

Step (6-c):

Examples of the methods for preparing the compound (I'-V') include a method of cyclizing the compound (XXV) by a method similar to the method of Preparation method 5, Step (5-d).

[Preparation Method 7]

(Scheme 7)

[Formula 73]

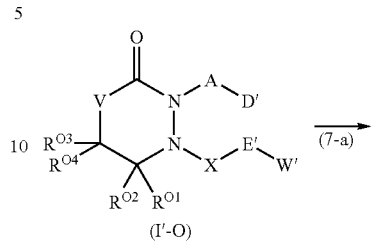

(I'-O)

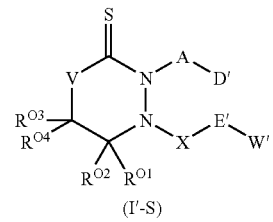

(I'-S)

Examples of the method for preparing the compounds represented by the general formula (I'-S) [henceforth simply referred to as "compound (I'-S)"], which constitute a part of Compound (I) of the invention, of which substituent D, E and/or W may be protected, include, for example, a method of performing the reaction steps described below in accordance with Scheme 7. The compounds represented by the general formula (I'-O) [henceforth simply referred to as "compound (I'-O)"] can be synthesized by any one of Preparation methods 1 to 6. Although the compound (I'-O), per se, may be Compound (I) of the invention, when the compound contains a protective group, it can be subjected to deprotection and thereby converted into Compound (I) of the invention. Similarly, although the compound (I'-S), per se, may be Compound (I) of the invention, when the compound contains a protective group, it can be subjected to deprotection and thereby converted into Compound (I) of the invention. In Scheme 7, V', $R^{O1}$ to $R^{O4}$, A, D', X, E', and W' have the same meanings as those defined above.

Step (7-a):

Examples of the methods for preparing the compound (I'-S) include a method of thiocarbonylating a compound (I'-O) in an inert solvent. Examples of the inert solvent used for this method include dichloromethane, chloroform, tetrahydrofuran, dioxane, diethyl ether, toluene and the like is, and these solvents can be used as a simple solvent or a mixed solvent. Examples of the thiocarbonylation reagent include the Lawesson's reagent [2,4-bis(4-methoxyphenyl)-1,3-dithia-2,4-diphosphetane-2,4-disulfide], diphosphorous pentoxide and the like, and these reagents are used in an amount of, for example, usually 1 to 20 fold moles, preferably 1 to 5 fold moles, based on the compound (I'-O). As the reaction temperature, an appropriate temperature from room temperature to the reflux temperature of the solvent is generally chosen. The reaction time is generally 0.5 to 72 hours, preferably 1 to 48 hours. However, since the progress of the reaction can be monitored by thin layer chromatography (TLC), high performance liquid chromatography (HPLC) or the like, it is usually preferred that the reaction is terminated when a maximum yield of the compound (I'-S) is obtained.

[Preparation Method 8]

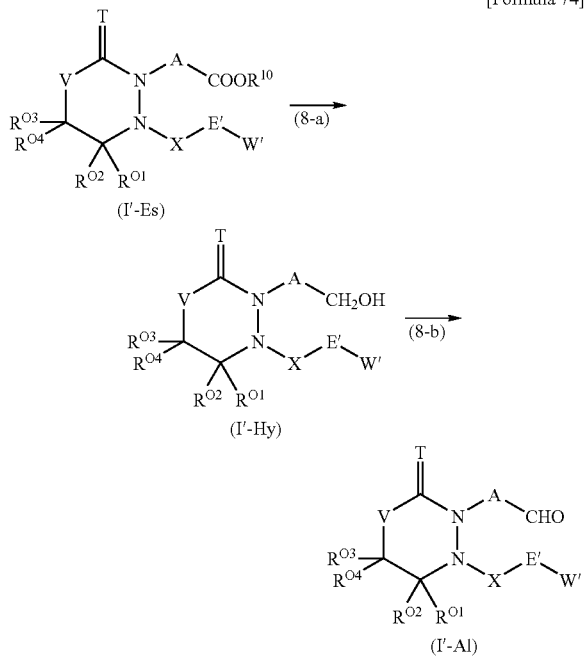

(Scheme 8)

[Formula 74]

Examples of the method for preparing the compounds represented by the general formula (I'-Hy) or (I'-Al) [henceforth simply referred to as "compound (I'-Hy)" and "compound (I'-Al)", respectively], which constitute a part of Compound (I) of the invention, of which substituent E and/or W may be protected, include, for example, a method of performing the reaction steps described below in accordance with Scheme 8. The compounds represented by the general formula (I'-Es) [henceforth simply referred to as "compound (I'-Es)"] can be synthesized by any of the methods of Preparation methods 1 to 7. Although the compound (I'-Es), per se, may be Compound (I) of the invention, when the compound contains a protective group, it can be subjected to deprotection and thereby converted into Compound (I) of the invention. Similarly, although the compound (I'-Hy) or compound (I'-Al), per se, may be Compound (I) of the invention, when the compound contains a protective group, it can be subjected to deprotection and thereby converted into Compound (I) of the invention. In Scheme 8, T, V, $R^{O1}$ to $R^{O4}$, A, $R^{10}$, X, E', and W' have the same meanings as those defined above.

Step (8-a):

Examples of the methods for preparing the compound (I'-Hy) include a method of reducing a compound represented by the general formula (I'-Es) [henceforth simply referred to as "compound (I'-Es)"] in an inert solvent. The aforementioned reduction reaction is a known reaction, and can be performed by, for example, a reaction in an organic solvent (tetrahydrofuran, dimethoxyethane, diethyl ether, dioxane, methanol, ethanol, isopropanol and the like) or an aqueous solution thereof in the presence of a reducing agent (sodium borohydride, lithium borohydride and the like) at −10 to 70° C.

Step (8-b):

Examples of the methods for preparing the compound (I'-Al) include a method of oxidizing the compound (I'-Hy) in an inert solvent. The oxidation reaction is a known reaction, and examples of the methods include, for example (1) a method of using the Swern oxidation, (2) a method of using a Dess-Martin regent, (3) a method of using a TEMPO regent and the like.

These methods are specifically explained below.

(1) The method of using the Swern oxidation is performed by, for example, reacting oxalyl chloride and dimethyl sulfoxide at −78° C. in an organic solvent (chloroform, dichloromethane and the like), reacting a compound (I'-Hy) with the resulting solution, and further reacting the product with a tertiary amine (triethylamine, diisopropylethylamine, N-methylmorpholine, N-ethylpiperidine, diazabicyclo[5,4,0]undec-7-ene and the like) at −78 to 20° C.

(2) The method of using the Dess-Martin regent is performed by, for example, performing the reaction in an organic solvent (single or mixed solvent of chloroform, dichloromethane, 1,2-dichloroethane, tetrahydrofuran, acetonitrile, t-butylalcohol and the like) in the presence of the Dess-Martin regent [1,1,1-triacetoxy-1,1-dihydro-1,2-benziodoxol-3-(1H)-one] in the presence or absence of a base (pyridine and the like) at 0 to 40° C.

(3) The method of using the TEMPO regent is performed by, for example, performing the reaction in a single or mixed solvent of organic solvents (chloroform, dichloromethane, tetrahydrofuran, toluene, acetonitrile, ethyl acetate and the like), water and the like in the presence of the TEMPO regent (2,2,6,6,-tetramethyl-1-piperidinyloxy free radical) and a reoxidation agent (aqueous hydrogen peroxide, sodium hypochlorite, 3-chloroperbenzoic acid, iodobenzenediacetate, potassium peroxymonosulfate and the like) in the presence or absence of a quaternary ammonium salt (tetra-n-butylammonium chloride, tetra-n-butylammonium bromide and the like) at 20 to 60° C.

In addition to those mentioned above, oxidation reactions are not particularly limited so long as the reactions can easily and selectively oxidize an alcohol into an aldehyde. For example, the reactions can be chosen by examination according to various reactions such as the Jones oxidation, oxidation with PCC, and oxidation using sulfur trioxide/pyridine complex, methods described in ordinary chemical articles such as Jikken Kagaku Koza (Lecture of Experiment Chemistry), 4th-edition, Ed. by the Chemical Society of Japan, Vol. 23, references cited therein and the like.

[Preparation Method 9]

(Scheme 9)

[Formula 75]

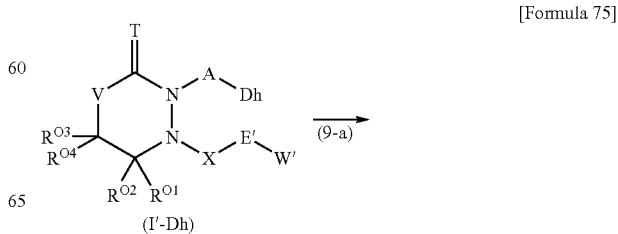

-continued

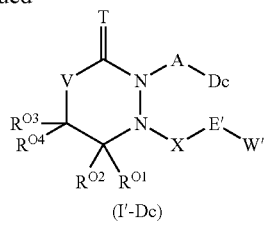

(I'-Dc)

Examples of the methods for preparing the compounds represented by the general formula (I'-Dc) [henceforth simply referred to as "compound (I'-Dc)"], which constitute a part of Compound (I) of the invention, of which substituent E and/or W may be protected, include, for example, a method of performing the reaction steps described below in accordance with Scheme 9. The compounds represented by the general formula (I'-Dh) [henceforth simply referred to as the "compound (I'-Dh)"] can be synthesized by any of the methods of Preparation methods 1 to 8. Although the compound (I'-Dh), per se, may be Compound (I) of the invention, when the compound contains a protective group, it can be subjected to deprotection and thereby converted into Compound (I) of the invention. Similarly, although the compound (I'-Dc), per se, may be Compound (I) of the invention, when the compound contains a protective group, it can be subjected to deprotection and thereby converted into Compound (I) of the invention. In Scheme 9, the group Dh represents hydroxyl group, or —CH$_2$OH group, the group Dc represents a —O-M$_m$-H group, or a —OC(O)—R$^{D9}$ group, and T, V, R$^{O1}$ to R$^{O4}$, A, X, E', W', M, m, and R$^{D9}$ have the same meanings as those defined above.

Step (9-a):

Examples of the methods for preparing the compound (I'-Dc) include a method of esterifying the hydroxyl group of the compound (I'-Dh) by using a compound (Dc-I) represented by the following formula:

HO-(M)$_m$-H        (Dc-I)

(wherein M and m have the same meanings as those defined above) [henceforth simply referred to as "compound (Dc-I)"], or a compound (Dc-II) represented by the following formula:

HO$_2$C—R$^{D9}$        (Dc-II)

(wherein R$^{D9}$ has the same meaning as that defined above) [henceforth simply referred to as "compound (Dc-II)"].

The esterification reaction is a known reaction, and examples of the method include, for example, (1) a method of using an acid halide, (2) a method of using a mixed acid anhydride, (3) a method of using a condensation agent and the like. These methods are specifically explained below.

(1) The method of using an acid halide can be performed by, for example, reacting a carboxylic acid with an acid-halidation agent (oxalyl chloride, thionyl chloride and the like) in a single or mixed solvent of organic solvents (chloroform, dichloromethane, tetrahydrofuran, toluene and the like) or without solvent at an appropriate temperature of from −20° C. to the reflux temperature of the solvent, and reacting the resulting acid halide with an alcohol in the presence of a base (pyridine, triethylamine, dimethylaniline, dimethylaminopyridine, diisopropylethylamine and the like) in an inert organic solvent (single or mixed solvent of chloroform, dichloromethane, diethyl ether, and tetrahydrofuran) at a temperature of −10 to 40° C. Further, the esterification can also be performed by a reaction with an acid halide in an organic solvent (dioxane, tetrahydrofuran and the like) using an aqueous alkaline solution (aqueous sodium hydrogencarbonate, aqueous sodium hydroxide and the like) at a temperature of −10 to 40° C.

(2) The method of using a mixed acid anhydride can be performed by, for example, reacting a carboxylic acid with an acid halide (pivaloyl chloride, tosyl chloride, mesyl chloride and the like), or an acid derivative (ethyl chloroformate, isobutyl chloroformate and the like) in an organic solvent (single or mixed solvent of chloroform, dichloromethane, diethyl ether, and tetrahydrofuran) or without solvent in the presence of a base (pyridine, triethylamine, dimethylaniline, dimethylaminopyridine, diisopropylethylamine and the like) at a temperature of −10 to 40° C., and reacting the resulting mixed acid anhydride with an alcohol in an organic solvent (single or mixed solvent of chloroform, dichloromethane, diethyl ether, and tetrahydrofuran) at a temperature of −10 to 40° C.

(3) The method of using a condensation agent is performed by, for example, reacting a carboxylic acid and an alcohol in an organic solvent (single or mixed solvent of chloroform, dichloromethane, diethyl ether, and tetrahydrofuran) or without solvent in the presence or absence of a base (pyridine, triethylamine, dimethylaniline, dimethylaminopyridine, diisopropylethylamine and the like) using a condensation agent {1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, 1-propylphosphonic acid cyclic anhydride (PPA) and the like}, and 1-hydroxybenztriazole (HOBT) or the like, if needed, at a temperature of −10 to 40° C.

All of these reactions of (1), (2) and (3) are desirably performed under an inert gas (argon, nitrogen and the like) atmosphere and an anhydrous condition.

As other esterification reactions, there are known "esterification with alcohol" described in ordinary chemical articles, for example, Shin-Jikken Kagaku Koza (New Lecture of Experiment Chemistry), Ed. by the Chemical Society of Japan, Vol. 14, p. 1002, "esterification with O-alkylation agent", ibid., the same volume, p. 1002, "esterification with halogenated alkyl", ibid., the same volume, p. 1008, "esterification reaction using a dehydration agent", ibid, vol. 22, p. 45 and the like, and the method can be selected by examining the methods described in these articles, references cited therein and the like.

[Preparation Methods 10 and 11]

(Scheme 10)

[Formula 76]

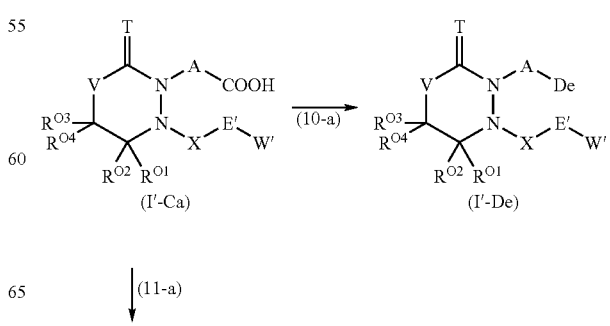

-continued

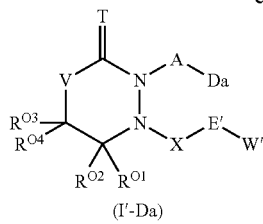

(I'-Da)

Examples of the methods for preparing the compounds represented by the general formula (I'-De) or the general formula (I'-Da) [henceforth simply referred to as the "compound (I'-De)" or "compound (I'-Da)"], which constitute a part of Compound (I) of the invention, of which substituent E and/or W may be protected, include, for example, a method of performing the reaction steps described below in accordance with Scheme 10. The compound represented by the general formula (I'-Ca) [henceforth simply referred to as "compound (I'-Ca)"] can be synthesized by any of the methods of Preparation methods 1 to 7. Although the compound (I'-Ca), per se, may be Compound (I) of the invention, when the compound contains a protective group, it can be subjected to deprotection and thereby converted into Compound (I) of the invention. Similarly, although the compound (I'-De) or compound (I'-Da), per se, may be Compound (I) of the invention, when the compound contains a protective group, it can be subjected to deprotection and thereby converted into Compound (I) of the invention. In Scheme 10, the group De represents —CO-OR$^{D1'}$, —COOR$^{D8}$, or a —COO-Z$^{1'}$-Z$^{2'}$-Z$^{3'}$ group, the group R$^{D1'}$ represents an alkyl group having 1 to 4 carbon atoms, phenyl group, an alkyl group having 1 to 4 carbon atoms substituted with phenyl group, or a biphenyl group, Z$^{1'}$, Z$^{2'}$, and Z$^{3'}$ have the same meanings as those of Z$^1$, Z$^2$, and Z$^3$, respectively, when the -Z$^{1'}$-Z$^{2'}$-Z$^{3'}$ group contains hydroxyl group, amino group, carboxyl group, or formyl group, these substituents may be protected, the group Da represents a —C(O)N(R$^{D2}$)SO$_2$R$^{D3}$ group, a —C(O)NR$^{D5}$R$^{D6}$ group, a —C(O)N(R$^{D5}$)SO$_2$R$^{D7}$ group, or a —C(O)-(M)$_m$-OH group, and T, V, R$^{O1}$ to R$^{O4}$, A, X, E', W', R$^{D8}$, Z$^1$, Z$^2$, Z$^3$, R$^{D2}$, R$^{D3}$, R$^{D5}$, R$^{D6}$, R$^{D7}$, M, and m have the same meanings as those defined above.

Step (10-a):

Examples of the methods for preparing the compound (I'-De) include a method of esterifying a compound (I'-Ca). The compound can be prepared by subjecting the carboxyl group of a compound (I'-Ca) and a compound (De-I) represented by the following formula:

R$^{50}$—R$^{D1'}$ (De-I)

(wherein R$^{50}$ represents hydroxyl group, or a halogen atom, and R$^{D1'}$ has the same meaning as that defined above) [henceforth simply referred to as "compound (De-I)"], a compound (De-II) represented by the following formula:

R$^{50}$—R$^{D8}$ (De-II)

(wherein R$^{50}$ and R$^{D8}$ have the same meanings as those defined above) [henceforth simply referred to as "compound (De-II)"], or a compound (De-III) represented by the following formula:

R$^{50}$-Z$^{1'}$-Z$^{2'}$-Z$^{3'}$ (De-III)

(wherein R$^{50}$, Z$^{1'}$, Z$^{2'}$, and Z$^{3'}$ have the same meanings as those defined above) [henceforth simply referred to as "compound (De-III)"] to an esterification reaction, and subjecting the resultant to a deprotection reaction for a protective group as required.

Examples of the methods for the esterification reaction for the compounds wherein R$^{50}$ in the compounds (De-I), (De-II), and (De-III) represents hydroxyl group include a method similar to the method of Preparation method 9, Step (9-a).

The esterification reaction for the compounds wherein R$^{50}$ in the compounds (De-I), (De-II), and (De-III) represents a halogen atom can be performed by, for example, a reaction in an organic solvent (single or mixed solvent of N,N-dimethylformamide, tetrahydrofuran, dioxane, diethyl ether, and dimethylacetoamide) in the presence of a base (potassium carbonate, cesium carbonate, sodium carbonate, potassium hydrogencarbonate, sodium hydrogencarbonate, potassium hydroxide, sodium hydroxide and the like) at a temperature of 0 to 150° C.

Step (11-a):

Examples of the methods for preparing the compound (I'-Da) include a method of amidating a compound (I'-Ca). The compound can be prepared by subjecting the carboxyl group of the compound (I'-Ca) and a compound (Da-I) represented by the following formula:

H—N(R$^{D2}$)SO$_2$R$^{D3}$ (Da-I)

(wherein R$^{D2}$ and R$^{D3}$ have the same meanings as those defined above) [henceforth simply referred to as "compound (Da-I)"], a compound (Da-II) represented by the following formula:

H—NR$^{D5}$R$^{D6}$ (Da-II)

(wherein R$^{D5}$ and R$^{D6}$ have the same meanings as those defined above) [henceforth simply referred to as "compound (Da-II)"], a compound (Da-III) represented by the following formula:

H—(R$^{D5}$)SO$_2$R$^{D7}$ (Da-III)

(wherein R$^{D5}$ and R$^{D7}$ have the same meanings as those defined above) [henceforth simply referred to as "compound (Da-III)"], or a compound (Da-IV) represented by the following formula:

H-(M)$_m$-OH (Da-IV)

(wherein M and m have the same meanings as those defined above) [henceforth simply referred to as "compound (Da-IV)"] to an amidation reaction, and subjecting the resultant to a deprotection reaction for a protective group, if needed.

The amidation reaction is a known reaction, and examples of the method include, for example, (1) a method of using an acid halide, (2) a method of using a mixed acid anhydride, (3) a method of using a condensation agent and the like. These methods are specifically explained below.

(1) The method of using an acid halide can be performed by, for example, reacting a carboxylic acid with an acid-halidation agent (oxalyl chloride, thionyl chloride and the like) in a single or mixed solvent of organic solvents (chloroform, dichloromethane, tetrahydrofuran, toluene and the like) or without solvent at an appropriate temperature of from −20° C. to the reflux temperature of the solvent, and reacting the resulting acid halide with an amine or sulfonamide in the presence of a base (pyridine, triethylamine, dimethylaniline, dimethylaminopyridine, diisopropylethylamine and the like) in an inert organic solvent (single or mixed solvent of chloroform, dichloromethane, diethyl ether, and tetrahydrofuran) at a temperature of −10 to 40°

C. Further, the amidation can also be performed by a reaction with an acid halide in an organic solvent (dioxane, tetrahydrofuran and the like) using an aqueous alkaline solution (aqueous sodium hydrogencarbonate, aqueous sodium hydroxide and the like) at a temperature of −10 to 40° C.

(2) The method of using a mixed acid anhydride can be performed by, for example, reacting a carboxylic acid with an acid halide (pivaloyl chloride, tosyl chloride, mesyl chloride and the like), or an acid derivative (ethyl chloroformate, isobutyl chloroformate and the like) in an organic solvent (single or mixed solvent of chloroform, dichloromethane, diethyl ether, and tetrahydrofuran) or without solvent in the presence of a base (pyridine, triethylamine, dimethylaniline, dimethylaminopyridine, diisopropylethylamine and the like) at a temperature of −10 to 40° C., and reacting the resulting mixed acid anhydride with an amine or sulfonamide in an organic solvent (single or mixed solvent of chloroform, dichloromethane, diethyl ether, and tetrahydrofuran) at a temperature of −10 to 40° C.

(3) The method of using a condensation agent is performed by, for example, reacting a carboxylic acid and an amine or sulfonamide in an organic solvent (single or mixed solvent of chloroform, dichloromethane, diethyl ether, and tetrahydrofuran) or without solvent in the presence or absence of a base (pyridine, triethylamine, dimethylaniline, dimethylaminopyridine, diisopropylethylamine and the like) using a condensation agent {1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, 1-propylphosphonic acid cyclic anhydride (PPA) etc}, and 1-hydroxybenztriazole (HOBT) or the like, if needed, at a temperature of −10 to 40° C.

Any of these reactions of (1), (2) and (3) are desirably performed under an inert gas (argon, nitrogen and the like) atmosphere and an anhydrous condition.

As other amidation reactions, known reactions include "reaction of carboxylic acid with amine or ammonia" described in ordinary chemical articles, for example, Shin-Jikken Kagaku Koza (New Lecture of Experiment Chemistry), Ed. by the Chemical Society of Japan, Vol. 14, p. 1136, "reaction with an amidation agent", ibid., the same volume, p. 1141, "synthesis from an acid halide", ibid., the same volume, p. 1142 and the like, and the method can be selected by examining the methods described in these articles, references cited therein and the like.

[Preparation Method 12]

(Scheme 11)

[Formula 77]

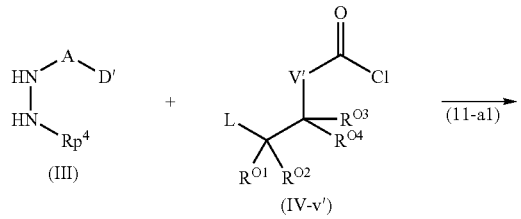

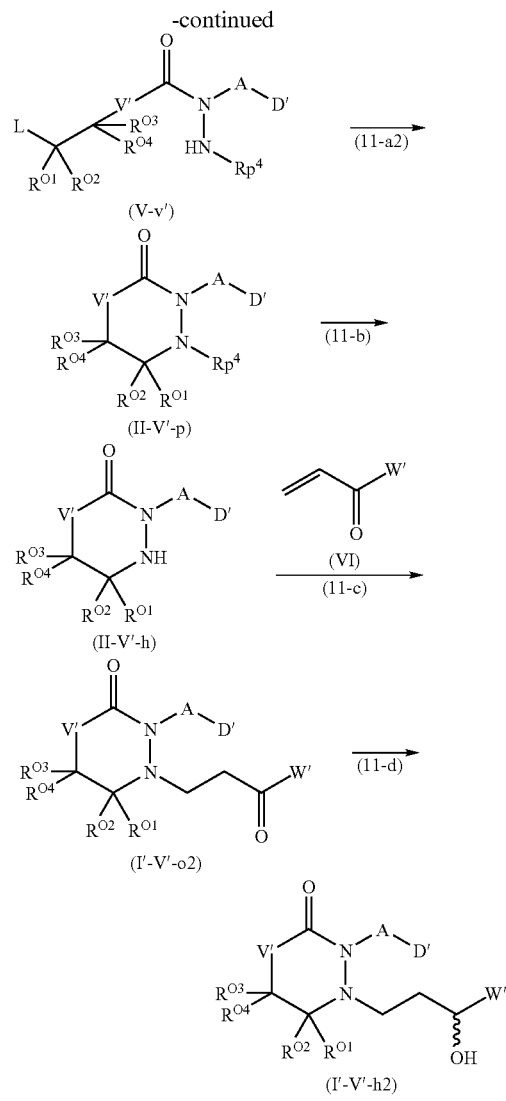

Examples of the methods for preparing the compounds represented by the general formula (I'-V'-o2) or the general formula (I'-V'-h2) [henceforth simply referred to as "compound (I'-V'-o2)" and "compound (I'-V'-h2)", respectively], which constitute a part of Compound (I) of the invention, of which substituent D and/or W may be protected, and the compounds represented by the general formula (II-V'-p) or the general formula (II-V'-h) [henceforth simply referred to as "compound (II-V'-p)" and "compound (II-V'-h)", respectively], which constitute a part of Compound (II) of the present invention, of which substituent D may be protected include, for example, a method of performing the reaction steps described below according to Scheme 11. Although these compound (I'-V'-o2) and compound (I'-V'-h2), per se, may be Compound (I) of the invention, when the compounds contain a protective group, they can be converted into Compound (I) of the invention by deprotection. Similarly, the compound (II-V'-p) and compound (II-V'-h), per se, may also be Compound (II) of the present invention, when the compounds contain a protective group, they can be converted into Compound (II) of the invention by deprotection. In Scheme 11, W', V', L, $R^{O1}$ to $R^{O4}$, A, D', and $Rp^4$ have the same meanings as those defined above.

Step (11-a1):

Examples of the methods for preparing the compounds represented by the general formula (V-v'), which are intermediates of the target compounds, include a method similar to the method of Preparation method 1, Step (1-a1) mentioned above.

The compound (IV-v') is commercially available, or can be synthesized by known methods or similar methods.

Step (11-a2):

Examples of the methods for preparing the compound (II-V'-p) include a method similar to the method of Preparation method 1, Step (1-a2) mentioned above.

Step (11-b):

Examples of the methods for preparing the compound (II-V'-h) include a method similar to the method of Preparation method 1, Step (1-b) mentioned above.

Step (11-c):

Examples of the methods for preparing the compound (I'-V'-o2) include a method similar to the method of Preparation method 1, Step (1-c) mentioned above.

Step (11-d):

Examples of the methods for preparing the compound (I'-V'-h2) include a method similar to the method of Preparation method 1, Step (1-d) mentioned above.

When the desired compound as the compound (I'-V'-h2) is an optically active isomer, the target substance can be obtained by subjecting the ketone or carbonyl group in the compound (I'-V'-o2) to asymmetric reduction. Asymmetric reduction reactions are well known, and examples include, for example, (1) a method of using an optically active phosphine ligand-rhodium complex, (2) a method of using a BINAP-ruthenium complex, (3) a method of using asymmetric hydrosilylation, (4) a method of using asymmetrically-modified lithium aluminum hydride, (5) a method of using borate and borane, (6) a method of using an enzyme or microorganism and the like.

Specific examples include a method of reducing a compound (I'-V'-o2) with $BH_3$ in an inert solvent in the presence of an oxaborolidine [e.g., (R)-2-methyl-CBS-oxaborolidine regent, (S)-isomer thereof and the like], which is commercially available or can be obtained by a known method. Examples of the inert solvent used for this method include, for example, tetrahydrofuran, dioxane, diethyl ether, toluene and the like, and these solvents can be used alone or as a mixed solvent. The oxaborolidine is used in an amount of, for example, usually a catalytic amount to 2 fold moles, preferably 0.01 to 1 fold mole, most preferably 0.02 to 0.1 fold mole, based on the compound (I'-V'-o2). Preferred examples of $BH_3$ used for the reaction include boron-THF complex, boron-dimethyl sulfide complex and the like, and they are used in an amount of, for example, usually 0.8 to 10 fold moles, preferably 1 to 2 fold moles. The reaction temperature is, for example, generally −100 to 50° C., preferably −100 to 0° C., most preferably −70 to −10° C. The reaction time is generally 0.5 to 72 hours, preferably 1 to 48 hours. However, since the progress of the reaction can be monitored by thin layer chromatography (TLC), high performance liquid chromatography (HPLC) or the like, and the optical purity of the product can be confirmed by HPLC using an asymmetric column or the like, it is usually preferred that the reaction is terminated when a maximum yield and optical purity of the compound (I'-V'-h2) are obtained.

The methods of the asymmetric reduction are not limited to these methods, and the preparation can be attained according to the methods described in ordinary chemical articles, for example, Jikken Kagaku Koza (Lecture of Experiment Chemistry), 4th-edition, Ed. by the Chemical Society of Japan, Vol. 26, pp. 23-26, Maruzen, references cited in this literature and the like.

The compound (IV-v') is commercially available, or can be synthesized by known methods or similar methods.

[Preparation Method 13]

(Scheme 12)

[Formula 78]

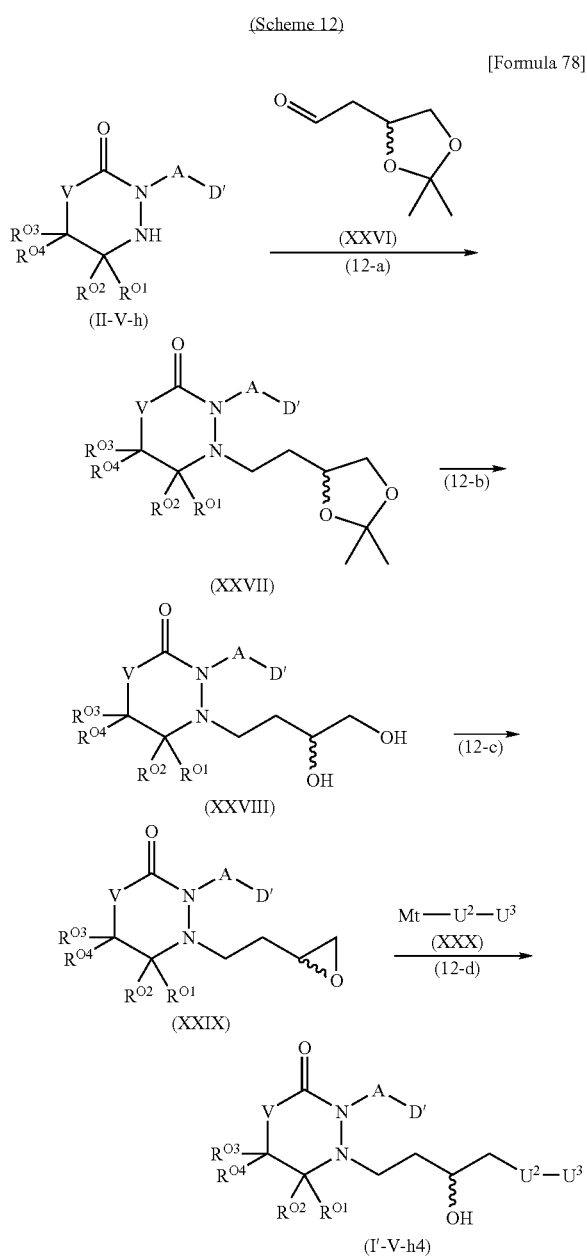

Examples of the method for preparing the compounds represented by the general formula (I'-V-h4) [henceforth simply referred to as "compound (I'-V-h4)"], which constitute a part of Compound (I) of the invention, of which substituent D may be protected, include, for example, a method of performing the reaction steps described below in accordance with Scheme 12. Although the compound (I'-V-h4), per se, may be Compound (I) of the invention, when the compound contains a protective group, it can be subjected to deprotection and thereby converted into Compound (I) of the invention. In Scheme 12, Mt represents lithium atom, or halogenated magnesium atom, and V, $R^{O1}$ to $R^{O4}$, A, D', $U^2$, and $U^3$ have the same meanings as those defined above.

Step (12-a):

Examples of the methods for preparing the compounds represented by the general formula (XXVII) [henceforth simply referred to as "compound (XXVII)"], which are intermediates of the target compounds, include a method of subjecting a compound (II-V-h) that can be prepared by a method similar to those of Preparation methods 1 and 2 [henceforth referred to as "compound (II-V-h)"] and a compound (XXVI) to a reductive amination reaction in an organic solvent. The compound (XXVI) is used in an amount of, for example, usually 0.5 to 10 fold moles, preferably 0.9 to 2 fold moles, based on the compound (II-V-h). Examples of the organic solvent used include, for example, dichloromethane, dichloroethane, tetrahydrofuran, dimethoxyethane, diethyl ether and the like These solvents can be used alone or a mixed solvent. Examples of the reducing agent used include sodium cyanoborohydride, sodium borohydride, sodium triacetoxyborohydride, pyridine borane and the like. These agents are used in an amount of, for example, usually 1 to 5 fold moles, preferably 1 to 3 fold moles, based on the compound (II-V-h). If needed, a desiccant such as sodium sulfate, magnesium sulfate, molecular sieves, and tetramethyl ortho-formate can be used. The reaction temperature is, for example, generally −10 to 100° C., preferably 0 to 50° C. The reaction time is generally 0.5 to 72 hours, preferably 1 to 48 hours. However, since the progress of the reaction can be monitored by thin layer chromatography (TLC), high performance liquid chromatography (HPLC) or the like, it is usually preferred that the reaction is terminated when a maximum yield of the compound (XXVII) is obtained.

The compound (XXVI) is commercially available, or can be synthesized by known methods or similar methods.

Step (12-b):

Examples of the methods for preparing the compounds represented by the general formula (XXVIII) [henceforth simply referred to as "compound (XXVIII)"] include a method of subjecting the aforementioned compound (XXVII) to a deprotection reaction in an organic solvent in the presence of an acid. Examples of the organic solvent used for this method include, for example, halogenated hydrocarbons such as dichloromethane and chloroform, ethers such as tetrahydrofuran, dioxane, and diethyl ether, and alcohols such as methanol and ethanol. These solvents can be used alone or a mixed solvent. Examples of the acid used in the aforementioned reaction include, for example, organic acids such as acetic acid, trifluoroacetic acid, methanesulfonic acid, p-toluenesulfonic acid, camphorsulfonic acid, and inorganic acids such as hydrochloric acid and sulfuric acid. These acids are used in an amount of, for example, usually 1 to 20 fold moles, preferably 1 to 10 fold moles, based on the compound (XXVII). The reaction temperature is, for example, −10 to 100° C. The reaction time is generally 0.5 to 72 hours, preferably 0.5 to 48 hours. However, since the progress of the reaction can be monitored by thin layer chromatography (TLC), high performance liquid chromatography (HPLC) or the like, it is usually preferred that the reaction is terminated when a maximum yield of the compound (XXVIII) is obtained.

Step (12-c):

Examples of the methods for preparing the compounds represented by the general formula (XXIX) [henceforth simply referred to as "compound (XXIX)"] include (1) a method of cyclizing the aforementioned compound (XXVIII) in an organic solvent in the presence of a phosphine and a diazocarbonyl compound, and (2) a method of cyclizing the compound in an organic solvent in the presence of a base and a sulfonic acid halide.

(1) Examples of the organic solvent used for this method include, for example, halogenated hydrocarbons such as dichloromethane and chloroform, ethers such as tetrahydrofuran, dioxane, and diethyl ether, N,N-dimethylformamide, acetonitrile and the like. These solvents can be used alone or a mixed solvent. Examples of the phosphine used in the aforementioned reaction include, for example, triphenylphosphine, trimethylphosphine, tributylphosphine and the like. These phosphines are used in an amount of, for example, usually 1 to 20 fold moles, preferably 1 to 10 fold moles, based on the compound (XXVIII). Examples of the diazocarbonyl compound used for the reaction include, for example, N,N,N',N'-tetramethylazodicarboxamide, di-t-butylazodicarboxylate, diethylazodicarboxylate, diisopropylazodicarboxylate and the like. These compounds are used in an amount of, for example, usually 1 to 20 fold moles, preferably 1 to 10 fold moles, based on the compound (XXVIII). The reaction temperature is, for example, generally −30 to 120° C., preferably −20 to 100° C. The reaction time is generally 0.5 to 72 hours, preferably 0.5 to 48 hours. However, since the progress of the reaction can be monitored by thin layer chromatography (TLC), high performance liquid chromatography (HPLC) or the like, it is usually preferred that the reaction is terminated when a maximum yield of the compound (XXIX) is obtained.

(2) Examples of the organic solvent used for this method include, for example, halogenated hydrocarbons such as dichloromethane and chloroform, ethers such as tetrahydrofuran, dioxane, and diethyl ether, N,N-dimethylformamide, acetonitrile and the like. These solvents can be used alone or a mixed solvent. Examples of the base used for the aforementioned reaction include, for example, alkali metal compounds such as sodium hydrogencarbonate, sodium hydroxide, sodium hydride, potassium carbonate, sodium carbonate, potassium hydroxide, and sodium methylate, and organic tertiary amines such as pyridine, trimethylamine, triethylamine, diisopropylethylamine, and N-methylmorpholine. These bases are used in an amount of, for example, usually 1 to 50 fold moles, preferably 1 to 20 fold moles, based on the compound (XXVIII). Examples of the sulfonic acid halide used include, for example, sulfonic acid halides such as mesyl chloride, and tosyl chloride. These halides are used in an amount of, for example, usually 0.8 to 5 fold moles, preferably 0.8 to 2 fold moles, based on the compound (XXVIII). The reaction temperature is, for example, generally −30 to 120° C., preferably −20 to 80° C. The reaction time is generally 0.5 to 72 hours, preferably 0.5 to 48 hours. However, since the progress of the reaction can be monitored by thin layer chromatography (TLC), high performance liquid chromatography (HPLC) or the like, it is usually preferred that the reaction is terminated when a maximum yield of the compound (XXIX) is obtained.

Step (12-d):

Examples of the methods for preparing the compound (I'-V-h4) include a method of cleaving the ring of the aforementioned compound (XXIX) with a compound represented by the general formula (XXX) [henceforth simply referred to as "compound (XXX)"] in an organic solvent. Examples of the organic solvent used in this method include, for example, halogenated hydrocarbons such as dichloromethane and chloroform, ethers such as tetrahydrofuran, dioxane, and diethyl ether and the like. These solvents can be used alone or a mixed solvent. The compound (XXX) is used in an amount of, for example, usually 1 to 10 fold moles, preferably 1 to 5 fold moles, based on the compound (XXIX). If needed, a copper regent such as copper(I) iodide, copper(I) chloride, copper cyanide, and lithium tetrachlorocuprate can be used as a catalyst. The reaction temperature is, for example, generally −50 to 50° C., preferably −30 to 30° C. The reaction time is generally 0.25 to 48 hours, preferably 0.5 to 24 hours. However, since the progress of the reaction can be monitored by thin layer chromatography (TLC), high performance liquid chromatography (HPLC) or the like, it is usually preferred that the reaction is terminated when a maximum yield of the compound (I'-V-h4) is obtained.

The compound (XXX) is commercially available, or can be synthesized by known methods or similar methods.

The preparation methods for Compound (I) of the invention and Compound (II) of the present invention are not limited to the methods described herein. For example, the compounds of the present invention can be prepared by modifying or converting substituents of compounds as precursors of the compounds of the present invention using one or a combination of two or more of reactions described in ordinary chemical articles and the like.

Examples of the preparation method for Compound (I) of the present invention which contains an asymmetric carbon in E or a moiety other than E include, besides the preparation methods based on asymmetric reduction mentioned above, a method of using a commercially available starting material (or starting material that can be prepared by a known method or a method similar to a known method) of which moiety corresponding to the asymmetric carbon is originally optically active. A method is also available in which the compound of the present invention or a precursor thereof is separated as an optically active isomer by a conventional method. Examples of such method include, for example, a method utilizing high performance liquid chromatography (HPLC) using a chiral column, the classical fractional crystallization for separation of optically active substances comprising formation of a salt with an optically active regent, separation by fractional crystallization or the like, and conversion of the salt into a compound of free form, a method comprising condensation with an optically active regent to form a diastereomer, successive separation and purification, followed by decomposition and the like. When a precursor is separated to obtain an optically active substance, optically active Compound (I) of the present invention can then be prepared by performing the aforementioned preparation methods.

When Compound (I) of the present invention contains an acidic functional group such as carboxyl group, phenolic hydroxyl group, or tetrazole ring, the compound can be converted into pharmaceutically acceptable salt (e.g., inorganic salts with sodium, ammonia and the like, or organic salts with triethylamine and the like) by a known means. For example, when an inorganic salt is to be obtained, it is preferable to dissolve Compound (I) of the present invention in water containing at least 1 equivalence of hydroxide, carbonate, bicarbonate or the like corresponding to a desired inorganic salt. For the reaction, a water-miscible inactive organic solvent such as methanol, ethanol, acetone, and dioxane may be mixed. For example, by using sodium hydroxide, sodium carbonate, or sodium hydrogencarbonate, a solution of sodium salt can be obtained.

When Compound (I) of the present invention contains amino group, another basic functional group, or an aromatic ring which itself has a basic property (e.g., pyridine ring and the like), the compound can also be converted into a pharmaceutically acceptable salt (e.g., salts with inorganic acids such as hydrochloric acid and sulfuric acid, or salts with organic acids such as acetic acid and citric acid) by a known means. For example, when a salt with an inorganic acid is to be obtained, it is preferable to dissolve Compound (I) of the present invention in water containing at least 1 equivalence of a desired inorganic acid. For the reaction, a water-miscible inactive organic solvent such as methanol, ethanol, acetone, and dioxane may be mixed. For example, by using hydrochloric acid, a solution of hydrochloride can be obtained.

If a solid salt is desired, a solution may be evaporated, or a water-miscible organic solvent having polarity to some extent, such as butanol or ethyl methyl ketone, can be added to obtain a solid salt thereof.

The various compounds disclosed by the present invention can be purified by known methods such as variety of chromatography techniques (column chromatography, flash column chromatography, thin layer chromatography, high performance liquid chromatography).

The compounds of the present invention and pharmaceutically acceptable salts thereof have no toxicity as demonstrated in the examples mentioned later, and have an osteogenesis promoting action, and therefore they are useful as active ingredients of medicaments.

The compounds of the present invention and pharmaceutically acceptable salts thereof can be expected to systemically exhibit bone density increasing action and bone strength increasing action, or exhibit an action of promoting local bone morphogenesis/osteogenesis. The osteogenesis promoting action of the compounds of the present invention and pharmaceutically acceptable salts thereof can be evaluated, for example, by using bone marrow cells isolated from experimental animals such as rats or human and cultured, and using number of formed calcified bone-like nodes, alkaline phosphatase activity, which is a differentiation marker of osteoblasts or the like as a marker. Further, it can also be evaluated by using pathological model animals such as reduced bone mass model rats subjected to sciatic nerve resection and ovariectomy and the like with bone density or bone strength of appendicular skeletons or the like as a marker.

The medicament of the present invention containing a compound represented by the general formula (I) or a pharmaceutically acceptable salt thereof as an active ingredient can promote osteogenesis in vertebrates including humans, preferably mammals, and the medicament is useful for, for example, prophylactic and/or therapeutic treatment of skeletal diseases such as osteoporosis and fracture. Further, the medicament of the present invention is also useful as a medicament for promoting bone regeneration after a surgical medical treatment.

Examples of the skeletal diseases include various diseases in which uncoupling of bone resorption and bone formation arises in bone remodeling due to various causes, exhibiting, as a result, decrease of bone density and/or degradation of osseous tissues and/or decrease of bone strength. A typical example of such skeletal diseases is osteoporosis.

Osteoporosis is a disease characterized by fracture liability due to reduction in bone mass, decay of bone microstructures, or increase of bone fragility, and refers to the disease defined in the World Congress on Osteoporosis (venue: Amsterdam) in 1996 (Yoshizo Yamamoto "Definition of osteoporosis and diagnosis criteria in Japan", CLINICAL CALCIUM. Vol. 11, pp. 19-24, 2001). Osteoporosis is generally classified into primary osteoporosis in which any underlying disease does not exist, and secondary osteoporosis associated with other diseases such as various endocrinologic diseases and hemopathies.

Examples of the primary osteoporosis include juvenile osteoporosis and involutional osteoporosis. Examples of the involutional osteoporosis include postmenopausal or postovariectomic osteoporosis and senile osteoporosis.

Examples of the secondary osteoporosis include immobility osteoporosis due to prolonged bed rest or agravity stimulus, drug osteoporosis due to long-term administration of corticosteroid and the like, osteoporosis caused by endocrinologic diseases such as Cushing's syndrome and other hypogonadism of which major cause is hypersecretion of endogenous steroids, primary hyperparathyroidism or secondary hyperparathyroidism, hyperthyroidism, hypoparathyroidism, renal osteodystrophy, and diabetes, osteoporosis caused by hemopathies such as multiple myeloma and malignant lymphoma, osteoporosis caused by inflammatory diseases such as rheumatoid arthritis, osteoporosis caused by genetic diseases such as osteogenesis imperfecta, homocystinuria and Marfan's syndrome and the like.

Examples of skeletal diseases other than osteoporosis include osteomalacia, osteitis fibrosa, aplastic bone, dialytic osteopathia, osteopenia resulting from tumors such as multiple myeloma, osteopenia resulting from administration of drugs such as steroids, osteopenia and arthritis resulting from inflammation, periodontal diseases, cancer bone metastasis, hypercalcemia, Paget's disease of bone, ankylosing spondylitis, bone defects (alveolar bone defect, mandible defect, childhood idiopathic bone defect and the like), chronic rheumatoid arthritis, osteoarthritis, destruction of joint tissues and the like.

Examples of other skeletal diseases include abnormal osseous tissues caused by dynamic load. Examples of such skeletal diseases include, for example, fracture, refracture and the like. Femoral neck fracture, compressed fracture of spine vertebra, fracture of distal end of radius, fracture of proximal end of humerus and the like due to osteoporosis as a causative disease are also included in this category.

In addition to the diseases mentioned above, any diseases are encompasses within the scope of the term "skeletal diseases" used in the specification so long as they are diseases in which uncoupling of bone resorption and bone formation arises in bone remodeling, and as a result exhibit decrease of bone density and/or degradation of osseous tissues and/or decrease of bone strength, and the diseases can be subjected by prophylactic and/or therapeutic treatment using the medicament of the present invention.

The medicament of the present invention can also be applied, in addition to the prophylactic and/or therapeutic treatment of the aforementioned diseases, as a medicament for promoting bone regeneration along with a surgical medical treatment. Examples of such medical practice include bone repair and/or bone reconstruction after surgical extraction of primary malignant tumors such as myeloma, bone sarcoma, chondrosarcoma, Ewing sarcoma, malignant fibrous histiocytoma, and fibrosarcoma, or bone metastasis lesions of lung cancer, gastric cancer, breast cancer, liver cancer and the like.

Examples of the surgical medical treatment further include joint replacement, repair of vertebral canal (spine fusion surgery, pexis of vertebral canal, posterior lumbar interbody fusion (PLIF)), enlargement of vertebral canal, osteotomy, bone extension, dentistry reconstruction, cranial defect reconstruction, cranioplasty, ilium spacer pexis by bony support, hetero-osteoplasty, bone homograft, bone autograft and the like. Alternative therapies for bone graft are also included in the surgical medical treatment. The term "surgical medical treatment" used in the specification must be construed in the broadest sense thereof including invasive operations conducted in the field of surgery such as brain surgery, chest surgery, and abdominal surgery, field of orthopedic surgery, field of plastic surgery and the like (e.g., thoracotomy operation, artificial joint substitution operation and the like), bloodless treatments (e.g., immobilization by gypsum of fracture sites and the like) and the like, and should not be construed in any limitative sense.

In addition to the medical practices mentioned above, any medical practices may be subjects applicable with the medicament of the present invention, so long as improvement in vital prognosis, QOL, and ADL of patients can be expected by promoting osteogenesis.

The medicament of the present invention is preferably used as an osteogenesis promotion agent. The medicament of the present invention is more preferably used as an agent for prophylactic and/or therapeutic treatment of a skeletal disease, and the medicament may also be more preferably used to promote bone regeneration at the time of surgical medical treatment. Furthermore, the medicament of the present invention may most preferably be used for prophylactic and/or therapeutic treatment of osteoporosis and/or fracture, and may also most preferably be used to promote bone regeneration at the time of bone repair and/or bone reconstruction. It will be readily understood by those skilled in the art that the medicament for prophylactic and/or therapeutic treatment according to the present invention include as an embodiment a medicament for preventing or suppressing progression of pathological conditions.

The compounds represented by the aforementioned general formula (I) promote cAMP production in human $EP_4$ receptor-expressing cells, and exhibit a binding activity to human $EP_4$ receptor and an osteogenesis promotion action through promotion of cAMP production in the presence of a cyclooxygenase 2 (COX-2) inhibitor in rat bone marrow cells. Therefore, it is clearly understood that the compounds are $EP_4$ agonists. The specificity (selectivity) for $EP_4$ can be evaluated by, for example, performing measurement of agonistic activity and receptor binding test using cells in which each of human $EP_1$, $EP_2$, and $EP_3$ receptors is expressed to calculate a ratio of Ki values.

Ratio of $Ki$ values (time)=Dissociation constant $Ki$ for each receptor/Dissociation constant $Ki$ for $EP_4$ Since $PGE_2$ have side reactions which should be avoided for continuous administration for a long period of time, such as the algesic action and oxytocic action, the compounds of the present invention are required to have high specificity for $EP_4$, and they preferably satisfy a condition of the ratio of Ki values≧1000, more preferably the ratio of Ki values≧3000, extremely preferably the ratio of Ki values≧10000. Therefore, the medicament of the present invention can be applied for various diseases as an $EP_4$ agonist, and is useful as a prophylactic and/or therapeutic agent for, for example, glaucoma, hypertonia oculi, tear gland-associated diseases, myocardial ischemia, hypertension, bronchitis, pulmonary fibrosis, versicular emphysema, chronic obstructive respiratory disease, thrombosis, hepatitis, nephritis (renal failure), stomatitis, alimentary canal ulcers such as gastric ulcer and duodenal ulcer, ulcerative colitis, Crohn's disease, asthma, nerve cell death, arthritis, immune diseases (autoimmune diseases such as rheumatoid arthritis, multiple sclerosis, amyotrophic lateral sclerosis, Sjoegren's syndrome and systemic erythematodes, rejection after organ transplantation and the like), systemic inflammatory response syndrome, sepsis, hemophagocytic syndrome, macrophage activation syndrome, Still disease, Kawasaki disease, thermal burn, systemic granuloma, multiple organ failure, shock, cervical canal obstruction, anomaly in sleep, baldness, psilosis and the like. It is especially useful as a prophylactic and/or therapeutic agent for glaucoma, hypertonia oculi, alimentary canal ulcers such as gastric ulcer and duodenal ulcer, and ulcerative colitis, and the medicament is highly useful as a prophylactic and/or therapeutic agent for glaucoma and ulcerative colitis among others.

The compounds of the present invention exhibit superior stability in stability evaluation in a stress test, a long-term storage test, and an accelerated test, and exhibit superior solubility in various solvents. Therefore, they are useful as active ingredients of medicaments.

The compounds of the present invention are still more useful as active ingredients of medicaments, also because they exhibit superior metabolic stability.

The medicament of the present invention can be prepared as a medicament comprising a compound represented by the formula (I) or a pharmaceutically acceptable salt thereof as an active ingredient. For example, a compound or a salt thereof, which is administered as a prodrug and produces the compound represented by the formula (1) or a pharmaceutically acceptable salt thereof after in vivo metabolism, also falls within the scope of the medicament of the present invention.

The administration route of the medicament of the present invention is not particularly limited. It is selected from, for example, oral administration, subcutaneous administration, intracutaneous administration, intramuscular injection, intravenous administration, transnasal administration, transvaginal administration, transrectal administration, local administration at pathological lesion and the like. The medicament of the present invention exhibits superior effect as a medicament via at least one of administration route among the administration routes.

A compound represented by the formula (1) or a pharmaceutically acceptable salt thereof, per se, may be used as the medicament of the present invention. However, it is preferable to add one or more kinds of pharmaceutically acceptable carriers to the compound represented by the formula (1) or a pharmaceutically acceptable salt thereof to prepare a pharmaceutical composition and administer the composition. Further, as the active ingredient of the medicament of the present invention, a hydrate or solvate of a compound represented by the general formula (I) or a pharmaceutically acceptable salt thereof may be used.

Examples of formulations for preparing the aforementioned pharmaceutical composition include tablet, powder, granule, syrup, suspension, capsule, inhalant, injection and the like. For the manufacture of these formulations, various carriers suitable for these preparations are used. For example, examples of the carrier for oral preparations include excipients, binders, lubricants, fluid accelerators, and colorants. Further, examples of the method for using the composition as an inhalants include a method of inhaling powder of the pharmaceutical composition or a liquid dosage form prepared by dissolving or suspending the pharmaceutical composition in a solvent as it is, or inhaling mist thereof by using a sprayer called atomizer or nebulizer. When the composition is formulated as an injection, water for injection, physiological saline, glucose aqueous solution, vegetable oil for injection, propylene glycol, polyethylene glycol and the like can generally be used as a diluent. Disinfectants, antiseptics, stabilizers, isotonic agents, soothing agents and the like may be further added, as required. A clathrate compound in which the compound of the present invention is clathrated in cyclodextrin may be prepared, and used as the medicament of the present invention.

When the aforementioned agent for prophylactic and/or therapeutic treatment is administered, an appropriate dosage form can be suitably chosen and administered via an appropriate route. For example, the agent can be orally administered in the form of tablet, powder, granule, syrup, suspension, capsule or the like. The agent can be also administered via the respiratory tract in the form of an inhalant. In addition, the agent can be administered subcutaneously, intracutaneously, intravascularly, intramuscularly, or intraperitoneally in the form of an injection including drip infusion. Furthermore, the agent can be administered transmucosally in the form of sublingual tablet or suppository, and can be administered percutaneously in the form of gel, lotion, ointment, cream, or spray. In addition, the agent can also be administered as a prolonged action drug, for example, a sustained-release injection (e.g., microcapsule formulation, microsphere formulation, nanosphere formulation and the like), or an embedding formulation (e.g., film formulation and the like).

When the medicament of the present invention is used to promote bone regeneration at the time of various surgical medical treatments, the medicament can be directly administered to a fracture site or a local site subjected to bone repair and/or bone reconstruction and the like In such a case, the compound can be directly injected to a local site together with an appropriate non-hydrophilic solvent, or the compound can also be formulated in an appropriate carrier such as biodegradable polymers, and used as a medicament molded into a rod shape, needle shape, spherical shape, film shape or the like, or in the form of ointment, cream, or gel, or sustained release microcapsule (e.g., microcapsule formulation, microsphere formulation, nanosphere formulation and the like) by embedding or injecting the formulation in a fracture site and the like Examples of the biodegradable high molecular polymer include, for example, aliphatic acid polyesters (polymers and copolymers of one or more kinds of $\alpha$-hydroxycarboxylic acids, hydroxydicarboxylic acids, lactic acid/caprolactone, valerolactone and the like, mixtures thereof), derivatives thereof (polylactic acids, polyglycolic acids, block polymers of polyethylene glycol and the like), poly-$\alpha$-cyanoacrylates, poly-$\beta$-hydroxybutyric acids, polyalkylene oxalates, poly-ortho-esters, polyortho-carbonates, polycarbonates, polyamino acids, hyaluronic acid esters, polystyrene groups, polymethacrylic acids, copolymers of acrylic acid and methacrylic acid, polyamino acids, decyne stearate, ethylcellulose, acetylcellulose, nitrocellulose, maleic anhydride copolymers, ethylene vinyl acetate copolymers, polyvinyl acetates, polyacrylamides, collagen, gelatin, fibrin, bone meal, bone cement and the like.

The biodegradable high molecular polymer may consist of one kind of substance, a copolymer or a simple mixture of two or more kinds of substances (e.g., poly-D,L-lactic acid/glycolate copolymer (PLGA) and the like), or a complex (PLGA/gelatin sponge complex) or a simple mixture, and the polymerization scheme may be any of random, block, and graft polymerizations.

The medicament of the present invention can also be applied or adsorbed on an artificial bone (implant), bone prostheses (hydroxyapatite, $\beta$-tricalcium phosphate and the like) and the like consisting of a highly biocompatible material (metal, calcium, ceramics, polymer materials and the like) together with an appropriate solvent or carrier, or embedded therein, and administered to a local site.

The medicament of the present invention is selectively acts on or binds to the $EP_4$ receptor, but does not act on or bind to $EP_1$ receptor, $EP_2$ receptor, $EP_3$ receptor, DP receptors, FP receptors, IP receptors, TP receptors, PPARα receptor, PPARδ receptor, PPARγ receptor, S1P receptors (e.g., S1P1 receptor, S1P2 receptor, S1P3 receptor and the like), $LTB_4$ receptors (e.g., BLT1, BLT2 and the like), LPA receptors (e.g., LPA1 receptor, LPA2 receptor, LPA3 receptor and the like), and cannabinoid receptors (e.g., CB1 receptor, CB2 receptor and the like), or more weakly acts on or binds to these receptors compared with the $EP_4$ receptor. Therefore, the medicament of the present invention induces few adverse effects caused by receptors other than the $EP_4$ receptor, and can be safely used for vertebrates including human, preferably mammals including human.

The medicament of the present invention is verified to exhibit extremely low toxicity in an acute toxicity test, sub-acute toxicity test, chronic toxicity test, reproduction toxicity test and the like, and is also verified to exhibit extremely low toxicity in an antigenic test, mutagenicity test, local irritation test, hemolysis test, hERG test and the like. Therefore, the medicament can be safely used for vertebrates including human, preferably mammals including human.

Further, the medicament of the present invention has very little influence (inhibition or induction) on drug metabolizing enzymes, and the medicament is metabolized through two or more kinds of metabolic pathways. Therefore, the medicament causes no problem of interaction with a drug used in combination, and can be safely used for vertebrates including human, preferably mammals including human.

The medicament of the present invention is also verified to be highly safe also on the basis of observation of various symptoms in a general pharmacological test (general symptoms and behaviors, central nervous system, vegetative nervous system and smooth muscles, respiratory organs and circulatory systems, digestive system, water and electrolyte metabolism), and can be safely used for vertebrates including human, preferably mammals including human.

The administration period of the medicament of the present invention is not particularly limited. In principle, the medicament is administered during a period where it is judged that clinical symptoms of a disease are observable, and it is common to continue the administration for several weeks to one year. However, it is also possible to extend the administration period depending on pathological conditions, or continue the administration even after recovery of the clinical symptoms. The medicament may also be prophylactically administered by a decision of a medical doctor even if a clinical symptom is not observable. The dose of the medicament of the present invention is not particularly limited. For oral administration, the medicament may generally be administered in an amount of, for example, 0.01 to 2000 mg per day as the active ingredient once or several times as divided portions. As for administration frequency in the above case, the medicament may be administered once a month to every day, and the medicament may preferably be administered once to three times per week or five times per week, or every day.

Further, for example, when the medicament of the present invention is directly administered to a local site of fracture, bone repair, bone reconstruction and the like to promote osteoanagenesis during a surgical medical treatment, 0.01 to 1000 mg of the active ingredient can generally be administered for adults per one time. As for the administration frequency in the above case, the medicament can be administered at a frequency of once per six months to every day, preferably once per three months to once per one month, or once per week.

The daily dose and/or dose per one time, administration period, and administration frequency may be suitably increased or decreased depending on various factors such as the age, weight, degree of physical healthiness of a patient, a type and severity of a disease to be treated, administration route, dosage form (sustained release property of carrier for active ingredient and the like) and the like.

Further, when a skeletal disease is prevented and/or treated with the medicament of the present invention, or when the medicament of the present invention is used for promoting bone regeneration in a surgical medical treatment, the medicament of the present invention can be used together with one or more kinds of medicaments selected from the group consisting of bone activating agents, osteogenesis promoting agents, bone resorption suppressing agents, bone metabolism improving agents, sexual hormone preparations, and calcium preparations, simultaneously or at different times. Further, the medicament of the present invention can also be prepared as a so-called combined drug together with the medicaments exemplified above and then administered. The aforementioned combined drug include a dosage form as a complete mixture of active ingredients in the same manner as typical compositions, and further include a dosage form, kit and package including a non-mixed combination of ingredients separately administered from two or more containers each of which contains each active ingredient.

Examples of the bone activating agents usable in combination with the medicament of the present invention include, for example, vitamin D or vitamin D derivatives such as calcitriol, alfacalcidol, OCT, and ED-71, examples of the osteogenesis promoting agents include, for example, menatetrenone, teriparatide, somatropin, insulin-like growth factor-I (IGF-I), bone morphogenetic proteins (BMPs), basic fibroblast growth factor (bFGF), transforming growth factor-β (TGF-β), $EP_2$ agonist, LRP5 agonist, anti-SOST antibody, GSK-3 inhibitor, Dkk1 inhibitor, calcilytics, growth hormone secretagogues and the like, examples of the bone resorption suppressing agents include, for example, elcatonin, calcitonin salmon, etidronate, pamidronate, clodronate, alendronate, incadronate, risedronate, minodronate, ibandronate, cathepsin K inhibitors, osteoprotegerin, anti-RANKL antibodies and the like, examples of the bone metabolism improving agents include, for example, fluoride, strontium ranelate, ipriflavone and the like, examples of the sexual hormone preparations include, for example, estriol, estradiol, conjugated estrogen, progesterone, medroxyprogesterone, testosterone, metyltestosterone, mestanolone, stanozolol, metenolone, nandrolone, selective estrogen receptor modulators (SERM: raloxifen, lasofoxifene, bazedoxifene, ospemifene, arzoxifene, CHF4227, PSK-3471 and the like), selective androgen receptor modulators (SARM) and the like, and examples of the calcium preparations include, for example, calcium carbonate, calcium lactate, calcium gluconate, calcium acetate, calcium chloride, calcium citrate, calcium hydrogenphosphate, calcium L-aspartate and the like. It can also be used together with various kinds of drugs for skeletal diseases to be created in the future. These combined drugs are not limited so long as the combinations are clinically meaningful.

When the medicament of the present invention is used as an $EP_4$ agonist, the medicament of the present invention may be used together with one or more kinds of drugs generally used for the purpose of prophylactic and/or therapeutic treatment of objective diseases, for example, glaucoma, hypertonia oculi, tear gland-associated diseases, myocardial ischemia, hypertension, bronchitis, pulmonary fibrosis, versicular emphysema, chronic obstructive respiratory disease, thrombosis, hepatitis, nephritis (renal failure), stomatitis, alimentary canal ulcers such as gastric ulcer and duodenal ulcer, ulcerative colitis, Crohn's disease, asthma, nerve cell death, arthritis, immune diseases (autoimmune diseases such as rheumatoid arthritis, multiple sclerosis, amyotrophic lateral sclerosis, Sjoegren's syndrome and systemic erythematodes, rejection after organ transplantation and the like), systemic inflammatory response syndrome, sepsis, hemophagocytic syndrome, macrophage activation syndrome, Still disease, Kawasaki disease, thermal burn, systemic granuloma, multiple organ failure, shock, cervical canal obstruction, anomaly in sleep, baldness, psilosis and the like, simultaneously or at different timings. Further, the medicament of the present invention can also be prepared as a so-called combined drug together with the drugs exemplified above and then administered. The aforementioned combined drug include a dosage form as a complete mixture of active ingredients in the same manner as typical compositions, and further include a dosage form, kit and package including a non-mixed combination of ingredients separately administered from two or more containers each of which contains each active ingredient.

For example, for the purpose of prophylactic and/or therapeutic treatment of alimentary canal ulcer, the medicament of the present invention can be used together with steroid hormones, salazosulfapyridine, immunosuppressants, and various kinds of drugs for alimentary canal ulcer to be created in the future. Further, for the purpose of prophylactic and/or therapeutic treatment of glaucoma, for example, the medicament of the present invention can be used together with prostaglandin F2α derivatives such as xalatan, β-blockers, carbonate dehydrarase inhibitors, α 1-blockers, αβ-blockers, angiotensin II antagonists, and various kinds of drugs for glaucoma to be created in the future. These drugs used in combination are not limited, so long as the combinations are clinically meaningful.

It should be understood that the medicament of the present invention can be administered with a prophylactic or therapeutic agent of which purpose is different from that of the prophylactic and/or therapeutic treatment according to the present invention.

EXAMPLES

The present invention will be explained more specifically with reference to examples, test examples and the like. However, the scope of the present invention is not limited to the following examples and the like.

In the examples, for thin layer chromatography (TLC), Precoated Silica Gel 60 F254 (produced by Merck, product number: 5715-1M)) was used. After development with chloroform:methanol (1:0 to 1:1), acetonitrile:acetic acid:water (200:1:1 to 100:4:4), or ethyl acetate:hexane (1:0 to 0:1), spots were observed by UV irradiation (254 nm) or coloration with ninhydrine or dinitrophenylhydrazine solution in hydrochloric acid.

As for column chromatography, the indication of "Quad" means use of "Quad 1 preparative chromatography system" (produced by Biotage), and one or several columns selected from cartridge columns KP-Sil-12M, 40S and 40M produced by the same manufacturer were used depending on the amount of sample. The indication of "Flash" means that means use of "Flash column system" (produced by Biotage), and one or several of the columns produced by the same manufacturer were used depending on the amount of sample. Further, the indication of "Flash column chromatography" means that usual column chromatography was performed by using Silica gel 60N (spherical shape, neutral, 40 to 100 μm, produced by Kanto Kagaku) depending on the amount of sample.

Preparative thin layer chromatography (henceforth abbreviated as "PTLC") was performed by using one or several PLC plates, Silica Gel 60 F254 (20×20 cm, layer thickness: 2 mm, with concentration zone (4 cm), produced by Merck, Product number: 13793-1M), depending on the amount of sample.

Mass spectrometry was performed by Method A or B described below. The "RT" values as measurement data indicate retention times (minute) in liquid chromatography. No indication of elution condition for the data of liquid chromatography mass spectrometry (LCMS) means that the measurement was performed by Method A. When the measurement was performed under other conditions, the conditions are indicated.

Method A

Measurement was performed by liquid chromatography mass spectrometry (LCMS). Platform-LC type mass spectrometer (produced by Micromass) was used as the mass spectrometer, and the measurement was performed by the electrospray ionization (ESI) method. As the liquid chromatography apparatus, an apparatus produced by Waters was used. As the separation column, Develosil C30-UG-5 (50×4.6 mm, produced by Nomura Kagaku) was used. Elution was generally performed at a flow rate of 2 ml/minute using Solution A [water containing 0.1% (v/v) acetic acid] and Solution B [acetonitrile containing 0.1% (v/v) acetic acid] as solvents. As for the elution condition, elution was performed with a linear gradient of 5 to 98% (v/v) of Solution B from 0 to 4 minutes and then 98% of Solution B for 6 minutes.

Method B

Platform-LC type mass spectrometer (produced by Micromass) was used as the mass spectrometer, and the measurement was performed by the electrospray ionization (ESI) method. As the liquid chromatography apparatus, an apparatus produced by GILSON was used. As the separation column, Develosil C30-UG-5 (50×4.6 mm, produced by Nomura Kagaku) was used. Elution was performed at a flow rate of 2 ml/minute using Solution A [water containing 0.1% (v/v) acetic acid] and Solution B [acetonitrile containing 0.1% (v/v) acetic acid] as solvents, with a linear gradient of 5 to 98% (v/v) of Solution B from 0 to 5 minutes and then 98% of Solution B for 5 minutes.

Method C

Measurement was performed by fast atomic bombardment mass spectrometry (FAB-MS) by using JEOL-JMS-SX102 (produced by JEOL) as a mass spectrometer.

For drying organic solvents, anhydrous magnesium sulfate or anhydrous sodium sulfate was used.

The manufacturers of the regents used may sometimes be indicated with the following abbreviations: Tokyo Chemical Industry: TCI, Aldrich: ALD, Kanto Kagaku: KANT, Wako Pure Chemical Industries: WAKO, Kokusan Kagaku Kogyo: KOKUSAN, Lancaster: LANC, Maybridge: MAYB, OAKWOOD: OA, Matrix Scientific: MS, Alfa Aesar: ALF, ASDI: ASDI, and Asta Tech: AST.

Names of the regents, solvents and the like may sometimes be indicated with the following abbreviations: tetrahydrofuran: THF, N,N-dimethylformamide: DMF, dimethyl sulfoxide: DMSO, triethylamine: TEA, diisopropylethylamine:

DIEA, trifluoroacetic acid: TFA, N-ethyl-N'-3-dimethylaminopropylcarbodiimide hydrochloride: WSC.HCl, and 1-hydroxybenzotriazole: HOBT.

Example II-a01

Synthesis of methyl 4-(2-bromoethyl)benzoate (Intermediate ia-01) (Preparation method ia-1)

A solution of 4-(2-bromoethyl)benzoic acid (4.58 g, TCI) in a mixture of dichloromethane (50 ml) and methanol (50 ml) was added dropwise with a 2.0 M solution of (trimethylsilyl)diazomethane in hexane (11.0 ml, ALD) over 10 minutes, and the mixture was stirred at room temperature for 2 hours. The reaction solution was concentrated under reduced pressure, and then the residue was purified by column chromatography (Flash, hexane:ethyl acetate=15:1) to obtain the title compound (Intermediate ia-01, 4.32 g).

Synthesis of t-butyl 2-{2-[(4-methoxycarbonyl)phenyl]ethyl}hydrazinecarboxylate (Intermediate ia-02) (Preparation Method ia-2)

A solution of Intermediate ia-01 (4.28 g) in acetonitrile (50 ml) was added with t-butyl carbazate (11.64 g, WAKO), sodium hydrogencarbonate (7.40 g), and sodium iodide (700 mg), and the mixture was refluxed for 24 hours by heating. The insoluble solid was removed by filtration, and then the filtrate was concentrated under reduced pressure. The residue was added with ethyl acetate (150 ml), and washed successively with purified water (75 ml), and saturated brine. The organic layer was dried, and then the solvent was evaporated under reduced pressure. The residue was purified by column chromatography (Flash, hexane:ethyl acetate=5:1) to obtain the title compound (Intermediate ia-02, 3.67 g).

Synthesis of t-butyl 2-{2-[(4-methoxycarbonyl)phenyl]ethyl}-3-oxotetrahydro-pyridazine-1-carboxylate (Compound No. II-a01) (Preparation Method 1-1a)

A solution of Intermediate ia-02 (1.0 g) in acetonitrile (20 ml) was successively added with potassium carbonate (939 mg), and 4-chlorobutyryl chloride (419 µl, WAKO) under ice cooling, and the mixture was warmed to room temperature, and stirred for 30 minutes. The reaction mixture was added with water (50 ml), and extracted with ethyl acetate (50 ml×2). The organic layers were combined, washed with saturated brine, and dried, and then the solvent was evaporated under reduced pressure. A solution of the residue in DMF (20 ml) was added with a 60% sodium hydride (89 mg, KANTO) in DMF (10 ml) under ice cooling, and the mixture was warmed to room temperature, and stirred for 30 minutes. The reaction mixture was added with water (100 ml), and extracted with ethyl acetate (50 ml×3). The organic layers were combined, washed with saturated brine, and dried, and then the solvent was evaporated under reduced pressure to obtain the title compound (Compound No. II-a1, 995 mg). Mass (LCMS): 363 (M$^+$+1), RT=4.60.

Example II-a02

Synthesis of methyl 4-[2-(6-oxotetrahydropyridazin-1-yl)ethyl]benzoate (Compound No. II-a02) (Preparation Method 1-1b)

A solution of Compound No. II-a01 (200 mg) in dichloromethane (2 ml) was added with TFA (2 ml) under ice cooling, and the mixture was warmed to room temperature, and stirred for 1 hour. The reaction solution was concentrated under reduced pressure, and then the residue was added with saturated aqueous sodium hydrogencarbonate, and extracted with ethyl acetate (50 ml×2). The organic layers were combined, washed with saturated brine, and dried, and then the solvent was evaporated under reduced pressure to obtain the title compound (Compound No. II-a2, 140 mg). Mass (LCMS): 263 (M$^+$+1), RT=3.55.

Example IAO-E001

Synthesis of N-methoxy-N-methyl-2-[3-(trifluoromethyl)phenyl]acetamide (Intermediate pa-01) (Preparation Method pa-1)

A solution of 3-(trifluoromethyl)phenylacetic acid (1.00 g, TCI) in DMF (15 ml) was added with WSC HCl (1.28 g, KOKUSAN), HOBT (794 mg, KOKUSAN), and DIEA (1.02 ml, ALD), and the mixture was stirred at room temperature for 30 minutes. The reaction mixture was added with a solution of N,O-dimethylhydroxylamine hydrochloride (956 mg, WAKO) in DMF (5 ml) added with DIEA (1.74 ml) and stirred for 20 minutes at room temperature beforehand, and the mixture was stirred at room temperature for 16 hours. The reaction mixture was added with ethyl acetate (150 ml), successively washed with 1 N aqueous hydrochloric acid, purified water, saturated aqueous sodium hydrogencarbonate, and saturated brine and dried, and then the solvent was evaporated under reduced pressure to obtain the title compound (Intermediate pa-01, 893 mg).

Synthesis of methyl 4-[2-(2-{3-oxo-4-[3-(trifluoromethyl)phenyl]butyl}-6-oxotetrahydropyridazin-1-yl)ethyl]benzoate (Compound No. IAO-E001) (Preparation Method 1-1c)

A solution of Intermediate pa-01 (542 mg) in anhydrous THF (15 ml) cooled to −40° C. was added dropwise with a 1 M solution of vinylmagnesium bromide in THF (2.4 ml, ALD) over 10 minutes under an argon atmosphere, and the mixture was stirred for 10 minutes, warmed to room temperature, and further stirred for 30 minutes. The reaction mixture was poured into saturated aqueous ammonium chloride (40 ml), and extracted with ethyl acetate (40 ml×3). The organic layers were combined, washed with saturated brine, and dried, and then the solvent was evaporated under reduced pressure. A solution of this residue in ethanol (5 ml) was added with Compound No. II-a2 (115 mg) and TEA (0.12 ml), and the mixture was stirred at room temperature for 20 minutes, and then refluxed for 2 hours by heating. The reaction solution was concentrated under reduced pressure, and then the residue was purified by column chromatography (Flash, hexane:ethyl acetate=4:1) to obtain the title compound (Compound No. IAO-E001, 120 mg). Mass (LCMS): 477 (M$^+$+1), RT=4.83.

Example IAH-E001

Synthesis of methyl 4-[2-(2-{3-hydroxy-4-[3-(trifluoromethyl)phenyl]butyl}-6-oxotetrahydropyridazin-1-yl)ethyl]benzoate (Compound No. IAH-E001) (Preparation Method 1-1d)

A solution of Compound No. IAO-E001 (110 mg) in methanol (3 ml) was added with a solution of cerium chloride heptahydrate (86 mg, Wako) in purified water (1 ml), and the mixture was cooled to −15° C., then added with sodium borohydride (11 mg, WAKO), and stirred for 15 minutes. The reaction solution was added with saturated brine (25 ml), and the mixture was extracted with ethyl acetate (50 ml×2). The organic layers were combined, washed with saturated brine, and dried, and then the solvent was evaporated under reduced pressure. The residue was purified by column chromatography (Flash, hexane:ethyl acetate=5:1) to obtain the title compound (Compound No. IAH-E001, 90 mg). Mass (LCMS): 475 ($M^+$+1), RT=4.71.

Example IAH-H001

Synthesis of 4-[2-(2-{3-hydroxy-4-[3-(trifluoromethyl)phenyl]butyl}-6-oxotetrahydropyridazin-1-yl) ethyl]benzoic acid (Compound No. IAH-H001) (Preparation Method 1-1e)

A solution of Compound No. IAH-E001 (80 mg) in a mixture of methanol (1 ml) and THF (1 ml) was added with 2 N aqueous sodium hydroxide (418 µl), and the mixture was stirred at room temperature for 16 hours under a nitrogen gas atmosphere. The reaction mixture was added with 1 N aqueous hydrochloric acid (940 µl) under ice cooling, and the mixture was extracted with ethyl acetate (50 ml). The organic layer was washed with saturated brine, and dried, and then the solvent was evaporated under reduced pressure to obtain the title compound (Compound No. IAH-H001, 76 mg). Mass (LCMS): 465 ($M^+$+1), RT=4.23.

Examples IAH-H001a and IAH-H001b

Preparation of optically active substances of 4-[2-(2-{3-hydroxy-4-[3-(trifluoromethyl)-phenyl]butyl}-6-oxotetrahydropyridazin-1-yl)ethyl]benzoic acid (Compound Nos. IAH-H001a and IAH-H001b) by HPLC (Preparation Method 1-1f)

Preparative HPLC using CHIRALCEL AD column (4.6 mm×250 mm, produced by Daicel Chemical Industries) was performed by using a solution of Compound No. IAH-H001 (13.6 mg) dissolved in ethanol (1.0 ml) in a volume of 25 µl per 1 time to obtain the title compounds [Compound Nos. IAH-H001a, 5.3 mg (HPLC retention time: 21.83 minutes, optical purity: 100 ee %), and Compound No. IAH-H001b, 5.4 mg (HPLC retention time: 25.50 minutes, optical purity: 96.5ee %)]. The HPLC conditions were a column temperature of 40° C., monitoring by UV absorption at 254 nm, elution solvent of n-hexane [containing 0.1% (v/v) TFA]:ethanol [containing 0.1% (v/v) TFA]=85:15, and flow rate of 0.5 ml/minutes.

Example IAO-E002

Synthesis of methyl 4-{2-[2-(3-oxo-3-phenylpropyl)-6-oxotetrahydropyridazin-1-yl]ethyl}benzoate (Compound No. IAO-E002) (Preparation Method 1-1c')

A solution of Compound No. II-a2 (100 mg) in acetonitrile (2 ml) was added with β-chloropropiophenone (64 mg, TCI), and potassium carbonate (105 mg), and the mixture was stirred at 50° C. for 16 hours. The insoluble solid in the reaction solution was removed by filtration, and then the reaction solution was added with purified water (10 ml), and extracted with ethyl acetate (30 ml). The organic layer was washed with saturated brine, and dried, and then the solvent was evaporated under reduced pressure. The residue was purified by column chromatography (Flash, hexane:ethyl acetate=7:1) to obtain the title compound (Compound No. IAO-E002, 29 mg). Mass (LCMS): 395 ($M^+$+1).

Example IAH-E002

Synthesis of methyl 4-{2-[2-(3-hydroxy-3-phenylpropyl)-6-oxotetrahydropyridazin-1-yl] ethyl}benzoate (Compound No. IAH-E002) (Preparation Method 1-1d)

According to the procedures described in the synthesis method of Compound No. IAH-E001 provided that the reaction was performed under ice cooling for 30 minutes and at room temperature for 30 minutes, Compound No. IAO-E002 (28 mg) was used instead of Compound No. IAH-E001, and the material was reacted and treated to obtain the title compound (Compound No. IAH-E002, 28 mg). Mass (LCMS): 397 ($M^+$+1).

Example IAH-H002

Synthesis of 4-{2-[2-(3-hydroxy-3-phenylpropyl)-6-oxotetrahydropyridazin-1-yl]ethyl}]benzoic acid (Compound No. IAH-H002) (Preparation Method 1-1e)

According to the procedures described in the synthesis method of Compound No. IAH-H001, Compound No. IAH-E002 (28 mg) was used instead of Compound No. IAH-H001, and the material was reacted and treated to obtain the title compound (Compound No. IAH-H002, 13 mg). Mass (LCMS): 383 ($M^+$+1), RT=3.83.

Example IAO-E003

Synthesis of methyl 4-(2-{2-[3-oxo-3-(4-fluorophenyl)propyl]-6-oxotetrahydro-pyridazin-1-yl}ethyl) benzoate (Compound No. IAO-E003) (Preparation Method 1-1c')

According to the procedures described in the synthesis method of Compound No. IAO-E002, 3-chloro-4'-fluoropropiophenone (64 mg) was used instead of β-chloropropiophenone, and the material was reacted and treated to obtain the title compound (Compound No. IAO-E003, 50 mg). Mass (LCMS): 413 ($M^+$+1).

Example IAH-E003

Synthesis of methyl 4-(2-{2-[3-hydroxy-3-(4-fluorophenyl)propyl]-6-oxotetrahydropyridazin-1-yl}ethyl)benzoate (Compound No. IAH-E003) (Preparation Method 1-1d)

According to the procedures described in the synthesis method of Compound No. IAH-E001 provided that the reaction was performed under ice cooling for 30 minutes and at room temperature for 30 minutes, Compound No. IAO-E003 (49 mg) was used instead of Compound No. IAH-E001, and the material was reacted and treated to obtain the title compound (Compound No. IAH-E003, 48 mg). Mass (LCMS): 415 ($M^+$+1).

Example IAH-H003

Synthesis of 4-(2-{2-[3-hydroxy-3-(4-fluorophenyl)propyl]-6-oxotetrahydro-pyridazin-1-yl}ethyl)benzoic acid (Compound No. IAH-H003) (Preparation Method 1-1e)

According to the procedures described in the synthesis method of Compound No. IAH-H001, Compound No. IAH-E003 (48 mg) was used instead of Compound No. IAH-H001, and the material was reacted and treated to obtain the title compound (Compound No. IAH-H003, 27 mg). Mass (LCMS): 401 ($M^+$+1), RT=3.89.

Example IAO-E004

Synthesis of N-methoxy-N-methyl-2-[3-(4-fluorophenyl)phenyl]acetamide (Intermediate pa-02) (Preparation Method pa-1)

According to the procedures described in the synthesis method of Intermediate pa-01, 3-(4-fluorophenyl)benzoic acid (1.0 g, Array-BioPharm, Inc.) was used instead of 3-(trifluoromethyl)phenylacetic acid, and the material was reacted and treated to obtain the title compound (Intermediate pa-02, 758 mg).

Synthesis of methyl 4-[2-(2-{3-oxo-3-[3-(4-fluorophenyl)phenyl]propyl}-6-oxotetrahydropyridazin-1-yl)ethyl]benzoate (Compound No. IAO-E004) (Preparation Method 1-1c)

According to the procedures described in the synthesis method of Compound No. IAO-E001, Intermediate pa-02 (492 mg) was used instead of Intermediate pa-01, and the material was reacted and treated, and the resultant was further reacted with Compound No. II-a2 (100 mg) and treated to obtain the title compound (Compound No. IAO-E004, 183 mg). Mass (LCMS): 489 ($M^+$+1).

Example IAH-E004

Synthesis of methyl 4-[2-(2-{3-hydroxy-3-[3-(4-fluorophenyl)phenyl]propyl}-6-oxotetrahydropyridazin-1-yl)ethyl]benzoate (Compound No. IAH-E004) (Preparation Method 1-1d)

According to the procedures described in the synthesis method of Compound No. IAH-E001 provided that the reaction was performed under ice cooling for 30 minutes and at room temperature for 30 minutes, Compound No. IAO-E004 (50 mg) was used instead of Compound No. IAH-E001, and the material was reacted and treated to obtain the title compound (Compound No. IAH-E004, 49 mg). Mass (LCMS): 491 ($M^+$+1).

Example IAH-H004

Synthesis of 4-[2-(2-{3-hydroxy-3-[3-(4-fluorophenyl)phenyl]propyl}-6-oxotetrahydropyridazin-1-yl)ethyl]benzoic acid (Compound No. IAH-H004) (Preparation Method 1-1e)

According to the procedures described in the synthesis method of Compound No. IAH-H001, Compound No. IAH-E004 (48 mg) was used instead of Compound No. IAH-H001, and the material was reacted and treated to obtain the title compound (Compound No. IAH-H004, 14 mg). Mass (LCMS): 477 ($M^+$+1), RT=4.45.

Example II-b01

Synthesis of t-butyl 3-{2-(4-methoxycarbonylphenyl)ethyl}-2-oxo-2H-tetrahydro-1,3,4-oxadiazine-4-carboxylate (Compound No. II-b01) (Preparation Method 1-1a)

According to the procedures described in the synthesis method of Compound No. II-a01, 2-chloroethyl chloroformate (174 mg, TCI) was used instead of 4-chlorobutyryl chloride, and the material was reacted and treated to obtain the title compound (Compound No. II-b01, 347 mg). Mass (LCMS): 365 ($M^+$+1), RT=4.59.

Example II-b02

Synthesis of methyl 4-{2-(2-oxo-2H-tetrahydro-1,3,4-oxadiazin-3-yl)ethyl}benzoate (Compound No. II-b02) (Preparation Method 1-1b)

According to the procedures described in the synthesis method of Compound No. II-a02, Compound No. II-b01 (347 mg) was used instead of Compound No. II-a01, and the material was reacted and treated to obtain the title compound (Compound No. II-b02, 236 mg). Mass (LCMS): 265 ($M^+$+1), RT=3.06.

Example II-bs01

Synthesis of 2-[2-(1-{4-methoxycarbonyl}phenethyl)-t-butoxycarbonylhydrazine-1-carbonyl]mercaptoethyl octanoate (Intermediate ia-06) (Preparation Method id-1)

A solution of 2-mercaptoethyl octanoate (115.6 μl, WAKO) in dichloromethane (2.75 ml) was cooled to −4C, and added with pyridine (44 μl, KANT) and triphosgene (53.4 mg, TCI), and the mixture was stirred at −4° C. for 1 hour. Then, the mixture was added with Intermediate ia-02 (147 mg), and stirred at −4° C. for 2 hours. The reaction mixture was added with saturated aqueous sodium hydrogencarbonate (2 ml), and extracted with dichloromethane (10 ml×2). The organic layers were combined, washed with saturated brine, and dried, and then the solvent was evaporated under reduced pressure. The residue was purified by column chromatography (Flash, hexane:ethyl acetate=6:1) to obtain the title compound (Intermediate ia-06, 225.8 mg).

Synthesis of 2-[2-(1-{4-methoxycarbonyl}phenethyl)-t-butoxycarbonylhydrazine-1-carbonyl]mercaptoethanol (Intermediate ia-07) (Preparation Method id-2)

A solution of Intermediate ia-06 (225.8 mg) in methanol (4.3 ml) was cooled to 0° C., and added with a solution of sodium methylate in methanol (10.5 μl, 28% methanol solution, WAKO), and the mixture was stirred at 0° C. for 4 hours. The reaction mixture was neutralized by addition of 1 N aqueous hydrochloric acid (100 μl), and then was added with purified water (2 ml), and the mixture was extracted with chloroform (20 ml×2). The organic layers were combined, washed with saturated brine, and dried, and then the solvent was evaporated under reduced pressure to obtain the title compound (Intermediate ia-07).

Synthesis of t-butyl 3-[4-(4-methoxycarbonyl)phenethyl-2-oxo-2H-tetrahydroxy-1,3,4-thiadiazine-4-carboxylate (Compound No. II-bs01) (Preparation Method 1-1m)

A solution of Intermediate ia-07 in dichloromethane (4.3 ml) was added with triethylamine (120 μl, TCI), and tosyl chloride (164 mg, TCI), and the mixture was stirred at room temperature for 18 hours. The reaction mixture was added with purified water, and extracted with dichloromethane. The organic layer was dried, then the solvent was evaporated under reduced pressure, and the residue was purified by column chromatography (Flash, hexane:ethyl acetate=3:1). A solution of the resulting compound in DMF (3 ml) was added with 60% sodium hydride (14.3 mg, KANT) under ice cooling, and the mixture was warmed to room temperature, and stirred for 3 hours. The reaction mixture was added with water (1 ml), and extracted with ethyl acetate (20 ml×2). The organic layers were combined, washed with saturated brine, and dried, and then the solvent was evaporated under reduced pressure to obtain the title compound (Compound No. II-bs01, 81.7 mg). Mass (LCMS): 381 ($M^+$+1), RT=4.67.

Example II-bs02

Synthesis of 3-[4-(4-methoxycarbonyl)phenethyl-2-oxo-2H-tetrahydroxy-1,3,4-thiadiazine (Compound No. II-bs02) (Preparation Method 1-1b)

According to the procedures described in the synthesis method of Compound No. II-a02, Compound II-bs01 (81.7 mg) was used instead of Compound No. II-a01, and the material was reacted and treated to obtain the title compound (Compound No. II-bs02, 47 mg). Mass (LCMS): 281 ($M^+$+1), RT=3.27.

Examples IAO-E005 to IAH-H056

Preparations of Compound Nos. IAO-E005 to IAH-H056 are shown in Tables A-1 to A-9. The meanings of the symbols used in the tables are as follows: Exp.: Example Compound No., Syn.: preparation method, SM1: Starting compound 1, and SM2: Starting compound 2. For "SM2", corresponding symbols, regent names and manufacturers are shown in Table CA-1. The starting materials for which the term "Synthesized material" is indicated in the column of "Manufacturer" were synthesized according to the procedures described in International Patent Publication WO00/03980.

"V", "$R^{D1}$", "E", and "W" represent substituents and functional groups in the following general formula (I-Exp-A).

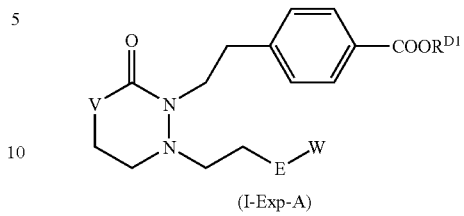

[Formula 79]

(I-Exp-A)

The liquid chromatography-mass spectrometry data are shown in the columns of "LCMS", and retention times in the liquid chromatography are shown in the columns of "RTime". Mass spectrometry data are shown in the columns of "Mass". The measurement conditions of the aforementioned liquid chromatography-mass spectrometry are shown in the columns of "Method".

Example IAO-E005

Synthesis of methyl 4-(2-{2-[3-oxo-4-(3-methoxyphenyl)butyl]-6-oxotetrahydro-pyridazin-1-yl}ethyl)benzoate (Compound No. IAO-E005) (Preparation method 1-1g)

A solution of 3-methoxyphenylacetic acid (665 mg, TCI, corresponding to "SM2" in the tables) in DCM (15 ml) was added with WSC.HCl (920 mg, KOKUSAN), N,O-dimethylhydroxylamine hydrochloride (780 mg, WAKO), dimethylaminopyridine (48 mg, TCI), and DIEA (1.65 g, ALD), and the mixture was stirred at room temperature for 5 hours. The reaction mixture was successively washed with 1 N aqueous hydrochloric acid, purified water, saturated aqueous sodium hydrogencarbonate, and saturated brine, and dried, and then the solvent was evaporated under reduced pressure. A solution of this residue in anhydrous THF (15 ml) was cooled to −40° C. under an argon atmosphere, and added dropwise over 10 minutes with a 1 M solution of vinylmagnesium bromide in THF (4.8 ml, ALD), and the mixture was stirred for 10 minutes, warmed to room temperature, and further stirred for 30 minutes. The reaction mixture was poured into saturated aqueous ammonium chloride (40 ml), and extracted with ethyl acetate (40 ml×3). The organic layers were combined, washed with saturated brine, and dried, and then the solvent was evaporated under reduced pressure. A solution of this residue in ethanol (5 ml) was added with Compound No. II-a02 (148 mg) (corresponding to "SM1" in the tables) and TEA (0.15 ml), and the mixture was stirred at room temperature for 20 minutes, and then refluxed for 2 hours by heating. The reaction solution was concentrated under reduced pressure, and then the residue was purified by column chromatography (Flash, ethyl acetate) to obtain the title compound (Compound No. IAO-E005, 190 mg). Mass (LCMS): 439 ($M^+$+1), RT=4.54.

Example IAH-E005

Synthesis of methyl 4-(2-{2-[3-hydroxy-4-(3-methoxyphenyl)butyl]-6-oxotetrahydro-pyridazin-1-yl}ethyl)benzoate (Compound No. IAH-E005) (Preparation method 1-1d)

According to the procedures described in the synthesis method of Compound No. IAH-E001, Compound No. IAO-E005 (190 mg) was used instead of Compound No. IAO-E001, and the material was reacted and treated to obtain the title compound (Compound No. IAH-E005, 184 mg). Mass (LCMS): 441 ($M^+$+1), RT=3.89.

Example IAH-H005

Synthesis of 4-(2-{2-[3-hydroxy-4-(3-methoxyphenyl)butyl]-6-oxotetrahydro-pyridazin-1-yl}ethyl)benzoic acid (Compound No. IAH-H005) (Preparation method 1-1e)

According to the procedures described in the synthesis method of Compound No. IAH-H001, Compound No. IAH-E005 (200 mg) was used instead of Compound No. IAH-E001, and the material was reacted and treated to obtain the title compound (Compound No. IAH-H005, 133 mg). Mass (LCMS): 426 ($M^+$+1), RT=3.88.

TABLE 74

Table-A-1

| Exp. | Syn. | SM1 | SM2 | V | $R^{D1}$ | E | W | LCMS RTime | Mass | Method |
|---|---|---|---|---|---|---|---|---|---|---|
| IAO-E005 | 1-1g | Exp. II-a02 | CA01 | $CH_2$ | Me | C=O | 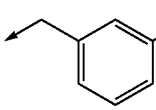 | 4.54 | 439 | A |
| IAH-E005 | 1-1d | IAO-E005 | | $CH_2$ | Me | CH(OH) | 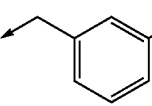 | 3.89 | 441 | B |
| IAH-H005 | 1-1e | IAH-E005 | | $CH_2$ | H | CH(OH) | 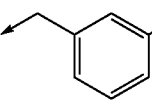 | 3.88 | 427 | A |
| IAO-E006 | 1-1g | Exp. II-a02 | CA02 | $CH_2$ | Me | C=O | 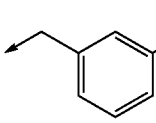 | 4.57 | 427 | A |
| IAH-E006 | 1-1d | IAO-E006 | | $CH_2$ | Me | CH(OH) | 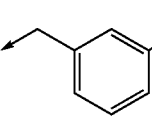 | 3.99 | 429 | B |
| IAH-H006 | 1-1e | IAH-E006 | | $CH_2$ | H | CH(OH) | 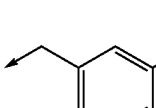 | 3.94 | 415 | A |
| IAO-E007 | 1-1g | Exp. II-a02 | CA03 | $CH_2$ | Me | C=O | 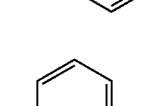 | 4.2 | 425 | B |
| IAH-E007 | 1-1d | IAO-E007 | | $CH_2$ | Me | CH(OH) | 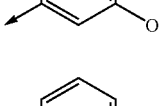 | | | |

TABLE 74-continued

Table-A-1

| Exp. | Syn. | SM1 | SM2 | V | $R^{D1}$ | E | W | LCMS RTime | Mass | Method |
|---|---|---|---|---|---|---|---|---|---|---|
| IAH-H007 | 1-1e | IAH-E007 | | $CH_2$ | H | CH(OH) | 3-OMe-phenyl | 3.79 | 413 | A |
| IAO-E008 | 1-1g | Exp. II-a02 | CA04 | $CH_2$ | Me | C=O | 3-F-phenyl | 4.21 | 413 | B |
| IAH-E008 | 1-1d | IAO-E008 | | $CH_2$ | Me | CH(OH) | 3-F-phenyl | 3.99 | 415 | B |
| IAH-H008 | 1-1e | IAH-E008 | | $CH_2$ | H | CH(OH) | 3-F-phenyl | 3.86 | 401 | A |
| IAO-E009 | 1-1g | Exp. II-a02 | CA05 | $CH_2$ | Me | C=O | 1-phenylcyclopropyl | 4.64 | 435 | B |
| IAH-E009 | 1-1d | IAO-E009 | | $CH_2$ | Me | CH(OH) | 1-phenylcyclopropyl | | | |
| IAH-H009 | 1-1e | IAH-E009 | | $CH_2$ | H | CH(OH) | 1-phenylcyclopropyl | 4.1 | 423 | A |
| IAO-E010 | 1-1g | Exp. II-b02 | CA06 | O | Me | C=O | 3-CF$_3$-benzyl | 4.42 | 479 | B |
| IAH-E010 | 1-1d | IAO-E010 | | O | Me | CH(OH) | 3-CF$_3$-benzyl | 4.23 | 481 | B |
| IAH-H010 | 1-1e | IAH-E010 | | O | H | CH(OH) | 3-CF$_3$-benzyl | 4.14 | 467 | A |

TABLE 75
Table-A-2
| Exp. | Syn. | SM1 | SM2 | V | R^D1 | E | W | LCMS RTime | Mass | Method |
|---|---|---|---|---|---|---|---|---|---|---|
| IAO-E011 | 1-1g | Exp. II-a02 | CA07 | CH$_2$ | Me | C=O | 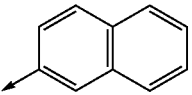 | 4.7 | 445 | B |
| IAH-E011 | 1-1d | IAO-E011 | | CH$_2$ | Me | CH(OH) | 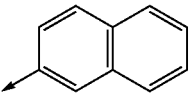 | | | |
| IAH-H011 | 1-1e | IAH-E011 | | CH$_2$ | H | CH(OH) | 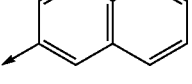 | 4.09 | 433 | A |
| IAO-E012 | 1-1g | Exp. II-a02 | CA08 | CH$_2$ | Me | C=O | 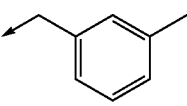 | 4.5 | 453 | A |
| IAH-E012 | 1-1d | IAO-E012 | | CH$_2$ | Me | CH(OH) | 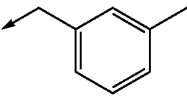 | | | |
| IAH-H012 | 1-1e | IAH-E012 | | CH$_2$ | H | CH(OH) | 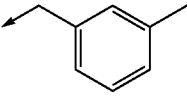 | 3.82 | 441 | A |
| IAO-E013 | 1-1g | Exp. II-b02 | CA08 | O | Me | C=O | 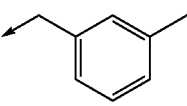 | 4.5 | 455 | A |
| IAH-E013 | 1-1d | IAO-E013 | | O | Me | CH(OH) | 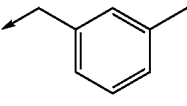 | | | |
| IAH-H013 | 1-1e | IAH-E013 | | O | H | CH(OH) | 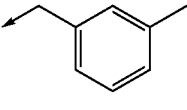 | 3.78 | 443 | A |
| IAO-E014 | 1-1g | Exp. II-a02 | CA09 | CH$_2$ | Me | C=O | 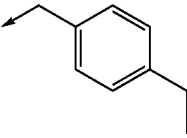 | 5.16 | 451 | A |
| IAH-E014 | 1-1d | IAO-E014 | | CH$_2$ | Me | CH(OH) | 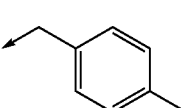 | | | |
| IAH-H014 | 1-1e | IAH-E014 | | CH$_2$ | H | CH(OH) | 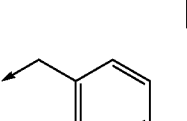 | 4.36 | 439 | A |

TABLE 75-continued

Table-A-2

| Exp. | Syn. | SM1 | SM2 | V | R^{D1} | E | W | LCMS RTime | Mass | Method |
|---|---|---|---|---|---|---|---|---|---|---|
| IAO-E015 | 1-1g | Exp. II-a02 | CA10 | CH$_2$ | Me | C=O | 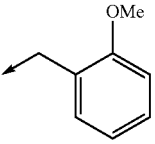 | 4.63 | 439 | A |
| IAH-E015 | 1-1d | IAO-E015 | | CH$_2$ | Me | CH(OH) | 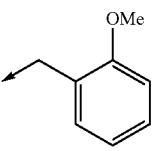 | | | |
| IAH-H015 | 1-1e | IAH-E015 | | CH$_2$ | H | CH(OH) | 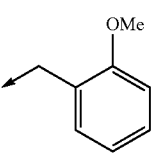 | 3.90 | 427 | A |
| IAO-E016 | 1-1g | Exp. II-a02 | CA11 | CH$_2$ | Me | C=O | 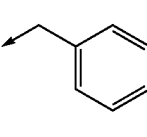 | 4.79 | 455 | A |
| IAH-E016 | 1-1d | IAO-E016 | | CH$_2$ | Me | CH(OH) | 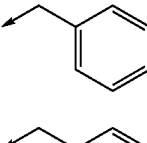 | | | |
| IAH-H016 | 1-1e | IAH-E016 | | CH$_2$ | H | CH(OH) | 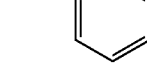 | 4.06 | 443 | A |

TABLE 76

Table-A-3

| Exp. | Syn. | SM1 | SM2 | V | R^{D1} | E | W | LCMS RTime | Mass | Method |
|---|---|---|---|---|---|---|---|---|---|---|
| IAO-E017 | 1-1g | Exp. II-a02 | CA12 | CH$_2$ | Me | C=O | 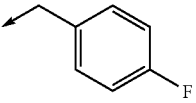 | 4.6 | 427 | A |
| IAH-E017 | 1-1d | IAO-E017 | | CH$_2$ | Me | CH(OH) | 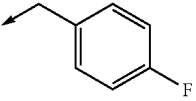 | | | |
| IAH-H017 | 1-1e | IAH-E017 | | CH$_2$ | H | CH(OH) | 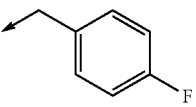 | 3.84 | 401 | A |
| IAO-E018 | 1-1g | Exp. II-a02 | CA13 | CH$_2$ | Me | C=O | 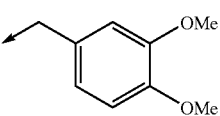 | 4.3 | 469 | A |

TABLE 76-continued
Table-A-3
| Exp. | Syn. | SM1 | SM2 | V | R$^{D1}$ | E | W | LCMS RTime | Mass | Method |
|---|---|---|---|---|---|---|---|---|---|---|
| IAH-E018 | 1-1d | IAO-E018 | | CH$_2$ | Me | CH(OH) | 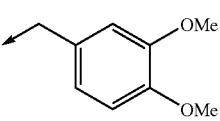 | | | |
| IAH-H018 | 1-1e | IAH-E018 | | CH$_2$ | H | CH(OH) | 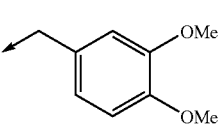 | 3.03 | 457 | A |
| IAO-E019 | 1-1g | Exp. II-a02 | CA14 | CH$_2$ | Me | C=O | 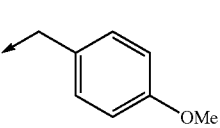 | 4.54 | 439 | A |
| IAH-E019 | 1-1d | IAO-E019 | | CH$_2$ | Me | CH(OH) | 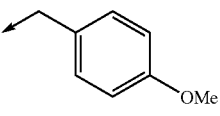 | | | |
| IAH-H019 | 1-1e | IAH-E019 | | CH$_2$ | H | CH(OH) | 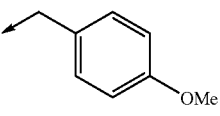 | 3.80 | 427 | A |
| IAO-E020 | 1-1g | Exp. II-a02 | CA15 | CH$_2$ | Me | C=O | 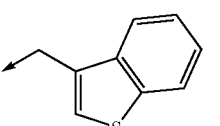 | 4.87 | 465 | A |
| IAH-E020 | 1-1d | IAO-E020 | | CH$_2$ | Me | CH(OH) | 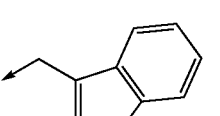 | | | |
| IAH-H020 | 1-1e | IAH-E020 | | CH$_2$ | H | CH(OH) | 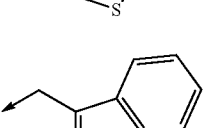 | 4.09 | 453 | A |
| IAO-E021 | 1-1g | Exp. II-a02 | CA16 | CH$_2$ | Me | C=O | 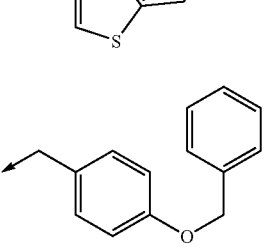 | 5.19 | 515 | A |
| IAH-E021 | 1-1d | IAO-E021 | | CH$_2$ | Me | CH(OH) | 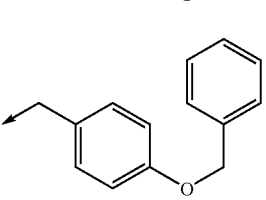 | | | |

TABLE 76-continued

Table-A-3

| Exp. | Syn. | SM1 | SM2 | V | R$^{D1}$ | E | W | LCMS RTime | Mass | Method |
|---|---|---|---|---|---|---|---|---|---|---|
| IAH-H021 | 1-1e | IAH-E021 | | CH$_2$ | H | CH(OH) | 4-benzyloxybenzyl | 4.41 | 503 | A |
| IAO-E022 | 1-1g | Exp. II-a02 | CA17 | CH$_2$ | Me | C=O | 2-CF$_3$-benzyl | 4.84 | 477 | A |
| IAH-E022 | 1-1d | IAO-E022 | | CH$_2$ | Me | CH(OH) | 2-CF$_3$-benzyl | | | |
| IAH-H022 | 1-1e | IAH-E022 | | CH$_2$ | H | CH(OH) | 2-CF$_3$-benzyl | 4.27 | 465 | A |

TABLE 77

Table-A-4

| Exp. | Syn. | SM1 | SM2 | V | R$^{D1}$ | E | W | LCMS RTime | Mass | Method |
|---|---|---|---|---|---|---|---|---|---|---|
| IAO-E023 | 1-1g | Exp. II-a02 | CA18 | CH$_2$ | Me | C=O | 4-CF$_3$-benzyl | 4.89 | 477 | A |
| IAH-E023 | 1-1d | IAO-E023 | | CH$_2$ | Me | CH(OH) | 4-CF$_3$-benzyl | | | |
| IAH-H023 | 1-1e | IAH-E023 | | CH$_2$ | H | CH(OH) | 4-CF$_3$-benzyl | 4.28 | 465 | A |
| IAO-E024 | 1-1g | Exp. II-a02 | CA19 | CH$_2$ | Me | C=O | 3-Cl-benzyl | 4.82 | 443 | A |
| IAH-E024 | 1-1d | IAO-E024 | | CH$_2$ | Me | CH(OH) | 3-Cl-benzyl | | | |

TABLE 77-continued
Table-A-4
| Exp. | Syn. | SM1 | SM2 | V | R$^{D1}$ | E | W | LCMS RTime | Mass | Method |
|---|---|---|---|---|---|---|---|---|---|---|
| IAH-H024 | 1-1e | IAH-E024 | | CH$_2$ | H | CH(OH) | 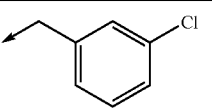 | 4.18 | 431 | A |
| IAO-E025 | 1-1g | Exp. II-a02 | CA20 | CH$_2$ | Me | C=O | 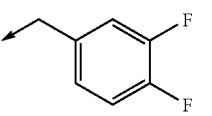 | 4.66 | 445 | A |
| IAH-E025 | 1-1d | IAO-E025 | | CH$_2$ | Me | CH(OH) | 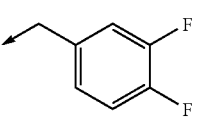 | | | |
| IAH-H025 | 1-1e | IAH-E025 | | CH$_2$ | H | CH(OH) | 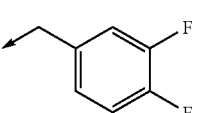 | 4.08 | 433 | A |
| IAO-E026 | 1-1g | Exp. II-a02 | CA21 | CH$_2$ | Me | C=O |  | 4.64 | 445 | A |
| IAH-E026 | 1-1d | IAO-E026 | | CH$_2$ | Me | CH(OH) | 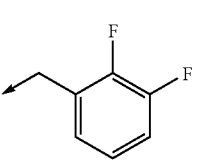 | | | |
| IAH-H026 | 1-1e | IAH-E026 | | CH$_2$ | H | CH(OH) |  | 4.06 | 433 | A |
| IAO-E027 | 1-1g | Exp. II-a02 | CA22 | CH$_2$ | Me | C=O | 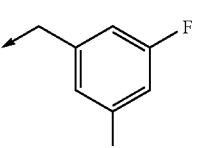 | 4.68 | 445 | A |
| IAH-E027 | 1-1d | IAO-E027 | | CH$_2$ | Me | CH(OH) | 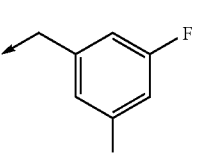 | | | |
| IAH-H027 | 1-1e | IAH-E027 | | CH$_2$ | H | CH(OH) | 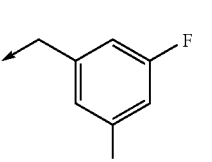 | 4.10 | 433 | A |

TABLE 77-continued

Table-A-4

| Exp. | Syn. | SM1 | SM2 | V | R$^{D1}$ | E | W | LCMS RTime | Mass | Method |
|---|---|---|---|---|---|---|---|---|---|---|
| IAO-E028 | 1-1g | Exp. II-a02 | CA23 | CH$_2$ | Me | C=O | 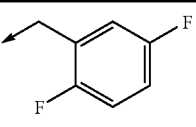 | 4.46 | 445 | A |
| IAH-E028 | 1-1d | IAO-E028 | | CH$_2$ | Me | CH(OH) | 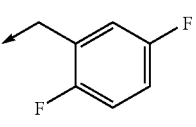 | | | |
| IAH-H028 | 1-1e | IAH-E028 | | CH$_2$ | H | CH(OH) | 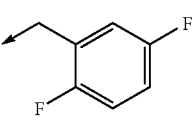 | 4.06 | 433 | A |

TABLE 78

Table-A-5

| Exp. | Syn. | SM1 | SM2 | V | R$^{D1}$ | E | W | LCMS RTime | Mass | Method |
|---|---|---|---|---|---|---|---|---|---|---|
| IAO-E029 | 1-1g | Exp. II-a02 | CA24 | CH$_2$ | Me | C=O | 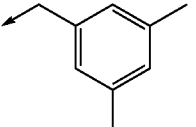 | 4.98 | 437 | A |
| IAH-E029 | 1-1d | IAO-E029 | | CH$_2$ | Me | CH(OH) | 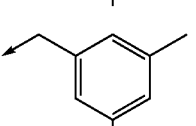 | | | |
| IAH-H029 | 1-1e | IAH-E029 | | CH$_2$ | H | CH(OH) | 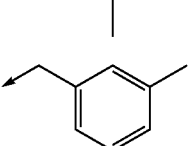 | 4.28 | 425 | A |
| IAO-E030 | 1-1g | Exp. II-a02 | CA25 | CH$_2$ | Me | C=O | 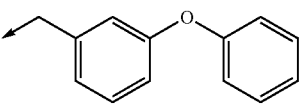 | 5.12 | 501 | A |
| IAH-E030 | 1-1d | IAO-E030 | | CH$_2$ | Me | CH(OH) | 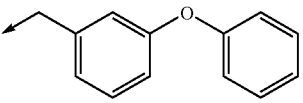 | | | |
| IAH-H030 | 1-1e | IAH-E030 | | CH$_2$ | H | CH(OH) | 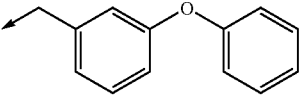 | 4.48 | 489 | A |
| IAO-E031 | 1-1g | Exp. II-a02 | CA26 | CH$_2$ | Me | C=O | 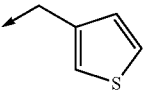 | 4.88 | 415 | A |

TABLE 78-continued
Table-A-5
| Exp. | Syn. | SM1 | SM2 | V | R<sup>D1</sup> | E | W | LCMS RTime | Mass | Method |
|---|---|---|---|---|---|---|---|---|---|---|
| IAH-E031 | 1-1d | IAO-E031 | | CH$_2$ | Me | CH(OH) | 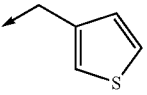 | | | |
| IAH-H031 | 1-1e | IAH-E031 | | CH$_2$ | H | CH(OH) | 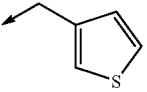 | 3.89 | 403 | A |
| IAO-E032 | 1-1g | Exp. II-a02 | CA27 | CH$_2$ | Me | C=O | 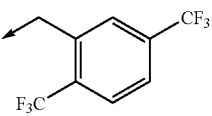 | 5.01 | 545 | A |
| IAH-E032 | 1-1d | IAO-E032 | | CH$_2$ | Me | CH(OH) | 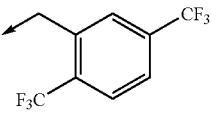 | | | |
| IAH-H032 | 1-1e | IAH-E032 | | CH$_2$ | H | CH(OH) | 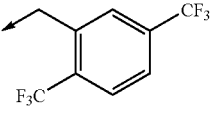 | 4.46 | 533 | A |
| IAO-E033 | 1-1g | Exp. II-a02 | CA28 | CH$_2$ | Me | C=O | 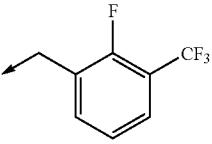 | 4.85 | 495 | A |
| IAH-E033 | 1-1d | IAO-E033 | | CH$_2$ | Me | CH(OH) | 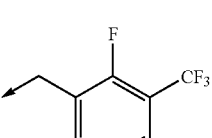 | | | |
| IAH-H033 | 1-1e | IAH-E033 | | CH$_2$ | H | CH(OH) | 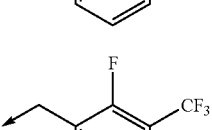 | 4.17 | 483 | A |
| IAO-E034 | 1-1g | Exp. II-a02 | CA29 | CH$_2$ | Me | C=O | 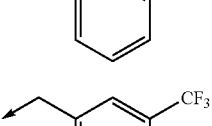 | 5.06 | 511 | A |
| IAH-E034 | 1-1d | IAO-E034 | | CH$_2$ | Me | CH(OH) | 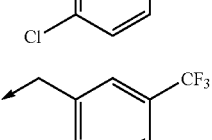 | | | |
| IAH-H034 | 1-1e | IAH-E034 | | CH$_2$ | H | CH(OH) | 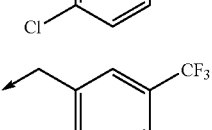 | 4.36 | 499 | A |

TABLE 79
Table-A-6
| Exp. | Syn. | SM1 | SM2 | V | R$^{D1}$ | E | W | LCMS RTime | Mass | Method |
|---|---|---|---|---|---|---|---|---|---|---|
| IAO-E035 | 1-1g | Exp. II-a02 | CA30 | CH$_2$ | Me | C=O | 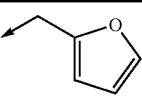 | 4.33 | 399 | A |
| IAH-E035 | 1-1d | IAO-E035 | | CH$_2$ | Me | CH(OH) | 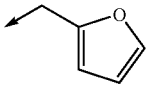 | | | |
| IAH-H035 | 1-1e | IAH-E035 | | CH$_2$ | H | CH(OH) | 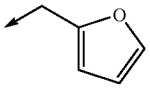 | 3.62 | 387 | A |
| IAO-E036 | 1-1g | Exp. II-a02 | CA31 | CH$_2$ | Me | C=O | 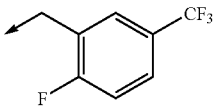 | 4.89 | 495 | A |
| IAH-E036 | 1-1d | IAO-E036 | | CH$_2$ | Me | CH(OH) | 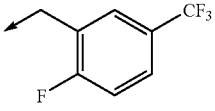 | | | |
| IAH-H036 | 1-1e | IAH-E036 | | CH$_2$ | H | CH(OH) | 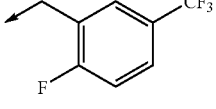 | 4.20 | 483 | A |
| IAO-E037 | 1-1g | Exp. II-a02 | CA32 | CH$_2$ | Me | C=O | 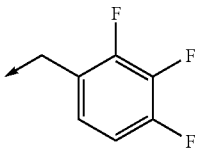 | 4.74 | 463 | A |
| IAH-E037 | 1-1d | IAO-E037 | | CH$_2$ | Me | CH(OH) |  | | | |
| IAH-H037 | 1-1e | IAH-E037 | | CH$_2$ | H | CH(OH) | 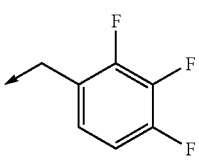 | 4.02 | 451 | A |
| IAO-E038 | 1-1g | Exp. II-a02 | CA33 | CH$_2$ | Me | C=O | 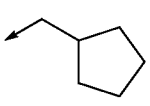 | 4.92 | 401 | A |
| IAH-E038 | 1-1d | IAO-E038 | | CH$_2$ | Me | CH(OH) | 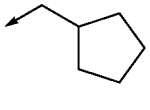 | | | |
| IAH-H038 | 1-1e | IAH-E038 | | CH$_2$ | H | CH(OH) | 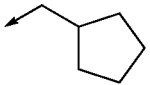 | 4.04 | 389 | A |

TABLE 79-continued

Table-A-6

| Exp. | Syn. | SM1 | SM2 | V | R^D1 | E | W | LCMS RTime | Mass | Method |
|---|---|---|---|---|---|---|---|---|---|---|
| IAO-E039 | 1-1g | Exp. II-a02 | CA34 | CH$_2$ | Me | C=O | 3-CF$_3$, 4-F benzyl | 4.92 | 495 | A |
| IAH-E039 | 1-1d | IAO-E039 | | CH$_2$ | Me | CH(OH) | 3-CF$_3$, 4-F benzyl | | | |
| IAH-H039 | 1-1e | IAH-E039 | | CH$_2$ | H | CH(OH) | 3-CF$_3$, 4-F benzyl | 4.18 | 483 | A |
| IAO-E040 | 1-1g | Exp. II-a02 | CA35 | CH$_2$ | Me | C=O | 3-OCF$_3$ benzyl | 4.95 | 493 | A |
| IAH-E040 | 1-1d | IAO-E040 | | CH$_2$ | Me | CH(OH) | 3-OCF$_3$ benzyl | | | |
| IAH-H040 | 1-1e | IAH-E040 | | CH$_2$ | H | CH(OH) | 3-OCF$_3$ benzyl | 4.19 | 481 | A |

TABLE 80

Table-A-7

| Exp. | Syn. | SM1 | SM2 | V | R^D1 | E | W | LCMS RTime | Mass | Method |
|---|---|---|---|---|---|---|---|---|---|---|
| IAO-E041 | 1-1g | Exp. II-a02 | CA36 | CH$_2$ | Me | C=O | 4-I benzyl | 5.04 | 535 | A |
| IAH-E041 | 1-1d | IAO-E041 | | CH$_2$ | Me | CH(OH) | 4-I benzyl | | | |
| IAH-H041 | 1-1e | IAH-E041 | | CH$_2$ | H | CH(OH) | 4-I benzyl | 4.20 | 523 | A |
| IAO-E042 | 1-1g | Exp. II-a02 | CA37 | CH$_2$ | Me | C=O | 3-CF$_3$, 5-F benzyl | | | |

TABLE 80-continued
Table-A-7
| Exp. | Syn. | SM1 | SM2 | V | R$^{D1}$ | E | W | LCMS RTime | Mass | Method |
|---|---|---|---|---|---|---|---|---|---|---|
| IAH-E042 | 1-1d | IAO-E042 | | CH$_2$ | Me | CH(OH) | 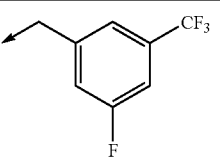 | 4.77 | 497 | A |
| IAH-H042 | 1-1e | IAH-E042 | | CH$_2$ | H | CH(OH) | 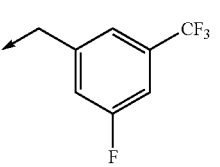 | 4.36 | 483 | A |
| IAO-E043 | 1-1g | Exp. II-a02 | CA38 | CH$_2$ | Me | C=O | 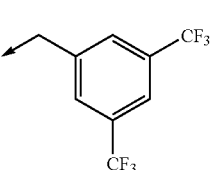 | | | |
| IAH-E043 | 1-1d | IAO-E043 | | CH$_2$ | Me | CH(OH) | 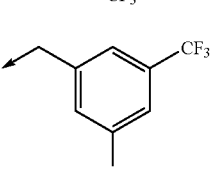 | 4.95 | 547 | B |
| IAH-H043 | 1-1e | IAH-E043 | | CH$_2$ | H | CH(OH) | 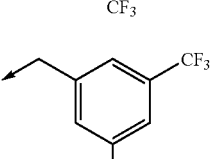 | 4.57 | 533 | A |
| IAO-E044 | 1-1g | Exp. II-a02 | CA39 | CH$_2$ | Me | C=O | 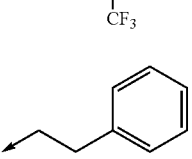 | 4.68 | 423 | A |
| IAH-E044 | 1-1d | IAO-E044 | | CH$_2$ | Me | CH(OH) | 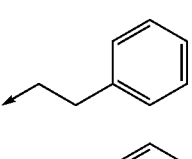 | 4.39 | 425 | B |
| IAH-H044 | 1-1e | IAH-E044 | | CH$_2$ | H | CH(OH) | 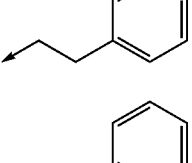 | 4.09 | 411 | A |
| IAO-E045 | 1-1g | Exp. II-a02 | CA40 | CH$_2$ | Me | C=O | 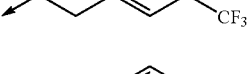 | 4.90 | 491 | B |
| IAH-E045 | 1-1d | IAO-E045 | | CH$_2$ | Me | CH(OH) | 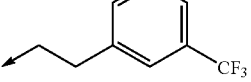 | 4.74 | 493 | A |

TABLE 80-continued

Table-A-7

| Exp. | Syn. | SM1 | SM2 | V | R<sup>D1</sup> | E | W | LCMS RTime | Mass | Method |
|---|---|---|---|---|---|---|---|---|---|---|
| IAH-H045 | 1-1e | IAH-E045 | | CH<sub>2</sub> | H | CH(OH) | 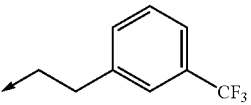 | 4.34 | 479 | A |
| IAO-E046 | 1-1g | Exp. II-a02 | CA41 | CH<sub>2</sub> | Me | C=O | 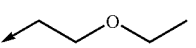 | 3.60 | 391 | B |
| IAH-E046 | 1-1d | IAO-E046 | | CH<sub>2</sub> | Me | CH(OH) | 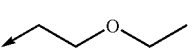 | 3.84 | 393 | A |
| IAH-H046 | 1-1e | IAH-E046 | | CH<sub>2</sub> | H | CH(OH) | 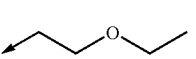 | 3.55 | 379 | A |

TABLE 81

Table-A-8

| Exp. | Syn. | SM1 | SM2 | V | R<sup>D1</sup> | E | W | LCMS RTime | Mass | Method |
|---|---|---|---|---|---|---|---|---|---|---|
| IAO-E047 | 1-1g | Exp. II-a02 | CA42 | CH<sub>2</sub> | Me | C=O | 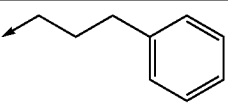 | 4.85 | 437 | A |
| IAH-E047 | 1-1d | IAO-E047 | | CH<sub>2</sub> | Me | CH(OH) | 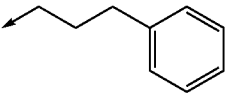 | | | |
| IAH-H047 | 1-1e | IAH-E047 | | CH<sub>2</sub> | H | CH(OH) | 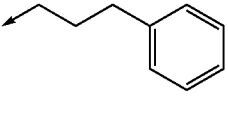 | 4.30 | 425 | A |
| IAO-E048 | 1-1g | Exp. II-a02 | CA43 | CH<sub>2</sub> | Me | C=O | 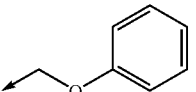 | | | |
| IAH-E048 | 1-1d | IAO-E048 | | CH<sub>2</sub> | Me | CH(OH) | 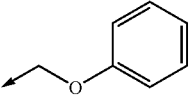 | | | |
| IAH-H048 | 1-1e | IAH-E048 | | CH<sub>2</sub> | H | CH(OH) | 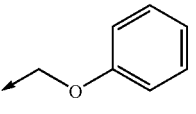 | 4.00 | 413 | A |
| IAO-E049 | 1-1g | Exp. II-a02 | CA44 | CH<sub>2</sub> | Me | C=O | 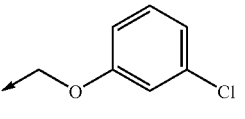 | 4.70 | 459 | A |
| IAH-E049 | 1-1d | IAO-E049 | | CH<sub>2</sub> | Me | CH(OH) | 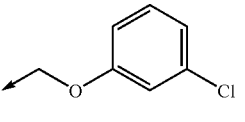 | | | |

TABLE 81-continued

Table-A-8

| Exp. | Syn. | SM1 | SM2 | V | $R^{D1}$ | E | W | LCMS RTime | Mass | Method |
|---|---|---|---|---|---|---|---|---|---|---|
| IAH-H049 | 1-1e | IAH-E049 | | $CH_2$ | H | CH(OH) | 3-Cl-phenoxymethyl | 4.27 | 447 | A |
| IAO-E050 | 1-1g | Exp. II-a02 | CA45 | $CH_2$ | Me | C=O | 3-OMe-phenoxymethyl | 4.44 | 455 | A |
| IAH-E050 | 1-1d | IAO-E050 | | $CH_2$ | Me | CH(OH) | 3-OMe-phenoxymethyl | | | |
| IAH-H050 | 1-1e | IAH-E050 | | $CH_2$ | H | CH(OH) | 3-OMe-phenoxymethyl | 4.00 | 443 | A |
| IAO-E051 | 1-1g | Exp. II-a02 | CA46 | $CH_2$ | Me | C=O | 3-Br-benzyl | 4.80 | 487 | A |
| IAH-E051 | 1-1d | IAO-E051 | | $CH_2$ | Me | CH(OH) | 3-Br-benzyl | | | |
| IAH-H051 | 1-1e | IAH-E051 | | $CH_2$ | H | CH(OH) | 3-Br-benzyl | 4.08 | 475 | A |
| IAO-E052 | 1-1g | Exp. II-a02 | CA47 | $CH_2$ | Me | C=O | 3-I-benzyl | 4.92 | 535 | A |
| IAH-E052 | 1-1d | IAO-E052 | | $CH_2$ | Me | CH(OH) | 3-I-benzyl | | | |
| IAH-H052 | 1-1e | IAH-E052 | | $CH_2$ | H | CH(OH) | 3-I-benzyl | 4.17 | 523 | A |

TABLE 82
Table-A-9
| Exp. | Syn. | SM1 | SM2 | V | R$^{D1}$ | E | W | LCMS RTime | Mass | Method |
|---|---|---|---|---|---|---|---|---|---|---|
| IAO-E053 | 1-1g | Exp. II-a02 | CA48 | CH$_2$ | Me | C=O | 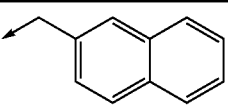 | 4.95 | 459 | A |
| IAH-E053 | 1-1d | IAO-E053 | | CH$_2$ | Me | CH(OH) | 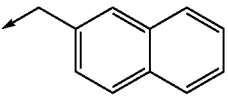 | | | |
| IAH-H053 | 1-1e | IAH-E053 | | CH$_2$ | H | CH(OH) | 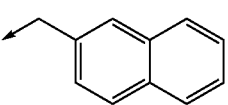 | 4.20 | 447 | A |
| IAO-E054 | 1-1g | Exp. II-a02 | CA49 | CH$_2$ | Me | C=O | 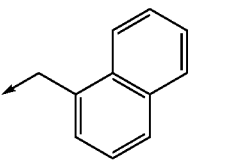 | 5.01 | 459 | A |
| IAH-E054 | 1-1d | IAO-E054 | | CH$_2$ | Me | CH(OH) | 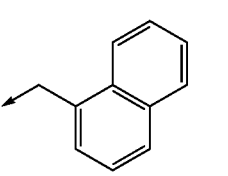 | | | |
| IAH-H054 | 1-1e | IAH-E054 | | CH$_2$ | H | CH(OH) | 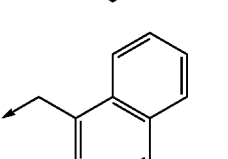 | 4.14 | 447 | A |
| IAO-E055 | 1-1g | Exp. II-a02 | CA50 | CH$_2$ | Me | C=O | 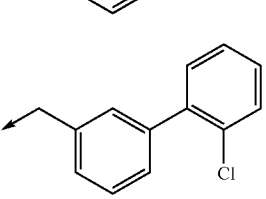 | 5.46 | 519 | B |
| IAH-E055 | 1-1d | IAO-E055 | | CH$_2$ | Me | CH(OH) | 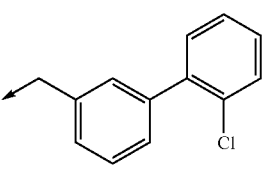 | | | |
| IAH-H055 | 1-1e | IAH-E055 | | CH$_2$ | H | CH(OH) | 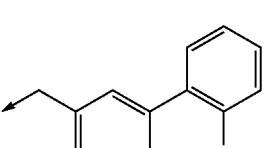 | 4.42 | 507 | A |
| IAO-E056 | 1-1g | Exp. II-a02 | CA51 | CH$_2$ | Me | C=O | 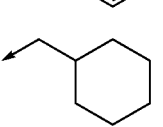 | 5.37 | 415 | B |

TABLE 82-continued

Table-A-9

| Exp. | Syn. | SM1 | SM2 | V | R^D1 | E | W | LCMS RTime | Mass | Method |
|---|---|---|---|---|---|---|---|---|---|---|
| IAH-E056 | 1-1d | IAO-E056 | | CH$_2$ | Me | CH(OH) | 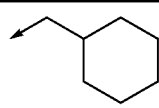 | | | |
| IAH-H056 | 1-1e | IAH-E056 | | CH$_2$ | H | CH(OH) | 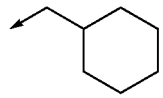 | 4.22 | 403 | A |

TABLE 83

Table-CA-1

| Symbol | Reagent | Manufacturer |
|---|---|---|
| CA01 | 3-Methoxyphenylacetic acid | TCI |
| CA02 | 3-Fluorophenylacetic acid | TCI |
| CA03 | 3-Methoxybenzoic acid | TCI |
| CA04 | 3-Fluorobenzoic acid | TCI |
| CA05 | 1-Phenyl-1-cyclopropanecarboxylic acid | ALD |
| CA06 | 3-Trifluoromethylphenylacetic acid | TCI |
| CA07 | 2-Naphthoic acid | TCI |
| CA08 | 3-Methoxymethylphenylacetic acid | Synthesized material |
| CA09 | 4-Isopropylphenylacetic acid | LANC |
| CA10 | 2-Methoxyphenylacetic acid | ALD |
| CA11 | 4-Methylthiophenylacetic acid | ALD |
| CA12 | 4-Fluorophenylacetic acid | TCI |
| CA13 | 3,4-Dimethoxyphenylacetic acid | TCI |
| CA14 | 4-Methoxyphenylacetic acid | TCI |
| CA15 | 2-(Benzo[b]thiophen-3-yl)acetic acid | LANC |
| CA16 | 4-Benzyloxyphenylacetic acid | OA |
| CA17 | 2-Trifluorophenylacetic acid | TCI |
| CA18 | 4-Trifluorophenylacetic acid | TCI |
| CA19 | 3-Chlorophenylacetic acid | TCI |
| CA20 | 3,4-Difluorophenylacetic acid | LANC |
| CA21 | 2,3-Difluorophenylacetic acid | LANC |
| CA22 | 3,5-Difluorophenylacetic acid | LANC |
| CA23 | 2,5-Difluorophenylacetic acid | ALD |
| CA24 | 3,5-Dimethylphenylacetic acid | ALF |
| CA25 | 3-Phenoxyphenylacetic acid | LANC |
| CA26 | Thiophene-3-acetic acid | TCI |
| CA27 | 5-Ditrifluoromethylphenylacetic acid | ALD |
| CA28 | 2-Fluoro-3-trifluoromethylphenylacetic acid | ALD |
| CA29 | 2-Chloro-5-trifluoromethylphenylacetic acid | ALF |
| CA30 | Furan-2-acetic acid | ASDI |
| CA31 | 2-Fluoro-5-trifluoromethylphenylacetic acid | MS |
| CA32 | 2,3,4-Trifluorophenylacetic acid | MS |
| CA33 | Cyclopentylacetic acid | TCI |
| CA34 | 4-Fluoro-3-trifluoromethylphenylacetic acid | ALD |
| CA35 | 3-Trifluoromethoxyphenylacetic acid | MS |
| CA36 | 4-Iodophenylacetic acid | LANC |
| CA37 | 3-Fluoro-5-trifluoromethylphenylacetic acid | MS |
| CA38 | 3,5-Ditrifluoromethylphenylacetic acid | TCI |
| CA39 | 3-Phenylpropionic acid | MS |
| CA40 | 3-(3-Trifluoromethylphenyl)propionic acid | MS |
| CA41 | 3-Ethoxypropanoic acid | TCI |
| CA42 | 4-Phenylbutanoic acid | TCI |
| CA43 | 3-Phenoxyacetic acid | TCI |
| CA44 | 3-(3-Chlorophenoxy)acetic acid | LANC |
| CA45 | 3-(3-Methoxyphenoxy)acetic acid | LANC |
| CA46 | 3-Bromophenylacetic acid | TCI |
| CA47 | 3-Iodophenylacetic acid | ALD |
| CA48 | 2-Naphthaleneacetic acid | TCI |
| CA49 | 1-Naphthaleneacetic acid | KANT |
| CA50 | 3-(2-Chlorophenyl)phenylacetic acid | AST |
| CA51 | 2-Cyclohexylacetic acid | TCI |

Examples IAO-E057 to IAH-H074

Preparations of Compound Nos. IAO-E057 to IAH-H074 are shown in Tables A-10 to A-12. The symbols used in the tables, "Exp.", "Syn.", and "SM1", have the same meanings as those defined above. For "SM2", corresponding symbols, regent names and manufacturers are shown in Tables CA-1 and CA-2. The starting materials for which the term "Synthesized material" is indicated in the columns of "Manufacturer" were synthesized according to the procedures described in International Patent Publication WO00/03980, and the starting materials for which the term "Synthesized material 2" is indicated were synthesized according to the procedures described below.

Synthesis of 2-(2,3-dihydro-1H-inden-1-yl)acetic acid (Starting compound CA52)

Synthesis of ethyl 2-(2,3-dihydroinden-1-yl-indene) acetate (Intermediate pb-01) (Preparation Method pb-1)

A solution of sodium hydride (2.72 g, WAKO) in anhydrous dimethoxyethane (32.5 mL) was added dropwise with ethyl diethylphosphonoacetate (23.4 ml, TCI) under ice cooling, and the mixture was stirred for 10 minutes, and then added dropwise with a solution of 1-indanone (TCI, 5.00 g) in anhydrous DME (32.5 ml). The mixture was stirred for 5 minutes, and then stirred for 18 hours under reflux by heating. The reaction mixture was concentrated, then added with water and ethyl acetate, successively washed with saturated aqueous ammonium chloride, and saturated brine, and dried, and then the solvent was evaporated under reduced pressure. The residue was purified by column chromatography (hexane alone) to obtain the title compound (Intermediate pb-01, 5.24 g).

Synthesis of ethyl 2-(2,3-dihydro-1H-inden-1-yl) acetate (Intermediate pb-02) (Preparation method pb-2)

A solution of Intermediate pb-01 (3.28 g) in ethanol (32 ml) was added with 10% palladium-carbon (32 mg, Merck), and the mixture was stirred at room temperature for 3 hours under a hydrogen atmosphere. The reaction mixture was filtered, and the solvent of the filtrate was evaporated under reduced pressure to obtain the title compound (Intermediate pb-02, 3.32 g).

Synthesis of 2-(2,3-dihydro-1H-inden-1-yl)acetic acid (Starting compound CA52) (Preparation method pb-3)

A solution of Intermediate pb-02 (3.32 g) in methanol (82 ml) was added with 2 N aqueous sodium hydroxide (16.4 ml), and the mixture was stirred at 60° C. for 1 hour. The reaction mixture was concentrated under reduced pressure, then neutralized with 1 N aqueous hydrochloric acid under ice cooling, and extracted with ethyl acetate. The organic layer was washed with saturated brine, and dried, and then the solvent was evaporated under reduced pressure to obtain the title compound (Starting compound CA52, 2.84 g).

Synthesis of 2-(5-fluoro-2,3-dihydro-1H-inden-1-yl) acetic acid (Starting compound CA53)

Synthesis of ethyl 2-(5-fluoro-2,3-dihydroinden-1-yl-indene)acetate (Intermediate pb-01) (Preparation method pb-1)

According to the procedures described in the synthesis method of Intermediate pb-01, 5-fluoro-1-indanone (5.32 g) was used instead of 1-indanone, and the material was reacted and treated to obtain the title compound (Intermediate pc-01, 5.24 g).

Synthesis of ethyl 2-(5-fluoro-2,3-dihydro-1H-inden-1-yl)acetate (Intermediate pc-02) (Preparation method pb-2)

According to the procedures described in the synthesis method of Intermediate pb-02, Intermediate pc-01 (2.54 g) was used instead of Intermediate pb-01, and the material was reacted and treated to obtain the title compound (Intermediate pc-02, 2.10 g).

Synthesis of 2-(5-fluoro-2,3-dihydro-1H-inden-1-yl) acetic acid (Starting compound CA53) (Preparation method pb-3)

According to the procedures described in the synthesis method of Example CA52, Intermediate pc-02 (1.09 g) was used instead of Intermediate pb-02, and the material was reacted and treated to obtain the title compound (Starting compound CA53, 890 mg).

Synthesis of 2-[2-(trifluoromethyl)phenyloxy]acetic acid (Starting compound CA54) (Preparation method pc-1)

A solution of 2-hydroxybenzotrifluoride (3.00 g, TCI) in a mixture of DMF (16.5 ml) and ethanol (1.8 ml) was added with sodium hydroxide (1.5 g, WAKO) and bromoacetic acid (2.6 g, TCI), and the mixture was stirred at 85° C. for 24 hours. The reaction mixture was added with diethyl ether and saturated brine, and successively washed with 1 N aqueous hydrochloric acid and saturated aqueous sodium carbonate. The layer produced between the aqueous layer and oil layer was dried to obtain a crude product of the title compound (Compound No. CA54, 2.36 g).

Synthesis of 3-[2-(trifluoromethyl)phenyl]propionic acid (Starting compound CA55)

Synthesis of ethyl 3-[2-(trifluoromethyl)phenyl]acrylate (Intermediate pd-01) (Preparation method pb-1)

According to the procedures described in the synthesis method of Intermediate pb-01, 2-Trifluoromethylbenzaldehyde (TCI, 3.19 ml) was used instead of 1-indanone, and the material was reacted and treated to obtain the title compound (Intermediate pd-01, 5.92 g).

Synthesis of ethyl 3-[2-(trifluoromethyl)phenyl]propionate (Intermediate pd-02) (Preparation method pb-2)

According to the procedures described in the synthesis method of Intermediate pb-02, Intermediate pd-01 (5.92 g) was used instead of Intermediate pb-01, and the material was reacted and treated to obtain the title compound (Intermediate pd-02, 5.95 g).

Synthesis of 3-[2-(trifluoromethyl)phenyl]propionic acid (Starting compound CA55) (Preparation method pb-3)

According to the procedures described in the synthesis method of Starting compound CA52, Intermediate pd-02 (5.92 g) was used instead of Intermediate pb-02, and the material was reacted and treated to obtain the title compound (Starting compound CA55, 5.00 g). "V", "$R^{D1}$", "E", and "W" represent substituents and functional groups in the following general formula (I-Exp-A).

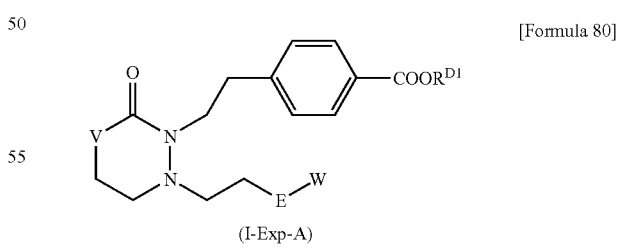

[Formula 80]

(I-Exp-A)

The liquid chromatography-mass spectrometry data are shown in the columns of "LCMS", and retention times in the liquid chromatography are shown in the columns of "RTime". Mass spectrometry data are shown in the columns of "Mass". The measurement conditions of the aforementioned liquid chromatography-mass spectrometry are shown in the columns of "Method".

TABLE 84
Table-A-10
| Exp. | Syn. | SM1 | SM2 | V | $R^{D1}$ | E | W | LCMS RTime | Mass | Method |
|---|---|---|---|---|---|---|---|---|---|---|
| IAO-E057 | 1-1g | Exp. II-a02 | CA06 | S | Me | C=O | 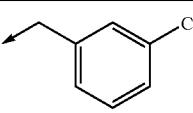 | 4.95 | 495 | A |
| IAH-E057 | 1-1d | IAO-E057 | | S | Me | CH(OH) | 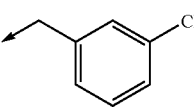 | 4.81 | 497 | B |
| IAH-H057 | 1-1e | IAH-E057 | | S | H | CH(OH) | 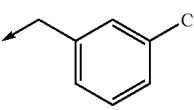 | 4.38 | 483 | A |
| IAO-E058 | 1-1g | Exp. II-a02 | CA19 | O | Me | C=O | 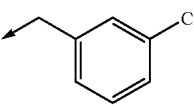 | 4.53 | 445 | B |
| IAH-E058 | 1-1d | IAO-E058 | | O | Me | CH(OH) | 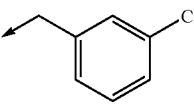 | 4.3 | 447 | B |
| IAH-H058 | 1-1e | IAH-E058 | | O | H | CH(OH) | 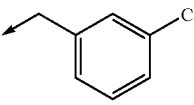 | 4.07 | 433 | A |
| IAO-E059 | 1-1g | Exp. II-a02 | CA34 | O | Me | C=O | 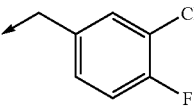 | 4.76 | 497 | A |
| IAH-E059 | 1-1d | IAO-E059 | | O | Me | CH(OH) | 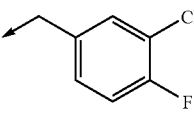 | | | |
| IAH-H059 | 1-1e | IAH-E059 | | O | H | CH(OH) | 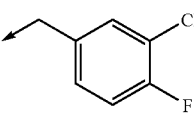 | 4.22 | 485 | A |
| IAO-E060 | 1-1g | Exp. II-a02 | CA56 | $CH_2$ | Me | C=O | 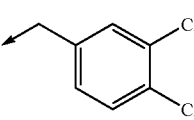 | 4.95 | 477 | B |
| IAH-E060 | 1-1d | IAO-E060 | | $CH_2$ | Me | CH(OH) | 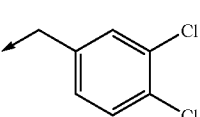 | 4.72 | 479 | B |
| IAH-H060 | 1-1e | IAH-E060 | | $CH_2$ | H | CH(OH) | 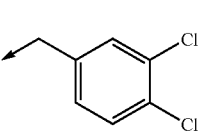 | 4.33 | 465 | A |

TABLE 84-continued
Table-A-10
| Exp. | Syn. | SM1 | SM2 | V | R^{D1} | E | W | LCMS RTime | Mass | Method |
|---|---|---|---|---|---|---|---|---|---|---|
| IAO-E061 | 1-1g | Exp. II-a02 | CA57 | CH$_2$ | Me | C=O | 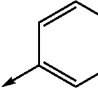 | 4.87 | 463 | A |
| IAH-E061 | 1-1d | IAO-E061 | | CH$_2$ | Me | CH(OH) | 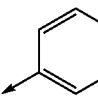 | 4.58 | 465 | A |
| IAH-H061 | 1-1e | IAH-E061 | | CH$_2$ | H | CH(OH) | 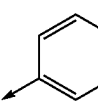 | 4.12 | 451 | A |
| IAO-E062 | 1-1g | Exp. II-a02 | CA52 | CH$_2$ | Me | C=O | 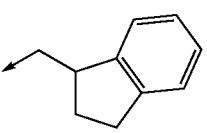 | 4.96 | 449 | A |
| IAH-E062 | 1-1d | IAO-E062 | | CH$_2$ | Me | CH(OH) | 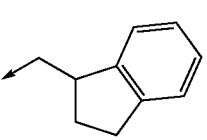 | 4.77 | 451 | A |
| IAH-H062 | 1-1e | IAH-E062 | | CH$_2$ | H | CH(OH) | 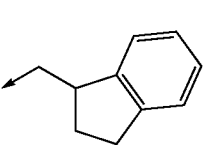 | 4.24 | 437 | A |
TABLE 85
Table-A-11
| Exp. | Syn. | SM1 | SM2 | V | R^{D1} | E | W | LCMS RTime | Mass | Method |
|---|---|---|---|---|---|---|---|---|---|---|
| IAO-E063 | 1-1g | Exp. II-a02 | CA53 | CH$_2$ | Me | C=O | 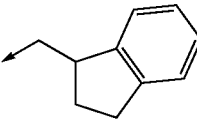 | 5 | 467 | B |
| IAH-E063 | 1-1d | IAO-E063 | | CH$_2$ | Me | CH(OH) | 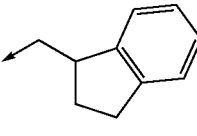 | 4.62 | 469 | B |
| IAH-H063 | 1-1e | IAH-E063 | | CH$_2$ | H | CH(OH) | 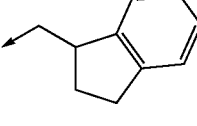 | 4.27 | 455 | A |

TABLE 85-continued

Table-A-11

| Exp. | Syn. | SM1 | SM2 | V | R$^{D1}$ | E | W | LCMS RTime | Mass | Method |
|---|---|---|---|---|---|---|---|---|---|---|
| IAO-E064 | 1-1g | Exp. II-a02 | CA54 | CH$_2$ | Me | C=O | 2-CF$_3$-phenyl-O-CH$_2$CH$_2$- | 4.53 | 493 | B |
| IAH-E064 | 1-1d | IAO-E064 | | CH$_2$ | Me | CH(OH) | 2-CF$_3$-phenyl-O-CH$_2$CH$_2$- | 4.42 | 495 | B |
| IAH-H064 | 1-1e | IAH-E064 | | CH$_2$ | H | CH(OH) | 2-CF$_3$-phenyl-O-CH$_2$CH$_2$- | 4.17 | 481 | A |
| IAO-E065 | 1-1g | Exp. II-a02 | CA55 | CH$_2$ | Me | C=O | 2-CF$_3$-phenyl-CH$_2$CH$_2$- | 4.97 | 491 | A |
| IAH-E065 | 1-1d | IAO-E065 | | CH$_2$ | Me | CH(OH) | 2-CF$_3$-phenyl-CH$_2$CH$_2$- | 4.80 | 493 | A |
| IAH-H065 | 1-1e | IAH-E065 | | CH$_2$ | H | CH(OH) | 2-CF$_3$-phenyl-CH$_2$CH$_2$- | 4.29 | 479 | A |
| IAO-E066 | 1-1g | Exp. II-a02 | CA19 | S | Me | C=O | 3-Cl-phenyl-CH$_2$- | | 461 | C |
| IAH-E066 | 1-1d | IAO-E066 | | S | Me | CH(OH) | 3-Cl-phenyl-CH$_2$- | | 463 | C |
| IAH-H066 | 1-1e | IAH-E066 | | S | H | CH(OH) | 3-Cl-phenyl-CH$_2$- | | 449 | C |
| IAO-E067 | 1-1g | Exp. II-a02 | CA34 | S | Me | C=O | 3-CF$_3$-4-F-phenyl-CH$_2$- | | 513 | C |

TABLE 85-continued
Table-A-11
| Exp. | Syn. | SM1 | SM2 | V | $R^{D1}$ | E | W | LCMS RTime | Mass | Method |
|---|---|---|---|---|---|---|---|---|---|---|
| IAH-E067 | 1-1d | IAO-E067 | | S | Me | CH(OH) | 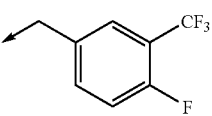 | | 515 | C |
| IAH-H067 | 1-1e | IAH-E067 | | S | H | CH(OH) | 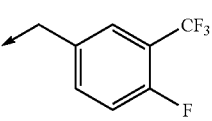 | | 501 | C |
| IAO-E068 | 1-1g | Exp. II-a02 | CA28 | S | Me | C=O | 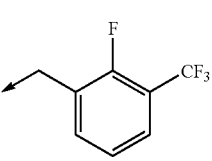 | | 513 | C |
| IAH-E068 | 1-1d | IAO-E068 | | S | Me | CH(OH) |  | | 515 | C |
| IAH-H068 | 1-1e | IAH-E068 | | S | H | CH(OH) | 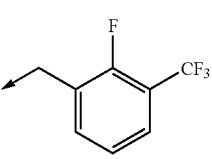 | | 501 | C |
TABLE 86
Table-A-12
| Exp. | Syn. | SM1 | SM2 | V | $R^{D1}$ | E | W | LCMS RTime | Mass | Method |
|---|---|---|---|---|---|---|---|---|---|---|
| IAO-E069 | 1-1g | Exp. II-bs02 | CA08 | S | Me | C=O | 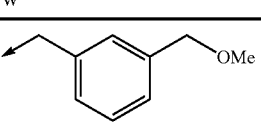 | | 471 | C |
| IAH-E069 | 1-1d | IAO-E069 | | S | Me | CH(OH) | 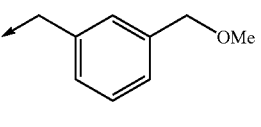 | | 473 | C |
| IAH-H069 | 1-1e | IAH-E069 | | S | H | CH(OH) | 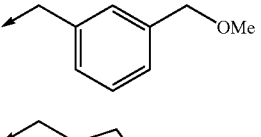 | | 459 | C |
| IAO-E070 | 1-1g | Exp. II-bs02 | CA33 | S | Me | C=O | 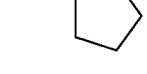 | | 419 | C |
| IAH-E070 | 1-1d | IAO-E070 | | S | Me | CH(OH) | 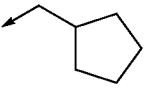 | | 421 | C |

TABLE 86-continued
Table-A-12
| Exp. | Syn. | SM1 | SM2 | V | R$^{D1}$ | E | W | LCMS RTime | Mass | Method |
|---|---|---|---|---|---|---|---|---|---|---|
| IAH-H070 | 1-1e | IAH-E070 | | S | H | CH(OH) | 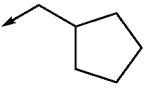 | | 407 | C |
| IAO-E071 | 1-1g | Exp. II-bs02 | CA41 | S | Me | C=O | 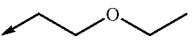 | | 409 | C |
| IAH-E071 | 1-1d | IAO-E071 | | S | Me | CH(OH) | 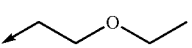 | | 411 | C |
| IAH-H071 | 1-1e | IAH-E071 | | S | H | CH(OH) | 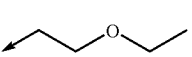 | | 397 | C |
| IAO-E072 | 1-1g | Exp. II-bs02 | CA46 | S | Me | C=O | 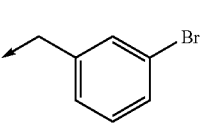 | | 505 | C |
| IAH-E072 | 1-1d | IAO-E072 | | S | Me | CH(OH) | 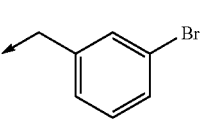 | | 507 | C |
| IAH-H072 | 1-1e | IAH-E072 | | S | H | CH(OH) | 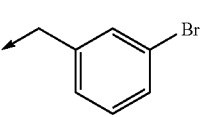 | | 493 | C |
| IAO-E073 | 1-1g | Exp. II-bs02 | CA47 | S | Me | C=O | 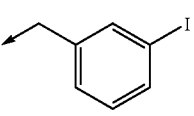 | | 553 | C |
| IAH-E073 | 1-1d | IAO-E073 | | S | Me | CH(OH) | 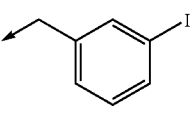 | | 555 | C |
| IAH-H073 | 1-1e | IAH-E073 | | S | H | CH(OH) | 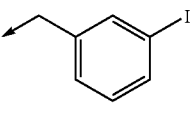 | | 541 | C |
| IAO-E074 | 1-1g | Exp. II-bs02 | CA48 | S | Me | C=O | 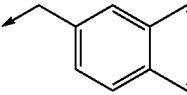 | | 477 | C |
| IAH-E074 | 1-1d | IAO-E074 | | S | Me | CH(OH) | 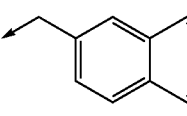 | | 479 | C |
| IAH-H074 | 1-1e | IAH-E074 | | S | H | CH(OH) | 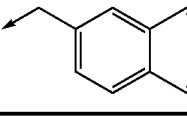 | | 465 | C |

TABLE 87

Table-CA-2

| Symbol | Reagent | Manufacturer |
|---|---|---|
| CA52 | 2-(2,3-Dihydro-1H-inden-1-yl)acetic acid | Synthesized material 2 |
| CA53 | 2-(5-Fluoro-2,3-dihydro-1H-inden-1-yl)acetic acid | Synthesized material 2 |
| CA54 | 2-[2-(Trifluoromethyl)phenyloxy]acetic acid | Synthesized material 2 |
| CA55 | 3-[2-(Trifluoromethyl)phenyl]propionic acid | Synthesized material 2 |
| CA56 | 3,4-Dichlorophenylacetic acid | TCI |
| CA57 | 4-(Trifluoromethyl)benzoic acid | TCI |

Example IAH-CE01

Synthesis of 2-(2,2-dimethyl-1,3-dioxolan-4-yl)acetaldehyde (Intermediate ia-03) (Preparation method ic-03)

A solution of 2-(2,2-dimethyl-1,3-dioxolan-4-yl)ethanol (530 mg, ALD) in dichloromethane (50 ml) was added with Dess-Martin periodinane[1,1,1-triacetoxy-1,1-dihydro-1,2-benziodoxol-3(1H)-one] (2.23 g, LANC), and the mixture was stirred at room temperature for 2 hours. The solvent was evaporated under reduced pressure, and the residue was purified by silica gel chromatography (flash column chromatography, hexane:ethyl acetate=2:1) to obtain the title compound (Intermediate ia-03).

Synthesis of methyl 4-[2-(2-{2-[2,2-dimethyl-1,3-dioxolane-4-]ethyl}-6-oxotetrahydropyridazin-1-yl)ethyl]benzoate (Intermediate ia-04) (Preparation method ic-2)

A solution of Intermediate ia-03 in dichloroethane (25 ml) was added with Compound No. II-a02 (655 mg), tetramethyl ortho-formate (547 µl, ALD), sodium triacetoxyborohydride (1.06 g, ALD), and acetic acid (286 µl), and the mixture was stirred at room temperature for 18 hours under a nitrogen atmosphere. The reaction mixture was neutralized by addition of saturated aqueous sodium hydrogencarbonate (10 ml), and then extracted with ethyl acetate (20 ml×2). The organic layers were combined, washed with saturated brine, and dried, and then the solvent was evaporated under reduced pressure to obtain the title compound (Intermediate ia-04).

Synthesis of methyl 4-[2-(2-{3,4-dihydroxybutyl}-6-oxotetrahydropyridazin-1-yl)ethyl]benzoate (Intermediate ia-05) (Preparation method ic-3)

A solution of Intermediate ia-04 in methanol (25 ml) was added with p-toluenesulfonic acid monohydrate (475.5 mg, WAKO), and the mixture was stirred at room temperature for 18 hours. The reaction mixture was neutralized by addition of saturated aqueous sodium hydrogencarbonate (10 ml), and then extracted with ethyl acetate (20 ml×2). The organic layers were combined, washed with saturated brine, and dried, and then the solvent was evaporated under reduced pressure. The residue was purified by column chromatography (Flash, chloroform:methanol=30:1) to obtain the title compound (Intermediate ia-05, 683.7 mg).

Synthesis of methyl 4-[2-(2-{2-[oxylan-2-yl]ethyl}-6-oxotetrahydropyridazin-1-yl)ethyl]benzoate (Compound No. IAH-CE01) (Preparation method ic-4)

A solution of Intermediate ic-05 (683 mg) in chloroform (65 ml) was added with triphenylphosphine (562 mg, WAKO) and diethyl azodicarboxylate (338 µl, LANC), and the mixture was stirred at 80° C. for 18 hours. The reaction mixture was added with purified water (40 ml), and extracted with chloroform (50 ml). The organic layers were combined, washed with saturated brine, and dried, and then the solvent was evaporated under reduced pressure. The residue was purified by column chromatography (Flash, chloroform:methanol=100:1) to obtain the title compound (Compound No. IAH-CE01, 483 mg). Mass (LCMS): 333 ($M^+$+1), RT=3.88.

Example IAH-E024b

Synthesis of methyl 4-[2-(2-{3-hydroxy-4-[3-(trifluoromethyl)phenyl]butyl}-6-oxotetrahydropyridazin-1-yl)ethyl]benzoate (Compound No. IAH-E024a) (Preparation method 1-11)

A solution of copper iodide (82.5 mg, WAKO) in anhydrous THF (1.5 ml) was cooled to −30° C. under a nitrogen atmosphere, and added dropwise with a 0.5 M solution of 3-chlorophenylmagnesium bromide in THF (1.73 ml, ALD) over 5 minutes, and the mixture was stirred for 15 minutes. Then, the reaction mixture was added dropwise with a solution of Compound No. IAH-CE01 (120 mg) in anhydrous THF (0.9 ml) at −30° C. over 5 minutes, and the mixture was stirred for 2 hours with gradually warming to 0° C. The reaction mixture was added with saturated aqueous ammonium chloride (2 ml), and extracted with chloroform (10 ml×2). The organic layers were combined, washed with saturated brine, and dried, and then the solvent was evaporated under reduced pressure. The residue was purified by column chromatography (Flash, chloroform:methanol=200:1) to obtain the title compound (Compound No. IAH-E024b, 146 mg). Mass (LCMS): 445 ($M^+$+1), RT=4.60.

Example IAH-H024b

Synthesis of 4-[2-(2-{4-[3-chlorophenyl]-3-hydroxybutyl}-6-oxotetrahydro-pyridazin-1-yl)ethyl]benzoic acid (Compound No. IAH-H024b) (Preparation method 1-1e)

According to the procedures described in the synthesis method of Compound No. IAH-H001, Compound No. IAH-E024b (143 mg) was used instead of IAH-E001, and the material was reacted and treated to obtain the title compound (Compound No. IAH-H024b, 69.6 mg). Mass (LCMS): 431 ($M^+$+1), RT=4.11.

Examples IAH-E075 to IAH-H080

Preparations of Compound Nos. IAH-E075 to IAH-H077 are shown in Table Ae-1. The symbols used in the table, "Exp.", "Syn.", and "SM1", have the same meanings as those defined above. For "SM2", corresponding symbols, regent names and preparation methods are shown in Table MG-1. The preparation methods are described below.

Synthesis of (benzo[b]thiophen-5-yl-)magnesium bromide (Compound No. MG01) (Preparation method mr-01)

A solution of magnesium (34 mg, WAKO) in dehydrated THF (0.7 ml) was added dropwise with a solution of 5-bromobenzo[b]thiophene (149.2 mg, MAYB) and dibromoethane (30 µl, WAKO) in dehydrated THF (0.7 ml) under an argon atmosphere, and the mixture was stirred at room temperature for 2 hours to obtain a THF solution of the title compound (Compound No. MG01).

Synthesis of (1-methyl-1H-indazol-5-yl-)magnesium bromide (Compound No. MG02) (Preparation method mr-02)

A solution of 1H-indazole-5-amine (15.32 g, TCI) in ice water (300 ml) was cooled to −5° C., added dropwise with concentrated hydrochloric acid (52.5 ml, KOKUSAN), and then added dropwise with a solution of sodium nitrite (8.74 g, WAKO) in purified water (45 ml) at −5° C., and the mixture was stirred for 20 minutes. The reaction mixture was added dropwise with a solution of potassium iodide (22.9 g, WAKO) in purified water (75 ml) at −5° C., and the mixture was stirred at 90° C. for 1.5 hours. The reaction mixture was cooled to room temperature, and the solid was taken by filtration. The resulting solid was dissolved in ethyl acetate (400 ml), and the solution was filtered. The filtrate was successively washed with 10% aqueous sodium sulfite (300 ml×3), and saturated brine, and dried, and then the solvent was evaporated under reduced pressure. A solution of the residue in DMF (50 ml) was added dropwise to a solution of sodium hydride washed with dehydrated THF (1.05 g, before washing with dehydrated THF, WAKO) in DMF (20 ml) at 0° C., and the mixture was stirred for 30 minutes. The mixture was added dropwise with methyl iodide (1.87 ml, TCI), stirred at 0° C. for 15 minutes, then warmed to room temperature, and stirred for 14.5 hours. The reaction mixture was added with purified water (100 ml) at 0° C., and extracted with ethyl acetate (150 ml×3). The organic layers were combined, washed with saturated brine, and dried, and then the solvent was evaporated under reduced pressure. A solution of this crude product (129 mg) in dehydrated THF (5 ml) was cooled to 0° C., added dropwise with i-propylmagnesium bromide (0.76 M THF solution, 855 µl, ALD), and the mixture was stirred at room temperature for 3 hours to obtain a THF solution of the title compound (Compound No. MG02).

Synthesis of (cyclobutylmethyl)magnesium bromide (Compound No. MG03) (Preparation method mr-01)

According to the procedures described in the synthesis method of Compound No. MG01, (bromomethyl)cyclobutane (104.3 mg, ALD) was used instead of 5-bromobenzo[b]thiophene, and the material was reacted to obtain a THF solution of the title compound (Compound No. MG03).

"V", "$R^{D1}$", and "W" represent substituents and functional groups in the following general formula (I-Exp-Ae).

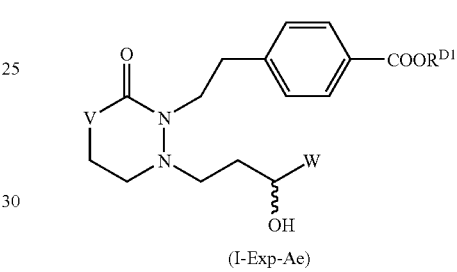

(I-Exp-Ae)

[Formula 81]

The liquid chromatography-mass spectrometry data are shown in the columns of "LCMS", and retention times in the liquid chromatography are shown in the columns of "RTime". Mass spectrometry data are shown in the columns of "Mass". The measurement conditions of the aforementioned liquid chromatography-mass spectrometry are shown in the columns of "Method".

TABLE 88

Table-Ae-1

| Exp. | Syn. | SM1 | SM2 | V | $R^{D1}$ | W | LCMS RTime | Mass | Method |
|---|---|---|---|---|---|---|---|---|---|
| IAH-E075 | 1-11 | IAH-CE01 | MG01 | $CH_2$ | Me | benzothiophen-5-ylmethyl | 4.62 | 467 | A |
| IAH-H075 | 1-1e | IAH-E066 | | $CH_2$ | H | benzothiophen-5-ylmethyl | 3.64 | 453 | B |
| IAH-E076 | 1-11 | IAH-CE01 | MG02 | $CH_2$ | Me | 1-methylindazol-5-ylmethyl | 4.06 | 465 | A |

TABLE 88-continued

Table-Ae-1

| Exp. | Syn. | SM1 | SM2 | V | $R^{D1}$ | W | LCMS RTime | Mass | Method |
|---|---|---|---|---|---|---|---|---|---|
| IAH-H076 | 1-1e | IAH-E067 | | $CH_2$ | H | 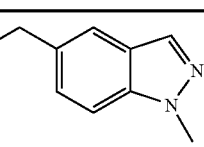 | 3.68 | 451 | A |
| IAH-E077 | 1-1l | IAH-CE01 | MG03 | $CH_2$ | Me |  | 4.58 | 403 | B |
| IAH-H077 | 1-1e | IAH-E068 | | $CH_2$ | H |  | 4.08 | 389 | A |
| IAH-E078 | 1-1l | IAH-CE01 | MG04 | $CH_2$ | Me | 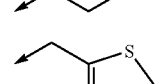 | 4.29 | 417 | A |
| IAH-H078 | 1-1e | IAH-E069 | | $CH_2$ | H | 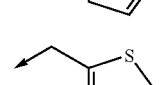 | 3.84 | 403 | A |
| IAH-E079 | 1-1d | IAH-CE01 | MG05 | $CH_2$ | Me | 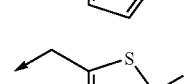 | 4.6 | 451 | B |
| IAH-H079 | 1-1e | IAH-E070 | | $CH_2$ | H | 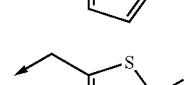 | 4.15 | 437 | A |
| IAH-E080 | 1-1d | IAH-CE01 | MG06 | $CH_2$ | Me | 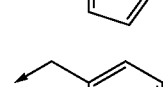 | 4.98 | 479 | B |
| IAH-H080 | 1-1e | IAH-E071 | | $CH_2$ | H | 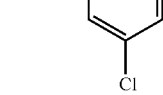 | 4.41 | 465 | A |

TABLE 89

Table-MG-1

| Symbol | Reagent | Preparation method, Manufacturer |
|---|---|---|
| MG01 | (Benzo[b]thiophen-5-yl-)magnesium bromide | mr-01 |
| MG02 | (1-Methyl-1H-indazol-5-yl-)magnesium bromide | mr-02 |
| MG03 | (Cyclobutylmethyl)magnesium bromide | mr-01 |
| MG04 | (Thiophen-2-yl-)magnesium bromide | ALD |
| MG05 | (5-Chlorothiophen-2-yl-)magnesium bromide | ALD |
| MG06 | (3,5-Dichlorophenyl)magnesium bromide | ALD |

Example II-c01

Synthesis of t-butyl 2-{[3-(methoxycarbonylmethyloxy)phenyl]methyl}-3-oxotetrahydropyridazine-1-carboxylate (Compound No. II-c01)

Synthesis of methyl 2-[(3-bromomethyl)phenyloxy]acetate (Intermediate ic-01) (Preparation method ia-1)

According to the procedures described in the synthesis method of Intermediate ia-01, 3-(bromomethyl)phenoxyacetic acid (5.0 g, LANC) was used instead of 4-(2-bromoethyl)benzoate, and the material was reacted and treated to obtain the title compound (Intermediate ic-01, 5.2 g).

Synthesis of t-butyl 2-{[3-(methoxycarbonylmethyloxy)phenyl]-methyl}hydrazine-1-carboxylate (Intermediate ic-02) (Preparation method ia-2)

According to the procedures described in the synthesis method of Intermediate ia-02, Intermediate ic-01 (5.2 g) was used instead of Intermediate ia-01, and the material was reacted and treated to obtain the title compound (Intermediate ic-02, 710 mg).

Synthesis of t-butyl 2-{[3-(methoxycarbonylmethyloxy)phenyl]-methyl}-3-oxotetrahydropyridazine-1-carboxylate (Compound No. II-c01) (Preparation method 1-1a)

According to the procedures described in the synthesis method of Compound No. II-a01, Intermediate ic-02 (355 mg) was used instead of Intermediate ia-02, and the material was reacted and treated to obtain the title compound (Compound No. II-c01, 194 mg). Mass (LCMS): 379 ($M^+$+1), RT=3.93 (LCMS measurement condition: Method B).

Example II-c02

Synthesis of methyl 2-{3-[(6-oxotetrahydropyridazin-1-yl)methyl]phenyloxy}acetate (Compound No. II-c02) (Preparation method 1-1b)

According to the procedures described in the synthesis method of Compound No. II-a02, Compound No. II-c01 (194 mg) was used instead of Compound No. II-a01, and the material was reacted and treated to obtain the title compound (Compound No. II-c02, 143 mg). Mass (LCMS): 279 ($M^+$+1), RT=3.33.

Example II-d01

Synthesis of methyl 3-(2-bromoethyloxy)benzoate (Intermediate id-01) (Preparation method ib-1)

A solution of 1,2-dibromoethane (15.4 g, TCI) in acetone (50 ml) was added with potassium carbonate (13.6 g), and added dropwise with a solution of methyl 3-hydroxybenzoate (5.0 g, TCI) in acetone (20 ml), and then the mixture was refluxed for 24 hours by heating. The insoluble solid was removed by filtration, and then the filtrate was concentrated under reduced pressure. The residue was purified by column chromatography (Flash, hexane:ethyl acetate=3:1) to obtain the title compound (Intermediate id-01, 3.18 g).

Synthesis of t-butyl 2-{2-[3-(methoxycarbonyl)phenyloxy]ethyl}hydrazine-1-carboxylate (Intermediate id-02) (Preparation method ia-2)

According to the procedures described in the synthesis method of Intermediate ia-02, Intermediate id-01 (3.18 g) was used instead of Intermediate ia-01, and the material was reacted and treated to obtain the title compound (Intermediate id-02, 1.58 g).

Synthesis of t-butyl 2-{2-[3-(methoxycarbonyl)phenyloxy]ethyl}-3-oxotetrahydro-pyridazine-1-carboxylate (Compound No. II-d01) (Preparation method 1-1a)

According to the procedures described in the synthesis method of Compound No. II-a01, Intermediate id-02 (790 mg) was used instead of Intermediate ia-02, and the material was reacted and treated to obtain the title compound (Compound No. II-d01, 693 mg). Mass (LCMS): 379 ($M^+$+1), RT=4.59.

Example II-d02

Synthesis of methyl 3-[2-(6-oxotetrahydropyridazin-1-yl)ethyloxy]benzoate (Compound No. II-d02) (Preparation method 1-1b)

According to the procedures described in the synthesis method of Compound No. II-a02, Compound No. II-d01 (693 mg) was used instead of Compound No. II-a01, and the material was reacted and treated to obtain the title compound (Compound No. II-d02, 511 mg). Mass (LCMS): 279 ($M^+$+1), RT=3.57.

Example II-do01

Synthesis of t-butyl 3-{2-[3-(methoxycarbonyl)phenyloxy]ethyl}-2-oxo-2H-tetrahydro-1,3,4-oxadiazine-4-carboxylate (Compound No. II-do01) (Preparation method 1-1a)

According to the procedures described in the synthesis method of Compound No. II-a01, Intermediate id-02 (3.5 g) was used instead of Intermediate ia-02, 2-chloroethyl chloroformate (1.78 g, TCI) was used instead of 4-chlorobutyryl chloride, and they were reacted and treated to obtain the title compound (Compound No. II-do01, 3.73 g). Mass (FAB-MS): 381 ($M^+$+1), Measurement condition: Method C.

Example II-do02

Synthesis of methyl 3-[2-(2-oxo-2H-tetrahydro-1,3,4-oxadiazine-3-yl)ethyloxy]benzoate (Compound No. II-do02) (Preparation method 1-1b)

According to the procedures described in the synthesis method of Compound No. II-a02, Compound No. II-do01 (3.73 g) was used instead of Compound No. II-a01, and the material was reacted and treated to obtain the title compound (Compound No. II-d02, 2.9 g). Mass (LCMS): 281 ($M^+$+1), RT=3.55.

Example II-e01

Synthesis of methyl 4-(2-bromoethyloxy)benzoate (Intermediate ie-01) (Preparation method ib-1)

Methyl 4-hydroxybenzoate (5.0 g, TCI) was used instead of methyl 3-hydroxybenzoate, and the material was reacted and treated to obtain the title compound (Intermediate ie-01, 3.29 g).

Synthesis of t-butyl 2-{2-[4-(methoxycarbonyl)phenyloxy]ethyl)hydrazine-1-carboxylate (Intermediate ie-02) (Preparation method ia-2)

According to the procedures described in the synthesis method of Intermediate ia-02, Intermediate ie-01 (3.29 g) was used instead of Intermediate ia-01, and the material was reacted and treated to obtain the title compound (Intermediate ie-02, 1.97 g).

Synthesis of t-butyl 2-[4-(methoxycarbonyl)phenyloxy]ethyl-3-oxotetrahydro-pyridazine-1-carboxylate (Compound No. II-e01) (Preparation method 1-1a)

According to the procedures described in the synthesis method of Compound No. II-a01, Intermediate ie-02 (985 mg) was used instead of Intermediate ia-02, and the material was reacted and treated to obtain the title compound (Compound No. II-e01, 911 mg). Mass (LCMS): 379 ($M^+$+1), RT=4.54.

Example II-e02

Synthesis of methyl 4-[2-(6-oxotetrahydropyridazin-1-yl)ethyloxy]benzoate (Compound No. II-e02) (Preparation method 1-1b)

According to the procedures described in the synthesis method of Compound No. II-a02, Compound No. II-e01 (911 mg) was used instead of Compound No. II-a01, and the material was reacted and treated to obtain the title compound (Compound No. II-e02, 624 mg). Mass (LCMS): 279 ($M^+$+1), RT=3.52.

Example II-f01

Synthesis of ethyl 3-(2-formylethyl)benzoate (Intermediate if-01) (Preparation method ib-2)

According to the procedures described in Journal of Organic Chemistry, vol. 57, 11, p. 3218, ethyl 3-iodobenzoate (4.0 g, TCI) was used instead of methyl 4-iodobenzoate, and the material was reacted and treated to obtain the title compound (Intermediate if-01, 539 mg).

Synthesis of t-butyl 2-{3-[3-(ethoxycarbonyl)phenyl]propyl}hydrazinecarboxylate (Intermediate if-02) (Preparation method ib-3)

According to the procedures described in Journal of Organic Chemistry, vol. 68, 18, p. 6899, Intermediate if-01 (539 mg) was used instead of 1-[(t-butyldimethylsilyloxy)-5-oxopentan-2-yl]acetate, and the material was reacted and treated to obtain the title compound (Intermediate if-02, 788 mg).

Synthesis of t-butyl 2-{3-[3-(ethoxycarbonyl)phenyl]propyl}-3-oxotetrahydro-pyridazine-1-carboxylate (Compound No. II-f01) (Preparation method 1-1a)

According to the procedures described in the synthesis method of Compound No. II-a01, Intermediate if-02 (788 mg) was used instead of Intermediate ia-02, and the material was reacted and treated to obtain the title compound (Compound No. II-f01, 860 mg). Mass (LCMS): 391 ($M^+$+1), RT=4.87 (LCMS measurement condition: Method B).

Example II-f02

Synthesis of ethyl 3-[3-(6-oxotetrahydropyridazin-1-yl)propyl]benzoate (Compound No. II-f02) (Preparation method 1-1b)

According to the procedures described in the synthesis method of Compound No. II-a02, Compound No. II-f01 (860 mg) was used instead of Compound No. II-a01, and the material was reacted and treated to obtain the title compound (Compound No. II-f02, 638 mg). Mass (LCMS): 291 ($M^+$+1), RT=3.41 (LCMS measurement condition: Method B).

Example II-g01

Synthesis of ethyl 4-(2-formylethyl)benzoate (Intermediate ig-01) (Preparation method ib-2)

According to the procedures described in Journal of Organic Chemistry, vol. 57, 11, p. 3218, ethyl 4-iodobenzoate (4.0 g, TCI) was used instead of methyl 4-iodobenzoate, and the material was reacted and treated to obtain the title compound (Intermediate ig-01, 2.8 g).

Synthesis of t-butyl 2-{3-[4-(ethoxycarbonyl)phenyl]propyl}hydrazinecarboxylate (Intermediate ig-02) (Preparation method ib-3)

According to the procedures described in Journal of Organic Chemistry, vol. 68, 18, p. 6899, Intermediate ig-01 (2.0 g) was used instead of 1-[(t-butyldimethylsilyloxy)-5-oxopentan-2-yl]acetate, and the material was reacted and treated to obtain the title compound (Intermediate ig-02, 2.1 g).

Synthesis of t-butyl 2-{3-[4-(ethoxycarbonyl)phenyl]propyl}-3-oxotetrahydro-pyridazine-1-carboxylate (Compound No. II-g01) (Preparation method 1-1a)

According to the procedures described in the synthesis method of Compound No. II-a01, Intermediate ig-02 (2.1 g) was used instead of Intermediate ia-02, and the material was reacted and treated to obtain the title compound (Compound No. I-g01, 2.5 g). Mass (LCMS): 391 ($M^+$+1), RT=4.85 (LCMS measurement condition: Method B).

Example II-g02

Synthesis of ethyl 4-[3-(6-oxotetrahydropyridazin-1-yl)propyl]benzoate (Compound No. II-g02) (Preparation method 1-1b)

According to the procedures described in the synthesis method of Compound No. II-a02, Compound No. II-g01 (2.5 g) was used instead of Compound No. II-a01, and the material was reacted and treated to obtain the title compound (Compound No. II-g02, 1.8 g). Mass (LCMS): 291 ($M^+$+1), RT=3.33 (LCMS measurement condition: Method B).

Example II-go01

Synthesis of t-butyl 3-{3-[4-(ethoxycarbonyl)phenyl]propyl}-2-oxo-2H-tetrahydro-1,3,4-oxadiazine-4-carboxylate (Compound No. II-go01) (Preparation method 1-1a)

According to the procedures described in the synthesis method of Compound No. II-a01, Intermediate ig-02 (8.36 g) was used instead of Intermediate ia-02, 2-chloroethyl chloroformate (4.08 g, TCI) was used instead of 4-chlorobutyryl chloride, and the material was reacted and treated to obtain the title compound (Compound No. II-go01, 8.42 g). Mass (FAB-MS): 393 ($M^+$+1), Measurement condition: Method C.

Example II-go02

Synthesis of ethyl 4-[3-(2-oxo-2H-tetrahydro-1,3,4-oxadiazine-3-yl)propyl]benzoate (Compound No. II-go02) (Preparation method 1-1b)

According to the procedures described in the synthesis method of Compound No. II-a02, Compound No. II-go01 (8.42 g) was used instead of Compound No. II-a01, and the material was reacted and treated to obtain the title compound (Compound No. II-g02, 6.44 g). Mass (LCMS): 293 (M$^+$+1), RT=3.89.

Example II-h01

Synthesis of t-butyl 2-{3-[5-(methoxycarbonyl)furan-2-yl]propyl}-3-oxotetrahydro-pyridazine-1-carboxylate Synthesis of methyl 5-(2-formylethyl)furan-2-carboxylate (Intermediate ih-01) (Preparation method ib-4)

A solution of 5-bromo-2-furancarboxylic acid methyl ester (816 mg, MAYB) in DMF (3 ml) was added with tetra-n-butylammonium chloride (1.1 g, TCI), sodium hydrogencarbonate (688 mg), palladium acetate (10.4 mg, WAKO), and allyl alcohol (346 mg, TCI), and the mixture was stirred at 60° C. for 20 hours. The reaction solution was added with distilled water (30 ml), and ethyl acetate (20 ml), and the insoluble solid was removed by filtration. The filtrate was extracted with ethyl acetate (50 ml×2). The organic layers were combined, washed with saturated brine, and dried, and then the filtrate was concentrated under reduced pressure. The residue was purified by column chromatography (Flash, hexane:ethyl acetate=4:1) to obtain the title compound (Intermediate ih-01, 204 mg).

Synthesis of t-butyl 2-{3-[5-(methoxycarbonyl)furan-2-yl]propyl}hydrazinecarboxylate (Intermediate ih-02) (Preparation method ib-3)

According to the procedures described in Journal of Organic Chemistry, vol. 68, 18, p. 6899, Intermediate ih-01 (204 mg) was used instead of 1-[(t-butyldimethylsilyloxy)-5-oxopentan-2-yl]acetic acid, and the material was reacted and treated to obtain the title compound (Intermediate ih-02, 118 mg).

Synthesis of t-butyl 2-{3-[5-(methoxycarbonyl)furan-2-yl]propyl}-3-oxotetrahydro-pyridazine-1-carboxylate (Compound No. II-h01) (Preparation method 1-1a)

According to the procedures described in the synthesis method of Compound No. II-a01, Intermediate ih-02 (118 mg) was used instead of Intermediate ia-02, and the material was reacted and treated to obtain the title compound (Compound No. II-h01, 76 mg). Mass (LCMS): 367 (M$^+$+1), RT=4.02 (LCMS measurement condition: Method B).

Example II-h02

Synthesis of methyl 5-(3-(6-oxotetrahydropyridazin-1-yl)propyl)furan-2-carboxylate (Compound No. II-h02) (Preparation method 1-1b)

According to the procedures described in the synthesis method of Compound No. II-a02, Compound No. II-h01 (76 mg) was used instead of Compound No. II-a01, and the material was reacted and treated to obtain the title compound (Compound No. II-h02, 40 mg). Mass (LCMS): 291 (M$^+$+1), RT=2.73 (LCMS measurement condition: Method B).

Example II-i01

Synthesis of ethyl 2-[2-(benzyloxy)ethoxy]isonicotinate (Intermediate ii-01) (Preparation method id-1)

A solution of ethyl 2-bromoisonicotinate (575 mg, MATRIX) in THF (25 ml) was added with ethylene glycol monobenzyl ether (710 µl, TCI), cooled to 0° C., and added with potassium t-butoxide (420 mg, TCI), and the mixture was stirred at room temperature for 3 hours. The reaction mixture was added with purified water (15 ml), and extracted with ethyl acetate (30 ml×2). The organic layers were combined, washed with saturated brine, and dried, and then the solvent was evaporated under reduced pressure. The residue was purified by column chromatography (Flash, hexane:ethyl acetate=10:1) to obtain the title compound (Intermediate ii-01).

Synthesis of ethyl 2-(2-hydroxyethoxy)isonicotinate (Intermediate ii-02) (Preparation method id-2)

A solution of Intermediate ii-01 in a mixture of methanol (10.8 ml) and ethyl acetate (2.2 ml) was added with Pd/C (39 mg, Merck), and added dropwise with two drops of concentrated hydrochloric acid, and the mixture was stirred at room temperature for 18 hours under a hydrogen atmosphere. The reaction mixture was filtered through Celite, and the solvent was evaporated under reduced pressure to obtain the title compound (Intermediate ii-02).

Synthesis of ethyl 2-(2-bromoethoxy)isonicotinate (Intermediate ii-03) (Preparation method id-3)

A solution of Intermediate ii-02 in dichloromethane (26 ml) was added with triphenylphosphine-polystyrene (3.54 g, NOVABIOCHEM), and carbon tetrabromide (645 mg, TCI), and the mixture was stirred at 50° C. for 1 hour. The reaction mixture was filtered, and the solvent was evaporated under reduced pressure to obtain the title compound (Intermediate ii-03).

Synthesis of t-butyl 2-{2-[(4-methoxycarbonyl)pyridyl]oxyethyl}hydrazinecarboxylate (Intermediate ii-04) (Preparation method ia-2)

According to the procedures described in the synthesis method of Intermediate ia-02, Intermediate ii-03 was used instead of Intermediate ia-01, and the material was reacted and treated to obtain the title compound (Intermediate ii-04).

Synthesis of t-butyl 2-{2-[(4-methoxycarbonyl)py-ridyl]oxyethyl}-3-oxotetrahydro-pyridazine-1-car-boxylate (Compound No. II-i01) (Preparation method 1-1a)

According to the procedures described in the synthesis method of Compound No. II-a01, Intermediate ii-04 was used instead of Intermediate ia-02, and the material was reacted and treated to obtain the title compound (Compound No. II-i01, 73.4 mg). Mass (LCMS): 394 (M$^+$+1), RT=3.74 (LCMS measurement condition: Method B).

Example II-i02

Synthesis of ethyl 2-[2-(6-oxotetrahydropyridazin-1-yl)ethoxy]isonicotinate (Compound No. II-i02) (Preparation method 1-1b)

According to the procedures described in the synthesis method of Compound No. II-a02, Compound No. II-i01 (73.4 mg) was used instead of Compound No. II-a01, and the material was reacted and treated to obtain the title compound (Compound No. II-i02, 38.1 mg). Mass (LCMS): 294 (M$^+$+1), RT=3.16 (LCMS measurement condition: Method A).

Example II-j01

Synthesis of t-butyl 2-[4-(benzyloxy)butyl]hydra-zine-1-carboxylate (Intermediate ij-02) (Preparation method ia-2)

According to the procedures described in the synthesis method of Intermediate ia-02, benzyl 4-bromobutyl ether (1.2 g, ALD) was used instead of Intermediate ia-01, and the material was reacted and treated to obtain a crude product of the title compound (Intermediate ij-02, 1.33 g).

Synthesis of t-butyl 2-[4-(benzyloxy)butyl]-3-oxotet-rahydropyridazine-1-carboxylate (Example II-j01) (Preparation method 1-1a)

According to the procedures described in the synthesis method of Compound No. II-a01, Intermediate ij-02 (1.33 g) was used instead of Intermediate ia-02, and the material was reacted and treated to obtain the title compound (Compound No. II-j01, 704 mg). Mass (LCMS): 363 (M$^+$+1), RT=4.76 (LCMS measurement condition: Method B).

Example II-j02

Synthesis of 1-benzyloxy-4-(6-oxotetrahydropy-ridazin-1-yl)butane (Example II-j02) (Preparation method 1-1b)

According to the procedures described in the synthesis method of Compound No. II-a02, Compound No. II-j01 (704 mg) was used instead of Compound No. IIa-01, and the material was reacted and treated to obtain the title compound (Compound No. II-j02, 391 mg). Mass (LCMS): 263 (M$^+$+1), RT=3.22 (LCMS measurement condition: Method B).

Example II-k01

Synthesis of 2-[4-(bromomethyl)phenyl]acetic acid (Intermediate ik-00) (Preparation method 1-1n)

According to the procedures described in International Patent Publication WO00/03980, p-tolylacetic acid (10 g, TCI) was used instead of m-tolylacetic acid, and the material was reacted and treated to obtain the title compound (Intermediate ik-00, 4.7 g).

Synthesis of methyl 2-[4-(bromomethyl)phenyl]acetate (Intermediate ik-01) (Preparation method ia-1)

According to the procedures described in the synthesis method of Intermediate ia-01, Intermediate ik-00 (4.7 g) was used instead of 4-(2-bromoethyl)benzoic acid, and the material was reacted and treated to obtain the title compound (Intermediate ik-01, 4.7 g).

Synthesis of t-butyl 2-[4-(2-methoxy-2-oxoethyl) benzyl]hydrazine-1-carboxylate (Intermediate ik-02) (Preparation method ia-2)

According to the procedures described in the synthesis method of Intermediate ia-02, Intermediate ik-01 (2.0 g) was used instead of Intermediate ia-01, and the material was reacted and treated to obtain the title compound (Intermediate ik-02, 611 mg).

Synthesis of t-butyl 2-[4-(2-methoxy-2-oxoethyl) benzyl]-3-oxotetrahydro-pyridazine-1-carboxylate (Compound No. II-k01) (Preparation method 1-1a)

According to the procedures described in the synthesis method of Compound No. II-a01, Intermediate ik-02 (611 mg) was used instead of Intermediate ia-02, and the material was reacted and treated to obtain the title compound (Compound No. II-k01, 219 mg). Mass (LCMS): 363 (M$^+$+1), RT=4.26 (LCMS measurement condition: Method B).

Example II-k02

Synthesis of methyl 2-{4-[(6-oxotetrahydropy-ridazin-1-yl)methyl]phenyl}acetate (Compound No. II-k02) (Preparation method 1-1b)

According to the procedures described in the synthesis method of Compound No. II-a02, Compound No. II-k01 (219 mg) was used instead of Compound No. II-a01, and the material was reacted and treated to obtain the title compound (Compound No. II-k02, 152 mg). Mass (LCMS): 263 (M$^+$+1), RT=3.37.

Example II-l01

Synthesis of methyl 2-[3-(bromomethyl)phenyl]acetate (Intermediate il-01) (Preparation method ia-1)

According to the procedures described in the synthesis method of Intermediate ia-01, 2-[3-(bromomethyl)phenyl] acetic acid (500 mg) synthesized according to the procedures described in International Patent Publication WO00/03980 was used instead of 4-(2-bromoethyl)benzoic acid, and the material was reacted and treated to obtain the title compound (Intermediate il-01, 471 mg).

Synthesis of t-butyl 2-[3-(2-methoxy-2-oxoethyl) benzyl]hydrazine-1-carboxylate (Intermediate il-02) (Preparation method ia-2)

According to the procedures described in the synthesis method of Intermediate ia-02, Intermediate il-01 (471 mg) was used instead of Intermediate ia-01, and the material was reacted and treated to obtain the title compound (Intermediate il-02, 121 mg).

Synthesis of t-butyl 2-[3-(2-methoxy-2-oxoethyl) benzyl]-3-oxotetrahydropyridazine-1-carboxylate (Compound No. II-101) (Preparation method 1-1a)

According to the procedures described in the synthesis method of Compound No. II-a01, Intermediate il-02 (121 mg) was used instead of Intermediate ia-02, and the material was reacted and treated to obtain the title compound (Compound No. II-101, 58 mg). Mass (LCMS): 363 (M$^+$+1), RT=4.09 (LCMS measurement condition: Method B).

Example II-102

Synthesis of methyl 2-{3-[(6-oxotetrahydropyridazin-1-yl)methyl]phenyl}acetate (Compound No. II-102) (Preparation method 1-1b)

According to the procedures described in the synthesis method of Compound No. II-a02, Compound No. II-101 (58 mg) was used instead of Compound No. II-a01, and the material was reacted and treated to obtain the title compound (Compound No. II-102, 33 mg). Mass (LCMS): 263 (M$^+$+1), RT=2.73 (LCMS measurement condition: Method B).

Example II-m01

Synthesis of ethyl 3-p-tolylacrylate (Intermediate im-00) (Preparation method pb-1)

According to the procedures described in the synthesis method of Intermediate pb-1, p-tolualdehyde (3.0 g, ADL) was used instead of 1-indanone, and the material was reacted and treated to obtain the title compound (Intermediate im-00, 4.8 g).

Synthesis of ethyl 3-[4-(bromomethyl)phenyl]acrylate (Intermediate im-01) (Preparation method 1-1n)

According to the procedures described in International Patent Publication WO00/03980, Intermediate im-00 (4.8 g) was used instead of m-tolylacetic acid, and the material was reacted and treated to obtain the title compound (Intermediate im-01, 3.45 g).

Synthesis of t-butyl 2-[4-(3-ethoxy-3-oxoprop-1-enyl)benzyl]hydrazine-1-carboxylate (Intermediate im-02) (Preparation method ia-2)

According to the procedures described in the synthesis method of Intermediate ia-02, Intermediate im-01 (3.45 g) was used instead of Intermediate ia-01, and the material was reacted and treated to obtain the title compound (Intermediate im-02, 1.17 g).

Synthesis of t-butyl 2-[4-(3-ethoxy-3-oxoprop-1-enyl)benzyl]-3-oxotetrahydro-pyridazine-1-carboxylate (Example II-m01) (Preparation method 1-1a)

According to the procedures described in the synthesis method of Compound No. II-a01, Intermediate im-02 (1.17 g) was used instead of Intermediate ia-02, and the material was reacted and treated to obtain the title compound (Compound No. II-m01, 1.5 g). Mass (LCMS): 389 (M$^+$+1), RT=4.66 (LCMS measurement condition: Method B).

Example II-m02

Synthesis of ethyl 3-{4-[(6-oxotetrahydropyridazin-1-yl)methyl]phenyl}acrylate (Example II-m02) (Preparation method 1-1b)

According to the procedures described in the synthesis method of Compound No. II-a02, Compound No. II-m01 (1.5 g) was used instead of Compound No. II-a01, and the material was reacted and treated to obtain the title compound (Compound No. II-m02, 1.2 g). Mass (LCMS): 289 (M$^+$+1), RT=3.36 (LCMS measurement condition: Method B).

Example II-o01

Synthesis of ethyl 3-m-tolylacrylate (Intermediate io-00) (Preparation method pb-1)

According to the procedures described in the synthesis method of Intermediate pb-1, m-tolualdehyde (3.0 g, ALD) was used instead of 1-indanone, and the material was reacted and treated to obtain the title compound (Intermediate io-00, 4.8 g).

Synthesis of ethyl 3-[3-(bromomethyl)phenyl]acrylate (Intermediate io-01) (Preparation method 1-1n)

According to the procedures described in International Patent Publication WO00/03980, Intermediate io-00 (1.0 g) was used instead of m-tolylacetic acid, and the material was reacted and treated to obtain the title compound (Intermediate io-01, 184 mg).

Synthesis of t-butyl 2-[3-(3-ethoxy-3-oxoprop-1-enyl)benzyl]hydrazine-1-carboxylate (Intermediate io-02) (Preparation method ia-2)

According to the procedures described in the synthesis method of Intermediate ia-02, Intermediate io-01 (184 mg) was used instead of Intermediate ia-01, and the material was reacted and treated to obtain the title compound (Intermediate io-02, 116 mg).

Synthesis of t-butyl 2-[3-(3-ethoxy-3-oxoprop-1-enyl)benzyl]-3-oxotetrahydro-pyridazine-1-carboxylate (Example II-o01) (Preparation method 1-1a)

According to the procedures described in the synthesis method of Compound No. II-a01, Intermediate io-02 (116 mg) was used instead of Intermediate ia-02, and the material was reacted and treated to obtain the title compound (Compound No. II-o01, 62 mg). Mass (LCMS): 389 (M$^+$+1), RT=4.93 (LCMS measurement condition: Method B).

Example II-o02

Synthesis of ethyl 3-{3-[(6-oxotetrahydropyridazin-1-yl)methyl]phenyl}acrylate (Example II-o02) (Preparation method 1-1b)

According to the procedures described in the synthesis method of Compound No. II-a02, Compound No. II-o01 (62 mg) was used instead of Compound No. II-a01, and the material was reacted and treated to obtain the title compound (Compound No. II-o02, 43 mg). Mass (LCMS): 289 ($M^++1$), RT=3.84.

Example ICO-E001

Synthesis of methyl 2-{3-[(2-{3-oxo-4-[3-(trifluoromethyl)phenyl]butyl}-6-oxotetrahydropyridazin-1-yl)methyl]phenyloxy}acetate (Compound No. ICO-E001) (Preparation method 1-1g)

According to the procedures described in the synthesis method of Compound No. IAO-E005, 3-(trifluoromethyl)phenylacetic acid (524 mg) was used instead of 3-methoxyphenylacetic acid, Compound No. II-c02 (143 mg) was used instead of Compound No. II-a02, and they were reacted and treated to obtain the title compound (Compound No. ICO-E001, 92 mg). Mass (LCMS): 493 ($M^++1$), RT=4.33 (LCMS measurement condition: Method B).

Example ICH-E001

Synthesis of methyl 2-{3-[(2-{3-hydroxy-4-[3-(trifluoromethyl)phenyl]butyl}-6-oxotetrahydropyridazin-1-yl)methyl]phenyloxy}acetate (Compound No. ICH-E001) (Preparation method 1-1d)

According to the procedures described in the synthesis method of Compound No. IAH-E001, Compound No. ICO-E001 (92 mg) was used instead of Compound No. IAO-E001, and the material was reacted and treated to obtain the title compound (Compound No. ICH-E001). Mass (LCMS): 495 ($M^++1$), RT=4.26 (LCMS measurement condition: Method B).

Example ICH-H001

Synthesis of 2-{3-[(2-{3-hydroxy-4-[3-(trifluoromethyl)phenyl]butyl}-6-oxotetrahydropyridazin-1-yl)methyl]phenyloxy}acetic acid (Compound No. ICH-H001) (Preparation method 1-1e)

According to the procedures described in the synthesis method of Compound No. IAH-H001, Compound No. ICH-E001 obtained in the example mentioned above was used instead of Compound No. IAH-E001, and the material was reacted and treated to obtain the title compound (Compound No. ICH-H001, 4 mg). Mass (LCMS): 481 ($M^++1$), RT=4.26.

Example IDO-E001

Synthesis of methyl 3-[2-(2-{3-oxo-4-[3-(trifluoromethyl)phenyl]butyl}-6-oxotetrahydropyridazin-1-yl)ethyloxy]benzoate (Compound No. IDO-E001) (Preparation method 1-1g)

According to the procedures described in the synthesis method of Compound No. IAO-E005, 3-(trifluoromethyl)phenylacetic acid (1.1 g) was used instead of 3-methoxyphenylacetic acid, Compound No. II-d02 (300 mg) was used instead of Compound No. II-a02, and they were reacted and treated to obtain the title compound (Compound No. IDO-E001, 35 mg). Mass (LCMS): 493 ($M^++1$), RT=4.60 (LCMS measurement condition: Method B).

Example IDH-E001

Synthesis of methyl 3-[2-(2-{3-hydroxy-4-[3-(trifluoromethyl)phenyl]butyl}-6-oxotetrahydropyridazin-1-yl)ethyloxy]benzoate (Compound No. IDH-E001) (Preparation method 1-1d)

According to the procedures described in the synthesis method of Compound No. IAH-E001, Compound No. IDO-E001 (35 mg) was used instead of Compound No. IAO-E001, and the material was reacted and treated to obtain the title compound (Compound No. IDH-E001). Mass (LCMS): 495 ($M^++1$), RT=4.48 (LCMS measurement condition: Method B).

Example IDH-H001

Synthesis of 3-[2-(2-{3-hydroxy-4-[3-(trifluoromethyl)phenyl]butyl}-6-oxotetrahydropyridazin-1-yl)ethyloxy]benzoic acid (Compound No. IDH-H001) (Preparation method 1-1e)

According to the procedures described in the synthesis method of Compound No. IAH-H001, Compound No. IDH-E001 obtained in the example mentioned above was used instead of Compound No. IAH-E001, and the material was reacted and treated to obtain the title compound (Compound No. IDH-H001, 9 mg). Mass (LCMS): 481 ($M^++1$), RT=4.27.

Examples IDO-E002 to IDH-H007

Preparations of Compound Nos. IDO-E002 to IDH-H007 are shown in Tables A-1 to A-9. The symbols used in the tables are as those defined above.

"V", "$R^{D1}$", "E", and "W" represent substituents and functional groups in the following general formula (I-Exp-D).

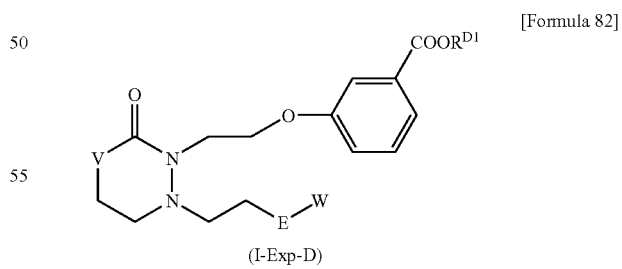

[Formula 82]

(I-Exp-D)

The liquid chromatography-mass spectrometry data are shown in the column of "LCMS", and retention times in the liquid chromatography are shown in the column of "RTime". Mass spectrometry data are shown in the column of "Mass". The measurement conditions of the aforementioned liquid chromatography-mass spectrometry are shown in the column of "Method".

TABLE 90
Table-D-1
| Exp. | Syn. | SM1 | SM2 | V | R^{D1} | E | W | LCMS RTime | Mass | Method |
|---|---|---|---|---|---|---|---|---|---|---|
| IDO-E002 | 1-1g | Exp. II-d02 | CA19 | CH$_2$ | Me | C=O | 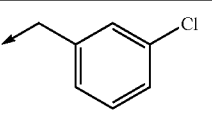 | 4.75 | 459 | A |
| IDH-E002 | 1-1d | IDO-E002 | | CH$_2$ | Me | CH(OH) | 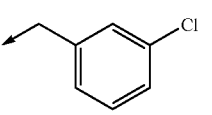 | 4.60 | 461 | A |
| IDH-H002 | 1-1e | IDH-E002 | | CH$_2$ | H | CH(OH) | 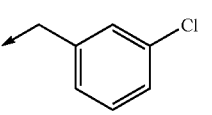 | 4.15 | 447 | A |
| IDO-E003 | 1-1g | Exp. II-d02 | CA34 | CH$_2$ | Me | C=O | 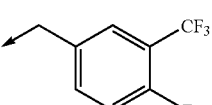 | 4.84 | 511 | A |
| IDH-E003 | 1-1d | IDO-E003 | | CH$_2$ | Me | CH(OH) | 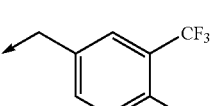 | 4.74 | 513 | A |
| IDH-H003 | 1-1e | IDH-E003 | | CH$_2$ | H | CH(OH) | 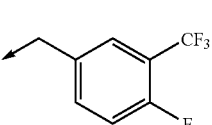 | 4.30 | 499 | A |
| IDO-E004 | 1-1g | Exp. II-d02 | CA28 | CH$_2$ | Me | C=O | 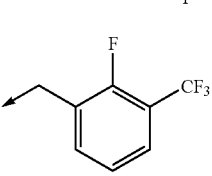 | 4.81 | 511 | A |
| IDH-E004 | 1-1d | IDO-E004 | | CH$_2$ | Me | CH(OH) | 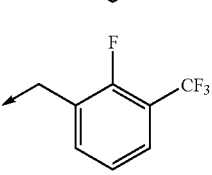 | 4.72 | 513 | A |
| IDH-H004 | 1-1e | IDH-E004 | | CH$_2$ | H | CH(OH) |  | 4.30 | 499 | A |
| IDO-E005 | 1-1g | Exp. II-d02 | CA08 | CH$_2$ | Me | C=O | 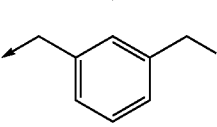 | 4.45 | 469 | A |
| IDH-E005 | 1-1d | IDO-E005 | | CH$_2$ | Me | CH(OH) | 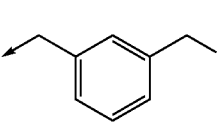 | 4.27 | 471 | A |

TABLE 90-continued

Table-D-1

| Exp. | Syn. | SM1 | SM2 | V | $R^{D1}$ | E | W | LCMS RTime | Mass | Method |
|---|---|---|---|---|---|---|---|---|---|---|
| IDH-H005 | 1-1e | IDH-E005 | | $CH_2$ | H | CH(OH) | 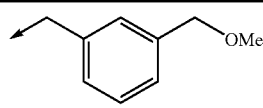 | 3.87 | 457 | A |
| IDO-E006 | 1-1g | Exp. II-do02 | CA06 | O | Me | C=O | 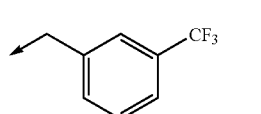 | 4.55 | 495 | B |
| IDH-E006 | 1-1d | IDO-E006 | | O | Me | CH(OH) | 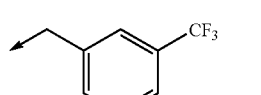 | 4.37 | 497 | B |
| IDH-H006 | 1-1e | IDH-E006 | | O | H | CH(OH) | 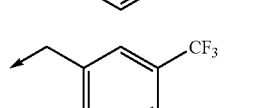 | 4.20 | 483 | A |
| IDO-E007 | 1-1g | Exp. II-do02 | CA08 | O | Me | C=O | 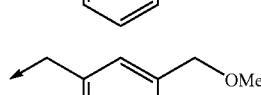 | 4.39 | 471 | A |
| IDH-E007 | 1-1d | IDO-E007 | | O | Me | CH(OH) | 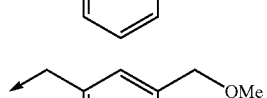 | 4.23 | 473 | A |
| IDH-H007 | 1-1e | IDH-E007 | | O | H | CH(OH) | 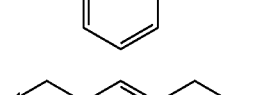 | 3.82 | 459 | A |

Example IEO-E001

Synthesis of methyl 4-[2-(2-{3-oxo-4-[3-(trifluoromethyl)phenyl]butyl}-6-oxotetrahydropyridazin-1-yl)ethyloxy]benzoate (Compound No. IEO-E001) (Preparation method 1-1g)

According to the procedures described in the synthesis method of Compound No. IAO-E005, 3-(trifluoromethyl)phenylacetic acid (1.1 g) was used instead of 3-methoxyphenylacetic acid, Compound No. II-e02 (300 mg) was used instead of Compound No. II-a02, and they were reacted and treated to obtain the title compound (Compound No. IEO-E001, 122 mg). Mass (LCMS): 493 ($M^+$+1), RT=4.49 (LCMS measurement condition: Method B).

Example IEH-E001

Synthesis of methyl 4-[2-(2-{3-hydroxy-4-[3-(trifluoromethyl)phenyl]butyl}-6-oxotetrahydropyridazin-1-yl)ethyloxy]benzoate (Compound No. IEH-E001) (Preparation method 1-1d)

According to the procedures described in the synthesis method of Compound No. IAH-E001, Compound No. IEO-E001 (122 mg) was used instead of Compound No. IAO-E001, and the material was reacted and treated to obtain the title compound (Compound No. IEH-E001). Mass (LCMS): 495 ($M^+$+1), RT=4.44 (LCMS measurement condition: Method B).

Example IEH-H001

Synthesis of 4-[2-(2-{3-hydroxy-4-[3-(trifluoromethyl)phenyl]butyl}-6-oxo-tetrahydropyridazin-1-yl)ethyloxy]benzoic acid (Compound No. IEH-H001) (Preparation method 1-1e)

According to the procedures described in the synthesis method of Compound No. IAH-H001, Compound No. IEH-E001 obtained in the example mentioned above was used instead of Compound No. IAH-E001, and the material was reacted and treated to obtain the title compound (Compound No. IEH-H001, 76 mg). Mass (LCMS): 481 ($M^+$+1), RT=4.18.

Example IFO-E001

Synthesis of methyl 3-[3-(2-{3-oxo-4-[3-(trifluoromethyl)phenyl]butyl}-6-oxotetrahydropyridazin-1-yl)propyl]benzoate (Compound No. IFO-E001) (Preparation method 1-1 g)

According to the procedures described in the synthesis method of Compound No. IAO-E005, 3-(trifluoromethyl)

phenylacetic acid (822 mg) was used instead of 3-methoxyphenylacetic acid, Compound No. II-f02 (234 mg) was used instead of Compound No. II-a02, and they were reacted and treated to obtain the title compound (Compound No. IFO-E001, 111 mg). Mass (LCMS): 505 (M$^+$+1), RT=5.08 (LCMS measurement condition: Method B).

Example IFH-E001

Synthesis of methyl 3-[3-(2-{3-hydroxy-4-[3-(trifluoromethyl)phenyl]butyl}-6-oxotetrahydropyridazin-1-yl)propyl]benzoate (Compound No. IFH-E001) (Preparation method 1-1d)

According to the procedures described in the synthesis method of Compound No. IAH-E001, Compound No. IFO-E001 (111 mg) was used instead of Compound No. IAO-E001, and the material was reacted and treated to obtain the title compound (Compound No. IFH-E001). Mass (LCMS): 507 (M$^+$+1), RT=4.98.

Example IFH-H001

Synthesis of 3-[3-(2-{3-hydroxy-4-[3-(trifluoromethyl)phenyl]butyl}-6-oxo-tetrahydropyridazin-1-yl)propyl]benzoic acid (Compound No. IFH-H001) (Preparation method 1-1e)

According to the procedures described in the synthesis method of Compound No. IAH-H001, Compound No. IFH-E001 obtained in the example mentioned above was used instead of Compound No. IAH-E001, and the material was reacted and treated to obtain the title compound (Compound No. IFH-H001, 92 mg). Mass (LCMS): 479 (M$^+$+1), RT=4.33.

Example IGO-E001

Synthesis of methyl 4-[3-(2-{3-oxo-4-[3-(trifluoromethyl)phenyl]butyl}-6-oxotetrahydropyridazin-1-yl)propyl]benzoate (Compound No. IGO-E001) (Preparation method 1-1g)

According to the procedures described in the synthesis method of Compound No. IAO-E005, 3-(trifluoromethyl)phenylacetic acid (822 mg) was used instead of 3-methoxyphenylacetic acid, Compound No. II-g02 (234 mg) was used instead of Compound No. II-a02, and they were reacted and treated to obtain the title compound (Compound No. IGO-E001, 211 mg). Mass (LCMS): 505 (M$^+$+1), RT=5.04.

Example IGH-E001

Synthesis of methyl 4-[3-(2-{3-hydroxy-4-[3-(trifluoromethyl)phenyl]butyl}-6-oxotetrahydropyridazin-1-yl)propyl]benzoate (Compound No. IGH-E001) (Preparation method 1-1d)

According to the procedures described in the synthesis method of Compound No. IAH-E001, Compound No. IGO-E001 (211 mg) was used instead of Compound No. IAO-E001, and the material was reacted and treated to obtain the title compound (Compound No. IGH-E001). Mass (LCMS): 507 (M$^+$+1), RT=4.96.

Example IGH-H001

Synthesis of 4-[3-(2-{3-hydroxy-4-[3-(trifluoromethyl)phenyl]butyl}-6-oxotetrahydropyridazin-1-yl)propyl]benzoic acid (Compound No. IGH-H001) (Preparation method 1-1e)

According to the procedures described in the synthesis method of Compound No. IAH-H001, Compound No. IGH-E001 obtained in the example mentioned above was used instead of Compound No. IAH-E001, and the material was reacted and treated to obtain the title compound (Compound No. IGH-H001, 77 mg). Mass (LCMS): 479 (M$^+$+1), RT=4.25.

Examples IGO-E002 to IGH-H010

Preparations of Compound Nos. IGO-E002 to IGH-H010 are shown in Tables G-1 and G-2. The symbols used in the tables have the same meanings as those defined above.

"V", "R$^{D1}$", "E", and "W" represent substituents and functional groups in the following general formula (I-Exp-G).

[Formula 83]

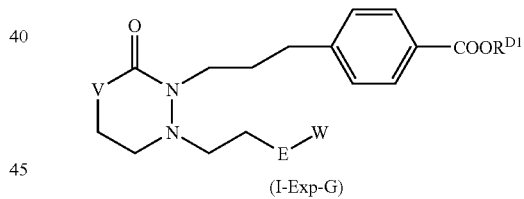

(I-Exp-G)

The liquid chromatography-mass spectrometry data are shown in the columns of "LCMS", and retention times in the liquid chromatography are shown in the columns of "RTime". Mass spectrometry data are shown in the columns of "Mass". The measurement conditions of the aforementioned liquid chromatography-mass spectrometry are shown in the columns of "Method".

TABLE 91

Table-G-1

| | | | | | | | | | LCMS | |
| Exp. | Syn. | SM1 | SM2 | V | R$^{D1}$ | E | W | RTime | Mass | Method |
| --- | --- | --- | --- | --- | --- | --- | --- | --- | --- | --- |
| IGO-E002 | 1-1g | Exp. II-g02 | CA19 | CH$_2$ | Et | C=O | ⌬-Cl (3-chlorobenzyl) | 5.01 | 471 | A |

TABLE 91-continued
Table-G-1
| Exp. | Syn. | SM1 | SM2 | V | R$^{D1}$ | E | W | LCMS RTime | Mass | Method |
|---|---|---|---|---|---|---|---|---|---|---|
| IGH-E002 | 1-1d | IDO-E002 | | CH$_2$ | Et | CH(OH) | 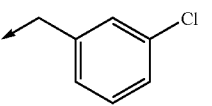 | 4.90 | 473 | A |
| IGH-H002 | 1-1e | IDH-E002 | | CH$_2$ | H | CH(OH) | 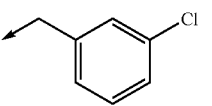 | 4.18 | 445 | A |
| IGO-E003 | 1-1g | Exp. II-g02 | CA34 | CH$_2$ | Et | C=O | 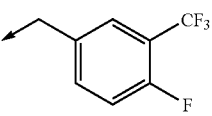 | 5.11 | 523 | A |
| IGH-E003 | 1-1d | IDO-E003 | | CH$_2$ | Et | CH(OH) | 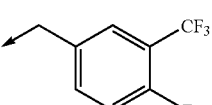 | 4.99 | 525 | A |
| IGH-H003 | 1-1e | IDH-E003 | | CH$_2$ | H | CH(OH) | 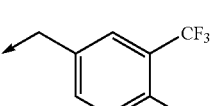 | 4.32 | 497 | A |
| IGO-E004 | 1-1g | Exp. II-g02 | CA28 | CH$_2$ | Et | C=O |  | 5.08 | 523 | A |
| IGH-E004 | 1-1d | IDO-E004 | | CH$_2$ | Et | CH(OH) | 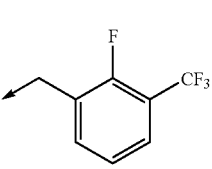 | 4.99 | 525 | A |
| IGH-H004 | 1-1e | IDH-E004 | | CH$_2$ | H | CH(OH) |  | 4.27 | 497 | A |
| IGO-E005 | 1-1g | Exp. II-g02 | CA08 | CH$_2$ | Et | C=O | 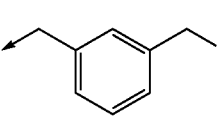 | 4.72 | 481 | A |
| IGH-E005 | 1-1d | IDO-E005 | | CH$_2$ | Et | CH(OH) | 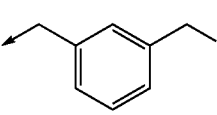 | 4.57 | 483 | A |
| IGH-H005 | 1-1e | IDH-E005 | | CH$_2$ | H | CH(OH) | 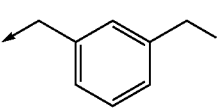 | 3.89 | 455 | A |

TABLE 92
Table-G-2
| Exp. | Syn. | SM1 | SM2 | V | R<sup>D1</sup> | E | W | LCMS RTime | Mass | Method |
|---|---|---|---|---|---|---|---|---|---|---|
| IGO-E006 | 1-1g | Exp. II-go02 | CA06 | O | Et | C=O | 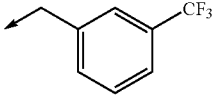 | 5.04 | 507 | B |
| IGH-E006 | 1-1d | IGO-E006 | | O | Et | CH(OH) | 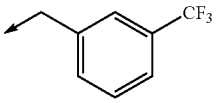 | 4.81 | 509 | B |
| IGH-H006 | 1-1e | IGH-E006 | | O | H | CH(OH) | 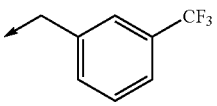 | 4.25 | 481 | A |
| IGO-E007 | 1-1g | Exp. II-go02 | CA19 | O | Et | C=O | 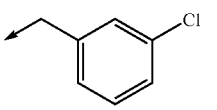 | 4.98 | 473 | A |
| IGH-E007 | 1-1d | IGO-E007 | | O | Et | CH(OH) | 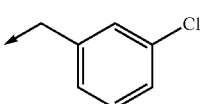 | 4.88 | 475 | A |
| IGH-H007 | 1-1e | IGH-E007 | | O | H | CH(OH) | 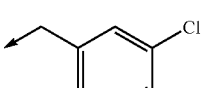 | 4.14 | 477 | A |
| IGO-E008 | 1-1g | Exp. II-go02 | CA34 | O | Et | C=O | 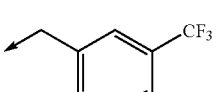 | 5.03 | 525 | A |
| IGH-E008 | 1-1d | IGO-E008 | | O | Et | CH(OH) | 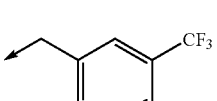 | 4.95 | 527 | A |
| IGH-H008 | 1-1e | IGH-E008 | | O | H | CH(OH) | 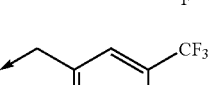 | 4.27 | 499 | A |
| IGO-E009 | 1-1g | Exp. II-go02 | CA28 | O | Et | C=O |  | 5.05 | 525 | A |
| IGH-E009 | 1-1d | IGO-E009 | | O | Et | CH(OH) | 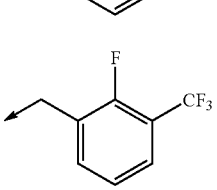 | 4.94 | 527 | A |

TABLE 92-continued

Table-G-2

| Exp. | Syn. | SM1 | SM2 | V | R$^{D1}$ | E | W | LCMS RTime | Mass | Method |
|---|---|---|---|---|---|---|---|---|---|---|
| IGH-H009 | 1-1e | IGH-E009 | | O | H | CH(OH) | 2-F, 3-CF$_3$-benzyl | 4.24 | 499 | A |
| IGO-E010 | 1-1g | Exp. II-go02 | CA08 | O | Et | C=O | 3-OMe-benzyl | 4.72 | 483 | A |
| IGH-E010 | 1-1d | IGO-E010 | | O | Et | CH(OH) | 3-OMe-benzyl | 4.55 | 485 | A |
| IGH-H010 | 1-1e | IGH-E010 | | O | H | CH(OH) | 3-OMe-benzyl | 3.85 | 425 | A |

Example IHO-E001

Synthesis of methyl 5-[3-(2-{3-oxo-4-[3-(trifluoromethyl)phenyl]butyl}-6-oxotetrahydropyridazin-1-yl)propyl]furan-2-carboxylate (Compound No. IHO-E001) (Preparation method 1-1g)

According to the procedures described in the synthesis method of Compound No. IAO-E005, 3-(trifluoromethyl)phenylacetic acid (153 mg) was used instead of 3-methoxyphenylacetic acid, and Compound No. II-h02 (40 mg) was used instead of Compound No. II-a02, and they were reacted and treated to obtain the title compound (Compound No. IHO-E001, 58 mg). Mass (LCMS): 481 (M$^+$+1), RT=4.57.

Example IHH-E001

Synthesis of methyl 5-[3-(2-{3-hydroxy-4-[3-(trifluoromethyl)phenyl]butyl}-6-oxotetrahydropyridazin-1-yl)propyl]furan-2-carboxylate (Compound No. IHH-E001) (Preparation method 1-1d)

According to the procedures described in the synthesis method of Compound No. IAH-E001, Compound No. IHO-E001 (58 mg) was used instead of Compound No. IAO-E001, and the material was reacted and treated to obtain the title compound (Compound No. IHH-E001). Mass (LCMS): 483 (M$^+$+1), RT=4.46.

Example IHH-H001

Synthesis of 5-[3-(2-{3-hydroxy-4-[3-(trifluoromethyl)phenyl]butyl}-6-oxotetrahydropyridazin-1-yl)propyl]furan-2-carboxylic acid (Compound No. IHH-H001) (Preparation method 1-1e)

According to the procedures described in the synthesis method of Compound No. IAH-H001, Compound No. IHH-E001 obtained in the example mentioned above was used instead of Compound No. IAH-E001, and the material was reacted and treated to obtain the title compound (Compound No. IHH-H001, 18 mg). Mass (LCMS): 469 (M$^+$+1), RT=4.07.

Example IIO-E001

Synthesis of ethyl 2-(2-{2-[3-oxo-4-(3-trifluoromethylphenyl)butyl]-6-oxotetrahydropyridazin-1-yl}ethoxy)isonicotinate (Compound No. IIO-E001) (Preparation method 1-1g)

According to the procedures described in the synthesis method of Compound No. IAO-E005, 3-(trifluoromethyl)phenylacetic acid (476 mg) was used instead of 3-methoxyphenylacetic acid, Compound No. II-i02 (56.4 mg) was used instead of Compound No. II-a02, and they were reacted and treated to obtain the title compound (Compound No. IIO-E001, 68.5 mg). Mass (LCMS): 508 (M$^+$+1), RT=4.16 (LCMS measurement condition: Method B).

Example IIH-E001

Synthesis of ethyl 2-(2-{2-[3-hydroxy-4-(3-trifluoromethylphenyl)butyl]-6-oxotetrahydropyridazin-1-yl}ethoxy)isonicotinate (Compound No. IIH-E001) (Preparation method 1-1d)

According to the procedures described in the synthesis method of Compound No. IAH-E001, Compound No. IIO-E001 (68.5 mg) was used instead of Compound No. IAO-E001, and the material was reacted and treated to obtain the title compound (Compound No. IIH-E001, 68.4 mg). Mass (LCMS): 510 (M$^+$+1), RT=3.92 (LCMS measurement condition: Method B).

Example IIH-H001

Synthesis of 2-(2-{2-[3-hydroxy-4-(3-trifluoromethylphenyl)butyl]-6-oxotetrahydropyridazin-1-yl}ethoxy)isonicotinic acid (Compound No. IIH-H001) (Preparation method 1-1e)

According to the procedures described in the synthesis method of Compound No. IAH-H001, Compound No. IIH-E001 (68.4 mg) was used instead of Compound No. IAH-E001, and the material was reacted and treated to obtain the title compound (Compound No. IIH-H001, 25.6 mg). Mass (LCMS): 482 ($M^{+}+1$), RT=3.64 (LCMS measurement condition: Method B).

Example IJO-E001

Synthesis of methyl 2-[(4-{3-oxo-4-[3-(trifluoromethyl)phenyl]butyl}-6-oxotetrahydropyridazin-1-yl)butoxy]acetate (Example IJO-E001) (Preparation method 1-1o)

A solution of 3-trifluoromethylphenylacetic acid (24.9 g, TCI) in DCM (240 ml) was added with WSC.HCl (27.6 g, KOKUSAN), N,O-dimethylhydroxylamine hydrochloride (24.1 g, ALD), dimethylaminopyridine (1.45 g, TCI), and DIEA (67.3 ml, WAKO), and the mixture was stirred at room temperature for 14 hours. The reaction mixture was added with ethyl acetate, successively washed with 1 N aqueous hydrochloric acid, saturated brine, saturated aqueous sodium hydrogencarbonate, and saturated brine, and dried, and then the solvent was evaporated under reduced pressure. A solution of 4.3 g of this residue in anhydrous THF (36 ml) was cooled to −40° C., and added dropwise with a 1 M solution of vinylmagnesium bromide in THF (20.9 ml, ALD) under a nitrogen gas atmosphere, and then the mixture was warmed to room temperature, and stirred for 60 minutes. The reaction mixture was successively washed with saturated aqueous ammonium chloride and saturated brine, and the solvent was evaporated under reduced pressure with ethanol substitution. A solution of Compound No. II-j02 (381 mg) in ethanol (20 ml) was added with TEA (0.41 ml), and a solution of a half amount of the residue obtained above in ethanol (1 ml), and the mixture was refluxed for 1 hour by heating. After 1 hour, the reaction mixture was added with the other half of the residue, and further refluxed for 1.5 hours by heating. The reaction solution was left to cool, then added with ethyl acetate, successively washed with 1 N aqueous hydrochloric acid, saturated brine, saturated aqueous sodium hydrogencarbonate, and saturated brine, and concentrated under reduced pressure. Then, the residue was purified by column chromatography (Flash, n-hexane/ethyl acetate=from 1:1) to obtain a coupling product (466 mg). Mass (LCMS): 477 ($M^{+}+1$), RT=5.00 (LCMS measurement condition: Method B).

A solution of the product in ethanol (5.5 ml) was added with 10% palladium/carbon (15 mg, Merck), and the mixture was stirred at room temperature for 13 hours under a hydrogen atmosphere. The reaction mixture was filtered, and the solvent of the filtrate was evaporated under reduced pressure. A solution of 336 mg of the residue in THF (2.9 ml) was cooled to 0° C., and added with potassium t-butoxide (149 mg, TCI) and methyl bromoacetate (133 μl, WAKO) under a nitrogen gas atmosphere, and the mixture was warmed to room temperature, and stirred for further 20 minutes. The reaction solution was cooled to 0° C., added with ethyl acetate, and 1 N hydrochloric acid, successively washed with saturated aqueous sodium hydrogencarbonate and saturated brine, and concentrated under reduced pressure. Then, the residue was purified by PTLC (developed 3 times with chloroform/methanol=12:1) to obtain the title compound (Compound No. IJO-E001, 108 mg). Mass (LCMS): 459 ($M^{+}+1$), RT=3.74 (LCMS measurement condition: Method B).

Example IJH-E001

Synthesis of methyl 2-[(4-{3-hydroxy-4-[3-(trifluoromethyl)phenyl]butyl}-6-oxotetrahydropyridazin-1-yl)butoxy]acetate (Example IJH-E001) (Preparation method 1-1d)

According to the procedures described in the synthesis method of Compound No. IAH-E001 except that the temperature condition, 0° C. to room temperature, was changed to −50° C. to 0° C., a mixture of Compound No. IJO-E001 (4 mg) was used instead of Compound No. IAO-E001, and the material was reacted and treated to obtain a crude product of the title compound (Compound No. IJH-E001). Mass (LCMS): 461 ($M^{+}+1$), RT=3.46 (LCMS measurement condition: Method B).

Example IJH-H001

Synthesis of 2-[(4-{3-hydroxy-4-[3-(trifluoromethyl)phenyl]butyl}-6-oxotetrahydropyridazin-1-yl)butoxy]acetic acid (Example IJH-E001) (Preparation method 1-1e)

According to the procedures described in the synthesis method of Compound No. IAH-H001, Compound No. IJH-E001 was used instead of Compound No. IAH-E001, and the material was reacted and treated to obtain a crude product of the title compound (Compound No. IJH-H001, 1.4 mg). Mass (LCMS): 447 ($M^{+}+1$), RT=3.04 (LCMS measurement condition: Method B).

Example IKO-E001

Synthesis of methyl 2-{4-[(2-{3-oxo-4-[3-(trifluoromethyl)phenyl]butyl}-6-oxotetrahydropyridazin-1-yl)methyl]phenyl}acetate (Compound No. IKO-E001) (Preparation method 1-1g)

According to the procedures described in the synthesis method of Compound No. IAO-E005, 3-(trifluoromethyl)phenylacetic acid (590 mg) was used instead of 3-methoxyphenylacetic acid, Compound No. II-k02 (152 mg) was used instead of Compound No. II-a02, and they were reacted and treated to obtain the title compound (Compound No. IKO-E001, 195 mg). Mass (LCMS): 477 ($M^{+}+1$), RT=4.64.

Example IKH-E001

Synthesis of methyl 2-{4-[(2-{3-hydroxy-4-[3-(trifluoromethyl)phenyl]butyl}-6-oxotetrahydropyridazin-1-yl)methyl]phenyl}acetate (Compound No. IKO-H001) (Preparation method 1-1d)

According to the procedures described in the synthesis method of Compound No. IAH-E001, Compound No. IKO-E001 (195 mg) was used instead of Compound No. IAO-E001, and the material was reacted and treated to obtain the title compound (Compound No. IKH-E001, 198 mg). Mass (LCMS): 479 ($M^{+}+1$), RT=4.49.

Example IKO-H001

Synthesis of 2-{4-[(2-{3-hydroxy-4-[3-(trifluoromethyl)phenyl]butyl}-6-oxotetrahydropyridazin-1-yl)methyl]phenyl}acetic acid (Compound No. IKO-H001) (Preparation method 1-1e)

According to the procedures described in the synthesis method of Compound No. IAH-H001, Compound No. IKH-E001 (198 mg) obtained in the example mentioned above was used instead of Compound No. IAH-E001, and the material was reacted and treated to obtain the title compound (Compound No. IKH-H001, 180 mg). Mass (LCMS): 465 (M$^+$+1), RT=4.12.

Example ILO-E001

Synthesis of methyl 2-{3-[(2-{3-oxo-4-[3-(trifluoromethyl)phenyl]butyl}-6-oxotetrahydropyridazin-1-yl)methyl]phenyl}acetate (Compound No. ILO-E001) (Preparation method 1-1g)

According to the procedures described in the synthesis method of Compound No. IAO-E005, 3-(trifluoromethyl)phenylacetic acid (128 mg) was used instead of 3-methoxyphenylacetic acid, Compound No. II-102 (33 mg) was used instead of Compound No. II-a02, and they were reacted and treated to obtain the title compound (Compound No. ILO-E001, 29 mg). Mass (LCMS): 477 (M$^+$+1), RT=4.48 (LCMS measurement condition: Method B).

Example ILH-E001

Synthesis of methyl 2-{3-[(2-{3-hydroxy-4-[3-(trifluoromethyl)phenyl]butyl}-6-oxotetrahydropyridazin-1-yl)methyl]phenyl}acetate (Compound No. ILO-H001) (Preparation method 1-1d)

According to the procedures described in the synthesis method of Compound No. IAH-E001, Compound No. ILO-E001 (29 mg) was used instead of Compound No. IAO-E001, and the material was reacted and treated to obtain the title compound (Compound No. ILH-E001, 30 mg). Mass (LCMS): 479 (M$^+$+1), RT=4.32 (LCMS measurement condition: Method B).

Example ILO-H001

Synthesis of 2-{3-[(2-{3-hydroxy-4-[3-(trifluoromethyl)phenyl]butyl}-6-oxotetrahydropyridazin-1-yl)methyl]phenyl}acetic acid (Compound No. ILO-H001) (Preparation method 1-1e)

According to the procedures described in the synthesis method of Compound No. IAH-H001, Compound No. ILH-E001 (30 mg) obtained in the example mentioned above was used instead of Compound No. IAH-E001, and the material was reacted and treated to obtain the title compound (Compound No. ILO-H001, 24 mg). Mass (LCMS): 465 (M$^+$+1), RT=4.20.

Example IMO-E001

Synthesis of ethyl 3-{4-[(2-{3-oxo-4-[3-(trifluoromethyl)phenyl]butyl}-6-oxotetrahydropyridazin-1-yl)methyl]phenyl}acrylate (Example IMO-E001) (Preparation method 1-1g)

According to the procedures described in the synthesis method of Compound No. IAO-E005, 3-(trifluoromethyl)phenylacetic acid (353 mg) was used instead of 3-methoxyphenylacetic acid, Compound No. II-m02 (100 mg) was used instead of Compound No. II-a02, and they were reacted and treated to obtain the title compound (Compound No. IMO-E001, 50 mg). Mass (LCMS): 503 (M$^+$+1), RT=4.79 (LCMS measurement condition: Method B).

Example IMH-E001

Synthesis of ethyl 3-{4-[(2-{3-hydroxy-4-[3-(trifluoromethyl)phenyl]butyl}-6-oxotetrahydropyridazin-1-yl)methyl]phenyl}acrylate (Example IMH-E001) (Preparation method 1-1d)

According to the procedures described in the synthesis method of Compound No. IAH-E001, Compound No. IMO-E001 (50 mg) was used instead of Compound No. IAO-E001, and the material was reacted and treated to obtain the title compound (Compound No. IMH-E001, 41 mg). Mass (LCMS): 505 (M$^+$+1), RT=4.62 (LCMS measurement condition: Method B).

Example IMH-H001

Synthesis of 3-{4-[(2-{3-hydroxy-4-[3-(trifluoromethyl)phenyl]butyl}-6-oxotetrahydropyridazin-1-yl)methyl]phenyl}acrylic acid (Example IMH-H001) (Preparation method 1-1e)

According to the procedures described in the synthesis method of Compound No. IAH-H001, Compound No. IMH-E001 (20 mg) obtained in the example mentioned above was used instead of Compound No. IAH-E001, and the material was reacted and treated to obtain the title compound (Compound No. IMH-H001, 14 mg). Mass (LCMS): 477 (M$^+$+1), RT=4.17.

Example INH-E001

Synthesis of ethyl 3-{4-[(2-{3-hydroxy-4-[3-(trifluoromethyl)phenyl]butyl}-6-oxotetrahydropyridazin-1-yl)methyl]phenyl}propionate (Example INH-E001) (Preparation method pb-2)

According to the procedures described in the synthesis method of Intermediate pb-02, Compound No. IMH-E001 (20 mg) obtained in the example mentioned above was used instead of Intermediate pb-01, and the material was reacted and treated to obtain the title compound (Compound No. INH-E001, 20 mg). Mass (LCMS): 507 (M$^+$+1), RT=4.66 (LCMS measurement condition: Method B).

Example INH-H001

Synthesis of 3-{4-[(2-{3-hydroxy-4-[3-(trifluoromethyl)phenyl]butyl}-6-oxotetrahydropyridazin-1-yl)methyl]phenyl}propionic acid (Example INH-H01) (Preparation method 1-1e)

According to the procedures described in the synthesis method of Compound No. IAH-H001, Compound No. INH-E001 (20 mg) obtained in the example mentioned above was used instead of Compound No. IAH-E001, and the material was reacted and treated to obtain the title compound (Compound No. INH-H001, 12 mg). Mass (LCMS): 479 ($M^++1$), RT=4.21.

Example IOO-E001

Synthesis of ethyl 3-{3-[(2-{3-oxo-4-[3-(trifluoromethyl)phenyl]butyl}-6-oxotetrahydropyridazin-1-yl)methyl]phenyl}acrylate (Example IOO-E001) (Preparation method 1-1g)

According to the procedures described in the synthesis method of Compound No. IAO-E005, 3-(trifluoromethyl)phenylacetic acid (152 mg) was used instead of 3-methoxyphenylacetic acid, Compound No. II-o02 (43 mg) was used instead of Compound No. II-a02, and they were reacted and treated to obtain the title compound (Compound No. IOO-E001, 67 mg). Mass (LCMS): 503 ($M^++1$), RT=4.98.

Example IOH-E001

Synthesis of ethyl 3-{3-[(2-{3-hydroxy-4-[3-(trifluoromethyl)phenyl]butyl}-6-oxotetrahydropyridazin-1-yl)methyl]phenyl}acrylate (Example IOH-E001) (Preparation method 1-1d)

According to the procedures described in the synthesis method of Compound No. IAH-E001, Compound No. IOO-E001 (67 mg) was used instead of Compound No. IAO-E001, and the material was reacted and treated to obtain the title compound (Compound No. IOH-E001, 64 mg). Mass (LCMS): 505 ($M^++1$), RT=4.87.

Example IOH-H001

Synthesis of 3-{3-[(2-{3-hydroxy-4-[3-(trifluoromethyl)phenyl]butyl}-6-oxotetrahydropyridazin-1-yl)methyl]phenyl}acrylic acid (Example IOH-H001) (Preparation method 1-1e)

According to the procedures described in the synthesis method of Compound No. IAH-H001, Compound No. IOH-E001 (32 mg) obtained in the example mentioned above was used instead of Compound No. IAH-E001, and the material was reacted and treated to obtain the title compound (Compound No. IOH-H001, 28 mg). Mass (LCMS): 477 ($M^++1$), RT=4.22.

Example IPH-E001

Synthesis of ethyl 3-{3-[(2-{3-hydroxy-4-[3-(trifluoromethyl)phenyl]butyl}-6-oxotetrahydropyridazin-1-yl)methyl]phenyl}propionate (Example IPH-E001) (Preparation method pb-2)

According to the procedures described in the synthesis method of Intermediate pb-02, Compound No. IOH-E001 (32 mg) obtained in the example mentioned above was used instead of Intermediate pb-01, and the material was reacted and treated to obtain the title compound (Compound No. IPH-E001, 32 mg). Mass (LCMS): 507 ($M^++1$), RT=4.81.

Example IPH-H001

Synthesis of 3-{3-[(2-{3-hydroxy-4-[3-(trifluoromethyl)phenyl]butyl}-6-oxotetrahydropyridazin-1-yl)methyl]phenyl}propionic acid (Example IPH-H001) (Preparation method 1-1e)

According to the procedures described in the synthesis method of Compound No. IAH-H001, Compound No. IPH-E001 (32 mg) obtained in the example mentioned above was used instead of Compound No. IAH-E001, and the material was reacted and treated to obtain the title compound (Compound No. IPH-H001, 24 mg). Mass (LCMS): 479 ($M^++1$), RT=4.26.

Examples IAH-H024a and IAH-H024b

Preparation of optically active substances of 4-[2-(2-{4-[3-chlorophenyl]-3-hydroxybutyl}-6-oxotetrahydropyridazin-1-yl)ethyl]benzoic acid (Compound No. IAH-H024a and Compound No. IAH-H024b) by HPLC (Preparation method 1-1f)

Preparative HPLC using CHIRALCEL AS column (4.6 mm×250 mm, produced by Daicel Chemical Industries) was performed by using a solution of Compound No. IAH-H024 (10.6 mg) dissolved in ethanol (1.0 ml) in a volume of 25 μl per 1 time to obtain the title compounds [Compound Nos. IAH-H024a, 0.9 mg (HPLC retention time: 22.32 minutes, optical purity: 93.4 ee %), and Compound No. IAH-H024b, 1.3 mg (HPLC retention time: 24.63 minutes, optical purity: 94.8 ee %)]. The HPLC conditions were a column temperature of 40° C., monitoring by UV absorption at 254 nm, elution solvent of n-hexane [containing 0.1% (v/v) TFA]: ethanol [containing 0.1% (v/v) TFA]=80:20, and flow rate of 0.5 ml/minutes.

Example ITH-E001

Synthesis of methyl 4-[2-(2-{3-hydroxy-4-[3-(trifluoromethyl)phenyl]butyl}-6-thioxotetrahydropyridazin-1-yl)ethyl]benzoate (Compound No. ITH-E001) (Preparation method 1-1h)

A solution of Compound No. IAH-E001 (23.9 mg) in toluene (500 μl) was added with the Lawesson's reagent [2,4-bis(4-methoxyphenyl)-1,3-dithia-2,4-diphosphetane-2,4-disulfide] (20.2 mg), and the mixture was stirred at 60° C. for 2 hours under a nitrogen gas atmosphere. The reaction mixture was left to cool to room temperature, the solvent was evaporated under reduced pressure, and then the residue was purified by column chromatography (Flash, chloroform:methanol=100:1) to obtain the title compound (ITH-E001, 24.8 mg). Mass (LCMS): 495($M^++1$), RT=5.23 (LCMS measurement condition: Method B).

Example ITH-H001

Synthesis of 4-[2-(2-{3-hydroxy-4-[3-(trifluoromethyl)phenyl]butyl}-6-thioxotetrahydropyridazin-1-yl)ethyl]benzoic acid (Compound No. ITH-H001) (Preparation method 1-1e)

According to the procedures described in the synthesis method of Compound No. IAH-H001, Compound No. ITH-E001 (24.8 mg) was used instead of Compound No. IAH-E001, and the material was reacted and treated to obtain the title compound (Compound No. ITH-H001, 8.5 mg). Mass (LCMS): 481 ($M^+$+1), RT=4.53 (LCMS Measurement condition: Method B).

Formulation example will be specifically mentioned below. However, formulation is not limited to the following example.

Formulation Example 1

Solutions were prepared, in which each of the test compounds used in Test Example 2 was dissolved in a suitable solvent (20 to 50% PEG 400, 15% cyclodextrin and the like).

Test Example 1

Bone Nodule Formation Action in Rat Bone Marrow Cells

In order to investigate osteogenesis promoting action of the compounds of the present invention, the compounds were made to act on cultured rat bone marrow cells, and the number of formed bone nodule was counted.

(1) Measurement Method

As rat bone marrow cells, mesenchymal cells (KEM100) derived from rat bone marrow purchased from Dainippon Pharmaceutical were used. The cells stored in liquid nitrogen were thawed at 37° C., then suspended in a phosphate-buffered saline, and centrifuged at 900 rpm for 5 minutes. The supernatant was removed, and the cells were suspended again in a MEM culture medium (produced by GIBCO) containing 10% fetal bovine serum (produced by GIBCO). After the number of cells was counted, the cells were inoculated on a 12-well plate (produced by IWAKI) at a cell density of $1\times10^4$ cells/$cm^2$, and cultured at 37° C. in a 5% $CO_2$ incubator. From the next day of the inoculation, the medium was exchanged with the α MEM culture medium containing 10% fetal bovine serum every 2 or 3 days, and the cells were proliferated to the confluent state. The addition of the compound was conducted from the next day after the cells reached confluent. All the compounds were dissolved in dimethyl sulfoxide at a concentration of 100 mM, and further dissolved at a concentration of 0.01 nM to 100 μM in αMEM culture medium containing 10% fetal bovine serum, 5 mM β-glycerophosphoric acid (produced by Sigma), and 50 μg/ml of ascorbic acid (produced by Wako Pure Chemical Industries). The medium was exchanged every 2 or 3 days, and the cells were fixed with a formalin solution in phosphate buffer 21 to 28 days after the addition of the compounds, subjected to von Kossa staining, and observed under a microscope to count the numbers of mineralized bone nodule formed.

(2) Measurement Results

The test compound (Compound No. IAH-H001) exhibited an bone nodule formation promoting action in a dose-dependent manner in a concentration ranging from 1 nM to 10 μM, and thus was confirmed to have an osteogenesis promoting action. The test compound exhibited no cytotoxicity in the above concentrations.

Test Example 2

Bone Mass Increasing Action in Osteoporosis Model Rats

In order to investigate bone mass increasing action of the compounds of the present invention, they were given to osteoporosis model rats, and bone densities were measured.

(1) Measurement Method

Ovariectomy and left sciatic nerve excision were simultaneously performed in 7-week old female SD-IGS rats (Charles River Japan) under ether anesthesia.

In the same manner as that of Formulation Example 1, each of the compounds was dissolved in a suitable solvent (20 to 50% PEG 400, 15% cyclodextrin and the like), and orally administered at an appropriate dose (0.1 mg/kg, 1 mg/kg, 10 mg/kg, or 100 mg/kg) immediately after the surgical operation. Then, the compounds were administered once every day.

Three weeks after the start of the experiment, the rats were sacrificed, the left tibias were extracted, and surrounding tissues such as muscles were removed. Then, bone densities were measured by using a bone mineral analyzer DCS-600EX (produced by ALOKA).

(2) Measurement Results

The bone density decreased by 15% in average in the operation+solvent treatment group compared with the sham operation group. Whilst, in the group in which the rats were treated with representative compounds of Compound (I) of the present invention described in the specification (Example Compound Nos. IAH-H001a and IAH-H010), bone density was maintained or increased in the range of from decrease of 10% to increase of 15% compared with the sham operation group. From these results, it was confirmed that the compounds of the present invention were useful as a prophylactic and/or therapeutic agent for skeletal diseases. Moreover, no death and no $PGE_2$-like side reaction were observed in any of the compound treatment groups, and thus it was demonstrated that the compounds of the present invention were safely administrable.

Test Example 3

Bone Regeneration Promoting Action in Partial Cranial Bone Defect Model Rats

In order to investigate bone regeneration promoting action of the compounds of the present invention, they were locally given to partial cranial bone defect model rats, and pathological evaluation was performed.

(1) Measurement Method

The compounds were each dissolved in dimethyl sulfoxide or ethanol, and further dissolved in phosphate buffered physiological saline containing 100 mg/ml of fibrinogen and 0.2 mg/ml of aprotinin to prepare test solutions, which were stored with ice cooling.

Left parietal bones of 8-week old male SD-IGS rats (Charles River Japan) were perforated at the center with a diameter of 4.0 mm under nembutal anesthetization by using a trepan bar (produced by Micro Seiko) to create partial defect. Immediately after the operation, 25 μl of each test solution was dropped onto the defect portion, 5 mM aqueous calcium chloride containing 100 NIH units/ml of thrombin was further dropped onto the portion and solidified as gel, and then the epidermis was sutured.

Three weeks after the start of the experiment, the rats were sacrificed, and the same defects were created at the centers of right parietal bones. Then, the cranial bones were extracted, and after surrounding tissues were removed, soft X-ray photographs of the bones were taken. Binarization was performed with a threshold value of 50 by using an image analyzer Vidas (Zeiss) to obtain ratios of the osteoanagenesis regions (areas of light shadow regions of left side defect positions) to the total defect regions (areas of right side defects).

(2) Measurement Results

In the solvent-treated group, osteoanagenesis corresponding to increase of 15% in average was observed. Whilst in the groups in which representative compounds of Compound (I) of the present invention described in the specification were given (Example Compound Nos. IAH-H001a, IAH-H010, and IAH-H057, 1 µg/individual for each compound), osteoanagenesis was promoted within the range of increase of 20% to 60%. From the results, it was confirmed that the compounds of the present invention were useful as osteoanagenesis promotion agents for use in surgical medical treatments. Moreover, no death and no $PGE_2$-like side reaction were observed in any of the compound treatment groups, and thus it was demonstrated that the compounds of the present invention were safely administrable.

Test Example 4

Human Hepatic Microsome Metabolism Stability Test

In order to evaluate ability of the compounds to be metabolized in the liver, which is considered to greatly influence on the retention of drugs in blood, metabolic stability of the compounds of the present invention was examined by using human hepatic microsomes.

(1) Measurement Method

Test compounds were each dissolved and diluted in a buffer (100 mM Tris-HCl buffer (pH 7.4)), and added with human hepatic microsomes (5 mg/mL), as well as 13.2 mM NADP, 320 mM G6P, 8 U/mL of G6Pdase, 240 mM magnesium chloride, 200 mM UDP-GA, and 6.6 mM β-NAD (1:1:1:1:2:2) as a NADPH regeneration system, and the mixture was incubated at 37° C. After 20 minutes, the reaction was terminated with 100% acetonitrile, and measurement was performed by LC/MS or LC/MS/MS. The metabolic stability was represented with the liver intrinsic clearance (CLint) value.

(2) Measurement Results

Representative compounds of the objective Compound (I) described in the specification gave a typical CLint value of not more than 30 mL/min/kg, and thus it was considered that they were hardly metabolized in human liver, and extremely stable compounds.

Test Example 5

Agonist Activity Measurement Using Human $EP_4$ Receptor Expressing Cells

In order to investigate $EP_4$ receptor agonist activity of the compounds of the present invention, cAMP production was measured by using HEK293 in which the human $EP_4$ receptor was stably expressed.

(1) Measurement Method

As a result of searching for prostaglandin E receptors using Refseq Database, the gene information of human $EP_4$ (NM_000958) receptor was obtained. On the basis of the sequence information, the human $EP_4$ receptor gene was cloned by PCR using human cDNA as a template in a conventional manner to establish HEK293 in which the human $EP_4$ receptor was stably expressed. These cells were inoculated on a 96-well poly-D-lysine coated plate at a density of $2\times10^4$ cells/well, and cultured for 1 day. The medium in the wells was removed by aspiration, 80 µL of Dulbecco's modified Eagle's medium was added to each well, and the cells were incubated at 37° C. for 15 minutes. Then, 20 µL of an assay medium (Dulbecco's modified Eagle's medium containing 100 mM HEPES and 1 mM IBMX) containing $PGE_2$ or a test compound (at 5-fold concentration of the final concentration) was added to start the reaction, and the reaction was allowed at 37° C. for 30 minutes. Then, the medium was removed by aspiration, and the reaction was terminated by adding 100 µL of Assay/Lysis Buffer included in cAMP Screen Kit (produced by Applied Biosystems). Then, the cells were incubated at 37° C. for 30 minutes, and used as a sample for cAMP quantification. By using this sample, amount of cAMP in the sample was quantified according to the method attached to cAMP Screen Kit.

(2) Measurement Results

Increase of cAMP was observed at a test compound concentration of 10 µM for the compounds listed below with Example Compound Nos.: IAH-H001, IAH-H001a, IAH-H001b, IAH-E001, IAH-H002, IAH-H003, IAH-H004, IAH-H005, IAH-H006, IAH-H009, IAH-H010, IAH-H012, IAH-H013, IAH-H014, ICH-H001, IDH-H001, IEH-H001, IAH-H015, IAH-H016, IAH-H017, IAH-H018, IAH-H019, IAH-H020, IAH-H021, IAH-H022, IAH-H023, IAH-H024, IAH-H024a, IAH-H024b, IAH-H025, IAH-H026, IAH-H027, IAH-H028, IAH-H029, IAH-H030, IAH-H031, IAH-H032, IAH-H033, IAH-H034, IAH-H035, IAH-H036, IAH-H037, IAH-H038, IAH-H039, IAH-H040, IAH-H041, IFH-H001, IGH-H001, IAH-H042, IAH-H043, IAH-H044, IAH-H045, IAH-H046, IAH-H047, IAH-H048, IAH-H049, IAH-H050, IHH-H001, IAH-H051, IAH-H052, IAH-H053, IAH-H054, IAH-H055, IAH-H056, IAH-H060, IAH-H058, ITH-H001, IKH-H001, IOH-H001, IPH-H001, IGH-H002, IAH-H061, IDH-H006, ILH-H001, IAH-H063, IAH-H064, IGH-H003, IGH-H004, IGH-H005, IDH-H002, IDH-H003, IDH-H004, IDH-H005, IAH-H057, IGH-H006, IAH-H059, IGH-H007, IGH-H008, IGH-H009, IGH-H010, IDH-H007, IAH-H062, IAH-H065, IAH-H066, IAH-H067, and IAH-H068.

Test Example 6

Receptor Binding Test by Using Human EP Receptor Expressing Cells

In order to evaluate the selectivity for each EP receptor subtype, which is considered to greatly influence on the side reaction of drugs, $[^3H]PGE_2$ binding inhibitory activities of test compounds were measured in HEK293 in which human $EP_1$, human $EP_2$, human $EP_3$, or human $EP_4$ receptor was stably expressed.

(1) Measurement Method

As a result of searching for prostaglandin E receptors using Refseq Database, the gene information of human $EP_1$ (NM_000955), human $EP_2$ (NM_000956), human $EP_3$ (NM_198719), and human $EP_4$ (NM_000958) was obtained. On the basis of the sequence information, each receptor gene was cloned by PCR using human cDNA as a template in a conventional manner. First, by using the gene of human $EP_4$ receptor, HEK293 in which the human $EP_4$ receptor was stably expressed was established, and a membrane fraction was prepared. The membrane fraction was incubated at 30° C. for 90 minutes with a reaction mixture containing a test compound and [$^3$H]$PGE_2$ (200 μL/well). After the reaction, the reaction mixture was subjected to suction filtration under reduced pressure so that [$^3$H]$PGE_2$ binding to the membrane fraction was trapped on Unifilter Plate GF/C (produced by Packard), and binding radioactivity was measured by using a liquid scintillator.

The Kd value was obtained by Scatchard plot. Nonspecific bindings were obtained as bindings in the presence of excess amount (10 μM) of non-labelled $PGE_2$. The [$^3$H]$PGE_2$ binding inhibitory activity of a test compound was measured by adding [$^3$H]$PGE_2$ (1 nM) and a test compound at various concentrations. For the reaction, the following buffer was always used.

Buffer: 10 mM MES/NaOH (pH 6.0), 10 mM $MgCl2$, 1 mM EDTA, 0.1% BSA

The dissociation constant Ki of each compound was obtained in accordance with the following equation. [C] represents a concentration of [$^3$H]$PGE_2$ used for the binding inhibition test (1 nM in this test).

$$Ki=IC_{50}/(1+[C]/Kd).$$

Further, HEK293 in which each of human $EP_1$, human $EP_2$, and human $EP_3$ receptors was stably expressed was established, and a membrane fraction was prepared. By using each membrane fraction, Ki values of the test compound for human $EP_1$, human $EP_2$, and human $EP_3$ receptors were obtained in the same manner as the method used for $EP_4$ mentioned above. The ratios of Ki value for human $EP_4$ to Ki values for human $EP_1$, human $EP_2$, and human $EP_3$ were calculated. That is, a larger value of the ratio means binding to the human $EP_4$ receptor with higher selectivity.

(2) Measurement Results

For Example Compound No. IAH-H001a, the ratios of Ki values for the receptors were 80000 or more for human $EP_1$/human $EP_4$, 15000 for human $EP_2$/human $EP_4$, and 45000 or more for human $EP_3$/human $EP_4$. Therefore, it was proved that the compounds of the present invention selectively acted on $EP_4$.

Test Example 7

Action in Dextran Sulfate-Induced Inflammatory Intestinal Disease Model Mice (1) Measurement Method 8-Week old female C57BL/6J mice were allowed to take 7% dextran sulfate (henceforth abbreviated as "DSS") solution as drinking water ad libitum for 10 days to prepare inflammatory intestinal disease model. From the start of DSS intake, Example Compound Nos. IAH-H001a, IAH-H010 and IAH-H057 each dissolved in a suitable solvent (20 to 50% PEG 400 or 15% cyclodextrin) in the same manner as in Formulation Example 1 were given at appropriate doses (0.1 mg/kg, 1 mg/kg, 10 mg/kg, or 100 mg/kg) every day for 10 days (henceforth referred to as "medicament-treated groups"). Further, the solvent used for dissolving the compounds of the present invention was solely given to the mice made to take DSS (henceforth referred to as "solvent group"), and the solvent used for dissolving the compounds of the present invention was solely given every day to the mice allowed to take distilled water not containing DSS as drinking water ad libitum (henceforth referred to as "normal group"). The number of mice in each group was 10. After the start of intake of drinking water, body weight and clinical score were measured every other day. The clinical score was obtained as a sum of diarrhea score (normal: 0, loose stools: 2, diarrhea: 4) and bloody stool score (normal: 0, bleeding: 2, massive bleeding: 4). The mice were sacrificed 10 days after the start of intake of DSS containing water, and weights of the intestinal tracts of the large intestines were measured.

(2) Measurement Results

In the medicament-treated groups in which the mice were given with Example Compound Nos. IAH-H001a, IAH-H010, or IAH-H057, the diarrhea score and the bloody stool score were significantly improved and suppressed, and reduction of the large intestine weight was significantly suppressed compared with the solvent group. Therefore, it was confirmed that the compounds of the present invention were useful as a medicament for prophylactic and/or therapeutic treatment of ulcerative colitis or Crohn's disease, which are inflammatory intestinal diseases.

Test Example 8

Intraocular Pressure Lowering Action (1) Measurement Method

Male crab-eating monkeys with a body weight of 5 to 7.5 kg (5- to 10-year old) were used for the experiment. Example Compound Nos. IAH-H001a, IAH-H010, and IAH-H057 were each dissolved at various concentrations in water or physiological saline containing sodium hydroxide in an amount of the same equivalence as each compound. The intraocular pressure was measured immediately before a treatment with a test compound, then 50 μl of a solution containing each test compound was instilled, and the intraocular pressure was measured over time for 6 hours after the instillation. The intraocular pressure was measured under ketamine (5 to 10 mg/kg, intramuscular injection) anesthetization by using a pneumatic applanation tonometer. Each test compound was used in 3 monkeys, and the intraocular pressures before and after the instillation were compared.

(2) Measurement Results

Example Compound No. IAH-H001a, IAH-H010, and IAH-H057 exhibited significant intraocular pressure lowering action for the intraocular pressures after the instillation with each compound compared with the intraocular pressures before the instillation. Therefore, it was confirmed that the compounds of the present invention were useful as a medicament for prophylactic and/or therapeutic treatment of glaucoma.

INDUSTRIAL APPLICABILITY

The compounds of the present invention exhibit potent osteogenesis promotion action, when they are administered in free forms or in the forms of salts to human or animals, and they are useful as active ingredients of, for example, medicaments for prophylactic and/or therapeutic treatment of skeletal diseases such as osteoporosis and fracture, and medicaments for promoting osteoanagenesis in surgical medical treatments. The compounds of the present invention are also useful as active ingredients of medicaments for prophylactic and/or therapeutic treatment of glaucoma, ulcerative colitis and the like.

The invention claimed is:
1. A compound represented by the formula (I) or a salt thereof:

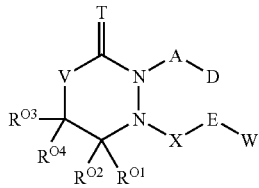 (I)

wherein T represents (1) oxygen atom, or (2) sulfur atom;
V represents a sulfur atom;
$R^{O1}$, $R^{O2}$, $R^{O3}$, and $R^{O4}$ independently represent (1) hydrogen atom, or (2) an alkyl group having 1 to 4 carbon atoms;
A represents $A^1$ or $A^2$;
$A^1$ represents (1) a linear alkylene group having 2 to 8 carbon atoms which may be substituted with one or two alkyl groups having 1 to 4 carbon atoms, (2) a linear alkenylene group having 2 to 8 carbon atoms which may be substituted with one or two alkyl groups having 1 to 4 carbon atoms, or (3) a linear alkynylene group having 2 to 8 carbon atoms which may be substituted with one or two alkyl groups having 1 to 4 carbon atoms;
$A^2$ represents a -$G^1$-$G^2$-$G^3$- group;
$G^1$ represents (1) a linear alkylene group having 1 to 4 carbon atoms which may be substituted with one or two alkyl groups having 1 to 4 carbon atoms, (2) a linear alkenylene group having 2 to 4 carbon atoms which may be substituted with one or two alkyl groups having 1 to 4 carbon atoms, or (3) a linear alkynylene group having 2 to 4 carbon atoms which may be substituted with one or two alkyl groups having 1 to 4 carbon atoms;
$G^2$ represents (1) a —$Ar^1$— group, (2) a —Y—$Ar^1$— group, (3) a —$Ar^1$—Y— group, or (4) a —Y— group, Y represents (1) —S— group, (2) —S(O)— group, (3) —S(O)$_2$— group, (4) —O— group, or (5) a —N($R^{G1}$)— group;
$R^{G1}$ represents (1) hydrogen atom, (2) an alkyl group having 1 to 4 carbon atoms, or (3) an acyl group having 2 to 6 carbon atoms; the group $Ar^1$ represents (1) a radical of a carbocyclic compound (ca1), or (2) a radical of a heterocyclic compound (qa1); the group $Ar^1$ may be substituted with 1 or the same or different 2 to 4 of groups $R^1$;
the group $R^1$ represents (1) an alkyl group having 1 to 4 carbon atoms, (2) an alkoxy group having 1 to 4 carbon atoms, or (3) a halogen atom;
$G^3$ represents (1) a single bond, (2) a linear alkylene group having 1 to 4 carbon atoms which may be substituted with one or two alkyl groups having 1 to 4 carbon atoms, (3) a linear alkenylene group having 2 to 4 carbon atoms which may be substituted with one or two alkyl groups having 1 to 4 carbon atoms, or (4) a linear alkynylene group having 2 to 4 carbon atoms which may be substituted with one or two alkyl groups having 1 to 4 carbon atoms (provided that when $G^2$ represents the —$Ar^1$—Y— group, or the —Y— group, $G^3$ represents any of those defined above except for a single bond);
D represents $D^1$ or $D^2$;
$D^1$ represents (1) a —$COOR^{D1}$ group, (2) tetrazol-5-yl group, or (3) a —C(O)N($R^{D2}$)SO$_2$R$^{D3}$ group;
$R^{D1}$ represents (1) hydrogen atom, (2) an alkyl group having 1 to 4 carbon atoms, (3) phenyl group, (4) an alkyl group having 1 to 4 carbon atoms substituted with phenyl group, or (5) a biphenyl group;
$R^{D2}$ represents (1) hydrogen atom, or (2) an alkyl group having 1 to 4 carbon atoms;
$R^{D3}$ represents (1) an alkyl group having 1 to 4 carbon atoms, or (2) phenyl group;
$D^2$ represents (1) a —CH$_2$OR$^{D4}$ group, (2) a —OR$^{D4}$ group, (3) formyl group, (4) a —C(O)NR$^{D5}$R$^{D6}$ group, (5) a —C(O)N(R$^{D5}$)SO$_2$R$^{D7}$ group, (6) a —C(O)-M$_m$-OH group, (7) a —O-M$_m$-H group, (8) a —COOR$^{D8}$ group, (9) a —OC(O)—R$^{D9}$ group, (10) a —COO-Z$^1$-Z$^2$-Z$^3$ group, or (11) a substituent selected from the group consisting of the substituents $D^{2a1}$, $D^{2a2}$, $D^{2a3}$, $D^{2a4}$ and $D^{2a5}$ represented by the following formulas:

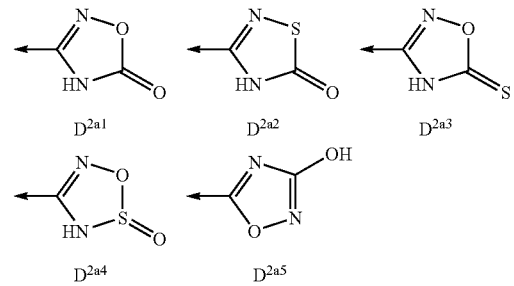

(wherein the arrows indicate a bond with the group A);
$R^{D4}$ represents (1) hydrogen atom, or (2) an alkyl group having 1 to 4 carbon atoms;
$R^{D5}$ and $R^{D6}$ independently represent (1) hydrogen atom or (2) an alkyl group having 1 to 4 carbon atoms, or (3) $R^{D5}$ and $R^{D6}$ may bind to each other to form a saturated monocyclic heterocyclic ring (qb1) together with the nitrogen atom to which they bind;
$R^{D7}$ represents an alkyl group having 1 to 4 carbon atoms substituted with phenyl group;
$R^{D8}$ represents (1) an alkyl group having 1 to 4 carbon atoms substituted with a biphenyl group which may be substituted with 1 to 3 substituents selected from the group consisting of an alkyl group having 1 to 4 carbon atoms, an alkoxy group having 1 to 4 carbon atoms, and a halogen atom, or (2) a biphenyl group which may be substituted with 1 to 3 substituents selected from the group consisting of an alkyl group having 1 to 4 carbon atoms, an alkoxy group having 1 to 4 carbon atoms, and a halogen atom;
$R^{D9}$ represents (1) phenyl group, or (2) an alkyl group having 1 to 4 carbon atoms; M represents a divalent group obtained by eliminating, from a compound having amino group and carboxyl group, hydrogen atom of the amino group and hydroxyl group of the carboxyl group;
m represents an integer of 1 or 2;
$Z^1$ represents (1) an alkylene group having 1 to 8 carbon atoms, (2) an alkenylene group having 2 to 8 carbon atoms, or (3) an alkynylene group having 2 to 8 carbon atoms;
$Z^2$ represents (1) —C(O)— group, (2) —OC(O)— group, (3) —COO— group, (4) a —C(O)N(R$^{Z1}$)— group, (5) a —N(R$^{Z2}$)C(O)— group, (6) —O— group, (7) —S— group, (8) —S(O)$_2$— group, (9) a —S(O)$_2$N(R$^{Z2}$)— group, (10) a —N(R$^{Z2)S(O)}$)$_2$— group, (11) a —N(R$^{Z3}$)— group, (12) a —N(R$^{Z4}$)C(O)N(R$^{Z5}$)— group, (13) a —N(R$^{Z6}$)C(O)O— group, (14) a —OC(O)N(R$^{Z7}$)— group, or (15) —OC(O)O— group;

$Z^3$ represents (1) hydrogen atom, (2) an alkyl group having 1 to 4 carbon atoms, (3) an alkenyl group having 2 to 4 carbon atoms, (4) an alkynyl group having 2 to 4 carbon atoms, (5) a ring Z, or (6) an alkyl group having 1 to 4 carbon atoms substituted with an alkoxy group having 1 to 4 carbon atoms, an alkylthio group having 1 to 4 carbon atoms, a —N($R^{Z8}$)($R^{Z9}$) group, or a ring Z;

the ring Z represents (1) a radical of a carbocyclic compound (ca2), or (2) a radical of a heterocyclic compound (qa2);

$R^{Z1}$, $R^{Z2}$, $R^{Z3}$, $R^{Z4}$, $R^{Z5}$, $R^{Z6}$, $R^{Z7}$, $R^{Z8}$, and $R^{Z9}$ independently represent hydrogen atom, or an alkyl group having 1 to 4 carbon atoms; or $R^{Z1}$ and $Z^3$ may form a saturated monocyclic heterocyclic ring (qb2) together with the nitrogen atom to which they bind;

X represents (1) ethylene group, (2) trimethylene group, or (3) —CH$_2$CH=CH— group;

E represents (1) —CH(OH)— group, or (2) —C(O)— group;

W represents (1) a group Wa represented by the following formula:

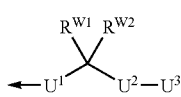
(Wa)

(wherein the arrow indicates a bond with the group E), or (2) a group $Ar^2$;

$R^{W1}$ and $R^{W2}$ independently represent (1) hydrogen atom, (2) an alkyl group having 1 to 4 carbon atoms, or (3) fluorine atom, or (4) $R^{W1}$ and $R^{W2}$ may bind to each other to form a 3- to 7- membered saturated cycloalkane (cb) together with the carbon atom to which they bind; the saturated cycloalkane (cb) may be substituted with 1 or the same or different 2 to 4 alkyl groups having 1 to 4 carbon atoms;

$U^1$ represents (1) a single bond, (2) an alkylene group having 1 to 4 carbon atoms, (3) an alkenylene group having 2 to 4 carbon atoms, or (4) an alkynylene group having 2 to 4 carbon atoms;

$U^2$ represents (1) a single bond, (2) an alkylene group having 1 to 4 carbon atoms, (3) an alkenylene group having 2 to 4 carbon atoms, (4) an alkynylene group having 2 to 4 carbon atoms, (5) —O— group, (6) —S— group, (7) —S(O)— group, (8) —S(O)$_2$— group, (9) a —N($R^{U1}$)— group, (10) —C(O)— group, (11) a —C(O)N($R^{U2}$)— group, (12) a —N($R^{U2}$)C(O)— group, (13) a —S(O)$_2$N($R^{U2}$)— group, or (14) a —N($R^{U2}$)S(O)$_2$ group;

$R^{U1}$ represents (1) hydrogen atom, (2) an alkyl group having 1 to 4 carbon atoms, or (3) an acyl group having 2 to 6 carbon atoms;

$R^{U2}$ represents (1) hydrogen atom, or (2) an alkyl group having 1 to 4 carbon atoms;

$U^3$ represents (1) an alkyl group having 1 to 8 carbon atoms which may be substituted with 1 or the same or different 2 to 4 substituents selected from the group consisting of an alkyl group having 1 to 4 carbon atoms, a halogen atom, hydroxyl group, an alkoxy group having 1 to 4 carbon atoms, an alkylthio group having 1 to 4 carbon atoms, and a —N($R^{U3}$)($R^{U4}$) group, (2) an alkenyl group having 2 to 8 carbon atoms which may be substituted with 1 or the same or different 2 to 4 substituents selected from the group consisting of an alkyl group having 1 to 4 carbon atoms, a halogen atom, hydroxyl group, an alkoxy group having 1 to 4 carbon atoms, an alkylthio group having 1 to 4 carbon atoms, and a —N($R^{U3}$)($R^{U4}$) group, (3) an alkynyl group having 2 to 8 carbon atoms which may be substituted with 1 or the same or different 2 to 4 substituents selected from the group consisting of an alkyl group having 1 to 4 carbon atoms, a halogen atom, hydroxyl group, an alkylthio group having 1 to 4 carbon atoms, and a —N($R^{U3}$)($R^{U4}$) group, (4) an alkyl group having 1 to 8 carbon atoms substituted with a group $Ar^3$, or (5) a group $Ar^3$;

$R^{U3}$ and $R^{U4}$ independently represent (1) hydrogen atom, or (2) an alkyl group having 1 to 4 carbon atoms, or (3) $R^{U3}$ and $R^{U4}$ may bind to each other to form a saturated monocyclic heterocyclic ring (qb3) together with the nitrogen atom to which they bind; the group $Ar^2$ and the group $Ar^3$ independently represent (1) a radical of a carbocyclic compound (ca3), or (2) a radical of a heterocyclic compound (qa3); the group $Ar^2$ and the group $Ar^3$ may be substituted with 1 or the same or different 2 to 4 of groups $R^2$;

$R^2$ represents (1) an alkyl group having 1 to 4 carbon atoms, (2) an alkoxy group having 1 to 4 carbon atoms, (3) an alkylthio group having 1 to 4 carbon atoms, (4) a halogen atom, (5) hydroxyl group, (6) nitro group, (7) a —N($R^{41}$)($R^{42}$) group, (8) an alkyl group having 1 to 4 carbon atoms substituted with an alkoxy group having 1 to 4 carbon atoms, (9) an alkyl group having 1 to 4 carbon atoms substituted with 1 to 3 halogen atoms, (10) an alkyl group having 1to 4 carbon atoms substituted with an alkoxy group having 1 to 4 carbon atoms substituted with 1to 3 halogen atoms, (11) an alkyl group having 1 to 4 carbon atoms substituted with a —N($R^{41}$)($R^{42}$) group, (12) a group $Ar^4$, (13) a —O—$Ar^4$ group, (14) an alkyl group having 1 to 4 carbon atoms substituted with a group $Ar^4$ (15) an alkenyl group having 2 to 4 carbon atoms substituted with a group $Ar^4$, (16) an alkynyl group having 2 to 4 carbon atoms substituted with a group $Ar^4$, (17) an alkoxy group having 1 to 4 carbon atoms substituted with a group $Ar^4$, (18) an alkyl group having 1 to 4 carbon atoms substituted with a —O—$Ar^4$ group, (19) a —COO$R^{43}$ group, (20) an alkoxy group having 1 to 4 carbon atoms substituted with 1 to 3 halogen atoms, (21) formyl group, (22) an alkyl group having 1 to 4 carbon atoms substituted with hydroxyl group, (23) an acyl group having 2 to 6 carbon atoms, (24) oxo group, or (25) thioxo group;

$R^{41}$ $R^{42}$ and independently represent (1) hydrogen atom, or (2) an alkyl group having 1 to 4 carbon atoms, or (3) $R^{41}$ and $R^{42}$ may bind to each other to form a saturated monocyclic heterocyclic ring (qb4) together with the nitrogen atom to which they bind;

$R^{43}$ represents (1) hydrogen atom, or (2) an alkyl group having 1 to 4 carbon atoms;

the group $Ar^4$ represents (1) a radical of a carbocyclic compound (ca4), or (2) a radical of a heterocyclic compound (qa4);

radicals of a carbocyclic compound ca1, ca2, ca3, and ca4 independently represent a radical of a completely unsaturated, or partially or completely saturated monocyclic compound having 3 to 11 carbon atoms, or a radical of condensed bicyclic carbocyclic compound having 8 to 11 carbon atoms;

the group $Ar^4$ may be substituted with 1 or the same or different 2 to 4 of groups $R^3$;

$R^3$ represents (1) an alkyl group having 1 to 4 carbon atoms, (2) an alkenyl group having 2 to 4 carbon atoms, (3) an alkynyl group having 2 to 4 carbon atoms, (4) an alkoxy group having 1 to 4 carbon atoms, (5) an alkyl group having 1 to 4 carbon atoms substituted with an alkoxy group having 1 to 4 carbon atoms, (6) a halogen atom, (7) hydroxyl group, (8) an alkyl group having 1 to 4 carbon atoms substituted with 1 to 3 halogen atoms, or (9) an alkyl group having 1 to 4 carbon atoms substituted with an alkoxy group having 1 to 4 carbon atoms substituted with 1 to 3 halogen atoms; radicals of a heterocyclic compound qa1, qa2, qa3, and qa4 independently represent a radical of a completely unsaturated, or partially or completely saturated monocyclic compound having 3 to 11 ring-constituting atoms (the monocyclic compound contains, as the ring-constituting atoms, one or more hetero atoms, which may be the same or different, selected from the group consisting of nitrogen atom, oxygen atom, and sulfur atom), or a radical of a condensed bicyclic heterocyclic compound (qa) having 7 to 11 ring-constituting atoms, the heterocyclic compound (qa) contains 1 to 4 hetero atoms, which may be the same or different, selected from the group consisting of nitrogen atom, oxygen atom, and sulfur atom as the ring-constituting atoms;

radicals of a saturated monocyclic heterocyclic compound qb1, qb2, qb3, and qb4 independently represent a radical of a 5- to 7-membered nitrogen-containing saturated monocyclic heterocyclic compound (qb), and the heterocyclic compound (qb) may further contain one ring-constituting hetero atom selected from the group consisting of nitrogen atom, oxygen atom, and sulfur atom, and may be substituted with 1 or the same or different 2 to 4 alkyl groups having 1 to 4 carbon atoms.

2. The compound or a salt thereof according to claim 1, which compound is represented by the general formula (I-F):

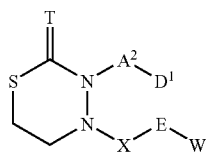

(I-F)

(wherein T, $A^2$, $D^1$, X, E, and W have the same meanings as those defined above).

3. A pharmaceutical composition comprising the compound or a pharmaceutically acceptable salt thereof according to claim 1 or 2 as an active ingredient and a pharmaceutically acceptable carrier.

4. A method of treating or reducing the risk of contracting glaucoma or ulcerative colitis, which comprises administering to a mammal in need thereof a therapeutically effective amount of the pharmaceutical composition according to claim 3.

5. A compound represented by the formula (II) or a salt thereof:

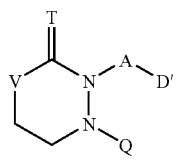

(II)

wherein D' have the same meaning as that of D mentioned below, or when D represents carboxyl group, the carboxyl group may be protected with a group $Rp^1$, when D contains hydroxyl group, the hydroxyl group may be protected with a group $Rp^2$, or when D contains formyl group, the formyl group may be protected with a group $Rp^3$;

D represents $D^1$ or $D^2$;

$D^1$ represents (1) a —$COOR^{D1}$ group, (2) tetrazol-5-yl group, or (3) a —$C(O)N(R^{D2})SO_2R^{D3}$ group;

$R^{D1}$ represents (1) hydrogen atom, (2) an alkyl group having 1 to 4 carbon atoms, (3) phenyl group, (4) an alkyl group having 1 to 4 carbon atoms substituted with phenyl group, or (5) a biphenyl group;

$R^{D2}$ represents (1) hydrogen atom, or (2) an alkyl group having 1 to 4 carbon atoms;

$R^{D3}$ represents (1) an alkyl group having 1 to 4 carbon atoms, or (2) phenyl group:

$D^2$ represents (1) a —$CH_2OR^{D4}$ group, (2) a —$OR^{D4}$ group, (3) formyl group, (4) a —$C(O)NR^{D5}R^{D6}$ group, (5) a —$C(O)N(R^{D5})SO_2R^{D7}$ group, (6) a —$C(O)-M_m$-OH group, (7) a —O—$M_m$—H group, (8) a —$COOR^{D8}$ group, (9) a —$OC(O)$—$R^{D9}$ group, (10) a —$COO-Z^1$-$Z^2$-$Z^3$ group, or (11) a substituent selected from the group consisting of the substituents $D^{2a1}$, $D^{2a2}$, $D^{2a3}$, $D^{2a4}$, and $D^{2a5}$ represented by the following formulae:

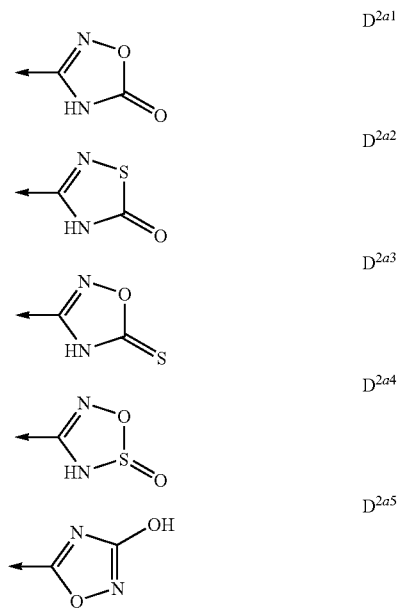

(wherein the arrows indicate a bond with the group A);

$R^{D4}$ represents (1) hydrogen atom, or (2) an alkyl group having 1 to 4 carbon atoms;

$R^{D5}$ and $R^{D6}$ independently represent (1) hydrogen atom, or (2) an alkyl group having 1 to 4 carbon atoms, or (3) $R^{D5}$ and $R^{D6}$ may bind to each other to form a saturated monocyclic heterocyclic ring (gb1) together with the nitrogen atom to which they bind;

$R^{D7}$ represents an alkyl group having 1 to 4 carbon atoms substituted with phenyl group;

$R^{D8}$ represents (1) an alkyl group having 1 to 4 carbon atoms substituted with a biphenyl group which may be substituted with 1 to 3 substituents selected from the group consisting of an alkyl group having 1 to 4 carbon atoms, an alkoxy group having 1 to 4 carbon atoms, and a halogen atom, or (2) a biphenyl group which may be substituted with 1 to 3 substituents selected from the group consisting of an alkyl group having 1 to 4 carbon atoms, an alkoxy group having 1 to 4 carbon atoms, and a halogen atom;

$R^{D9}$ represents (1) phenyl group, or (2) an alkyl group having 1 to 4 carbon atoms;

M represents a divalent group obtained by eliminating, from a compound having amino group and carboxyl group, hydrogen atom of the amino group and hydroxyl group of the carboxyl group;

m represents an integer of 1 or 2;

$Z^1$ represents (1) an alkylene group having 1 to 8 carbon atoms, (2) an alkenylene group having 2 to 8 carbon atoms, or (3) an alkynylene group having 2 to 8 carbon atoms;

$Z^2$ represents (1) —C(O)— group, (2) —OC(O)— group, (3) —COO— group, (4) a —C(O)N($R^{Z1}$)— group, (5) a —N($R^{Z2}$)C(O)— group, (6) —O— group, (7) —S— group, (8) —S(O)$_2$— group, (9) a —S(O)$_2$N($R^{Z2}$)— group, (10) a —N($R^{Z2}$)S(O)$_2$— group, (11) a —N($R^{Z3}$)— group, (12) a —N($R^{Z4}$)C(O)N($R^{Z5}$)— group, (13) a —N($R^{Z6}$)C(O)O— group, (14) a —OC(O)N($R^{Z7}$)— group, or (15) —OC(O)O— group;

$Z^3$ represents (1) hydrogen atom, (2) an alkyl group having 1 to 4 carbon atoms, (3) an alkenyl group having 2 to 4 carbon atoms, (4) an alkynyl group having 2 to 4 carbon atoms, (5) a ring Z, or (6) an alkyl group having 1 to 4 carbon atoms substituted with an alkoxy group having 1 to 4 carbon atoms, an alkylthio group having 1 to 4 carbon atoms, a —N($R^{Z8}$)($R^{Z9}$) group, or a ring Z;

the ring Z represents (1) a radical of a carbocyclic compound (ca2), or (2) a radical of a heterocyclic compound (qa2): $R^{Z1}$, $R^{Z2}$, $R^{Z3}$, $R^{Z4}$, $R^{Z5}$, $R^{Z6}$, $R^{Z7}$, $R^{Z8}$, and $R^{Z9}$ independently represent hydrogen atom, or an alkyl group having 1 to 4 carbon atoms:

or $R^{Z1}$ and $Z^3$ may form a saturated monocyclic heterocyclic ring (qb2) together with the nitrogen atom to which they bind;

wherein $Rp^3$ is acetal group;

wherein $Rp^4$ is 1 or more of the groups individual selected from -$Ap^1$-$Rp^5$, —C(O)$Rp^6$, and —COOR$p^6$, wherein $Ap^1$ and $Rp^5$ are the same as those mentioned above;

Q represents hydrogen atom, or a protective group $Rp^4$ of amino group;

wherein T represents (1) oxygen atom, or (2) sulfur atom;

A represents $A^1$ or $A^2$;

$A^1$ represents (1) a linear alkylene group having 2 to 8 carbon atoms which may be substituted with one or two alkyl groups having 1 to 4 carbon atoms, (2) a linear alkenylene group having 2 to 8 carbon atoms which may be substituted with one or two alkyl groups having 1 to 4 carbon atoms, or (3) a linear alkynylene group having 2 to 8 carbon atoms which may be substituted with one or two alkyl groups having 1 to 4 carbon atoms;

$A^2$ represents a -$G^1$-$G^2$-$G^3$- group;

$G^1$ represents (1) a linear alkylene group having 1 to 4 carbon atoms which may be substituted with one or two alkyl groups having 1 to 4 carbon atoms, (2) a linear alkenylene group having 2 to 4 carbon atoms which may be substituted with one or two ailed groups having 1 to 4 carbon atoms, or (3) a linear alkynylene group having 2 to 4 carbon atoms which may be substituted with one or two alkyl groups having 1 to 4 carbon atoms;

$G^2$ represents (1) a —$Ar^1$— group, (2) a —Y—$Ar^1$— group, (3) a —$Ar^1$—Y— group, or (4) a —Y— group, Y represents (1) —S— group, (2) —S(O)— group, (3) —S(O)$_2$— group, (4) —O— group, or (5) a —N($R^{G1}$)— group;

$R^{G1}$ represents (1) hydrogen atom, (2) an alkyl group having 1 to 4 carbon atoms, or (3) an acyl group having 2 to 6 carbon atoms;

the group $Ar^1$ represents (1) a radical of a carbocyclic compound (ca1), or (2) a radical of a heterocyctic compound (qa1); the group $Ar^1$ may be substituted with 1 or the same or different 2 to 4 of groups $R^1$;

the group $R^1$ represents (1) an alkyl group having 1 to 4 carbon atoms, (2) an alkoxy group having 1 to 4 carbon atoms, or (3) a halogen atom;

$G^3$ represents (1) a single bond, (2) a linear alkylene group having 1 to 4 carbon atoms which may be substituted with one or two alkyl groups having 1 to 4 carbon atoms, (3) a linear alkenylene group having 2 to 4 carbon atoms which may be substituted with one or two alkyl groups having 1 to 4 carbon atoms, or (4) a linear alkynylene group having 2 to 4 carbon atoms which may be substituted with one or two alkyl groups having 1 to 4 carbon atoms (provided that when $G^2$ represents the —$Ar^1$—Y— group, or the —Y— group, $G^3$ represents any of those defined above except for a single bond); and V represents a sulfur atom;

wherein $Rp^1$ is an alkyl group having 1 to 4 carbon atoms, an alkenyl group having 2 to 4 carbon atoms, an alkyl group having 1 to 4 carbon atoms substituted with an alkoxy group having 1 to 4 carbon atoms, an alkyl group having 1 to 4 carbon atoms substituted with 1 to 3 halogen atoms and -$Ap^1$-$Rp^5$ wherein -$Ap^1$ is a single bond, methylene group, or —CH$_2$C(O)—, and $Rp^5$ is phenyl group which may be substituted with 1 or the same or different 2 or more of Xp, where Xp represents an alkyl group having 1 to 4 carbon atoms, hydroxyl group, a halogen atom, trifluoromethyl group, nitro group, an alkoxy group having 1 to 4 carbon atoms, or a mono- or dialkylamino group having 1 to 4 carbon atoms in each alkyl group;

wherein $Rp^2$ is an alkyl group having 1 to 4 carbon atoms, an alkenyl group having 2 to 4 carbon atoms, an alkyl group having 1 to 4 carbon atoms substituted with an alkoxy group having 1 to 4 carbon atoms, an alkyl group having 1 to 4 carbon atoms substituted with 1 to 3 halogen atoms, a silyl group substituted with the same or different 3 of alkyl groups having 1 to 4 carbon atoms or phenyl groups, tetrahydropyranyl group, tetrahydrofuryl group, propargyl group, a group -$Ap^1$-$Rp^5$, a group —CH$_2$—$Ap^2$—$Rp^6$, a group —C(O)$Rp^6$, a group —COOR$p^6$, wherein $Ap^2$ is oxygen atom or sulfur atom, $Rp^6$ is hydrogen atom, an alkyl group having 1 to 4 carbon atoms, trimethylsilylethyl group, chloromethyl group, trichloromethyl group, trifluoromethyl group, 9-fluorenylmethyl group, adamantyl group, allyl group, and a group -$Ap^1$-$Rp^5$, wherein $Ap^1$ and $Rp^5$ are the same as those mentioned above.

* * * * *